United States Patent
Van Den Brink et al.

(10) Patent No.: US 10,407,501 B2
(45) Date of Patent: Sep. 10, 2019

(54) HUMANIZED OR CHIMERIC CD3 ANTIBODIES

(71) Applicant: GENMAB A/S, Copenhagen V (DK)

(72) Inventors: Edward Norbert Van Den Brink, Halfweg (NL); Joost J. Neijssen, Werkhoven (NL); Aran Frank Labrijn, Utrecht (NL); Joyce Meesters, Utrecht (NL); Janine Schuurman, Utrecht (NL); Isil Altintas, Utrecht (NL); Paul Parren, Utrecht (NL); Rik Rademaker, Utrecht (NL)

(73) Assignee: GENMAB A/S, Copenhagen V (DK)

( * ) Notice: Subject to any disclaimer, the term of this patent is extended or adjusted under 35 U.S.C. 154(b) by 268 days.

(21) Appl. No.: 15/110,414

(22) PCT Filed: Jan. 8, 2015

(86) PCT No.: PCT/EP2015/050276
§ 371 (c)(1),
(2) Date: Jul. 8, 2016

(87) PCT Pub. No.: WO2015/104346
PCT Pub. Date: Jul. 16, 2015

(65) Prior Publication Data
US 2016/0333095 A1    Nov. 17, 2016

(30) Foreign Application Priority Data

Jan. 9, 2014  (DK) .................................. 2014 00009
Jan. 9, 2014  (WO) ................. PCT/EP2014/050340
Jul. 4, 2014  (WO) ................. PCT/EP2014/064326

(51) Int. Cl.
| | |
|---|---|
| C07K 16/28 | (2006.01) |
| C07K 16/10 | (2006.01) |
| C07K 16/32 | (2006.01) |
| C07K 16/42 | (2006.01) |
| G01N 33/68 | (2006.01) |
| A61K 39/00 | (2006.01) |

(52) U.S. Cl.
CPC ...... *C07K 16/2809* (2013.01); *C07K 16/1063* (2013.01); *C07K 16/2863* (2013.01); *C07K 16/2887* (2013.01); *C07K 16/2896* (2013.01); *C07K 16/32* (2013.01); *C07K 16/4241* (2013.01); *G01N 33/6872* (2013.01); *A61K 2039/505* (2013.01); *C07K 2317/24* (2013.01); *C07K 2317/31* (2013.01); *C07K 2317/33* (2013.01); *C07K 2317/41* (2013.01); *C07K 2317/51* (2013.01); *C07K 2317/515* (2013.01); *C07K 2317/52* (2013.01); *C07K 2317/524* (2013.01); *C07K 2317/526* (2013.01); *C07K 2317/53* (2013.01); *C07K 2317/56* (2013.01); *C07K 2317/565* (2013.01); *C07K 2317/567* (2013.01); *C07K 2317/71* (2013.01); *C07K 2317/732* (2013.01); *C07K 2317/734* (2013.01); *C07K 2317/74* (2013.01); *C07K 2317/75* (2013.01); *C07K 2317/90* (2013.01); *C07K 2317/92* (2013.01); *G01N 2333/7051* (2013.01)

(58) Field of Classification Search
None
See application file for complete search history.

(56) References Cited

U.S. PATENT DOCUMENTS

| | | | | |
|---|---|---|---|---|
| 8,236,308 | B2 * | 8/2012 | Kischel | C07K 16/2809 424/136.1 |
| 2013/0129730 | A1 * | 5/2013 | Kufer | C07K 16/2809 424/135.1 |
| 2014/0112914 | A1 * | 4/2014 | Nezu | C07K 16/30 424/133.1 |
| 2015/0166661 | A1 * | 6/2015 | Chen | C07K 16/2809 424/135.1 |
| 2015/0337049 | A1 | 11/2015 | Labrijn et al. | |
| 2016/0168247 | A1 | 6/2016 | Van Den Brink et al. | |
| 2017/0355767 | A1 | 12/2017 | Engelberts et al. | |

FOREIGN PATENT DOCUMENTS

| | | | | |
|---|---|---|---|---|
| EP | 0 629 240 | A1 | 12/1994 | |
| WO | 92/22653 | A1 | 12/1992 | |
| WO | WO-2004035607 | A2 * | 4/2004 | ......... C07K 16/2887 |
| WO | 2007/042261 | A2 | 4/2007 | |
| WO | 2008/119567 | A2 | 10/2008 | |
| WO | 2011066501 | A1 | 6/2011 | |
| WO | WO-2012073985 | A1 * | 6/2012 | ............. C07K 16/30 |
| WO | 2012/113813 | A1 | 8/2012 | |
| WO | 2012143524 | A2 | 10/2012 | |
| WO | 2012/162067 | A2 | 11/2012 | |

(Continued)

OTHER PUBLICATIONS

Letter of F. Hoffmann-La Roche Ag, filed to the European Patent Register on Mar. 22, 2013 in connection with their opposition to the EP2155788 patent, 39 pages. (Year: 2013).*

(Continued)

*Primary Examiner* — Zachary S Skelding
(74) *Attorney, Agent, or Firm* — Nelson Mullins Riley & Scarborough LLP; Jane E. Remillard, Esq.; Christopher L. Frank

(57) ABSTRACT

The present invention relates to humanized or chimeric antibodies binding CD3. It furthermore relates to bispecific antibodies, compositions, pharmaceutical compositions, use of said antibodies in the treatment of a disease, and method of treatment.

19 Claims, 26 Drawing Sheets
Specification includes a Sequence Listing.

(56) References Cited

FOREIGN PATENT DOCUMENTS

WO            2015001085 A1     1/2015

OTHER PUBLICATIONS

Document D17 filed in conjunction with the letter of F. Hoffmann-La Roche Ag on Mar. 22, 2013, pp. 1-4. (Year: 2013).*
Morgan et al. (Molecular Therapy vol. 18 No. 4, 843-851, 2010). (Year: 2010).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Labrijn et al. (Proc Natl Acad Sci USA. Mar. 11, 2013;110(13):5145-50 and Supplemental data pp. 1-10) (Year: 2013).*
Bokemeyer, C. et al., "Safety of catumaxomab: Cytokine release-related symptoms as a possible predictive factor for efficacy in a pivotal phase II/III trial in malignant ascites," J Clin Oncol., 4 pages, (Meeting Abstracts), Abstract No. 3036 (2009).
Bruhns, P. et al., "Specificity and affinity of human Fcgamma receptors and their polymorphic variants for human IgG subclasses," Blood, vol. 113(16): 3716-3725 (2009).
Bryson, C. et al., "Prediction of immunogenicity of therapeutic proteins: validity of computational tools," Biodrugs, vol. 24 (1): 1-8 (2010).
Canfield, S. et al, "The Binding Affinity of Human IgG for its High Affinity Fc Receptor Is Determined by Multiple Amino Acids in the CH2 Domain and Is Modulated by the Hinge Region," J. Exp. Med., vol. 173: 1483-1491 (1991).
Dall'Acqua, W.F., et al, "Modulation of the effector functions of a human IgG1 through engineering of its hinge region," J Immunol., vol. 177(2): 1129-1138 (2006).
Duncan, A.R. et al., "The binding site for C1q on IgG," Nature, vol. 332 (6166): 738-740 (1988).
Heiss, M.M. et al., "The trifunctional antibody catumaxomab for the treatment of malignant ascites due to epithelial cancer: Results of a prospective randomized phase II/III trial," Int J Cancer, vol. 127(9): 2209-2221 (2010).
Herold, KC et al., "A single course of anti-CD3 monoclonal antibody hOKT3gamma1(Ala-Ala) results in improvement in C-peptide responses and clinical parameters for at least 2 years after onset of type 1 diabetes," Diabetes, vol. 54(6):1763-1769 (2005).
Hezareh, M. et al., "Effector function activities of a panel of mutants of a broadly neutralizing antibody against human immunodeficiency virus type I," Journal of Virology, The American Society for Micro-Biology, US, vol. 75 (24): 12161-12168 (2001).
Hinojosa, L.E., et al., "Construction of a Recombinant Non-Mitogenic Anti-Human CD3 Antibody," Hybridoma, vol. 29 (2): 115-124 (2010).
Idusogie, E.E., et al., "Mapping of the C1q binding site on rituxan, a chimeric antibody with a human IgG1 Fc," J Immunol., vol. 164 (8): 4178-4184 (2000).
International Preliminary Report on Patentability, PCT/EP2015/050276, dated Jul. 12, 2016, 8 pages.
International Search Report and Written Opinion, PCT/EP2015/050276, dated Mar. 13, 2015, 13 pages.
Jing, Li, et al., "Phase I trial of a humanized, Fc receptor nonbinding anti-CD3 antibody, hu12F6mu in patients receiving renal allografts," MABS, vol. 2 (4): 449-456 (2010).
Jones, K. et al., "Evolving novel anti-HER2 strategies," Lancet Oncol., vol. 10 (12): 1179-1187 (2009).
Kiewe, P. et al., "Phase I trial of the trifunctional anti-HER2 x anti-CD3 antibody ertumaxomab in metastatic breast cancer," Clin Cancer Res., vol. 12(10): 3085-3091 (2006).
Leabman, M et al., "Effects of altered Fc gamma R binding on antibody pharmacokinetics in cynomolgus monkeys," Mabs, vol. 5(6): 896-903 (2013).
Li, B. et al., "Construction and characterization of a humanized anti-human CD3 monoclonal antibody 12F6 with effective Immuno-regulation functions," Immunology, Blackwell Publishing, Oxford, GB, vol. 116 (4):487-498 (2010).
Lightle, S. et al., "Mutations within a human IgG2 antibody form distinct and homogeneous disulfide isomers but do not affect Fc gamma receptor or C1q binding," Protein Science, vol. 19 (4): 753-762 (2010).
Linke, R. et al., "Catumaxomab: clinical development and future directions," Mabs, vol. 2 (2): 129-136 (2010).
Lum and Thakur, "Targeting T cells with bispecific antibodies for cancer therapy," BioDrugs, vol. 25(6): 365-379 (2011).
Müller and Kontermann, "Bispecific antibodies for cancer immunotherapy: Current perspectives," BioDrugs, vol. 24(2): 89-98 (2010).
Oganesyan, V. et al., "Structural characterization of a human Fc fragment engineered for lack of effector functions," Acta Cryst., vol. D64: 700-704 (2008).
Parren, P.W. et al., "On the interaction of IgG subclasses with the low affinity Fc gamma RIIa (CD32) on human monocytes, neutrophils, and platelets, Analysis of a functional polymorphism to human IgG2," J. Clin Invest., vol. 90 (4): 1537-1546 (1992).
Perry, L.C. et al., "New approaches to prediction of immune responses to therapeutic proteins during preclinical development," Drugs, R.D., vol. 9 (6): 385-396 (2008).
Ruf, P. et al, "Pharmacokinetics, immunogenicity and bioactivity of the therapeutic antibody catumaxomab intraperitoneally administered to cancer patients," Br J Clin Pharmacol, vol. 69(6): 617-625 (2010).
Shields, Robert L. et al., "High Resolution Mapping of the Binding Site on Human IgG1 for FcgammaRI, FcgammaRII, FcgammaRII, and FcRn and Design of IgG1 Variants with Improved Binding to the FcgammaR," The Journal of Biological Chemistry, vol. 276(9):6591-6604 (2001).
Staerz, U.D. et al, "Hybrid antibodies can target sites for attack by T cells," 1985, Nature, vol. 314 (6012): 628-631 (1985).
Woodle, E.S., "Phase I trial of a humanized, Fc receptor nonbinding OKT3 antibody, huOKT3 gamma 1(Ala-Ala) in the treatment of acute renal allograft rejection," Transplantation, Williams and Wilkins, US, Baltimore, vol. 68(5): 608-616(1999).
Xu, D. et al., "In vitro characterization of five humanized OKT3 effector function variant antibodies," Cell Immunol., vol. 200(1): 16-26 (2000).
Office Action, U.S. Appl. No. 14/760,157, dated Feb. 7, 2019.
Office Action, U.S. Appl. No. 14/760,157, dated Aug. 27, 2018.
Office Action, U.S. Appl. No. 14/902,757, dated Mar. 14, 2019.
Office Action, U.S. Appl. No. 15/541,594, dated Nov. 27, 2018.
U.S. Appl. No. 14/760,157, filed Jul. 9, 2015, Aran Frank Labrijn.
U.S. Appl. No. 14/902,757, filed Jan. 4, 2016, Edward Van Den Brink.
U.S. Appl. No. 15/541,594, filed Jul. 5, 2017, Patrick Engelberts.
U.S. Appl. No. 15/744,317, filed Jan. 12, 2018, Rik Rademaker.
Office Action, U.S. Appl. No. 14/760,157, dated Apr. 9, 2018.
Office Action, U.S. Appl. No. 14/760,157, dated Sep. 20, 2017.
Office Action, U.S. Appl. No. 14/760,157, dated Feb. 17, 2017.
Office Action, U.S. Appl. No. 14/902,757, dated Jul. 30, 2018.
Office Action, U.S. Appl. No. 14/902,757, dated Dec. 18, 2017.
Office Action, U.S. Appl. No. 15/541,594, dated May 29, 2018.

* cited by examiner

| Antibody | EC50 (µg/mL) |
|---|---|
| IgG1-huCD3-H1L1 | 0.07 |
| IgG1-huCD3-H1L2 | 0.08 |
| IgG1-huCD3-H1L3 | 0.06 |
| IgG1-huCD3-H3L3 | 0.02 |
| IgG1-huCD3-H4L1 | 0.05 |
| IgG1-huCD3-H3L1-LFLEDA | 0.04 |
| IgG1-CD3-LFLEDA | 0.08 |

| Antibody | EC50 (µg/mL) |
|---|---|
| bsIgG1 CD3 x HER2 | 0.68 |
| bsIgG1 CD3 x b12-LFLEDA | 0.75 |
| bsIgG1 huCD3-H3L1xHER2-LFLEDA | 0.28 |
| IgG1-huCD3-H3L1-LFLEDA | 0.04 |
| IgG1-CD3-LFLEDA | 0.07 |

SEQUENCE LISTING

<160> NUMBER OF SEQ ID NOS: 60

<210> SEQ ID NO 1
<211> LENGTH: 8
<212> TYPE: PRT
<213> ORGANISM: Mus musculus

<400> SEQUENCE: 1

Gly Phe Thr Phe Asn Thr Tyr Ala
1               5

<210> SEQ ID NO 2
<211> LENGTH: 10
<212> TYPE: PRT
<213> ORGANISM: Mus musculus

<400> SEQUENCE: 2

Ile Arg Ser Lys Tyr Asn Asn Tyr Ala Thr
1               5                   10

<210> SEQ ID NO 3
<211> LENGTH: 16
<212> TYPE: PRT
<213> ORGANISM: Mus musculus

<400> SEQUENCE: 3

Val Arg His Gly Asn Phe Gly Asn Ser Tyr Val Ser Trp Phe Ala Tyr
1               5                   10                  15

<210> SEQ ID NO 4
<211> LENGTH: 9
<212> TYPE: PRT
<213> ORGANISM: Mus musculus

<400> SEQUENCE: 4

Thr Gly Ala Val Thr Thr Ser Asn Tyr
1               5

<210> SEQ ID NO 5
<211> LENGTH: 9
<212> TYPE: PRT
<213> ORGANISM: Mus musculus

<400> SEQUENCE: 5

Ala Leu Trp Tyr Ser Asn Leu Trp Val
1               5

<210> SEQ ID NO 6
<211> LENGTH: 125
<212> TYPE: PRT
<213> ORGANISM: homo sapiens

<400> SEQUENCE: 6

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

-continued

Ala Tyr Trp Gly Gln Gly Thr Leu Val Thr Val Ser Ser
            115                 120                 125

<210> SEQ ID NO 7
<211> LENGTH: 125
<212> TYPE: PRT
<213> ORGANISM: homo sapiens

<400> SEQUENCE: 7

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 8
<211> LENGTH: 125
<212> TYPE: PRT
<213> ORGANISM: homo sapiens

<400> SEQUENCE: 8

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 9
<211> LENGTH: 125
<212> TYPE: PRT
<213> ORGANISM: homo sapiens

<400> SEQUENCE: 9

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr

```
                    20                  25                  30
Ala Met Asn Trp Val Arg Gln Ala Pro Gly Lys Gly Leu Glu Trp Val
                35                  40                  45

Ala Arg Ile Arg Ser Lys Tyr Asn Asn Tyr Ala Thr Tyr Tyr Ala Asp
         50                  55                  60

Ser Val Lys Asp Arg Phe Thr Ile Ser Arg Asp Asp Ser Lys Ser Ile
 65                  70                  75                  80

Leu Tyr Leu Gln Met Asn Ser Leu Lys Thr Glu Asp Thr Ala Met Tyr
                 85                  90                  95

Tyr Cys Val Arg His Gly Asn Phe Gly Asn Ser Tyr Val Ser Trp Phe
                100                 105                 110

Ala Tyr Trp Gly Gln Gly Thr Met Val Thr Val Ser Ser
            115                 120                 125

<210> SEQ ID NO 10
<211> LENGTH: 109
<212> TYPE: PRT
<213> ORGANISM: homo sapiens

<400> SEQUENCE: 10

Gln Ala Val Val Thr Gln Glu Pro Ser Phe Ser Val Ser Pro Gly Gly
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
                35                  40                  45

Leu Ile Gly Gly Thr Asn Lys Arg Ala Pro Gly Val Pro Ala Arg Phe
             50                  55                  60

Ser Gly Ser Leu Ile Gly Asp Lys Ala Ala Leu Thr Ile Thr Gly Ala
 65                  70                  75                  80

Gln Ala Asp Asp Glu Ser Ile Tyr Phe Cys Ala Leu Trp Tyr Ser Asn
                 85                  90                  95

Leu Trp Val Phe Gly Gly Gly Thr Lys Leu Thr Val Leu
                100                 105

<210> SEQ ID NO 11
<211> LENGTH: 109
<212> TYPE: PRT
<213> ORGANISM: homo sapiens

<400> SEQUENCE: 11

Gln Ala Val Val Thr Gln Glu Pro Ser Phe Ser Val Ser Pro Gly Gly
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Thr Pro Gly Gln Ala Phe Arg Gly
                35                  40                  45

Leu Ile Gly Gly Thr Asn Lys Arg Ala Pro Gly Val Pro Ala Arg Phe
             50                  55                  60

Ser Gly Ser Ile Leu Gly Asn Lys Ala Ala Leu Thr Ile Thr Gly Ala
 65                  70                  75                  80

Gln Ala Asp Asp Glu Ser Ile Tyr Phe Cys Ala Leu Trp Tyr Ser Asn
                 85                  90                  95

Leu Trp Val Phe Gly Gly Gly Thr Lys Leu Thr Val Leu
                100                 105
```

<210> SEQ ID NO 12
<211> LENGTH: 109
<212> TYPE: PRT
<213> ORGANISM: homo sapiens

<400> SEQUENCE: 12

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 13
<211> LENGTH: 186
<212> TYPE: PRT
<213> ORGANISM: homo sapiens

<400> SEQUENCE: 13

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
            115                 120                 125

Tyr Trp Ser Lys Asn Arg Lys Ala Lys Ala Lys Pro Val Thr Arg Gly
        130                 135                 140

Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
            180                 185

<210> SEQ ID NO 14
<211> LENGTH: 150
<212> TYPE: PRT
<213> ORGANISM: homo sapiens

<400> SEQUENCE: 14

```
Phe Lys Ile Pro Ile Glu Glu Leu Glu Asp Arg Val Phe Val Asn Cys
1               5                   10                  15

Asn Thr Ser Ile Thr Trp Val Glu Gly Thr Val Gly Thr Leu Leu Ser
                20                  25                  30

Asp Ile Thr Arg Leu Asp Leu Gly Lys Arg Ile Leu Asp Pro Arg Gly
            35                  40                  45

Ile Tyr Arg Cys Asn Gly Thr Asp Ile Tyr Lys Asp Lys Glu Ser Thr
        50                  55                  60

Val Gln Val His Tyr Arg Met Cys Gln Ser Cys Val Glu Leu Asp Pro
65              70                  75                  80

Ala Thr Val Ala Gly Ile Ile Val Thr Asp Val Ile Ala Thr Leu Leu
                85                  90                  95

Leu Ala Leu Gly Val Phe Cys Phe Ala Gly His Glu Thr Gly Arg Leu
                100                 105                 110

Ser Gly Ala Ala Asp Thr Gln Ala Leu Leu Arg Asn Asp Gln Val Tyr
            115                 120                 125

Gln Pro Leu Arg Asp Arg Asp Asp Ala Gln Tyr Ser His Leu Gly Gly
130                 135                 140

Asn Trp Ala Arg Asn Lys
145                 150

<210> SEQ ID NO 15
<211> LENGTH: 330
<212> TYPE: PRT
<213> ORGANISM: homo sapiens

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65              70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 17
<211> LENGTH: 119
<212> TYPE: PRT
<213> ORGANISM: homo sapiens

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Phe Trp Val Arg Gln Ala Pro Gly Lys Gly Leu Glu Trp Val
        35                  40                  45

Ala Thr Ile Ser Arg Tyr Ser Arg Tyr Ile Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Leu Tyr Gly Ser Ser Pro Asp Tyr Trp Gly Gln Gly
            100                 105                 110

Thr Leu Val Thr Val Ser Ser
        115

<210> SEQ ID NO 18
<211> LENGTH: 106
<212> TYPE: PRT
<213> ORGANISM: homo sapiens

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Val
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Ser Gly Thr Lys Leu Glu Met Arg
            100                 105

<210> SEQ ID NO 19
<211> LENGTH: 121
```

<212> TYPE: PRT
<213> ORGANISM: homo sapiens

<400> SEQUENCE: 19

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
                100                 105                 110

Gln Gly Thr Leu Val Thr Val Ser Ser
            115                 120
```

<210> SEQ ID NO 20
<211> LENGTH: 107
<212> TYPE: PRT
<213> ORGANISM: homo sapiens

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
                100                 105
```

<210> SEQ ID NO 21
<211> LENGTH: 177
<212> TYPE: PRT
<213> ORGANISM: Macaca fascicularis

<400> SEQUENCE: 21

```
Gln Asp Gly Asn Glu Glu Met Gly Ser Ile Thr Gln Thr Pro Tyr Gln
1               5                   10                  15

Val Ser Ile Ser Gly Thr Thr Val Ile Leu Thr Cys Ser Gln His Leu
                20                  25                  30

Gly Ser Glu Ala Gln Trp Gln His Asn Gly Lys Asn Lys Glu Asp Ser
            35                  40                  45

Gly Asp Arg Leu Phe Leu Pro Glu Phe Ser Glu Met Glu Gln Ser Gly
    50                  55                  60

Tyr Tyr Val Cys Tyr Pro Arg Gly Ser Asn Pro Glu Asp Ala Ser His
```

```
                65                  70                  75                  80
His Leu Tyr Leu Lys Ala Arg Val Cys Glu Asn Cys Met Glu Met Asp
                    85                  90                  95

Val Met Ala Val Ala Thr Ile Val Ile Val Asp Ile Cys Ile Thr Leu
                100                 105                 110

Gly Leu Leu Leu Val Tyr Tyr Trp Ser Lys Asn Arg Lys Ala Lys
            115                 120                 125

Ala Lys Pro Val Thr Arg Gly Ala Gly Ala Gly Gly Arg Gln Arg Gly
            130                 135                 140

Gln Asn Lys Glu Arg Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 22
<211> LENGTH: 177
<212> TYPE: PRT
<213> ORGANISM: Macaca mulatta

<400> SEQUENCE: 22

Gln Asp Gly Asn Glu Glu Met Gly Ser Ile Thr Gln Thr Pro Tyr His
1               5                   10                  15

Val Ser Ile Ser Gly Thr Thr Val Ile Leu Thr Cys Ser Gln His Leu
                20                  25                  30

Gly Ser Glu Val Gln Trp Gln His Asn Gly Lys Asn Lys Glu Asp Ser
            35                  40                  45

Gly Asp Arg Leu Phe Leu Pro Glu Phe Ser Glu Met Glu Gln Ser Gly
        50                  55                  60

Tyr Tyr Val Cys Tyr Pro Arg Gly Ser Asn Pro Glu Asp Ala Ser His
65                  70                  75                  80

His Leu Tyr Leu Lys Ala Arg Val Cys Glu Asn Cys Met Glu Met Asp
                    85                  90                  95

Val Met Ala Val Ala Thr Ile Val Ile Val Asp Ile Cys Ile Thr Leu
                100                 105                 110

Gly Leu Leu Leu Val Tyr Tyr Trp Ser Lys Asn Arg Lys Ala Lys
            115                 120                 125

Ala Lys Pro Val Thr Arg Gly Ala Gly Ala Gly Gly Arg Gln Arg Gly
            130                 135                 140

Gln Asn Lys Glu Arg Pro Pro Val Pro Asn Pro Asp Tyr Glu Pro
145                 150                 155                 160

Ile Arg Lys Gly Gln Gln Asp Leu Tyr Ser Gly Leu Asn Gln Arg Arg
                165                 170                 175

Ile

<210> SEQ ID NO 23
<211> LENGTH: 330
<212> TYPE: PRT
<213> ORGANISM: homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30
```

-continued

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 24
<211> LENGTH: 330
<212> TYPE: PRT
<213> ORGANISM: homo sapiens

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 330
<212> TYPE: PRT
<213> ORGANISM: homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
```

```
                115                 120                 125
Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 330
<212> TYPE: PRT
<213> ORGANISM: homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 125
<212> TYPE: PRT
<213> ORGANISM: Mus musculus

<400> SEQUENCE: 27

Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125

<210> SEQ ID NO 28
<211> LENGTH: 109
<212> TYPE: PRT
<213> ORGANISM: Mus musculus

<400> SEQUENCE: 28

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30
```

```
Asn Tyr Ala Asn Trp Val Gln Glu Lys Pro Asp His Leu Phe Thr Gly
            35                  40                  45

Leu Ile Gly Gly Thr Asn Lys Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

Leu Trp Val Phe Gly Gly Gly Thr Lys Leu Thr Val Leu
                100                 105
```

<210> SEQ ID NO 29
<211> LENGTH: 122
<212> TYPE: PRT
<213> ORGANISM: homo sapiens

<400> SEQUENCE: 29

```
Glu Val Gln Leu Val Glu Ser Gly Gly Gly Leu Val Gln Pro Asp Arg
 1               5                  10                  15

Ser Leu Arg Leu Ser Cys Ala Ala Ser Gly Phe Thr Phe His Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Thr Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Tyr Gly Met Asp Val Trp
                100                 105                 110

Gly Gln Gly Thr Thr Val Thr Val Ser Ser
            115                 120
```

<210> SEQ ID NO 30
<211> LENGTH: 107
<212> TYPE: PRT
<213> ORGANISM: homo sapiens

<400> SEQUENCE: 30

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
                100                 105
```

<210> SEQ ID NO 31
<211> LENGTH: 106

```
<212> TYPE: PRT
<213> ORGANISM: homo sapiens

<400> SEQUENCE: 31

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 32
<211> LENGTH: 109
<212> TYPE: PRT
<213> ORGANISM: homo sapiens

<400> SEQUENCE: 32

Gln Ala Val Val Thr Gln Glu Pro Ser Leu Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Asn Arg Ala Pro Gly Val Pro Ala Arg Phe
50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 33
<211> LENGTH: 109
<212> TYPE: PRT
<213> ORGANISM: homo sapiens

<400> SEQUENCE: 33

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
```

```
                    85                  90                  95
Leu Trp Val Phe Gly Gly Gly Thr Lys Leu Thr Val Leu
                100                 105

<210> SEQ ID NO 34
<211> LENGTH: 8
<212> TYPE: PRT
<213> ORGANISM: homo sapiens

<400> SEQUENCE: 34

Gly Phe Thr Phe His Asp Tyr Ala
1               5

<210> SEQ ID NO 35
<211> LENGTH: 8
<212> TYPE: PRT
<213> ORGANISM: homo sapiens

<400> SEQUENCE: 35

Ile Ser Trp Asn Ser Gly Thr Ile
1               5

<210> SEQ ID NO 36
<211> LENGTH: 15
<212> TYPE: PRT
<213> ORGANISM: homo sapiens

<400> SEQUENCE: 36

Ala Lys Asp Ile Gln Tyr Gly Asn Tyr Tyr Gly Met Asp Val
1               5                   10                  15

<210> SEQ ID NO 37
<211> LENGTH: 6
<212> TYPE: PRT
<213> ORGANISM: homo sapiens

<400> SEQUENCE: 37

Gln Ser Val Ser Ser Tyr
1               5

<210> SEQ ID NO 38
<211> LENGTH: 9
<212> TYPE: PRT
<213> ORGANISM: homo sapiens

<400> SEQUENCE: 38

Gln Gln Arg Ser Asn Trp Pro Ile Thr
1               5

<210> SEQ ID NO 39
<211> LENGTH: 122
<212> TYPE: PRT
<213> ORGANISM: homo sapiens

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
        50                  55                  60
```

```
Lys Gly Arg Phe Thr Ile Ser Arg Asp Asn Ala Lys Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 40
<211> LENGTH: 107
<212> TYPE: PRT
<213> ORGANISM: homo sapiens

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Ile
                 85                  90                  95

Thr Phe Gly Gln Gly Thr Arg Leu Glu Ile Lys
            100                 105

<210> SEQ ID NO 41
<211> LENGTH: 8
<212> TYPE: PRT
<213> ORGANISM: homo sapiens

<400> SEQUENCE: 41

Gly Phe Thr Phe Asn Asp Tyr Ala
1               5

<210> SEQ ID NO 42
<211> LENGTH: 8
<212> TYPE: PRT
<213> ORGANISM: homo sapiens

<400> SEQUENCE: 42

Ile Ser Trp Asn Ser Gly Ser Ile
1               5

<210> SEQ ID NO 43
<211> LENGTH: 15
<212> TYPE: PRT
<213> ORGANISM: homo sapiens

<400> SEQUENCE: 43

Ala Lys Asp Ile Gln Tyr Gly Asn Tyr Tyr Tyr Gly Met Asp Val
1               5                   10                  15

<210> SEQ ID NO 44
<211> LENGTH: 6
<212> TYPE: PRT
```

<213> ORGANISM: homo sapiens

<400> SEQUENCE: 44

Gln Ser Val Ser Ser Tyr
1               5

<210> SEQ ID NO 45
<211> LENGTH: 9
<212> TYPE: PRT
<213> ORGANISM: homo sapiens

<400> SEQUENCE: 45

Gln Gln Arg Ser Asn Trp Pro Ile Thr
1               5

<210> SEQ ID NO 46
<211> LENGTH: 125
<212> TYPE: PRT
<213> ORGANISM: homo sapiens

<400> SEQUENCE: 46

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
        35                  40                  45

Ser Ile Ile Gly Thr Gly Gly Val Thr Tyr Tyr Ala Asp Ser Val Lys
    50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
        115                 120                 125

<210> SEQ ID NO 47
<211> LENGTH: 107
<212> TYPE: PRT
<213> ORGANISM: homo sapiens

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 48
<211> LENGTH: 8
<212> TYPE: PRT
<213> ORGANISM: homo sapiens

<400> SEQUENCE: 48

Gly Phe Thr Phe Ser Tyr His Ala
1               5

<210> SEQ ID NO 49
<211> LENGTH: 7
<212> TYPE: PRT
<213> ORGANISM: homo sapiens

<400> SEQUENCE: 49

Ile Gly Thr Gly Gly Val Thr
1               5

<210> SEQ ID NO 50
<211> LENGTH: 19
<212> TYPE: PRT
<213> ORGANISM: homo sapiens

<400> SEQUENCE: 50

Ala Arg Asp Tyr Tyr Gly Ala Gly Ser Phe Tyr Asp Gly Leu Tyr Gly
1               5                   10                  15

Met Asp Val

<210> SEQ ID NO 51
<211> LENGTH: 6
<212> TYPE: PRT
<213> ORGANISM: homo sapiens

<400> SEQUENCE: 51

Gln Ser Val Ser Ser Tyr
1               5

<210> SEQ ID NO 52
<211> LENGTH: 9
<212> TYPE: PRT
<213> ORGANISM: homo sapiens

<400> SEQUENCE: 52

Gln Gln Arg Ser Asp Trp Pro Leu Thr
1               5

<210> SEQ ID NO 53
<211> LENGTH: 123
<212> TYPE: PRT
<213> ORGANISM: homo sapiens

<400> SEQUENCE: 53

Ala Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Gly Asp Tyr
                20                  25                  30

Thr Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Asp Asn Gln Tyr Gly Ser Gly Ser Thr Tyr Gly Leu Gly Val
            100                 105                 110

Trp Gly Gln Gly Thr Leu Val Thr Val Ser Ser
        115                 120

<210> SEQ ID NO 54
<211> LENGTH: 107
<212> TYPE: PRT
<213> ORGANISM: homo sapiens

<400> SEQUENCE: 54

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 55
<211> LENGTH: 8
<212> TYPE: PRT
<213> ORGANISM: homo sapiens

<400> SEQUENCE: 55

Gly Phe Thr Phe Gly Asp Tyr Thr
1               5

<210> SEQ ID NO 56
<211> LENGTH: 8
<212> TYPE: PRT
<213> ORGANISM: homo sapiens

<400> SEQUENCE: 56

Ile Ser Trp Asn Ser Gly Ser Ile
1               5

<210> SEQ ID NO 57
<211> LENGTH: 16
<212> TYPE: PRT
<213> ORGANISM: homo sapiens

<400> SEQUENCE: 57

Thr Lys Asp Asn Gln Tyr Gly Ser Gly Ser Thr Tyr Gly Leu Gly Val
1               5                   10                  15

<210> SEQ ID NO 58
<211> LENGTH: 6
<212> TYPE: PRT
<213> ORGANISM: homo sapiens

<400> SEQUENCE: 58

```
Gln Ser Val Ser Ser Tyr
1               5

<210> SEQ ID NO 59
<211> LENGTH: 9
<212> TYPE: PRT
<213> ORGANISM: homo sapiens

<400> SEQUENCE: 59

Gln Gln Arg Ser Asn Trp Pro Leu Thr
1               5

<210> SEQ ID NO 60
<211> LENGTH: 9
<212> TYPE: PRT
<213> ORGANISM: Mus musculus

<400> SEQUENCE: 60

Ala Leu Trp Tyr Ser Asn His Trp Val
1               5
```

HUMANIZED OR CHIMERIC CD3 ANTIBODIES

RELATED APPLICATIONS

This application is a 35 U.S.C. 371 national stage filing of International Application No. PCT/EP2015/050276, filed Jan. 8, 2015, which claims priority to International Application No. PCT/EP2014/050340, filed Jan. 9, 2014, International Application No. PCT/EP2014/064326, filed Jul. 4, 2014 and Danish Patent Application No. PA 2014 00009, filed Jan. 9, 2014. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Jul. 8, 2016, is named GMI_147USD_Sequence_Listing.txt and is 53,067 bytes in size.

FIELD OF INVENTION

The present invention relates to a humanized or chimeric antibody binding to human CD3, compositions comprising said humanized or chimeric antibody, and use of said humanized or chimeric antibodies in treatment of a disease.

BACKGROUND

The Cluster of Differentiation 3 (CD3) has been known for many years and therefore has been subject of interest in many aspects. Specifically antibodies raised against CD3 or the T-cell Receptor Complex, which CD3 is part of, are known. An in vitro characterization of five humanized OKT3 effector function variant antibodies has been described [1].

Treatment with the anti-CD3 monoclonal antibody hOKT3 gamma1(Ala-Ala) results in improved C-peptide responses and clinical parameters for at least 2 years after onset of type 1 diabetes in absence of continued immunosuppressive medications [2].

A promising approach to improve targeted antibody therapy is by delivering cytotoxic cells specifically to the antigen-expressing cancer cells. This concept of using T-cells for efficient killing of tumor cells has been described [3]. However, initial clinical studies were rather disappointing mainly due to low efficacy, severe adverse effects (cytokine storm) and immunogenicity of the bispecific antibodies [4]. Advances in the design and application of bispecific antibodies have partially overcome the initial barrier of cytokine storm and improved clinical effectiveness without dose-limiting toxicities [5].

For example, certain bispecific antibodies targeting with one arm the antigen on the tumor cell and with the other arm for instance CD3 on T cells, provide Fc receptor binding by the Fc region. Upon binding, a complex of T cells, tumor cells and effector cells that bind the antibody Fc region is formed, leading to killing of the tumor cells [4]. Catumaxomab consists of a mouseIgG2a/ratIgG2b heterodimer and has been found successful for the treatment of cancer-associated ascites after intraperitoneal application [6]. However, the mouse/rat hybrid is immunogenic [7] and cannot be applied for long-term intravenous treatment in humans. Frequent treatment-related adverse events attributed to catumaxomab included cytokine-release-related symptoms (i.e. pyrexia, nausea, vomiting, chills, tachycardia and hypotension) [8]-[9], which relate to the effector functions of the Fc region of catumaxomab. Another antibody is ertumaxomab (HER2×CD3), which induces cytotoxicity in cell lines with low HER2 expression. Ertumaxomab has been in Phase II clinical development for metastatic breast cancer [10]-[11].

CD3 antibodies cross-reactive to cynomolgus and/or rhesus monkey CD3 have been described [12]-[13], however, further improvements for such cross-reactive antibodies are needed.

SUMMARY OF INVENTION

It is an object of the present invention to provide humanized or chimeric CD3 antibodies. Thus, in one aspect, the present invention relates to a humanized or chimeric antibody binding to human CD3, wherein said antibody comprises a binding region comprising heavy chain variable (VH) region CDR1, CDR2, and CDR3 having the sequences as set forth in SEQ ID NOs: 1, 2, and 3, respectively, and light chain variable (VL) region CDR1, CDR2, and CDR3 having the sequences as set forth in SEQ ID NO: 4, the sequence GTN, and the sequence as set forth in SEQ ID NO: 5 or SEQ ID NO:60, respectively.

in one aspect, the present invention relates to a humanized or chimeric antibody binding to human CD3, wherein said antibody comprises a binding region comprising heavy chain variable (VH) region CDR1, CDR2, and CDR3 having the sequences as set forth in SEQ ID NOs: 1, 2, and 3, respectively, and light chain variable (VL) region CDR1, CDR2, and CDR3 having the sequences as set forth in SEQ ID NO: 4, the sequence GTN, and the sequence as set forth in SEQ ID NO: 5, respectively.

In another aspect, the present invention relates to a bispecific antibody comprising a first binding region of an antibody according to the invention, and a second binding region which binds a different target than said first antigen binding region.

In another aspect, the present invention relates to a nucleic acid construct encoding one or more amino acid sequences according to the invention.

In another aspect, the present invention relates to an expression vector comprising (i) a nucleic acid sequence encoding a heavy chain sequence of a humanized or chimeric antibody according to the invention, (ii) a nucleic acid sequence encoding a light chain sequence of a humanized or chimeric antibody according to the invention, or (iii) both (i) and (ii).

In another aspect, the present invention relates to a host cell comprising an expression vector according to the invention.

In another aspect, the present invention relates to a composition comprising the antibody or bispecific antibody according to the invention.

In another aspect, the present invention relates to a pharmaceutical composition comprising the antibody or bispecific antibody according to the invention and a pharmaceutical acceptable carrier In another aspect, the present invention relates to the antibody or bispecific antibody, the composition, or the pharmaceutical composition according to the invention for use as a medicament.

In another aspect, the present invention relates to the antibody or bispecific antibody, the composition, or the pharmaceutical composition according to the invention for use in the treatment of a disease.

In another aspect, the present invention relates to a method of treatment of a disease comprising administering the antibody or bispecific antibody, the composition, or the pharmaceutical composition according to the invention, to a subject in need thereof.

In one aspect, the present invention relates to a method of diagnosing a disease characterized by involvement or accumulation of CD3-expression cells, comprising administering the humanized or chimeric antibody, the composition or the pharmaceutical composition according to the invention to a subject, optionally wherein said humanized or chimeric antibody is labeled with a detectable agent.

In another aspect, the present invention relates to a method for producing an antibody or a bispecific antibody according to the invention, comprising the steps of a) culturing a host cell according to the invention, and b) purifying the antibody from the culture media.

In another aspect, the present invention relates to a diagnostic composition comprising an antibody or bispecific antibody according to the invention.

In another aspect, the present invention relates to a method for detecting the presence of CD3 antigen, or a cell expressing CD3, in a sample comprising the steps of a) contacting the sample with an antibody or bispecific antibody according to the invention, under conditions that allow for formation of a complex between the antibody or bispecific antibody and CD3, and b) analyzing whether a complex has been formed.

In another aspect, the present invention relates to a kit for detecting the presence of CD3 antigen, or a cell expressing CD3, in a sample comprising i) an antibody or bispecific antibody according to the invention, and ii) instructions for use of the kit.

In another aspect, the present invention relates to an anti-idiotypic antibody which binds to an antibody according to the invention.

BRIEF DESCRIPTION OF FIGURES

FIG. 19: Sequence alignment of heavy chain (VH) and light chain (VL) variable regions of humanized CD3 antibodies according to the present invention.

DETAILED DESCRIPTION

Figure 1A:
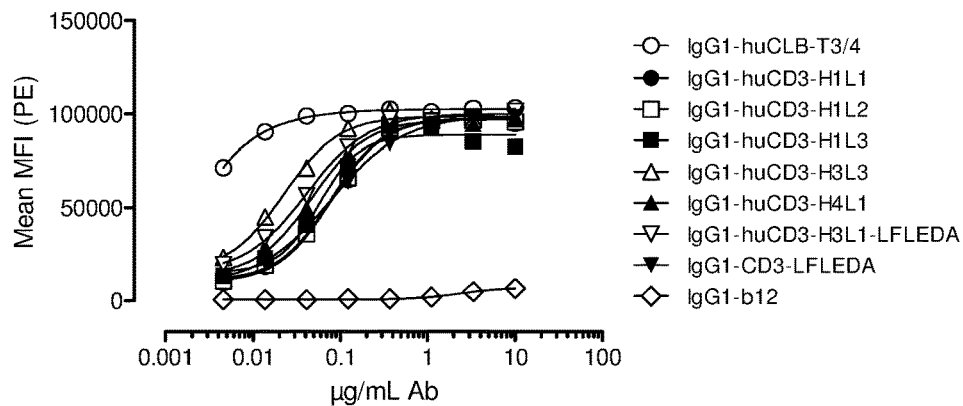
FIGS. 1A and 1B: Shows binding curves of (FIG. 1A) monospecific antibody variants of IgG1-huCD3 and (FIG. 1B) bispecific antibody variants bsIgG1 huCD3×HER2 to the human T-cell line Jurkat. Data shown are mean fluorescence intensities (MFI) of one representative experiment, as described in Example 2. The tables show the antibody concentrations (μg/mL) that result in half-maximal binding (EC50).

In one aspect, the present invention relates to a humanized or chimeric antibody binding to human CD3, wherein said antibody comprises a binding region comprising heavy chain variable (VH) region CDR1, CDR2, and CDR3 having the sequences as set forth in SEQ ID NOs: 1, 2, and 3, respectively, and light chain variable (VL) region CDR1, CDR2, and CDR3 having the sequences as set forth in SEQ ID NO: 4, the sequence GTN, and the sequence as set forth in SEQ ID NO: 5 or SEQ ID NO:60, respectively.

In one embodiment, the present invention relates to a humanized or chimeric antibody binding to human CD3, wherein said antibody comprises a binding region comprising heavy chain variable (VH) region CDR1, CDR2, and CDR3 having the sequences as set forth in SEQ ID NOs: 1, 2, and 3, respectively, and light chain variable (VL) region CDR1, CDR2, and CDR3 having the sequences as set forth in SEQ ID NO: 4, the sequence GTN, and the sequence as set forth in SEQ ID NO: 5, respectively.

The term "antibody" as used herein is intended to refer to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The binding region (or binding domain which may also be used herein, both terms having the same meaning) which interacts with an antigen, comprises variable regions of both the heavy and light chains of the immunoglobulin molecule. The constant regions of the antibodies (Abs) may mediate the binding of the immunoglobulin to host tissues or factors, including various cells of the immune system (such as effector cells and T-cells) and components of the complement system such as C1q, the first component in the classical pathway of complement activation. As indicated above, the term antibody as used herein, unless otherwise stated or clearly contradicted by context, includes fragments of an antibody that retain the ability to specifically interact, such as bind, to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab A/S); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; and (iv) a Fv fragment consisting essentially of the $V_L$ and $V_H$ domains of a single arm of an antibody. Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "immunoglobulin heavy chain", "heavy chain of an immunoglobulin" or "heavy chain" as used herein is intended to refer to one of the chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The heavy chain constant region may further comprise a hinge region. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance [14]). Within the structure of the immunoglobulin, the two heavy chains are inter-connected via disulfide bonds in the so-called "hinge region". Equally to the heavy chains each light chain is typically comprised of several regions; a light chain variable region (abbreviated herein as VL) and a light chain constant region (abbreviated herein as CL). The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see [15]). CDR sequences may be determined by use of the method provided by IMGT [16]-[17].

The term "isotype" as used herein, refers to the immunoglobulin class (for instance IgG1, IgG2, IgG3, IgG4, IgD, IgA, IgE, or IgM) or any allotype thereof, such as IgG1m (za) and IgG1m(f) [SEQ ID NO:15]) that is encoded by heavy chain constant region genes. Thus, in one embodiment, the antibody comprises a heavy chain of an immunoglobulin of the IgG1 class or any allotype thereof. Further, each heavy chain isotype can be combined with either a kappa (κ) or lambda (λ) light chain.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in [18]. Thus, the chimeric may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may for typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see [19]-[20]). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The humanized or chimeric antibody according to any aspect or embodiment of the present invention may be termed "humanized or chimeric CD3 antibody", "humanized or chimeric antibody of the invention", "CD3 antibody", or "CD3 antibody of the invention", which all have the same meaning and purpose unless otherwise contradicted by context.

The amino acid sequence of an antibody of non-human origin is distinct from antibodies of human origin, and therefore a non-human antibody is potentially immunogenic when administered to human patients. However, despite the non-human origin of the antibody, its CDR segments are responsible for the ability of the antibody to bind to its target antigen and humanization aims to maintain the specificity and binding affinity of the antibody. Thus, humanization of non-human therapeutic antibodies is performed to minimize its immunogenicity in man while such humanized antibodies at the same time maintain the specificity and binding affinity of the antibody of non-human origin.

The term "binding region" as used herein, refers to a region of an antibody which is capable of binding to any molecule, such as a polypeptide, e.g. present on a cell, bacterium, or virion.

The term "binding" as used herein, refers to the binding of an antibody to a predetermined antigen or target to which binding typically is with an affinity corresponding to a $K_D$ of about $10^{-6}$ M or less, e.g. $10^{-7}$ M or less, such as about $10^{-8}$ M or less, such as about $10^{-9}$ M or less, about $10^{-19}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The degree with which the affinity is lower is dependent on the $K_D$ of the antibody, so that when the $K_D$ of the antibody is very low (that is, the antibody is highly specific), then the degree with which the affinity for the antigen is lower than the affinity for a non-specific antigen may be at least 10,000 fold. The term "$K_D$" (M), as used herein, refers to the dissociation equilibrium constant of a particular antibody-antigen interaction.

The term "human CD3" as used herein, refers to the human Cluster of Differentiation 3 protein which is part of the T-cell co-receptor protein complex and is composed of four distinct chains. CD3 is also found in other species, and thus, the term "CD3" may be used herein and is not limited to human CD3 unless contradicted by context. In mammals, the complex contains a CD3γ (gamma) chain (human CD3γ chain Swissprot P09693, or cynomolgus monkey CD3γ Swissprot Q95LI7), a CD3δ (delta) chain (human CD3δ Swissprot P04234, or cynomolgus monkey CD3δ Swissprot Q95LI8), two CD3ε (epsilon) chains (human CD3ε Swissprot P07766; or cynomolgus CD3ε Swissprot Q95LI5), rhesus CD3ε (Swissprot G7NCB9), and a CD3ζ-chain (zeta) chain (human CD3ζ Swissprot P20963, cynomolgus monkey CD3ζ Swissprot Q09TK0). These chains associate with a molecule known as the T-cell receptor (TCR) and generate an activation signal in T lymphocytes. The TCR and CD3 molecules together comprise the TCR complex.

It is within the knowledge of the skilled person that amino acid sequences referred to as Swissprot numbers include a signal peptide which is removed after translation of the protein. Thus, proteins, such as CD3, present on cell surfaces do not include the signal peptide. In particular, the amino acid sequences listed in Table 1 do not contain such signal peptide. Such proteins as listed in Table 1 may be termed "mature proteins". Thus, SEQ ID NO:14 shows the amino acid sequence of mature human CD3δ (delta), SEQ ID NO:13 shows the amino acid sequence of mature human CD3ε (epsilon), SEQ ID NO:21 shows the amino acid sequence of mature cynomolgus CD3ε, and SEQ ID NO:22 shows the amino acid sequence of mature rhesus CD3ε. Thus, the term "mature" as used herein, refers to a protein which does not comprise any signal or leader sequence.

It is well-known that signal peptide sequence homology, length, and the cleavage site position, varies significantly between different proteins. Signal peptides may be determined by different methods, e.g. SEQ ID NO:13 of the present invention has been determined according to the SignalP application (available on http://www.cbs.dtu.dk/services/SignalP/).

In a particular embodiment, the humanized or chimeric antibody of the present invention binds the epsilon chain of CD3, such as the epsilon chain of human CD3 (SEQ ID NO:13). In yet another particular embodiment, the humanized or chimeric antibody binds an epitope within amino acids 1-27 of the N-terminal part of human CD3ε (epsilon) (SEQ ID NO:13). In such a particular embodiment, the antibody may even further cross-react with other non-human primate species, such as cynomolgus monkeys (cynomolgus CD3 epsilon SEQ ID NO:21) and/or rhesus monkeys (rhesus CD3 epsilon SEQ ID NO:22).

The term "cross-react" as used herein, refers to the ability of an antibody, such as a humanized or chimeric antibody according to the invention, to bind its target on different species. In particular, the humanized CD3 antibody exemplified in the examples described herein, has the ability to both bind human (Example 2), cynomolgus (Example 2) and rhesus monkey CD3.

An antibody according to the present invention comprising the CDR sequences as defined herein, further comprising framework regions may differ in sequence outside the CDR sequences but still retains the full binding ability as compared the original antibody. Thus, the present invention also relates to antibodies comprising an amino acid sequence of the variable region having a certain sequence identity to any sequence herein described.

The term "sequence identity" as used in the context of the present invention, refers to the percent identity between two sequences as a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller [21]. In addition, the percent identity between two amino acid sequences may be determined using the Needleman and Wunsch algorithm [22]. Multiple alignments are preferably performed using the Clustal W algorithm [23] (as used e.g., in Vector NTI Advance® software version 11.5; Invitrogen Inc.).

Thus, in one embodiment, the VH region has at least 90%, at least 95%, at least 97%, or at least 99% amino acid sequence identity to at least one amino acid sequence as set forth in the VH sequences selected from the group consisting of:
  a) a VH sequence as set forth in SEQ ID NO:6;
  b) a VH sequence as set forth in SEQ ID NO:8;
  c) a VH sequence as set forth in SEQ ID NO:7; and
  d) a VH sequence as set forth in SEQ ID NO:9.

In one particular embodiment, the VH region has at least 96% amino acid sequence identity to at least one amino acid sequence as set forth in the VH sequences selected from the group consisting of:
  a) a VH sequence as set forth in SEQ ID NO:6;
  b) a VH sequence as set forth in SEQ ID NO:8;
  c) a VH sequence as set forth in SEQ ID NO:7; and
  d) a VH sequence as set forth in SEQ ID NO:9.

In one embodiment, the VL region has at least 90%, at least 95%, at least 97%, or at least 99% amino acid sequence identity to at least one amino acid sequence as set forth in the VL sequences selected from the group consisting of:
  a) a VL sequence as set forth in SEQ ID NO:10;
  b) a VL sequence as set forth in SEQ ID NO:11; and
  c) a VL sequence as set forth in SEQ ID NO:12.

In one particular embodiment, the VL region has at least 95% amino acid sequence identity to at least one amino acid sequence as set forth in the VL sequences selected from the group consisting of:
  a) a VL sequence as set forth in SEQ ID NO:10;
  b) a VL sequence as set forth in SEQ ID NO:11; and
  c) a VL sequence as set forth in SEQ ID NO:12.

In one embodiment, the VH region is selected from the group consisting of:
  a) a VH sequence as set forth in SEQ ID NO:6;
  b) a VH sequence as set forth in SEQ ID NO:8;
  c) a VH sequence as set forth in SEQ ID NO:7; and
  d) a VH sequence as set forth in SEQ ID NO:9.

In one embodiment, the VL region is selected from the group consisting of:

a) a VL sequence as set forth in SEQ ID NO:10;
b) a VL sequence as set forth in SEQ ID NO:11; and
c) a VL sequence as set forth in SEQ ID NO:12.

In one embodiment, only one of either the VH or VL sequence is 100% identical to one of the sequences disclosed herein whereas the other may have a sequence identity of at least 90%, at least 95%, at least 97%, or at least 99% amino acid sequence identity with one of the sequences herein disclosed.

In one particular embodiment, the VH sequence has at least 97% amino acid sequence identity to at least one amino acid sequence as set forth in the VH sequences selected from the group consisting of:
  a) a VH sequence as set forth in SEQ ID NO:6;
  b) a VH sequence as set forth in SEQ ID NO:7;
  c) a VH sequence as set forth in SEQ ID NO:8; and
  d) a VH sequence as set forth in SEQ ID NO:9;
and the VL sequence has at least 95% amino acid sequence identity to at least one amino acid sequence as set forth in the VL sequences selected from the group consisting of:
  i. a VL sequence as set forth in SEQ ID NO: 10;
  ii. a VL sequence as set forth in SEQ ID NO:11; and
  iii. a VL sequence as set forth in SEQ ID NO:12.

In one embodiment, the VH and VL sequences are selected from the group consisting of:
  a) a VH and a VL sequence having at least 90% identity to the sequences set forth in SEQ ID NOs:6 and 10, respectively; 7 and 10, respectively; 8 and 10, respectively; 9 and 10, respectively; 6 and 11, respectively; 7 and 11, respectively; 8 and 11, respectively; 9 and 11, respectively; 6 and 12, respectively; 7 and 12, respectively; 8 and 12, respectively; and 9 and 12, respectively;
  b) a VH and a VL sequence having at least 95% identity to the sequences set forth in SEQ ID NOs:6 and 10, respectively; 7 and 10, respectively; 8 and 10, respectively; 9 and 10, respectively; 6 and 11, respectively; 7 and 11, respectively; 8 and 11, respectively; 9 and 11, respectively; 6 and 12, respectively; 7 and 12, respectively; 8 and 12, respectively; and 9 and 12, respectively;
  c) a VH and a VL sequence having at least 97% identity to the sequences set forth in SEQ ID NOs:6 and 10, respectively; 7 and 10, respectively; 8 and 10, respectively; 9 and 10, respectively; 6 and 11, respectively; 7 and 11, respectively; 8 and 11, respectively; 9 and 11, respectively; 6 and 12, respectively; 7 and 12, respectively; 8 and 12, respectively; and 9 and 12, respectively;
  d) a VH and a VL sequence having at least 99% identity to the sequences set forth in SEQ ID NOs:6 and 10, respectively; 7 and 10, respectively; 8 and 10, respectively; 9 and 10, respectively; 6 and 11, respectively; 7 and 11, respectively; 8 and 11, respectively; 9 and 11, respectively; 6 and 12, respectively; 7 and 12, respectively; 8 and 12, respectively; and 9 and 12, respectively;
  e) a VH and a VL sequence having at least 100% identity to the sequences set forth in SEQ ID NOs:6 and 10, respectively; 7 and 10, respectively; 8 and 10, respectively; 9 and 10, respectively; 6 and 11, respectively; 7 and 11, respectively; 8 and 11, respectively; 9 and 11, respectively; 6 and 12, respectively; 7 and 12, respectively; 8 and 12, respectively; and 9 and 12, respectively;
  f) a VH sequence having at least 90% identity to the sequence set forth in SEQ ID NO:6 and a VL sequence having at least 95% identity to the sequence set forth in SEQ ID NO:10, 11, or 12;
  g) a VH sequence having at least 90% identity to the sequence set forth in SEQ ID NO:6 and a VL sequence having at least 97% identity to the sequence set forth in SEQ ID NO:10, 11, or 12;
  h) a VH sequence having at least 90% identity to the sequence set forth in SEQ ID NO:6 and a VL sequence having at least 99% identity to the sequence set forth in SEQ ID NO:10, 11, or 12;
  i) a VH sequence having at least 90% identity to the sequence set forth in SEQ ID NO:6 and a VL sequence having at least 100% identity to the sequence set forth in SEQ ID NO:10, 11, or 12;
  j) a VH sequence having at least 95% identity to the sequence set forth in SEQ ID NO:6 and a VL sequence having at least 90% identity to the sequence set forth in SEQ ID NO:10, 11, or 12;
  k) a VH sequence having at least 95% identity to the sequence set forth in SEQ ID NO:6 and a VL sequence having at least 97% identity to the sequence set forth in SEQ ID NO:10, 11, or 12;
  l) a VH sequence having at least 95% identity to the sequence set forth in SEQ ID NO:6 and a VL sequence having at least 99% identity to the sequence set forth in SEQ ID NO:10, 11, or 12;
  m) a VH sequence having at least 95% identity to the sequence set forth in SEQ ID NO:6 and a VL sequence having at least 100% identity to the sequence set forth in SEQ ID NO:10, 11, or 12;
  n) a VH sequence having at least 97% identity to the sequence set forth in SEQ ID NO:6 and a VL sequence having at least 90% identity to the sequence set forth in SEQ ID NO:10, 11, or 12;
  o) a VH sequence having at least 97% identity to the sequence set forth in SEQ ID NO:6 and a VL sequence having at least 95% identity to the sequence set forth in SEQ ID NO:10, 11, or 12;
  p) a VH sequence having at least 97% identity to the sequence set forth in SEQ ID NO:6 and a VL sequence having at least 99% identity to the sequence set forth in SEQ ID NO:10, 11, or 12;
  q) a VH sequence having at least 97% identity to the sequence set forth in SEQ ID NO:6 and a VL sequence having at least 100% identity to the sequence set forth in SEQ ID NO:10, 11, or 12;
  r) a VH sequence having at least 99% identity to the sequence set forth in SEQ ID NO:6 and a VL sequence having at least 90% identity to the sequence set forth in SEQ ID NO:10, 11, or 12;
  s) a VH sequence having at least 99% identity to the sequence set forth in SEQ ID NO:6 and a VL sequence having at least 95% identity to the sequence set forth in SEQ ID NO:10, 11, or 12;
  t) a VH sequence having at least 99% identity to the sequence set forth in SEQ ID NO:6 and a VL sequence having at least 97% identity to the sequence set forth in SEQ ID NO:10, 11, or 12;
  u) a VH sequence having at least 99% identity to the sequence set forth in SEQ ID NO:6 and a VL sequence having at least 100% identity to the sequence set forth in SEQ ID NO:10, 11, or 12;
  v) a VH sequence having at least 100% identity to the sequence set forth in SEQ ID NO:6 and a VL sequence having at least 90% identity to the sequence set forth in SEQ ID NO:10, 11, or 12;

x) a VH sequence having at least 100% identity to the sequence set forth in SEQ ID NO:6 and a VL sequence having at least 95% identity to the sequence set forth in SEQ ID NO:10, 11, or 12;

y) a VH sequence having at least 100% identity to the sequence set forth in SEQ ID NO:6 and a VL sequence having at least 97% identity to the sequence set forth in SEQ ID NO:10, 11, or 12;

z) a VH sequence having at least 100% identity to the sequence set forth in SEQ ID NO:6 and a VL sequence having at least 99% identity to the sequence set forth in SEQ ID NO:10, 11, or 12;

aa) a VH sequence having at least 90% identity to the sequence set forth in SEQ ID NO:7 and a VL sequence having at least 95% identity to the sequence set forth in SEQ ID NO:10, 11, or 12;

ab a VH sequence having at least 90% identity to the sequence set forth in SEQ ID NO:7 and a VL sequence having at least 97% identity to the sequence set forth in SEQ ID NO:10, 11, or 12;

ac) a VH sequence having at least 90% identity to the sequence set forth in SEQ ID NO:7 and a VL sequence having at least 99% identity to the sequence set forth in SEQ ID NO:10, 11, or 12;

ad) a VH sequence having at least 90% identity to the sequence set forth in SEQ ID NO:7 and a VL sequence having at least 100% identity to the sequence set forth in SEQ ID NO:10, 11, or 12;

ae) a VH sequence having at least 95% identity to the sequence set forth in SEQ ID NO:7 and a VL sequence having at least 90% identity to the sequence set forth in SEQ ID NO:10, 11, or 12;

af) a VH sequence having at least 95% identity to the sequence set forth in SEQ ID NO:7 and a VL sequence having at least 97% identity to the sequence set forth in SEQ ID NO:10, 11, or 12;

ag) a VH sequence having at least 95% identity to the sequence set forth in SEQ ID NO:7 and a VL sequence having at least 99% identity to the sequence set forth in SEQ ID NO:10, 11, or 12;

ah) a VH sequence having at least 95% identity to the sequence set forth in SEQ ID NO:7 and a VL sequence having at least 100% identity to the sequence set forth in SEQ ID NO:10, 11, or 12;

ai) a VH sequence having at least 97% identity to the sequence set forth in SEQ ID NO:7 and a VL sequence having at least 90% identity to the sequence set forth in SEQ ID NO:10, 11, or 12;

aj) a VH sequence having at least 97% identity to the sequence set forth in SEQ ID NO:7 and a VL sequence having at least 95% identity to the sequence set forth in SEQ ID NO:10, 11, or 12;

ak) a VH sequence having at least 97% identity to the sequence set forth in SEQ ID NO:7 and a VL sequence having at least 99% identity to the sequence set forth in SEQ ID NO:10, 11, or 12;

al) a VH sequence having at least 97% identity to the sequence set forth in SEQ ID NO:7 and a VL sequence having at least 100% identity to the sequence set forth in SEQ ID NO:10, 11, or 12;

am) a VH sequence having at least 99% identity to the sequence set forth in SEQ ID NO:7 and a VL sequence having at least 90% identity to the sequence set forth in SEQ ID NO:10, 11, or 12;

an) a VH sequence having at least 99% identity to the sequence set forth in SEQ ID NO:7 and a VL sequence having at least 95% identity to the sequence set forth in SEQ ID NO:10, 11, or 12;

ao) a VH sequence having at least 99% identity to the sequence set forth in SEQ ID NO:7 and a VL sequence having at least 97% identity to the sequence set forth in SEQ ID NO:10, 11, or 12;

ap) a VH sequence having at least 99% identity to the sequence set forth in SEQ ID NO:7 and a VL sequence having at least 100% identity to the sequence set forth in SEQ ID NO:10, 11, or 12;

aq) a VH sequence having at least 100% identity to the sequence set forth in SEQ ID NO:7 and a VL sequence having at least 90% identity to the sequence set forth in SEQ ID NO:10, 11, or 12;

ar) a VH sequence having at least 100% identity to the sequence set forth in SEQ ID NO:7 and a VL sequence having at least 95% identity to the sequence set forth in SEQ ID NO:10, 11, or 12;

as) a VH sequence having at least 100% identity to the sequence set forth in SEQ ID NO:7 and a VL sequence having at least 97% identity to the sequence set forth in SEQ ID NO:10, 11, or 12;

at) a VH sequence having at least 100% identity to the sequence set forth in SEQ ID NO:7 and a VL sequence having at least 99% identity to the sequence set forth in SEQ ID NO:10, 11, or 12;

ba) a VH sequence having at least 90% identity to the sequence set forth in SEQ ID NO:8 and a VL sequence having at least 95% identity to the sequence set forth in SEQ ID NO:10, 11, or 12;

bb a VH sequence having at least 90% identity to the sequence set forth in SEQ ID NO:8 and a VL sequence having at least 97% identity to the sequence set forth in SEQ ID NO:10, 11, or 12;

bc) a VH sequence having at least 90% identity to the sequence set forth in SEQ ID NO:8 and a VL sequence having at least 99% identity to the sequence set forth in SEQ ID NO:10, 11, or 12;

bd) a VH sequence having at least 90% identity to the sequence set forth in SEQ ID NO:8 and a VL sequence having at least 100% identity to the sequence set forth in SEQ ID NO:10, 11, or 12;

be) a VH sequence having at least 95% identity to the sequence set forth in SEQ ID NO:8 and a VL sequence having at least 90% identity to the sequence set forth in SEQ ID NO:10, 11, or 12;

bf) a VH sequence having at least 95% identity to the sequence set forth in SEQ ID NO:8 and a VL sequence having at least 97% identity to the sequence set forth in SEQ ID NO:10, 11, or 12;

bg) a VH sequence having at least 95% identity to the sequence set forth in SEQ ID NO:8 and a VL sequence having at least 99% identity to the sequence set forth in SEQ ID NO:10, 11, or 12;

bh) a VH sequence having at least 95% identity to the sequence set forth in SEQ ID NO:8 and a VL sequence having at least 100% identity to the sequence set forth in SEQ ID NO:10, 11, or 12;

bi) a VH sequence having at least 97% identity to the sequence set forth in SEQ ID NO:8 and a VL sequence having at least 90% identity to the sequence set forth in SEQ ID NO:10, 11, or 12;

bj) a VH sequence having at least 97% identity to the sequence set forth in SEQ ID NO: and a VL sequence having at least 95% identity to the sequence set forth in SEQ ID NO:10, 11, or 12;

bk) a VH sequence having at least 97% identity to the sequence set forth in SEQ ID NO:8 and a VL sequence having at least 99% identity to the sequence set forth in SEQ ID NO:10, 11, or 12;

bl) a VH sequence having at least 97% identity to the sequence set forth in SEQ ID NO:8 and a VL sequence having at least 100% identity to the sequence set forth in SEQ ID NO:10, 11, or 12;

bm) a VH sequence having at least 99% identity to the sequence set forth in SEQ ID NO:8 and a VL sequence having at least 90% identity to the sequence set forth in SEQ ID NO:10, 11, or 12;

bn) a VH sequence having at least 99% identity to the sequence set forth in SEQ ID NO:8 and a VL sequence having at least 95% identity to the sequence set forth in SEQ ID NO:10, 11, or 12;

bo) a VH sequence having at least 99% identity to the sequence set forth in SEQ ID NO:8 and a VL sequence having at least 97% identity to the sequence set forth in SEQ ID NO:10, 11, or 12;

bp) a VH sequence having at least 99% identity to the sequence set forth in SEQ ID NO:8 and a VL sequence having at least 100% identity to the sequence set forth in SEQ ID NO:10, 11, or 12;

bq) a VH sequence having at least 100% identity to the sequence set forth in SEQ ID NO:8 and a VL sequence having at least 90% identity to the sequence set forth in SEQ ID NO:10, 11, or 12;

br) a VH sequence having at least 100% identity to the sequence set forth in SEQ ID NO:8 and a VL sequence having at least 95% identity to the sequence set forth in SEQ ID NO:10, 11, or 12;

bs) a VH sequence having at least 100% identity to the sequence set forth in SEQ ID NO:8 and a VL sequence having at least 97% identity to the sequence set forth in SEQ ID NO:10, 11, or 12;

bt) a VH sequence having at least 100% identity to the sequence set forth in SEQ ID NO:8 and a VL sequence having at least 99% identity to the sequence set forth in SEQ ID NO:10, 11, or 12;

ca) a VH sequence having at least 90% identity to the sequence set forth in SEQ ID NO:9 and a VL sequence having at least 95% identity to the sequence set forth in SEQ ID NO:10, 11, or 12;

cb a VH sequence having at least 90% identity to the sequence set forth in SEQ ID NO:9 and a VL sequence having at least 97% identity to the sequence set forth in SEQ ID NO:10, 11, or 12;

cc) a VH sequence having at least 90% identity to the sequence set forth in SEQ ID NO:9 and a VL sequence having at least 99% identity to the sequence set forth in SEQ ID NO:10, 11, or 12;

cd) a VH sequence having at least 90% identity to the sequence set forth in SEQ ID NO:9 and a VL sequence having at least 100% identity to the sequence set forth in SEQ ID NO:10, 11, or 12;

ce) a VH sequence having at least 95% identity to the sequence set forth in SEQ ID NO:9 and a VL sequence having at least 90% identity to the sequence set forth in SEQ ID NO:10, 11, or 12;

cf) a VH sequence having at least 95% identity to the sequence set forth in SEQ ID NO:9 and a VL sequence having at least 97% identity to the sequence set forth in SEQ ID NO:10, 11, or 12;

cg) a VH sequence having at least 95% identity to the sequence set forth in SEQ ID NO:9 and a VL sequence having at least 99% identity to the sequence set forth in SEQ ID NO:10, 11, or 12;

ch) a VH sequence having at least 95% identity to the sequence set forth in SEQ ID NO:9 and a VL sequence having at least 100% identity to the sequence set forth in SEQ ID NO:10, 11, or 12;

ci) a VH sequence having at least 97% identity to the sequence set forth in SEQ ID NO:9 and a VL sequence having at least 90% identity to the sequence set forth in SEQ ID NO:10, 11, or 12;

cj) a VH sequence having at least 97% identity to the sequence set forth in SEQ ID NO:9 and a VL sequence having at least 95% identity to the sequence set forth in SEQ ID NO:10, 11, or 12;

ck) a VH sequence having at least 97% identity to the sequence set forth in SEQ ID NO:9 and a VL sequence having at least 99% identity to the sequence set forth in SEQ ID NO:10, 11, or 12;

cl) a VH sequence having at least 97% identity to the sequence set forth in SEQ ID NO:9 and a VL sequence having at least 100% identity to the sequence set forth in SEQ ID NO:10, 11, or 12;

cm) a VH sequence having at least 99% identity to the sequence set forth in SEQ ID NO:9 and a VL sequence having at least 90% identity to the sequence set forth in SEQ ID NO:10, 11, or 12;

cn) a VH sequence having at least 99% identity to the sequence set forth in SEQ ID NO:9 and a VL sequence having at least 95% identity to the sequence set forth in SEQ ID NO:10, 11, or 12;

co) a VH sequence having at least 99% identity to the sequence set forth in SEQ ID NO:9 and a VL sequence having at least 97% identity to the sequence set forth in SEQ ID NO:10, 11, or 12;

cp) a VH sequence having at least 99% identity to the sequence set forth in SEQ ID NO:9 and a VL sequence having at least 100% identity to the sequence set forth in SEQ ID NO:10, 11, or 12;

cq) a VH sequence having at least 100% identity to the sequence set forth in SEQ ID NO:9 and a VL sequence having at least 90% identity to the sequence set forth in SEQ ID NO:10, 11, or 12;

cr) a VH sequence having at least 100% identity to the sequence set forth in SEQ ID NO:9 and a VL sequence having at least 95% identity to the sequence set forth in SEQ ID NO:10, 11, or 12;

cs) a VH sequence having at least 100% identity to the sequence set forth in SEQ ID NO:9 and a VL sequence having at least 97% identity to the sequence set forth in SEQ ID NO:10, 11, or 12; and ct) a VH sequence having at least 100% identity to the sequence set forth in SEQ ID NO:9 and a VL sequence having at least 99% identity to the sequence set forth in SEQ ID NO:10, 11, or 12.

In one embodiment, the binding region comprises a VH and a VL selected from the group consisting of:

a) a VH sequence as set forth in SEQ ID NO:6, and a VL sequence as set forth in SEQ ID NO:10;

b) a VH sequence as set forth in SEQ ID NO:8, and a VL as set forth in SEQ ID NO:10;

c) a VH sequence as set forth in SEQ ID NO:9, and a VL sequence as set forth in SEQ ID NO:10;

d) a VH sequence as set forth in SEQ ID NO:6, and a VL sequence as set forth in SEQ ID NO:11;

e) a VH sequence as set forth in SEQ ID NO:6, and a VL sequence as set forth in SEQ ID NO:12;

f) a VH sequence as set forth in SEQ ID NO:7, and a VL sequence as set forth in SEQ ID NO:10;

g) a VH sequence as set forth in SEQ ID NO:7, and a VL sequence as set forth in SEQ ID NO:11;

h) a VH sequence as set forth in SEQ ID NO:7, and a VL sequence as set forth in SEQ ID NO:12;

i) a VH sequence as set forth in SEQ ID NO:8, and a VL sequence as set forth in SEQ ID NO:11;

j) a VH sequence as set forth in SEQ ID NO:8, and a VL sequence as set forth in SEQ ID NO:12;

k) a VH sequence as set forth in SEQ ID NO:9, and a VL sequence as set forth in SEQ ID NO:11; and l) a VH sequence as set forth in SEQ ID NO:9, and a VL sequence as set forth in SEQ ID NO:12.

In a particular embodiment, the binding region comprises a VH sequence and a VL sequence selected from the group consisting of;

a) a VH sequence as set forth in SEQ ID NO:6, and a VL sequence as set forth in SEQ ID NO:10;

b) a VH sequence as set forth in SEQ ID NO:8, and a VL sequence as set forth in SEQ ID NO:10; and c) a VH sequence as set forth in SEQ ID NO:9, and a VL sequence as set forth in SEQ ID NO:10.

The humanized antibody according to the present invention may be generated by comparison of the heavy and light chain variable region amino acid sequences against a database of human germline variable region sequences in order to identify the heavy and light chain human sequence with the appropriate degree of homology for use as human variable framework regions. A series of humanized heavy and light chain variable regions may be designed by grafting, e.g. the murine, CDRs onto the frameworks regions (identified as described above) and, if necessary, by back-mutation (mutation of one or more of the human amino acid residues in the framework regions back to the non-human amino acid at the specific position(s)) to the specific murine sequence of residues identified which may be critical to the restoration of the antibody binding efficiency. Variant sequences with the lowest incidence of potential T-cell epitopes may then be selected as determined by application of in silico technologies; iTope™ and TCED™ ([24], [25], and [26]).

Furthermore, the humanized antibodies according to the present invention may also be "deimmunized". Deimmunization may be desired, as within a protein sequence, such as a humanized antibody according to the present invention, the presence of human T-cell epitopes may increase the immunogenicity risk profile as they have the potential to activate helper T-cells. Such activation of helper T-cells may be avoided by deimmunization. Deimmunization may be performed by introducing a mutation in the amino acid sequence of the humanized antibody in order to remove the T-cell epitopes without significantly reducing the binding affinity of the antibody.

Thus, in one embodiment of the present invention, the humanized antibody may be produced by a method comprising the steps of (i) comparing the non-human full variable heavy chain sequence and/or the full variable light chain sequence to a database of human germline sequences, (ii) selecting the human germline sequence having the highest homology to the non-human sequence to obtain a humanized sequence, (iii) optimizing the humanized sequence by back-mutation(s) if required, and (iv) expressing the sequence in a suitable expression system.

Thus, a full-length antibody according to the present invention may be produced by a method comprising the steps of (i) comparing the non-human variable heavy chain sequence and the variable light chain sequences to a database of human germline sequences, (ii) selecting the human germline sequence having the highest homology to the non-human sequence, (iii) grafting of the non-human CDRs in to the selected human germ-line to obtain a humanized sequences, (iv) optimizing the humanized sequences by back-mutation(s) if required, (v) identifying constant heavy and light chain sequences, and (vi) expressing the complete heavy chain sequences and complete light chain sequences in suitable expression systems. A full-length antibody according to the present invention may, thus, be produced as described in Example 1. It is within the knowledge of the skilled person to produce a full-length antibody when starting out from either CDR sequences or full variable region sequences. Thus, the skilled person would know how to generate a full-length antibody according to the present invention.

The term "complete heavy chain sequences" as used herein, refers to a sequence consisting of variable heavy chain and constant heavy chain sequences.

The term "complete light chain sequences" as used herein, refers to a sequence consisting of variable light chain and constant light chain sequences.

Back-mutation(s) may be introduced by standard DNA mutagenesis. Such standard techniques for DNA mutagenesis are described in [18]. Alternatively, use of commercially available kits such as Quickchange™ Site-Directed Mutagenesis Kit (Stratagene), or the desired back-mutations may be introduced by de novo DNA synthesis.

Thus, in one embodiment, the antibody is a humanized antibody.

Chimeric antibodies may be generated by substituting all constant region sequences of a non-human (such as murine) antibody with constant region sequences of human origin. Thus, fully non-human variable region sequences are maintained in the chimeric antibody. Thus, a chimeric antibody according to the present invention may be produced by a method comprising the step of expressing the non-human variable heavy chain (SEQ ID NO:27), non-human variable light chain sequences (SEQ ID NO:28), human constant heavy chain and human constant light chain sequences in suitable expression systems, and thereby generating a full-length chimeric antibody. Alternative methods may be used. Such methods of producing a chimeric antibody is within the knowledge of the skilled person, and thus, the skilled person would know how to produce a chimeric antibody according to the present invention.

Thus, in one embodiment, the antibody is a chimeric antibody.

In one embodiment, the antibody is a full-length antibody. The term "full-length antibody" as used herein, refers to an antibody (e.g., a parent or variant antibody) which contains all heavy and light chain constant and variable domains correspond to those that are normally found in a wild-type antibody of that isotype.

In one embodiment, the antibody comprises an Fc region comprising a first and a second immunoglobulin heavy chain.

The term "Fc region" as used herein, refers to a region comprising, in the direction from the N- to C-terminal, at least a hinge region, a CH2 region and a CH3 region. An Fc region may further comprise a CH1 region at the N-terminal end of the hinge region.

The term "hinge region" as used herein refers to the hinge region of an immunoglobulin heavy chain. Thus, for example the hinge region of a human IgG1 antibody corresponds to amino acids 216-230 according to the Eu numbering as set forth in Kabat.

Unless otherwise stated or contradicted by context, the amino acids of the constant region sequences are herein numbered according to the Eu-index of numbering (described in [27]) and may be termed "according to the Eu numbering as set forth in Kabat", "Eu numbering according to Kabat", or "according to the Eu numbering system".

The term "CH1 region" or "CH1 domain" as used herein, refers to the CH1 region of an immunoglobulin heavy chain. Thus, for example the CH1 region of a human IgG1 antibody corresponds to amino acids 118-215 according to the Eu numbering system. However, the CH1 region may also be any of the other subtypes as described herein.

The term "CH2 region" or "CH2 domain" as used herein, refers to the CH2 region of an immunoglobulin heavy chain. Thus, for example the CH2 region of a human IgG1 antibody corresponds to amino acids 231-340 according to the Eu numbering system. However, the CH2 region may also be any of the other subtypes as described herein.

The term "CH3 region" or "CH3 domain" as used herein, refers to the CH3 region of an immunoglobulin heavy chain. Thus, for example the CH3 region of a human IgG1 antibody corresponds to amino acids 341-447 according to the Eu numbering system. However, the CH3 region may also be any of the other subtypes as described herein.

In one embodiment, the isotype of the immunoglobulin heavy chain is selected from the group consisting of IgG1, IgG2, IgG3, and IgG4. The immunoglobulin heavy chain may be any allotype within each of the immunoglobulin classes, such as IgG1m(f) (SEQ ID NO:15). Thus, in one particular embodiment, the isotype of the immunoglobulin heavy chains is an IgG1, or any allotype thereof, such as IgG1m(f) (SEQ ID NO:15).

When targeting the antigen CD3 which is part of the T-cell Receptor (TCR), the T-cell specific mechanisms of cell killing is desirable. Other effector functions, e.g. complement activation, may not be wanted, and therefore, reduction of effector functions is desirable. C1q binding is the first step in the complement cascade, and therefore serves as an indicator for complement-dependent cytotoxicity (CDC) capacity of antibodies. If binding of C1q to the antibody can be avoided, activation of the complement cascade can be avoided as well.

Thus, in one embodiment, the antibody comprises an Fc region which has been modified so that binding of C1q to said antibody is reduced compared to a wild-type antibody by at least 70%, at least 80%, at least 90%, at least 95%, at least 97%, at least 99%, or 100%, wherein C1q binding is determined by ELISA.

The term "modified" as used herein, refers to the amino acid sequence of an Fc region which is not identical to the amino acid sequence of a wild-type Fc region. I.e. amino acid residues in specific positions of the wild-type Fc region have been substituted, deleted or inserted in order to alter, for example, the binding site for C1q, binding site for other effector molecules or binding to Fc Receptors (FcRs). Such modification(s) of the amino acid sequence may be prepared by substituting one or more amino acids with a conservative amino acid or may be prepared by substituting one or more amino acids with an alternative amino acid which is physically and/or functionally similar to the amino acid present in the wild-type. Substitutions may also be prepared by substituting with a non-conservative amino acid.

In the context of the present invention, amino acids may be described as conservative or non-conservative amino acids, and may therefore be classified accordingly. Amino acid residues may also be divided into classes defined by alternative physical and functional properties. Thus, classes of amino acids may be reflected in one or both of the following tables:

Amino Acid Residue of Conservative Class

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

In the context of the present invention, a substitution in an antibody, such as a humanized or chimeric antibody, is indicated as:

Original amino acid-position-substituted amino acid;

Referring to the well-recognized nomenclature for amino acids, the three letter code, or one letter code, is used, including the codes Xaa and X to indicate any amino acid residue. Accordingly, the notation "L234F" or "Leu234Phe" means, that the antibody comprises a substitution of Leucine with Phenylalanine in amino acid position 234.

Substitution of an amino acid at a given position to any other amino acid is referred to as:

Original amino acid-position; or e.g. "L234".

For a modification where the original amino acid(s) and/or substituted amino acid(s) may comprise more than one, but not all amino acid(s), the more than one amino acid may be separated by "," or "/". E.g. the substitution of Leucine for Phenylalanine, Arginine, Lysine or Tryptophan in position 234 is:

"Leu234Phe,Arg,Lys,Trp" or "Leu234Phe/Arg/Lys/Trp" or "L234F,R,K,W" or "L234F/R/K/W" or "L234 to F, R, K or W"

Such designation may be used interchangeably in the context of the invention but have the same meaning and purpose.

Furthermore, the term "a substitution" embraces a substitution into any one of the other nineteen natural amino acids, or into other amino acids, such as non-natural amino acids. For example, a substitution of amino acid L in position 234 includes each of the following substitutions: 234A, 234C, 234D, 234E, 234F, 234G, 234H, 234I, 234K, 234M, 234N, 234Q, 234R, 234S, 234T, 234V, 234W, 234P, and 234Y. This is, by the way, equivalent to the designation 234X, wherein the X designates any amino acid other than the original amino acid. These substitutions can also be designated L234A, L234C, etc., or L234A,C, etc., or L234A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as L234del. Thus, in such embodiments, the Leucine in position 234 has been deleted from the amino acid sequence.

The terms "amino acid" and "amino acid residue" may herein be used interchangeably.

The term "C1q binding" as used herein, refers to the binding of C1q to an antibody, when said antibody is bound to its antigen. The term "bound to its antigen" as used herein, refers to binding of an antibody to its antigen both in vivo and in vitro.

The term "reduce" as used herein when referring to C1q binding, refers to the ability of the antibody according to the invention to reduce, minimize or even completely inhibit the binding of C1q to the antibody when compared to the C1q binding to a wild-type antibody.

The term "wild-type antibody" as used herein, in relation to use in comparison assays of an antibody according to the present invention, refers to an antibody which is identical to the antibody to be tested except for not being inert. In this context, the term "inert" refers to a modified Fc region having reduced or no binding of C1q as determined in Example 10, i.e. where C1q binding is determined by ELISA; reduced or no Fc-mediated T-cell proliferation as determined in Example 4, i.e. T-cell proliferation is measured in a peripheral blood mononuclear cell (PBMC)-based functional assay; and/or reduced or no Fc-mediated CD69 expression as determined in Example 3, i.e. Fc-mediated CD69 expression is determined in a PBMC-based functional assay. Thus, the wild-type antibody comprises the naturally occurring amino acids in the immunoglobulin heavy chains, i.e. an antibody which does not comprise any amino acid modifications which may alter or reduce the ability of the antibody to interact with e.g. C1q, Fc Receptors or the like. Thus, such a wild-type antibody will remain an activating antibody which is able to bind e.g. C1q. A wild-type antibody and an antibody of the present invention may comprise other amino acid modifications than those affecting the antibody's ability of inducing effector functions, in order to make the antibody a bispecific antibody or the like.

The term "ELISA" as used herein refers to enzyme-linked immunosorbent assay which is a test that uses antibodies and color change to identify a substance. A first specific antibody is attached to the plate surface. Thereby the protein from a sample is added wherein binding to said first specific antibody is tested. A second antibody binding the antibody from the sample is added. The second antibody is linked to an enzyme, and, in the final step, a substance containing the enzyme's substrate is added. The subsequent reaction produces a detectable signal, most commonly a color change in the substrate. The concept of the ELISA method is well-known within the art and various ways of performing an ELISA are contemplated to be part of a method to evaluate the antibody according to the invention. Thus, this interpretation is not to be understood as limiting as various forms of ELISAs may be performed such as described in Example 4.

Specifically, the ability of an antibody according to the present invention to bind C1q may be determined by ELISA comprising the steps of (i) coating said antibody on a 96-well plate, (ii) adding 3% serum, (iii) adding an anti-human C1q antibody, (iv) developing the plate, and (v) measuring $OD_{405}$ nm. Thus, in one embodiment, the antibody comprises an Fc region which has been modified so that binding of C1q to said antibody is reduced compared to a wild-type antibody by at least 70%, at least 80%, at least 90%, at least 95%, at least 97%, or 100%, wherein C1q binding is determined by ELISA comprising the steps of (i) coating said antibodies on a 96-well plate, (ii) adding 3% serum, (iii) adding an anti-human C1q, (iv) developing the plate, and (v) measuring $OD_{405}$ nm. Thus, in particular embodiment, binding of C1q is evaluated as described in Example 10.

The terms "Fc Receptor" or "FcR" as used herein, refers to a protein found on the surface of certain cells. FcRs bind to the Fc region of antibodies. There are several different types of FcRs which are classified based on the type of antibody they recognize. E.g. Fcγ (gamma) Receptors bind to antibodies of the IgG class.

The terms "Fcγ Receptor", "Fc gamma Receptor" or "FcγR" as used herein, refers to a group of Fc Receptors belonging to the immunoglobulin superfamily and is the most important Fc receptors for inducing phagocytosis of opsonized (coated) microbes. This family includes several members, FcγRI (CD64), FcγRIIa (CD32a), FcγRIIb (CD32b), FcγRIIIa (CD16a), FcγRIIIb (CD16b), which differ in their antibody affinities due to their different molecular structure.

Fc-mediated effector functions form part of the biological activity of human immunoglobulin G (IgG) molecules. Examples of such effector functions include e.g. antibody-dependent cell-mediated cytotoxicity (ADCC) and complement-dependent cytotoxicity (CDC) which are triggered by the binding of various effector molecules to the Fc region. In the context of the present invention, "Fc binding", "Fc Receptor binding", "FcR binding", and "binding of an antibody Fc region to FcR" refers to the binding of the Fc region to an Fc Receptor (FcR) or an effector molecule. The terms "FcγR binding" and "FcγRI binding" refer to binding to or with an Fc region to the Fc gamma Receptor and Fc gamma Receptor I, respectively. When a CD3 antibody binds T-cells, the wild-type Fc region of the CD3 antibody binds to FcRs present on other cells, e.g. monocytes, which leads to non-specific, Fc-mediated activation of the T-cell. Such non-specific, Fc-mediated activation of T-cells may be undesired. T-cells may also be activated by targeted, or target-specific, T-cell activation. Such targeted T-cell activation may be highly desirable for the treatment of a range of indications, such as cancer. The term "targeted T-cell activation" as used herein, refers to directing the T-cells to specific cells, such as tumor cells by use of a bispecific antibody comprising a first binding region binding a specific target, such as a tumor target on a tumor cell, and a second binding region binding a T-cell specific target, such as CD3. Thus, targeting of T-cells to specific cells, e.g. tumor cells, may be facilitated by use of a bispecific antibody, wherein one of the binding regions binds CD3 present on the T-cell and the other binding region binds a target specific antigen, e.g. on a tumor cell. Although, non-specific, Fc-mediated T-cells activation may still be possible and therefore such undesired non-specific, Fc-mediated T-cell activation via Fc-mediated cross-linking should be avoided and may be disabled by making the Fc region inert for such activity. Thereby, interaction between said inert Fc region with Fc Receptors present is prevented. A humanized antibody of the present invention has been proven to be inert when tested in several different assays, i.e. see Examples 3 to 5. Another tested CD3 antibody, huCLB-T3/4, comprising amino acid modifications in the Fc region also proved to be inert when tested in different assays, i.e. see Examples 7 to 10. The humanized CD3 antibody according to the present invention comprising the amino acid substitutions L234F, L235E, and D265A, as described in the Examples, showed low levels of CD69 expression on T-cells (Example 3), abrogation of Fc-mediated T-cell proliferation (Example 4), and no non-specific target killing when in the form of a bispecific antibody (Example 5). Thus, a humanized antibody of the present invention shows superior results in several assays when compared to a wild-type antibody.

An antibody according to the present invention may comprise modifications in the Fc region. When an antibody comprises such modifications it may become an inert, or non-activating, antibody. The term "inertness", "inert" or "non-activating" as used herein, refers to an Fc region which is at least not able to bind any Fcγ Receptors, induce Fc-mediated cross-linking of FcRs, or induce FcR-mediated cross-linking of target antigens via two Fc regions of individual antibodies, or is not able to bind C1q. The inertness of an Fc region of a humanized or chimeric CD3 antibody is advantageously tested using the antibody in a monospecific format although an inert Fc region so identified can be used in bispecific or other humanized or chimeric multispecific CD3 antibodies.

Several variants can be constructed to make the Fc region of an antibody inactive for interactions with Fc gamma Receptors and C1q for therapeutic antibody development. Examples of such variants are described herein.

Thus, in one embodiment, the antibody comprises an Fc region which has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

The term "reduce" as used herein, refers to a reduction of activity or expression when compared to a control protein, such as an antibody. In particular, the term "reduce" when referring to T-cell proliferation, refers to the ability of the antibody according to the invention to reduce, minimize or even completely inhibit the proliferation of T-cells when compared to the proliferation of T-cells bound by a wild-type antibody. The ability of an antibody to reduce T-cell proliferation may be evaluated by a PBMC-based functional assay, as described in Example 4 and Example 8. In one embodiment the assay is performed with human PBMCs. In another embodiment the assay is performed with cynomolgus PBMCs. In yet another embodiment, the assay is performed with rhesus PBMCs. Since the antibodies according to the present invention are cross-reactive, a PBMC-based assay as herein described may be performed with any species PBMCs to show reduction of T-cell proliferation as long as the species PBMC used are within the cross-reactivity spectra of the antibodies, e.g. human, cynomolgus or rhesus monkeys.

The term "peripheral blood mononuclear cell (PBMC)-based functional assay" as used herein refers to an assay used for evaluating a functional feature of the antibody of the present invention, such as the ability of said antibody to affect T-cell proliferation or CD69 expression, wherein the only cells present are peripheral blood mononuclear cells. Thus, in one embodiment, T-cell proliferation is measured by a method comprising the steps of incubating PBMCs with antibody in the range of 1-1000 ng/mL at 37° C. in a 5% (vol/vol) $CO_2$ humidified incubator for three days, adding a chemical compound, such as BrdU, which is incorporated into the DNA of proliferating cells, incubating for five hrs., pelleting cells, drying cells, optionally storing the cells at 4° C., coating cells to ELISA plates, incubating with anti-BrdU-peroxidase for 90 min at room temperature, developing for about 30 min with 1 mg/mL 2,2'-azino-bis (3-ethylbenzothiazoline-6-sulfonic acid), adding 100 μL 2% oxalic acid to stop the reaction, and measuring absorbance at 405 nm in a suitable microplate reader.

The term "proliferation" as used herein, refers to cell growth in the context of cell division.

The term "BrdU" as used herein, refers to 5-bromo-2'-deoxyuridine, which is a homologue to thymidine. When BrdU is added to cell culture for a limited period of time (e.g. 4 hours) it will be incorporated into the DNA of proliferating cells. After fixing the cells, detection of incorporated BrdU may be performed in an ELISA using anti-BrdU-peroxidase. BrdU incorporation is therefore a measure for proliferation.

In one embodiment, the antibody comprises an Fc region which has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

The term "reduce" as used herein, refers to a reduction of activity or expression when compared to a control protein, such as an antibody. In particular, the term "reduce" when referring to expression level of the T-cell activation marker CD69, refers to a reduction in expression level of CD69 when compared to expression level of CD69 when the T-cell is bound by a wild-type antibody provided that both the binding regions of the antibody binds CD3. An antibody's ability to reduce expression of CD69 may be evaluated by a PBMC-based functional assay, as described in Example 3 and Example 7. Thus, in one embodiment, expression of CD69 is measured by a method comprising the steps of incubating PBMCs with an antibody in the range of 1-1000 ng/mL at 37° C. in a 5% (vol/vol) $CO_2$ humidified incubator for 16-24 hrs, washing the cells, staining the cells at 4° C. with a mouse anti-human CD28-PE and mouse-anti-human CD69-APC antibody, and determining CD69-expression on CD28 positive cells by flow cytometry.

The term "CD69" as used herein, refers to Cluster of Differentiation 69 which is a human transmembrane C-Type lectin protein encoded by the CD69 gene. Activation of T lymphocytes and natural killer (NK) cells, both in vivo and in vitro, induces expression of CD69. CD69 function as a signal transmitting receptor involved in cellular activation events including proliferation, functions as a signal-transmitting receptor in lymphocytes, including natural killer cells and platelets, and the induction of specific genes.

The term "peripheral blood mononuclear cell (PBMC)-based functional assay" as used herein refers to an assay used for evaluating a functional feature of the antibody of the present invention, such as the ability of said antibody to affect T-cell proliferation or CD69 expression, wherein the only cells present are peripheral blood mononuclear cells. A PBMC-based functional assay as described in Example 3, 4, 5, and 7 comprises the steps of (i) incubating PBMCs with an antibody at 37° C. in a 5% (vol/vol) $CO_2$ humidified incubator for about 16-24 hrs, (ii) washing the cells, (iii) staining the cells at 4° C. with a mouse anti-human CD28-PE and mouse-anti-human CD69-APC antibody, and (iv) determining the CD69 expression on CD28 positive cells by flow cytometry, when CD69 expression is evaluated. Thus, in one embodiment, CD69 expression may be determined as described in Example 3, 4, 5, or 7.

Thus, amino acids in the Fc region that play a dominant role in the interactions with C1q and the Fc Gamma Receptors may be modified. Examples of amino acid positions that may be modified include positions L234, L235 and P331. Combinations thereof, such as L234F/L235E/P331S, can cause a profound decrease in binding to human CD64, CD32A, CD16 and C1q.

Hence, in one embodiment, the amino acid in at least one position corresponding to L234, L235 and P331, may be A, A and S, respectively ([1], [28]). Also, L234F and L235E amino acid substitutions can result in Fc regions with abrogated interactions with Fc Gamma Receptors and C1q ([29]-[30]). Hence, in one embodiment, the amino acids in the positions corresponding to L234 and L235, may be F and E, respectively. A D265A amino acid substitution can decrease binding to all Fc gamma Receptors and prevent ADCC ([31]). Hence, in one embodiment, the amino acid in the position corresponding to D265 may be A. Binding to C1q can be abrogated by mutating positions D270, K322, P329, and P331. Mutating these positions to either D270A or K322A or P329A or P331A can make the antibody deficient in CDC activity ([32]). Hence, in one embodiment, the amino acids in at least one position corresponding to D270, K322, P329 and P331, may be A, A, A, and A, respectively.

An alternative approach to minimize the interaction of the Fc region with Fc gamma Receptors and C1q is by removal of the glycosylation site of an antibody. Mutating position N297 to e.g. Q, A, and E removes a glycosylation site which is critical for IgG-Fc gamma Receptor interactions. Hence, in one embodiment, the amino acid in a position corresponding to N297, may be G, Q, A or E ([33]). Another alternative approach to minimize interaction of the Fc region with Fc gamma Receptors may be obtained by the following mutations; P238A, A327Q, P329A or E233P/L234V/L235A/G236del ([31]).

Alternatively, human IgG2 and IgG4 subclasses are considered naturally compromised in their interactions with C1q and Fc gamma Receptors although, interactions with Fcγ Receptors (Fc gamma Receptors) were reported ([34]-[35]). Mutations abrogating these residual interactions can be made in both isotypes, resulting in reduction of unwanted side-effects associated with FcR binding. For IgG2, these include L234A and G237A, and for IgG4, L235E. Hence, in one embodiment, the amino acid in a position corresponding to L234 and G237 in a human IgG2 heavy chain, may be A and A, respectively. In one embodiment, the amino acid in a position corresponding to L235 in a human IgG4 heavy chain, may be E.

Other approaches to further minimize the interaction with Fc gamma Receptors and C1q in IgG2 antibodies include those described in [36] and [37].

The hinge region of the antibody can also be of importance with respect to interactions with Fc gamma Receptors and complement ([38]-[39]). Accordingly, mutations in or deletion of the hinge region can influence effector functions of an antibody.

The term "cross-linking" as used herein, refers to the indirect bridging of antibody Fab arm(s) (monovalently or bivalently) bound to the target antigen by FcR-bearing cell through binding to the antibody Fc region. Thus, an antibody which binds its target antigen on target antigen-bearing cells may cross-link with another cell expressing FcRs.

The term "unspecific killing" as used herein, refers to the killing of cells by the cytotoxic function of T-cells or other effector cells, through tumor target antigen-independent activation of said cells. Thus, by unspecific killing is meant that the tumor-target bearing cells may be killed by e.g. cytotoxic T-cells and not by the antibody binding the tumor target by e.g. induction of CDC.

The present inventors have shown (see Examples 3 to 5, 7 to 10) that a non-activating Fc region may be obtained by modifying one or more of at least five specific amino acid positions in the Fc region.

Thus, in one embodiment, the antibody comprises a first and a second immunoglobulin heavy chain, wherein in at least one of said first and second immunoglobulin heavy chains one or more amino acids in the positions corresponding to positions L234, L235, D265, N297, and P331 in a human IgG1 heavy chain, are not L, L, D, N, and P, respectively.

In one embodiment, in both the first and second heavy chains one or more amino acids in the position corresponding to positions L234, L235, D265, N297, and P331 in a human IgG1 heavy chain, are not L, L, D, N, and P, respectively.

In another embodiment, in at least one of the first and second heavy chains one or more amino acids in the positions corresponding to positions L234, L235 and D265 in a human IgG1 heavy chain, are not L, L and D, respectively, and the amino acids in the positions corresponding to N297 and P331 in a human IgG1 heavy chain, are N and P, respectively.

The term "amino acid corresponding to positions" as used herein refers to an amino acid position number in a human IgG1 heavy chain. Unless otherwise stated or contradicted by context, the amino acids of the constant region sequences are herein numbered according to the Eu-index of numbering (described in [27]). Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present invention.

In the context of the present invention, the amino acid may be defined as described above.

The term "the amino acid is not" or similar wording when referring to amino acids in a heavy chain is to be understood to mean that the amino acid is any other amino acid than the specific amino acid mentioned. For example, the amino acid in the position corresponding to L234 in a human IgG1 heavy chain is not L, means that the amino acid may be any of the other naturally or non-naturally occurring amino acids than L.

In one embodiment, in at least one of said first and second heavy chains the amino acid in the position corresponding to position D265 in a human IgG1 heavy chain, is not D.

In one embodiment, in at least one of the first and second heavy chains the amino acid in the position corresponding to D265 in a human IgG1 heavy chain, is not D, and the amino acids in the positions corresponding to positions N297 and P331 in a human IgG1 heavy chain, are N and P, respectively.

In one embodiment, in at least one of said first and second heavy chains the amino acids in the positions corresponding to position D265 in a human IgG1 heavy chain is hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acid in the position corresponding to position D265 in a human IgG1 heavy chain is selected from the group of amino acids consisting of; A, C, F, G, H, I, L, M, R, T, V, W and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acid in the position corresponding to position D265 in a human heavy chain is selected from the group consisting of; C, E, H, K, N, Q, R, S, and T.

In another embodiment, in at least one of said first and second heavy chains the amino acid in the position corresponding to position D265 in a human IgG1 heavy chain is an aliphatic uncharged, aromatic or acidic amino acid.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acid in the position corresponding to position D265 in a human IgG1 heavy chain is selected from the group consisting of; A, G, I, L, and V.

The term "aromatic" as used herein in relation to amino acid residues, refers to any amino acid residue selected from the group consisting of: F, T, and W. Thus, in one embodiment, in at least one of said first and second heavy chains the amino acid in the position corresponding to position D265 in a human IgG1 heavy chain is selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acid in the position corresponding to position D265 in a human IgG1 heavy chain is selected from the group consisting of; D and E.

In a particular embodiment, in at least one of said first and second heavy chains the amino acid in the position corresponding to position D265 in a human IgG1 heavy chain is selected from the group consisting of; A, E, F, G, I, L, T, V, and W.

In one embodiment, in both said first and second heavy chains the amino acid in the position corresponding to position D265 in a human IgG1 heavy chain, is not D.

In one embodiment, in both the first and second heavy chains the amino acid in the position corresponding to D265 in a human IgG1 heavy chain, is not D, and the amino acids in the positions corresponding to positions N297 and P331 in a human IgG1 heavy chain, are N and P, respectively.

In one embodiment, in both said first and second heavy chains the amino acid in the position corresponding to position D265 in a human IgG1 heavy chain is hydrophobic or polar amino acid.

The term "hydrophobic" as used herein in relation to an amino acid residue, refers to an amino acid residue selected from the group consisting of; A, C, F, G, H, I, L, M, R, T, V, W, and Y. Thus, in one embodiment, in both said first and second heavy chains the amino acid in the position corresponding to position D265 in a human IgG1 heavy chain is selected from the group of amino acids consisting of; A, C, F, G, H, I, L, M, R, T, V, W and Y.

The term "polar" as used herein in relation to amino acid residues, refers to any amino acid residue selected from the group consisting of; C, D, E, H, K, N, Q, R, S, and T. Thus, in one embodiment, in both said first and second heavy chains the amino acid in the position corresponding to position D265 in a human heavy chain is selected from the group consisting of; C, E, H, K, N, Q, R, S, and T. In one embodiment, in both said first and second heavy chains the amino acid in the position corresponding to position D265 in a human IgG1 heavy chain is selected from the group of amino acids consisting of; A, C, F, G, H, I, L, M, R, T, V, W and Y.

In one embodiment, in both said first and second heavy chains the amino acids in the positions corresponding to position D265 in a human heavy chain is selected from the group consisting of; C, E, H, K, N, Q, R, S, and T.

In another embodiment, in both said first and second heavy chains the amino acid in the position corresponding to position D265 in a human IgG1 heavy chain is aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in both said first and second heavy chains the amino acid in the position corresponding to position D265 in a human IgG1 heavy chain is selected from the group consisting of; A, G, I, L, and V.

The term "aromatic" as used herein in relation to amino acid residues, refers to any amino acid residue selected from the group consisting of: F, T, and W. Thus, in one embodiment, in both said first and second heavy chains the amino acid in the position corresponding to position D265 in a human IgG1 heavy chain is selected from the group consisting of; F, T, and W.

The term "acidic" as used herein in relation to amino acid residues, refers to any amino acid residue chosen from the group consisting of: D and E. Thus, in one embodiment, in both said first and second heavy chains the amino acid in the position corresponding to position D265 in a human IgG1 heavy chain are selected from the group consisting of; D and E.

In a particular embodiment, in both said first and second heavy chains the amino acid in the position corresponding to position D265 in a human IgG1 heavy chain is selected from the group consisting of; A, E, F, G, I, L, T, V, and W.

In further embodiment, in at least one of said first and second heavy chains the amino acid in the position corresponding to position N297 in a human IgG1 heavy chain, is not N.

In one embodiment, in at least one of the first and second heavy chains the amino acid in the position corresponding to N297 in a human IgG1 heavy chain, is not N, and the amino acid in the position corresponding to position P331 in a human IgG1 heavy chain, is P.

In one embodiment, in both said first and second heavy chains the amino acid in the position corresponding to positions N297 in a human IgG1 heavy chain, is not N.

In one embodiment, in both the first and second heavy chains the amino acid in the position corresponding to N297 in a human IgG1 heavy chain, is not N, and the amino acid in the position corresponding to position P331 in a human IgG1 heavy chain, is P.

In further embodiment, in at least one of said first and second heavy chains the amino acids in the positions corresponding to positions L234 and L235 in a human IgG1 heavy chain, are not L and L, respectively.

In one embodiment, in at least one of the first and second heavy chains the amino acids in the positions corresponding to L234 and L235 in a human IgG1 heavy chain, are not L and L, respectively, and the amino acids in the positions corresponding to positions N297 and P331 in a human IgG1 heavy chain, are N and P, respectively.

In one embodiment, in at least one of said first and second heavy chains the amino acids corresponding to positions L234 and L235 in a human IgG1 heavy chain are selected from the group consisting of; A, C, D, E, F, G, H, I, K, M, N, P, Q, R, S, T, Y, V.

In one embodiment, in at least one of said first and second heavy chains the amino acids in the positions corresponding to positions L234 and L235 in a human IgG1 heavy chain are hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acids in the positions corresponding to positions L234 and L235 in a human IgG1 heavy chain are each selected from the group consisting of; A, C, F, G, H, I, M, R, T, V, W, and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acids in the positions corresponding to positions L234 and L235 in a human IgG1 heavy chain are each selected from the group of amino acids consisting of; C, D, E, H, K, N, Q, R, S, and T.

In a particular embodiment, in at least one of said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y.

In one embodiment, in both said first and second heavy chains the amino acids in the positions corresponding to positions L234 and L235 in a human IgG1 heavy chain, are not L and L, respectively.

In one embodiment, in both the first and second heavy chains the amino acids in the positions corresponding to L234 and L235 in a human IgG1 heavy chain, are not L and L, respectively, and the amino acids in the positions corresponding to positions N297 and P331 in a human IgG1 heavy chain, are N and P, respectively.

In one embodiment, in both said first and second heavy chains the amino acids in the positions corresponding to L234 and L235 in a human IgG1 heavy chain are hydrophobic or polar amino acids.

In one embodiment, in both said first and second heavy chains the amino acids in the positions corresponding to positions L234 and L235 in a human IgG1 heavy chain are each selected from the group consisting of; A, C, F, G, H, I, M, R, T, V, W, and Y.

In one embodiment, in both said first and second heavy chains the amino acids in the positions corresponding to positions L234 and L235 in a human IgG1 heavy chain are each selected from the group of amino acids consisting of; C, D, E, H, K, N, Q, R, S, and T.

In a particular embodiment, in both said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y.

In another embodiment, in at least one of said first and second heavy chains the amino acids in the positions corresponding to positions L234 and L235 in a human IgG1 heavy chain are aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acids in the positions corresponding to positions L234 and L235 in a human IgG1 heavy chain are each selected from the group consisting of; A, G, I, and V.

The term "aromatic" as used herein in relation to amino acid residues, refers to any amino acid residue selected from the group consisting of: F, T, and W. Thus, in one embodiment, in at least one of said first and second heavy chains the amino acids in the positions corresponding to positions L234 and L235 in a human IgG1 heavy chain are each selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acids in the positions corresponding to positions L234 and L235 in a human IgG1 heavy chain are each selected from the group consisting of; D and E.

In a particular embodiment, in at least one of said first and second heavy chains the amino acids in the positions corresponding to L234 and L235 are each selected from the group consisting of; A, D, E, F, G, I, T, V, and W.

In one embodiment, in at least one of said first and second heavy chains the amino acids in the positions corresponding to positions L234 and L235 in a human IgG1 heavy chain, are F and E; or A and A, respectively.

In one embodiment, in at least one of the first and second heavy chains the amino acids in the positions corresponding to L234 and L235 in a human IgG1 heavy chain, are F and E; or A and A, respectively, and the amino acids in the positions corresponding to positions N297 and P331 in a human IgG1 heavy chain, are N and P, respectively.

In one embodiment, in both said first and second heavy chains the amino acids in the positions corresponding to positions L234 and L235 in a human IgG1 heavy chain, are F and E; or A and A, respectively.

In one embodiment, in both the first and second heavy chains the amino acids in the positions corresponding to L234 and L235 in a human IgG1 heavy chain, are F and E; or A and A, respectively, and the amino acids in the positions corresponding to positions N297 and P331 in a human IgG1 heavy chain, are N and P, respectively.

In a particular embodiment, in at least one of said first and second heavy chains the amino acids in the positions corresponding to positions L234 and L235 in a human IgG1 heavy chain, are F and E, respectively.

In one embodiment, in both said first and second heavy chains the amino acids in the positions corresponding to positions L234 and L235 in a human IgG1 heavy chain, are F and E, respectively.

In one embodiment, in at least one of said first and second heavy chains at least the amino acids in the positions corresponding to positions L234 and L235 in a human IgG1 heavy chain, are A and A, respectively.

In one embodiment, in both said first and second heavy chains at least the amino acids in the positions corresponding to positions L234 and L235 in a human IgG1 heavy chain, are A and A, respectively.

In one embodiment, in at least one of said first and second heavy chains the amino acids in the positions corresponding to positions L234, L235, and D265 in a human IgG1 heavy chain, are not L, L, and D, respectively.

In one embodiment, in at least one of the first and second heavy chains the amino acids in the positions corresponding to L234, L235, and D265 in a human IgG1 heavy chain, are not L, L and D, respectively, and the amino acids in the positions corresponding to positions N297 and P331 in a human IgG1 heavy chain, are N and P, respectively.

In one embodiment, in at least one of said first and second heavy chains the amino acids corresponding to positions L234 and L235 in a human IgG1 heavy chain are selected from the group consisting of; A, C, D, E, F, G, H, I, K, M, N, P, Q, R, S, T, Y, V, and W, and the amino acid corresponding to position D265 is selected from the group consisting of; A, C, E, F, G, H, I, K, L, M, N, P, Q, R, S, T, Y, V, and W.

In one embodiment, in at least one of said first and second heavy chains the amino acids in the positions corresponding to positions L234, L235 and D265 in a human IgG1 heavy chain are hydrophobic or polar amino acids.

The term "hydrophobic" as used herein in relation to an amino acid residue, refers to an amino acid residue selected from the group consisting of; A, C, F, G, H, I, L, M, R, T, V, W, and Y. Thus, in one embodiment, in at least one of said first and second heavy chains the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

The term "polar" as used herein in relation to amino acid residues, refers to any amino acid residue selected from the group consisting of; C, D, E, H, K, N, Q, R, S, and T. Thus, in one embodiment, in at least one of said first and second heavy chains the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in at least one of said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In one embodiment, in both said first and second heavy chains the amino acids in the positions corresponding to L234, L235, and D265 in a human IgG1 heavy chain are hydrophobic or polar amino acids.

In one embodiment, in both said first and second heavy chains the amino acid in the position corresponding to position D265 in a human IgG1 heavy chain is selected from the group of amino acids consisting of; A, C, F, G, H, I, L, M, R, T, V, W and Y, and the amino acids in the positions corresponding to positions L234 and L235 in a human IgG1 heavy chain are each selected from the group consisting of; A, C, F, G, H, I, M, R, T, V, W, and Y.

In one embodiment, in both said first and second heavy chains the amino acids in the positions corresponding to positions L234 and L235 in a human IgG1 heavy chain are each selected from the group of amino acids consisting of; C, D, E, H, K, N, Q, R, S, and T, the amino acid in the position corresponding to position D265 in a human heavy chain is selected from the group consisting of; C, E, H, K, N, Q, R, S, and T.

In a particular embodiment, in both said first and second heavy chains the amino acids in the positions corresponding to positions L234 and L235 in a human IgG1 heavy chain are each selected from the group consisting of; A, C, D, E, F, G, H, I, K, M, N, Q, R, S, T, V, W, and Y, and the amino acid in the position corresponding to position D265 in a human IgG1 heavy chain is selected from the group consisting of; A, C, E, F, G, H, I, K, L, M, N, Q, R, S, T, V, W, and Y.

In another embodiment, in at least one of said first and second heavy chains the amino acids in the positions corresponding to positions L234, L235 and D265 in a human IgG1 heavy chain are aliphatic uncharged, aromatic or acidic amino acids.

The term "aliphatic uncharged" as used herein in relation to amino acid residues, refers to any amino acid residue selected from the group consisting of: A, G, I, L, and V. Thus, in one embodiment, in at least one of said first and second heavy chains the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

The term "aromatic" as used herein in relation to amino acid residues, refers to any amino acid residue selected from the group consisting of: F, T, and W. Thus, in one embodiment, in at least one of said first and second heavy chains the amino acids in the positions corresponding to positions L234, L235 and D265 in a human IgG1 heavy chain are each selected from the group consisting of; F, T, and W.

The term "acidic" as used herein in relation to amino acid residues, refers to any amino acid residue chosen from the group consisting of: D and E. Thus, in one embodiment, in at least one of said first and second heavy chains the amino acids in the positions corresponding to positions L234, L235, and D265 in a human IgG1 heavy chain are each selected from the group consisting of; D and E.

In a particular embodiment, in at least one of said first and second heavy chains the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in both said first and second heavy chains the amino acids in the positions corresponding to positions L234, L235 and D265 in a human IgG1 heavy chain, are not L, L, and D, respectively.

In one embodiment, in both the first and second heavy chains the amino acids in the positions corresponding to L234, L235, and D265 in a human IgG1 heavy chain, are not L, L, and D, respectively, and the amino acids in the positions corresponding to positions N297 and P331 in a human IgG1 heavy chain, are N and P, respectively.

In one embodiment, in both said first and second heavy chains the amino acids in the positions corresponding to L234, L235, and D265 in a human IgG1 heavy chain are aliphatic uncharged, aromatic or acidic amino acids.

In one embodiment, in both said first and second heavy chains the amino acid in the position corresponding to position D265 in a human IgG1 heavy chain is selected from the group consisting of; A, G, I, L, and V, and the amino acids in the positions corresponding to positions L234 and L235 in a human IgG1 heavy chain are each selected from the group consisting of; A, G, I, and V.

In one embodiment, in both said first and second heavy chains the amino acids in the positions corresponding to positions L234, L235, and D265 in a human IgG1 heavy chain are each selected from the group consisting of; D and E.

In a particular embodiment, in both said first and second heavy chains the amino acid in the position corresponding to position D265 in a human IgG1 heavy chain is selected from the group consisting of; A, E, F, G, I, L, T, V, and W, and the amino acids in the positions corresponding to L234 and L235 are each selected from the group consisting of; A, D, E, F, G, I, T, V, and W.

In one embodiment, in at least one of said first and second heavy chains the amino acids in the positions corresponding to positions L234, L235, and D265 in a human IgG1 heavy chain, are F, E, and A; or A, A, and A, respectively.

In one embodiment, in at least one of the first and second heavy chains the amino acids in the positions corresponding to L234, L235, and D265 in a human IgG1 heavy chain, are F, E, and A; or A, A, and A, respectively, and the amino acids in the positions corresponding to positions N297 and P331 in a human IgG1 heavy chain, are N and P, respectively.

In one embodiment, in both said first and second heavy chains the amino acids in the positions corresponding to positions L234, L235, and D265 in a human IgG1 heavy chain, are F, E, and A; or A, A, and A, respectively.

In one embodiment, in both the first and second heavy chains the amino acids in the positions corresponding to L234, L235, and D265 in a human IgG1 heavy chain, are F, E, and A; or A, A, and A, respectively, and the amino acids in the positions corresponding to positions N297 and P331 in a human IgG1 heavy chain, are N and P, respectively.

In a particular embodiment, in at least one of said first and second heavy chains the amino acids in the positions corresponding to positions L234, L235, and D265 in a human IgG1 heavy chain, are F, E, and A, respectively.

In one embodiment, in both said first and second heavy chains the amino acids in the positions corresponding to positions L234, L235, and D265 in a human IgG1 heavy chain, are F, E, and A, respectively.

In one embodiment, in at least one of said first and second heavy chains the amino acids in the positions corresponding to positions L234, L235, and D265 in a human IgG1 heavy chain, are A, A, and A, respectively.

In one embodiment, in both said first and second heavy chains the amino acids in the positions corresponding to positions L234, L235, and D265 in a human IgG1 heavy chain, are A, A, and A, respectively.

In another embodiment, in at least one of said first and second heavy chains the amino acids in the positions corresponding to positions L234, L235, D265, N297, and P331 in a human IgG1 heavy chain, are F, E, A, Q, and S, respectively.

In one embodiment, in both said first and second heavy chains the amino acids in the positions corresponding to positions L234, L235, D265, N297, and P331 in a human IgG1 heavy chain, are F, E, A, Q, and S, respectively.

In a particular embodiment, the antibody according to the invention, comprises a VH sequence as set out in SEQ ID NO:8, a VL sequence as set out in SEQ ID NO:10, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:8, a VL sequence as set out in SEQ ID NO:12, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:6, a VL sequence as set out in SEQ ID NO:10, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:6, a VL sequence as set out in SEQ ID NO:12, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:9, a VL sequence as set out in SEQ ID NO:10, and in at least one of the heavy chains the amino acids in positions corresponding to positions L234, L235, and D265 in a human IgG1 heavy chain, are F, E, and A, respectively.

In another embodiment, the antibody according to the invention, comprises a VH sequence as set out in SEQ ID NO:9, a VL sequence as set out in SEQ ID NO:12, and in at least one of the heavy chains the amino acids in positions corresponding to positions L234, L235, and D265 in a human IgG1 heavy chain, are F, E, and A, respectively.

In one aspect, the antibody according to the invention comprises the human IgLC2/IgLC3 constant domain lambda light chain of SEQ ID NO:31.

In one aspect, the antibodies according to the invention may be modified in the light chain (LC) and/or heavy chain (HC) to increase the expression level and/or production yield. In one embodiment, the antibodies according to the invention may be modified in the light chain (LC). Such modifications are known in the art and may be performed according to the methods described in e.g. Zheng, L., Goddard, J.-P., Baumann, U., & Reymond, J.-L. (2004). Expression improvement and mechanistic study of the retro-Diels-Alderase catalytic antibody 10F11 by site-directed mutagenesis. Journal of Molecular Biology, 341(3), 807-14. doi:10.1016/j.jmb.2004.06.014.

In one embodiment, the antibody according to the invention comprises a light chain (LC), wherein the amino acid in the position corresponding to position T41 in the lambda light chain of SEQ ID NO:10 is not T.

In one embodiment, the antibody according to the invention comprises a light chain (LC), wherein the amino acid in the position corresponding to position T41 in the lambda light chain of SEQ ID NO:10 is selected from H, I, K, L, Q, R and V.

In one embodiment, the antibody according to the invention comprises a light chain (LC), wherein the amino acid in the position corresponding to position T41 in the lambda light chain of SEQ ID NO:10 is H, K or R, such as K.

In one embodiment, the antibody according to the invention comprises a light chain (LC), wherein the amino acid in the position corresponding to position F10 in the lambda light chain of SEQ ID NO:10 is not F, and wherein one or more of the amino acid positions corresponding to the positions T41, K55, and L97 in the lambda light chain of SEQ ID NO:10 are not T, K and L, respectively.

In one embodiment, the antibody according to the invention comprises a light chain (LC), wherein the amino acids in the positions corresponding to positions F10, T41, K55, and L97 in the lambda light chain of SEQ ID NO:10 are not F, T, K and L, respectively.

In one embodiment the antibody according to the invention comprises a light chain (LC), wherein the amino acid in the position corresponding to position T41 is selected from H, I, K, L, Q, R or V, such as selected from H, K and R, such as K, and wherein the amino acids in the positions corresponding to positions F10, T41, K55, and L97 in the lambda light chain of SEQ ID NO:10 are L, K, N, and H, respectively.

In one embodiment, the antibody according to the invention comprises a light chain (LC), wherein the amino acids in the positions corresponding to positions R23 and A35 are not R and A, respectively.

In one embodiment, the antibody according to the invention comprises a light chain (LC), wherein the amino acid in the position corresponding to position R23 is selected from A, G, H, K, Q, S, and T, such as from A and G, and wherein the amino acid in the position corresponding to A35 is selected from I, L, M, P, V, G, F and W, such as from I, L, M, P, and V.

In one embodiment, the antibody according to the invention comprises a light chain (LC), wherein the amino acid in the position corresponding to position R23 is A or G, such as A, and the amino acid in the position corresponding to position A35 is P.

In one embodiment, the antibody according to the invention comprises a light chain (LC), wherein the amino acids in the positions corresponding to positions F10, R23, A35, R47, D71, A82, D83, S86, I87, and F89 in the lambda light chain of SEQ ID NO:10 are not F, R, A, R, D, A, D, S, I, and F, respectively.

In one embodiment, the antibody according to the invention comprises a light chain (LC), wherein the amino acid in the position corresponding to position R23 is selected from A, G, H, K, Q, S, and T, such as from A and G, wherein the amino acid in the position corresponding to A35 is selected from I, L, M, P, V, G, F and W, such as from I, L, M, P, and wherein the amino acids in the positions corresponding to positions F10, R47, D71, A82, D83, S86, I87, and F89 in the lambda light chain of SEQ ID NO:10 are L, T, G, P, E, A, E, and Y, respectively.

In one embodiment, the antibody according to the invention comprises a light chain (LC), wherein the amino acid in the position corresponding to position R23 is A or G, and wherein the amino acids in the positions corresponding to positions F10, A35, R47, D71, A82, D83, S86, I87, and F89 in the lambda light chain of SEQ ID NO:10 are L, P, T, G, P, E, A, E, and Y, respectively.

In one aspect, the antibodies according to the invention may be modified in the light chain (LC) to increase the affinity of the antibodies. Modifications that lead to increased antibody affinity are known in the art.

In one aspect, the antibodies according to the invention may be modified in the light chain (LC) to reduce the affinity of the antibodies. This may be advantageous in some settings and lead to increased efficacy. In particular low affinity of the CD3 arm may have an impact on the motility of T cells in circulation and at tumor site thus leading to better engagement of T cells with tumor cells, cf. Mølhøj et al, Molecular Immunology 44 (2007). In particular this may be useful in bispecific formats, in which the CD3 antibodies are used as one of the binding arms. Modifications that lead to reduced antibody affinity are known in the art, see for example Webster et al. Int J Cancer Suppl. 1988; 3:13-6.

In one embodiment, the antibody according to the invention comprises a light chain (LC), wherein
(i) the amino acid in the position corresponding to position F10 in the lambda light chain of SEQ ID NO:10 is not F, or
(ii) the amino acid in the position corresponding to position K55 in the lambda light chain of SEQ ID NO:10 is not K, or
(iii) the amino acid in the position corresponding to position F10 in the lambda light chain of SEQ ID NO:10 is not F, and the amino acid in the position corresponding to position K55 in the lambda light chain of SEQ ID NO:10 is not K.

In one embodiment, the antibody according to the invention comprises a constant light chain (LC), wherein
(i) the amino acid in the position corresponding to position F10 in the lambda light chain of SEQ ID NO:10 is L, or
(ii) the amino acid in the position corresponding to position K55 in the lambda light chain of SEQ ID NO:10 is N, or
(iii) the amino acid in the position corresponding to position F10 in the lambda light chain of SEQ ID NO:10 is L, and the amino acid in the position corresponding to position K55 in the lambda light chain of SEQ ID NO:10 is N.

In one embodiment, the antibody according to the invention comprises a light chain (LC), wherein the amino acids in the positions corresponding to positions F10, T41, K55, and L97 in the lambda light chain of SEQ ID NO:10 are not F, T, K and L, respectively. Such modifications serve both to increase the expression level and to reduce the affinity.

The antibody according to the invention comprises a light chain (LC), wherein the amino acids in the positions corresponding to positions F10, T41, K55, and L97 in the lambda light chain of SEQ ID NO:10 are L, K, N, and H, respectively. Such modifications serve both to increase the expression level and to reduce the affinity.

In one embodiment, the antibody according to the invention comprises a heavy chain (HC) and a light chain (LC), wherein the positions corresponding to positions L234, L235, and D265 in the human IgG1 heavy chain of SEQ ID NO:15 are F, E, and A, respectively, and wherein the position corresponding to F405 in in the human IgG1 heavy chain of SEQ ID NO:15 is L, and wherein (i) the positions corresponding to positions F10, T41, K55, and L97 in the lambda light chain of SEQ ID NO:10 are L, K, N, and H, respectively, or (ii) the position corresponding to position T41 in the lambda light chain of SEQ ID NO:10 is K.

In one embodiment, the antibody according to the invention comprises the heavy chain (HC) of SEQ ID NO:25 and the light chain (LC) of SEQ ID NO:32.

In one embodiment, the antibody according to the invention comprises the heavy chain (HC) of SEQ ID NO:25 and the light chain (LC) of SEQ ID NO:33.

In one aspect, the present invention relates to a multispecific antibody comprising at least a first binding region of an antibody according to any aspect or embodiment herein described, and one or more binding regions which binds one or more different targets than the first binding region. Such a multispecific antibody may be a bispecific antibody.

Thus, in one aspect, the present invention relates to a bispecific antibody comprising a first binding region of an antibody according to any aspect or embodiment herein described, and a second binding region which binds a different target than the first binding region.

The term "multispecific antibody" refers to an antibody having specificities for at least two different, such as at least three, typically non-overlapping, epitopes. Such epitopes may be on the same or different targets. If the epitopes are on different targets, such targets may be on the same cell or different cells or cell types.

The term "bispecific antibody" refers to an antibody having specificities for at least two different, typically non-overlapping, epitopes. Such epitopes may be on the same or different targets. If the epitopes are on different targets, such targets may be on the same cell or different cells or cell types.

In one embodiment, the bispecific antibody comprises a first and a second heavy chain.

The embodiments relating to modification of the Fc region and embodiments relating to specific amino acid substitutions are contemplated to be part of any bispecific antibody according to the invention. Thus, in one embodiment, at least one of the first and second heavy chains comprise one or more amino acids modified as defined in any embodiment herein described, such as those described to in relation to providing an inert Fc region. In one embodiment, both said first and second heavy chains comprise one or more amino acids modified as defined in any embodiment herein described, such as those described to in relation to providing an inert Fc region. Accordingly, the bispecific antibody comprises an Fc region modified according to any aspect or embodiment herein described; or at least one of said first and second heavy chains comprise one or more amino acids modified as defined in any aspect or embodiment herein described.

Thus, in one embodiment, the bispecific antibody comprises a first binding region comprising a VH sequence as set out in SEQ ID NO:8 and a VL sequence as set out in SEQ ID NO:10; and wherein the Fc region has been modified so that binding of C1q to said antibody is reduced compared to a wild-type antibody by at least 70%, at least 80%, at least 90%, at least 95%, at least 97%, or 100%, wherein C1q binding is determined by ELISA.

In one embodiment, the bispecific antibody comprises a first binding region comprising a VH sequence as set out in SEQ ID NO:8 and a VL sequence as set out in SEQ ID NO:12; and wherein the Fc region has been modified so that binding of C1q to said antibody is reduced compared to a wild-type antibody by at least 70%, at least 80%, at least 90%, at least 95%, at least 97%, or 100%, wherein C1q binding is determined by ELISA.

In one embodiment, the bispecific antibody comprises a first binding region comprising a VH sequence as set out in SEQ ID NO:6 and a VL sequence as set out in SEQ ID NO:10; and wherein the Fc region has been modified so that binding of C1q to said antibody is reduced compared to a wild-type antibody by at least 70%, at least 80%, at least 90%, at least 95%, at least 97%, or 100%, wherein C1q binding is determined by ELISA.

In one embodiment, the bispecific antibody comprises a first binding region comprising a VH sequence as set out in SEQ ID NO:6 and a VL sequence as set out in SEQ ID NO:12; and wherein the Fc region has been modified so that binding of C1q to said antibody is reduced compared to a wild-type antibody by at least 70%, at least 80%, at least 90%, at least 95%, at least 97%, or 100%, wherein C1q binding is determined by ELISA.

In one embodiment, the bispecific antibody comprises a first binding region comprising a VH sequence as set out in SEQ ID NO:9 and a VL sequence as set out in SEQ ID NO:10; and wherein the Fc region has been modified so that binding of C1q to said antibody is reduced compared to a wild-type antibody by at least 70%, at least 80%, at least 90%, at least 95%, at least 97%, or 100%, wherein C1q binding is determined by ELISA.

In one embodiment, the bispecific antibody comprises a first binding region comprising a VH sequence as set out in SEQ ID NO:9 and a VL sequence as set out in SEQ ID NO:12; and wherein the Fc region has been modified so that binding of C1q to said antibody is reduced compared to a wild-type antibody by at least 70%, at least 80%, at least 90%, at least 95%, at least 97%, or 100%, wherein C1q binding is determined by ELISA.

In another embodiment, the bispecific antibody comprises a first binding region comprising a VH sequence as set out in SEQ ID NO:8 and a VL sequence as set out in SEQ ID NO:10; and wherein the Fc region has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

In one embodiment, the bispecific antibody comprises a first binding region comprising a VH sequence as set out in SEQ ID NO:8 and a VL sequence as set out in SEQ ID NO:12; and wherein the Fc region has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

In one embodiment, the bispecific antibody comprises a first binding region comprising a VH sequence as set out in SEQ ID NO:6 and a VL sequence as set out in SEQ ID NO:10; and wherein the Fc region has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

In one embodiment, the bispecific antibody comprises a first binding region comprising a VH sequence as set out in SEQ ID NO:6 and a VL sequence as set out in SEQ ID NO:12; and wherein the Fc region has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

In one embodiment, the bispecific antibody comprises a first binding region comprising a VH sequence as set out in SEQ ID NO:9 and a VL sequence as set out in SEQ ID NO:10; and wherein the Fc region has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

In one embodiment, the bispecific antibody comprises a first binding region comprising a VH sequence as set out in SEQ ID NO:9 and a VL sequence as set out in SEQ ID NO:12; and wherein the Fc region has been modified so that said antibody mediates reduced Fc-mediated T-cell proliferation compared to a wild-type antibody by at least 50%, at least 60%, at least 70%, at least 80%, at least 90%, at least 99% or 100%, wherein said T-cell proliferation is measured in a peripheral blood mononuclear cell (PBMC)-based functional assay.

In another embodiment, the bispecific antibody comprises a first binding region comprising a VH sequence as set out in SEQ ID NO:8 and a VL sequence as set out in SEQ ID NO:10; and wherein the Fc region has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In one embodiment, the bispecific antibody comprises a first binding region comprising a VH sequence as set out in SEQ ID NO:8 and a VL sequence as set out in SEQ ID NO:12; and wherein the Fc region has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In one embodiment, the bispecific antibody comprises a first binding region comprising a VH sequence as set out in SEQ ID NO:6 and a VL sequence as set out in SEQ ID NO:10; and wherein the Fc region has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In one embodiment, the bispecific antibody comprises a first binding region comprising a VH sequence as set out in SEQ ID NO:6 and a VL sequence as set out in SEQ ID NO:12; and wherein the Fc region has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In one embodiment, the bispecific antibody comprises a first binding region comprising a VH sequence as set out in SEQ ID NO:9 and a VL sequence as set out in SEQ ID NO:10; and wherein the Fc region has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In one embodiment, the bispecific antibody comprises a first binding region comprising a VH sequence as set out in SEQ ID NO:9 and a VL sequence as set out in SEQ ID NO:12; and wherein the Fc region has been modified so that said antibody reduces Fc-mediated CD69 expression by at least 50%, at least 60%, at least 70%, at least 80%, at least 90%, at least 99% or 100% when compared to a wild-type antibody wherein said Fc-mediated CD69 expression is determined in a PBMC-based functional assay.

In a particular embodiment, the bispecific antibody comprises a first binding region comprising a VH sequence as set out in SEQ ID NO:8 and a VL sequence as set out in SEQ ID NO:10; and wherein in at least one of the first and second heavy chains the amino acids in the positions corresponding to positions L234, L235, and D265 in a human IgG1 heavy chain, are F, E, and A, respectively.

In another embodiment, the bispecific antibody comprises a first binding region comprising a VH sequence as set out in SEQ ID NO:8 and a VL sequence as set out in SEQ ID NO:12; and wherein in at least one of the first and second heavy chains the amino acids in the positions corresponding to positions L234, L235, and D265 in a human IgG1 heavy chain, are F, E, and A, respectively.

In another embodiment, the bispecific antibody comprises a first binding region comprising a VH sequence as set out in SEQ ID NO:6 and a VL sequence as set out in SEQ ID NO:10; and wherein in at least one of the first and second heavy chains the amino acids in the positions corresponding to positions L234, L235, and D265 in a human IgG1 heavy chain, are F, E, and A, respectively.

In another embodiment, the bispecific antibody comprises a first binding region comprising a VH sequence as set out in SEQ ID NO:6 and a VL sequence as set out in SEQ ID NO:12; and wherein in at least one of the first and second heavy chains the amino acids in the positions corresponding to positions L234, L235, and D265 in a human IgG1 heavy chain, are F, E, and A, respectively.

In another embodiment, the bispecific antibody comprises a first binding region comprising a VH sequence as set out in SEQ ID NO:9 and a VL sequence as set out in SEQ ID NO:10; and wherein in at least one of the first and second heavy chains the amino acids in the positions corresponding to positions L234, L235, and D265 in a human IgG1 heavy chain, are F, E, and A, respectively.

In another embodiment, the bispecific antibody comprises a first binding region comprising a VH sequence as set out in SEQ ID NO:9 and a VL sequence as set out in SEQ ID NO:12; and wherein in at least one of the first and second heavy chains the amino acids in the positions corresponding to positions L234, L235, and D265 in a human IgG1 heavy chain, are F, E, and A, respectively.

Examples of bispecific antibody molecules which may be used in the present invention comprise (i) a single antibody that has two arms comprising different antigen-binding regions, (ii) a single chain antibody that has specificity to two different epitopes, e.g., via two scFvs linked in tandem by an extra peptide linker; (iii) a dual-variable-domain antibody (DVD-Ig™), where each light chain and heavy chain contains two variable domains in tandem through a short peptide linkage ([40]); (iv) a chemically-linked bispecific (Fab')2 fragment; (v) a TandAb®, which is a fusion of two single chain diabodies resulting in a tetravalent bispecific antibody that has two binding sites for each of the target antigens; (vi) a flexibody, which is a combination of scFvs with a diabody resulting in a multivalent molecule; (vii) a so called "dock and lock" molecule (Dock-and-Lock®), based on the "dimerization and docking domain" in Protein Kinase A, which, when applied to Fabs, can yield a trivalent bispecific binding protein consisting of two identical Fab fragments linked to a different Fab fragment; (viii) a so-called Scorpion molecule, comprising, e.g., two scFvs fused to both termini of a human Fab-arm; and (ix) a diabody.

In one embodiment, the bispecific antibody of the present invention is a diabody, a cross-body, or a bispecific antibody obtained via a controlled Fab arm exchange, e.g. DuoBody® (such as described in [41]) as those described in the present invention.

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, Nanobodies®) wherein different single chain Fv molecules or different diabodies or different heavy-chain antibodies (e.g. domain antibodies, Nanobodies®) are fused to each other or to another protein or carrier molecule fused to heavy-chain constant-domains, Fc-regions or parts thereof.

Examples of IgG-like molecules with complementary CH3 domains molecules include but are not limited to the Triomab® (Trion Pharma/Fresenius Biotech, [42]), the Knobs-into-Holes (Genentech, [43]), CrossMAbs (Roche, [44]) and the electrostatically-matched (Amgen, [45]-[46]; Chugai, [47]; Oncomed, [48]), the LUZ-Y (Genentech), DIG-body and PIG-body (Pharmabcine), the Strand Exchange Engineered Domain body (SEEDbody)(EMD Serono, [49]), the Biclonics (Merus), FcΔAdp (Regeneron, [50]), bispecific IgG1 and IgG2 (Pfizer/Rinat, [51]), Azymetric scaffold (Zymeworks/Merck, [52]), mAb-Fv (Xencor, [53]), bivalent bispecific antibodies (Roche) and DuoBody® molecules (Genmab A/S, [41]).

Examples of recombinant IgG-like dual targeting molecules include but are not limited to Dual Targeting (DT)-Ig (GSK/Domantis), Two-in-one Antibody (Genentech), Cross-linked Mabs (Karmanos Cancer Center), mAb2 (F-Star, [54]), Zybodies™ (Zyngenia), approaches with common light chain (Crucell/Merus, [55]), KABodies (NovImmune) and CovX-Body® (CovX/Pfizer).

Examples of IgG fusion molecules include but are not limited to Dual Variable Domain (DVD)-Ig™ (Abbott, [56]), Dual domain double head antibodies (Unilever; Sanofi Aventis, [57]), IgG-like Bispecific (ImClone/Eli Lilly), Ts2Ab (MedImmune/AZ) and BsAb (Zymogenetics), HERCULES (Biogen Idec, [58]), scFv fusion (Novartis), scFv fusion (Changzhou Adam Biotech Inc, [59]) and TvAb (Roche, [59], [60]).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART™) (MacroGenics, [62], [63]) and Dual(ScFv)2-Fab (National Research Center for Antibody Medicine—China).

Examples of Fab fusion bispecific antibodies include but are not limited to F(ab)2 (Medarex/AMGEN), Dual-Action or Bis-Fab (Genentech), Dock-and-Lock® (DNL) (ImmunoMedics), Bivalent Bispecific (Biotecnol) and Fab-Fv (UCB-Celltech).

Examples of ScFv-, diabody-based and domain antibodies include but are not limited to Bispecific T Cell Engager (BITE®) (Micromet, Tandem Diabody (Tandab) (Affimed), Dual Affinity Retargeting Technology (DART™) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting Nanobodies® (Ablynx), dual targeting heavy chain only domain antibodies.

It is further contemplated that any monospecific antibody fulfilling the assay conditions herein described may form the basis of a bispecific antibody. I.e. a bispecific antibody wherein one of the binding regions binds CD3 may originate from any monospecific CD3 antibody tested in the functional assays and fulfilling the requirements stated herein. Such a bispecific antibody may be provided by the methods described in [41], which is hereby incorporated by reference.

Thus, in a particular embodiment, each of said first and second heavy chain comprises at least a hinge region, a CH2 and CH3 region, wherein in said first heavy chain at least one of the amino acids in the positions corresponding to a position selected from the group consisting of T366, L368, K370, D399, F405, Y407, and K409 in a human IgG1 heavy chain has been substituted, and in said second heavy chain at least one of the amino acids in the positions corresponding to a position selected from the group consisting of T366, L368, K370, D399, F405, Y407, and K409 in a human IgG1 heavy chain has been substituted, and wherein said first and said second heavy chains are not substituted in the same positions. In this context the term "substituted", refers to that the amino acid in a specific amino acid position has been substituted with another naturally or non-naturally occurring amino acid. Thus, a "substituted" amino acid in a position corresponding to the position in a human IgG1 heavy chain means the amino acid at the particular position is different from the naturally occurring amino acid in an IgG1 heavy chain.

In one embodiment, in said first heavy chain the amino acid in the position corresponding to K409 in a human IgG1 heavy chain is not K, L or M, and optionally the amino acid in the position corresponding to F405 in a human IgG1 heavy chain is F, and in said second heavy chain at least one of the amino acids in the positions corresponding to a position selected from the group consisting of; T366, L368, K370, D399, F405, and Y407 in a human IgG1 heavy chain has been substituted.

In one embodiment, in said first heavy chain the amino acid in the position corresponding to K409 in a human IgG1 heavy chain is not K, L or M, and in said second heavy chain the amino acid in the position corresponding to F405 in a human IgG1 heavy chain is not F and optionally the amino acid in the position corresponding to K409 in a human IgG1 heavy chain is K.

In one embodiment, in said first heavy chain, the amino acid in the position corresponding to F405 in a human IgG1 heavy chain is not F, R, and G, and in said second heavy chain the amino acids in the positions corresponding to a position selected form the group consisting of; T366, L368, K370, D399, Y407, and K409 in a human IgG1 heavy chain has been substituted.

In one embodiment, the amino acid in position corresponding to K409 in a human IgG1 heavy chain is not K, L or M in said first heavy chain, and the amino acid in position corresponding to F405 in a human IgG1 heavy chain is not F.

In a further embodiment, the amino acid in the position corresponding to F405 in a human IgG1 heavy chain is L in said first heavy chain, and the amino acid in the position corresponding to K409 in a human IgG1 heavy chain is R in said second heavy chain, or vice versa.

Thus, in one embodiment, the amino acid in the position corresponding to K409 in a human IgG1 heavy chain is R in the first heavy chain, and the amino acid in the position corresponding to F405 in a human IgG1 heavy chain is L in the second heavy chain.

In a further embodiment, the humanized or chimeric CD3 antibody of the invention contains in at least one of the first and second heavy chain one or more of the inactivating substitutions as disclosed in any one of the above embodiments, such as L234F, L235E, and D265A; and that the amino acid in the position corresponding to F405 is not F. In one embodiment the humanized or chimeric CD3 antibody of the invention contains in at least one of the first and second heavy chain one or more of the inactivating substitutions as disclosed in any one of the above embodiments, such as L234F, L235E, and D265A; and a further substitution in the K409 position, such as K409R. In particular, in one embodiment, the humanized or chimeric CD3 antibody of the invention contains in both the first and second heavy chain one or more of the inactivating substitutions as disclosed in any one of the above embodiments, such as L234F, L235E, and D265A; and a substitution in the F405 position, such as F405L. In one embodiment the humanized or chimeric CD3 antibody of the invention contains in both the first and second heavy chain one or more of the inactivating substitutions as disclosed in any one of the above embodiments, such as L234F, L235E, and D265A; and a further substitution in the K409 position, such as K409R. Such antibodies are useful for generating a bispecific antibody.

Accordingly, in a further embodiment, in at least one of the first and second heavy chains the amino acids in the positions corresponding to position L234, L235, and D265 in a human IgG1 heavy chain are F, E, and A, respectively, the amino acid in the position corresponding to F405 in a human IgG1 heavy chain is L in the first heavy chain, and the amino acid in the position corresponding to K409 in a human IgG1 heavy chain is R in the second heavy chain.

In one embodiment, in at least one of the first and second heavy chains the amino acids in the positions corresponding to L234, L235, D265, N297, and P331 in a human IgG1 heavy chain are F, E, A, N, and P respectively, the amino acid in the position corresponding to F405 in a human IgG1 heavy chain is L in the first heavy chain, and the amino acid in the position corresponding to K409 in a human IgG1 heavy chain is R in the second heavy chain.

In an alternative embodiment, in at least one of the first and second heavy chains the amino acids in the positions corresponding to position L234, L235, and D265 in a human IgG1 heavy chain are F, E, and A, respectively, the amino acid in the position corresponding to K409 in a human IgG1 heavy chain is R in the first heavy chain, and the amino acid in the position corresponding to F405 in a human IgG1 heavy chain is L in the second heavy chain.

In one embodiment, in at least one of the first and second heavy chains the amino acids in the positions corresponding to L234, L235, D265, N297, and P331 in a human IgG1 heavy chain are F, E, A, N, and P respectively, the amino acid in the position corresponding to K409 in a human IgG1 heavy chain is R in the first heavy chain, and the amino acid in the position corresponding to F405 in a human IgG1 heavy chain is L in the second heavy chain.

In another embodiment, in both the first and second heavy chains the amino acids in the positions corresponding to position L234, L235, and D265 in a human IgG1 heavy chain are F, E, and A, respectively, the amino acid in the position corresponding to F405 in a human IgG1 heavy chain is L in the first heavy chain, and the amino acid in the position corresponding to K409 in a human IgG1 heavy chain is R in the second heavy chain.

In one embodiment, in both the first and second heavy chains the amino acids in the positions corresponding to L234, L235, D265, N297, and P331 in a human IgG1 heavy chain are F, E, A, N, and P respectively, the amino acid in the position corresponding to F405 in a human IgG1 heavy chain is L in the first heavy chain, and the amino acid in the position corresponding to K409 in a human IgG1 heavy chain is R in the second heavy chain.

In an alternative embodiment, in both the first and second heavy chains the amino acids in the positions corresponding to position L234, L235, and D265 in a human IgG1 heavy chain are F, E, and A, respectively, the amino acid in the position corresponding to K409 in a human IgG1 heavy chain is R in the first heavy chain, and the amino acid in the position corresponding to F405 in a human IgG1 heavy chain is L in the second heavy chain.

In one embodiment, in both the first and second heavy chains the amino acids in the positions corresponding to L234, L235, D265, N297, and P331 in a human IgG1 heavy chain are F, E, A, N, and P respectively, the amino acid in the position corresponding to K409 in a human IgG1 heavy chain is R in the first heavy chain, and the amino acid in the position corresponding to F405 in a human IgG1 heavy chain is L in the second heavy chain.

As described herein, T-cell recruitment to specific target cells, such as cancer or tumor cells, provides a way of killing the target cells. The present inventors have shown that a bispecific CD3×HER2 antibody comprising the specific amino acid substitutions L234F, L235E, and D265A in both of the heavy chains, was able to induce killing of AU565 cells as described in Example 5. T-cell mediated killing may be obtained by a bispecific antibody targeting CD3 with the first binding region and another target with the second binding region. Thus, in one embodiment, the first binding region is according to any embodiments described herein for the humanized or chimeric CD3 antibody, and the second binding region binds a different target than the first binding region. It is to be understood that when the antibody is a bispecific antibody, at least one half of the antibody, i.e. one of the pair of heavy and light chains of the antibody, is a humanized or chimeric antibody as herein described. Thus, one half of the bispecific antibody is a humanized or chimeric antibody binding CD3 according to the present invention and the other half may be humanized, chimeric, fully non-human or fully human binding a second target. Thus, in one embodiment, the antibody comprises a first and a second heavy chain, a first and second light chain, wherein said first heavy and said first light chains are humanized or chimeric and are connected via disulfide bridges forming a first binding region; and said second heavy and light chains are fully human and are connected via disulfide bridges forming a second binding region, wherein said first binding region is according to any aspect or embodiment herein described, and said second binding region binds a different target. In one embodiment, the antibody comprises a first and a second heavy chain, a first and second light chain, wherein said first heavy and said first light chains are humanized or chimeric and are connected via disulfide bridges forming a first binding region; and said second heavy and light chains are humanized or chimeric and are connected via disulfide bridges forming a second binding region, wherein said first binding region is according to any aspect or embodiment herein described, and said second binding region binds a different epitope of CD3 than said first binding region.

Thus, in one embodiment, the bispecific antibody comprises a first binding region comprising a VH sequence as set out in SEQ ID NO:8, and a VL sequence as set out in SEQ ID NO:10; a second binding region comprising a VH sequence as set out in SEQ ID NO:19, and a VL sequence as set out in SEQ ID NO:20; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In one embodiment, the bispecific antibody comprises a first binding region comprising a VH sequence as set out in SEQ ID NO:8, and a VL sequence as set out in SEQ ID NO:10; a second binding region comprising a VH sequence as set out in SEQ ID NO:29, and a VL sequence as set out in SEQ ID NO:30; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:8, and a VL sequence as set out in SEQ ID NO:10; a second binding region comprising a VH sequence as set out in SEQ ID NO:19, and a VL sequence as set out in SEQ ID NO:20; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:8, and a VL sequence as set out in SEQ ID NO:10; a second binding region comprising a VH sequence as set out in SEQ ID NO:29, and a VL sequence as set out in SEQ ID NO:30; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:8, and a VL sequence as set out in SEQ ID NO:12; a second binding region comprising a VH sequence as set out in SEQ ID NO:19, and a VL sequence as set out in SEQ ID NO:20; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:8, and a VL sequence as set out in SEQ ID NO:12; a second binding region comprising a VH sequence as set out in SEQ ID NO:29, and a VL sequence as set out in SEQ ID NO:30; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:8, and a VL sequence as set out in SEQ ID NO:12; a second binding region comprising a VH sequence as set out in SEQ ID NO:19, and a VL sequence as set out in SEQ ID NO:20; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:8, and a VL sequence as set out in SEQ ID NO:12; a second binding region comprising a VH sequence as set out in SEQ ID NO:29, and a VL sequence as set out in SEQ ID NO:30; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:10; a second binding region comprising a VH sequence as set out in SEQ ID NO:19, and a VL sequence as set out in SEQ ID NO:20; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:10; a second binding region comprising a VH sequence as set out in SEQ ID NO:29, and a VL sequence as set out in SEQ ID NO:30; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:10; a second binding region comprising a VH sequence as set out in SEQ ID NO:19, and a VL sequence as set out in SEQ ID NO:20; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:10; a second binding region comprising a VH sequence as set out in SEQ ID NO:29, and a VL sequence as set out in SEQ ID NO:30; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:12; a second binding region comprising a VH sequence as set out in SEQ ID NO:19, and a VL sequence as set out in SEQ ID NO:20; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:12; a second binding region comprising a VH sequence as set out in SEQ ID NO:29, and a VL sequence as set out in SEQ ID NO:30; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:12; a second binding region comprising a VH sequence as set out in SEQ ID NO:19, and a VL sequence as set out in SEQ ID NO:20; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:6, and a VL sequence as set out in SEQ ID NO:12; a second binding region comprising a VH sequence as set out in SEQ ID NO:29, and a VL sequence as set out in SEQ ID NO:30; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:10; a second binding region comprising a VH sequence as set out in SEQ ID NO:19, and a VL sequence as set out in SEQ ID NO:20; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:10; a second binding region comprising a VH sequence as set out in SEQ ID NO:29, and a VL sequence as set out in SEQ ID NO:30; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:10; a second binding region comprising a VH sequence as set out in SEQ ID NO:19, and a VL sequence as set out in SEQ ID NO:20; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:10; a second binding region comprising a VH sequence as set out in SEQ ID NO:29, and a VL sequence as set out in SEQ ID NO:30; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:12; a second binding region comprising a VH sequence as set out in SEQ ID NO:19, and a VL sequence as set out in SEQ ID NO:20; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:12; a second binding region comprising a VH sequence as set out in SEQ ID NO:29, and a VL sequence as set out in SEQ ID NO:30; wherein in at least one of the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:12; a second binding region comprising a VH sequence as set out in SEQ ID NO:19, and a VL sequence as set out in SEQ ID NO:20; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

In another embodiment, the bispecific antibody comprises a first binding region comprising a VH sequence as set out in SEQ ID NO:9, and a VL sequence as set out in SEQ ID NO:12; a second binding region comprising a VH sequence as set out in SEQ ID NO:29, and a VL sequence as set out in SEQ ID NO:30; wherein in both the first and second heavy chains the amino acids in the positions corresponding to positions L234, L235, and D265 in a human IgG1 heavy chain, are F, E, and A, respectively; and wherein in the first heavy chain the amino acid in the position corresponding to position F405 in a human IgG1 heavy chain, is L, and in the second heavy chain the amino acid in the position corresponding to position K409 in a human IgG1 heavy chain, is R.

The term "disulfide bridges" as used herein refers to the covalent bond between two Cysteine residues, i.e. said interaction may also be designated a Cys-Cys interaction.

The term "target" as used herein, refers to a molecule to which the binding region of the antibody according to the invention binds. When used in the context of the binding of an antibody the term includes any antigen towards which the raised antibody is directed.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different target; and wherein in at least one of the first and second heavy chains the amino acids in the positions corresponding to positions L234, L235, and D265 in a human IgG1 heavy chain, are F, E, and A, respectively.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different epitope of CD3 than the first binding region; and wherein in at least one of the first and second heavy chains the amino acids in the positions corresponding to positions L234, L235, and D265 in a human IgG1 heavy chain, are F, E, and A, respectively.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different target; and wherein in both the first and second heavy chains the amino acids in the positions corresponding to positions L234, L235, and D265 in a human IgG1 heavy chain, are F, E, and A, respectively.

In one particular embodiment, the first heavy and the first light chains are humanized or chimeric and are connected via disulfide bridges forming a first binding region; and the second heavy and light chains are fully human and are connected via disulfide bridges forming a second binding region, wherein the first binding region is according to any aspect or embodiment herein described, and the second binding region binds a different epitope of CD3 than the first binding region; and wherein in both the first and second heavy chains the amino acids in the positions corresponding to positions L234, L235, and D265 in a human IgG1 heavy chain, are F, E, and A, respectively.

In one aspect, the bispecific antibody according to the invention comprises a second binding region which binds to human HER2 or human CD20.

In one embodiment, the bispecific antibody according to the invention comprises a second binding region which binds to human CD20.

In one embodiment, the second binding region may be derived from a full-length monoclonal CD20 antibody, such as an antibody disclosed in WO2004035607 (Genmab A/S), including ofatumumab (2F2), 11B8, and 7D8; an antibody disclosed in WO2005103081 (Genmab A/S), including 2C6; AME-133; TRU-015; IMMU-106; ocrelizumab (Gazyva®); tositumomab (Bexxar®); and rituximab (Rituxan®/MabThera®).

In one embodiment, the second binding region may be derived from a full-length monoclonal CD20 antibody, which antibody binds to an epitope on CD20, which does not comprise or require the amino acid residues alanine at position 170 or proline at position 172, but which comprises or requires the amino acid residues asparagine at position 163 and asparagine at position 166.

In one embodiment, the bispecific antibody according to the invention comprises a second binding region binding to human CD20, which binding region comprises:

(i) the VH CDR1 region of SEQ ID NO:34, the VH CDR2 region of SEQ ID NO:35, the VH CDR3 region of SEQ ID NO:36, the VL CDR1 region of SEQ ID NO:37, the VL CDR2 region of DAS, and the VL CDR3 region of SEQ ID NO:38, (ii) the VH CDR1 region of SEQ ID NO: 41, the VH CDR2 region of SEQ ID NO:42, the VH CDR3 region of SEQ ID NO:43, the VL CDR1 region of SEQ ID NO:44, the VL CDR2 region of DAS, and the VL CDR3 region of SEQ ID NO:45, (iii) the VH CDR1 region of SEQ ID NO:48, the VH CDR2 region of SEQ ID NO:49, the VH CDR3 region of SEQ ID NO:50, the VL CDR1 region of SEQ ID NO:51, the VL CDR2 region of DAS, and the VL CDR3 region of SEQ ID NO:52, or (iv) the VH CDR1 region of SEQ ID NO:55, the VH CDR2 region of SEQ ID NO:56, the VH CDR3 region of SEQ ID NO:57, the VL CDR1 region of SEQ ID NO:58, the VL CDR2 region of DAS, and the VL CDR3 region of SEQ ID NO:59.

In one embodiment, the bispecific antibody according to the invention comprises a second binding region binding to human CD20, which binding region comprises:

(i) a VH sequence which has at least 90%, at least 95%, at least 97%, or at least 99% amino acid sequence identity to the amino acid sequence as set forth in SEQ ID NO:29, and a VL sequence which has at least 90%, at least 95%, at least 97%, or at least 99% amino acid sequence identity to the amino acid sequence as set forth in SEQ ID NO:30, (ii) a VH sequence which has at least 90%, at least 95%, at least 97%, or at least 99% amino acid sequence identity to the amino acid sequence as set forth in SEQ ID NO:39, and a VL sequence which has at least 90%, at least 95%, at least 97%, or at least 99% amino acid sequence identity to the amino acid sequence as set forth in SEQ ID NO:40, (iii) a VH sequence which has at least 90%, at least 95%, at least 97%, or at least 99% amino acid sequence identity to the amino acid sequence as set forth in SEQ ID NO:46, and a VL sequence which has at least 90%, at least 95%, at least 97%, or at least 99% amino acid sequence identity to the amino acid sequence as set forth in SEQ ID NO:47, or (iv) a VH sequence which has at least 90%, at least 95%, at least 97%, or at least 99% amino acid sequence identity to the amino acid sequence as set forth in SEQ ID NO:53, and a VL sequence which has at least 90%, at least 95%, at least 97%, or at least 99% amino acid sequence identity to the amino acid sequence as set forth in SEQ ID NO:54.

In one embodiment, the bispecific antibody according to the invention comprises a second binding region binding to human CD20, which second binding region comprises:

(i) the VH sequence of SEQ ID NO: 29 and the VL sequence of SEQ ID NO:30, (ii) the VH sequence of SEQ ID NO:39, and the VL sequence of SEQ ID NO:40, (iii) the VH sequence of SEQ ID NO:46, and the VL sequence of SEQ ID NO:47, or (iv) the VH sequence of SEQ ID NO:53, and the VL sequence of SEQ ID NO:54.

Nucleic Acid Constructs, Expression Vectors, and Host Cells

In one aspect, the present invention relates to a nucleic acid construct encoding one or more sequences set out in Table 1. Thus, the present invention relates to a nucleic acid construct encoding any one of the sequences set out in SEQ ID NOs: 1, 2, 3, 4, 5, 6, 7, 8, 9, 10, 11, 12, 13, 14, 15, 16, 17, 18, 19, 20, 21, 22, 23, 24, 25, and 26.

In a further aspect, the invention relates to nucleic acid construct encoding a sequence of a humanized or chimeric CD3 antibody according to the present invention, to expression vectors comprising a nucleic acid construct according to the present invention, to host cells comprising such expression vectors, and to methods of producing such an antibody by culturing such host cells under appropriate conditions whereby the antibody is produced and, optionally, retrieved. Humanized CD3 antibodies may also be denoted as "huCD3".

In one embodiment, the invention provides an expression vector comprising (i) a nucleic acid sequence encoding a heavy chain sequence of a humanized or chimeric antibody according to the invention, (ii) a nucleic acid sequence encoding a light chain sequence of a humanized or chimeric antibody according to the invention, or (iii) both (i) and (ii). Thus, the expression vector comprises one or more nucleic acid constructs or nucleic acid sequences according to any aspect or embodiment herein described.

In one embodiment, the expression vector of the invention comprises a nucleic acid sequence encoding one or more of the heavy chain and light chain CDR sequences selected from the group consisting of: SEQ ID NOs.:1, 2, 3, 4, and 5; and the sequence GTN.

In one embodiment, the invention provides an expression vector comprising a nucleic acid sequence encoding one or more amino acid sequences selected from the group consisting of SEQ ID NOs: 6, 7, 8, 9, 10, 11, 12, 19, 20, 27, 28, 29, and 30, or any combination thereof. In another embodiment, the expression vector comprises a nucleic acid sequence encoding the VH CDR3 amino acid sequence as set forth in SEQ ID NO: 3. In another embodiment, the expression vector comprises a nucleic acid sequence encoding a VH amino acid sequence selected from SEQ ID NOs: 6, 7, 8, 9, 19, 27, and 29. In another embodiment, the expression vector comprises a nucleic acid sequence encoding a VL amino acid sequence selected from SEQ ID NOs: 10, 11, 12, 20, 28, and 30. In another embodiment, the expression vector comprises a nucleic acid sequence encoding the constant region of a human antibody light chain, of a human antibody heavy chain, or both. In another embodiment, the invention provides an expression vector comprising a nucleic acid sequence encoding the amino acid sequence according to SEQ ID NOs: 15, 16, 23, 24, 25, and 26.

In a particular embodiment, the expression vector comprises a nucleic acid sequence encoding a variant of one or more of the above amino acid sequences, said variant having at most 25 amino acid modifications, such as at most 20, such as at most 15, 14, 13, 12, or 11 amino acid modifications, such as 10, 9, 8, 7, 6, 5, 4, 3, 2, or 1 amino acid modifications, such as deletions or insertions, preferably substitutions, such as conservative or non-conservative substitutions, or at least 80% identity to any of said sequences, such as at least 85% identity or 90% identity or 95% identity, such as 96% identity or 97% identity or 98% identity or 99% identity to any of the afore-mentioned amino acid sequences. The present invention also relates to nucleic acid sequences different from the above mentioned nucleic acid sequences but which due to the variance of the genetic code encode the same amino acid sequence as an antibody of the present invention. E.g. the nucleic acid sequence may vary but result in an identical amino acid sequences as any amino acid sequence herein described. It is well-known for the skilled person how to identify such further nucleic acid sequences based on the genetic code.

In a further embodiment, the expression vector further comprises a nucleic acid sequence encoding the constant region of a light chain, a heavy chain or both light and heavy chains of an antibody, e.g. a human antibody.

Such expression vectors as described above may be used for recombinant production of antibodies of the invention.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a humanized or chimeric CD3 antibody-encoding nucleic acid is comprised in a naked DNA or RNA vector, including, for example, a linear expression element (as described in for instance [64]), a compacted nucleic acid vector (as described in for instance [65] and/or [66]), a plasmid vector such as pBR322, pUC 19/18, or pUC 118/119, a "midge" minimally-sized nucleic acid vector (as described in for instance [67]), or as a precipitated nucleic acid vector construct, such as a $CaPO_4^-$-precipitated construct (as described in for instance [68], [69], [70], and [71]). Such nucleic acid vectors and the usage thereof are well known in the art (see for instance [72] and [73]).

In one embodiment, the vector is suitable for expression of the humanized or chimeric CD3 antibody in a bacterial cell. Examples of such vectors include expression vectors such as BlueScript (Stratagene), pIN vectors ([74]), pET vectors (Novagen, Madison Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: [75] and [76]).

A nucleic acid construct and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle-targeting sequences (e. g., nuclear localization sequences, ER retention signals, mitochondrial transit sequences, chloroplast transit sequences), membrane localization/anchor sequences (e. g., stop transfer sequences, GPI anchor sequences), and the like which are well-known in the art.

In an expression vector of the invention, humanized or chimeric CD3 antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acid constructs and/or vectors may also comprise an inducible promoter as opposed to a constitutive promoter such as CMV IE (the skilled person will recognize that such terms are actually descriptors of a degree of gene expression under certain conditions).

In one embodiment, the humanized or chimeric CD3 antibody-encoding expression vector is positioned in and/or delivered to the host cell or host animal via a viral vector.

Such expression vectors may be used for recombinant production of humanized or chimeric CD3 antibodies.

In one aspect, the invention provides a host cell comprising an expression vector according to the invention.

In one aspect, the humanized or chimeric CD3 antibodies of any aspect or embodiment described herein are provided by use of recombinant eukaryotic, recombinant prokaryotic, or recombinant microbial host cell which produces the antibody. Accordingly, the invention provides a recombinant eukaryotic, recombinant prokaryotic, or recombinant microbial host cell, which produces a humanized or chimeric CD3 antibody or immunoglobulin as defined herein. Examples of host cells include yeast, bacterial and mammalian cells, such as CHO or HEK-293 cells. For example, in one embodiment, the host cell comprises a nucleic acid sequence stably integrated into the cellular genome that comprises a sequence coding for expression of a humanized or chimeric CD3 antibody described herein. In another embodiment, the host cell comprises a non-integrated nucleic acid sequence, such as a plasmid, cosmid, phagemid, or linear expression element, which comprises a sequence coding for expression of a humanized or chimeric CD3 antibody described herein.

The term "recombinant host cell" (or simply "host cell"), as used herein, is intended to refer to a cell into which an expression vector or nucleic acid construct or sequence has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, eukaryotic host cells, such as CHO cells, HEK-293 cells, PER.C6, NS0 cells, and lymphocytic cells, and prokaryotic cells such as *E. coli* and other eukaryotic hosts such as plant cells and fungi.

In a further aspect, the invention relates to a method for producing a humanized or chimeric CD3 antibody of the invention, said method comprising the steps of a) culturing a host cell of the invention as described herein above, and b) retrieving and/or purifying the antibody of the invention from the culture media.

In a further aspect, the nucleotide sequence encoding a sequence of a humanized or chimeric CD3 antibody further encodes a second moiety, such as a therapeutic polypeptide. Exemplary therapeutic polypeptides are described elsewhere herein. In one embodiment, the invention relates to a method for producing a humanized or chimeric CD3 antibody fusion protein, said method comprising the steps of a) culturing a host cell comprising an expression vector comprising such a nucleotide sequence, and b) retrieving and/or purifying the humanized or chimeric CD3 antibody fusion protein from the culture media.

Compositions

In one aspect, the invention provides a composition comprising the antibody or bispecific antibody according to any aspect and embodiment herein described.

In one aspect, the invention provides a pharmaceutical composition comprising the antibody or bispecific antibody as defined in any one of the aspects and embodiments herein described, and a pharmaceutically acceptable carrier.

The pharmaceutical compositions may be formulated with pharmaceutically acceptable carriers or diluents as well as any other known adjuvants and excipients in accordance with conventional techniques such as those disclosed in [77].

The pharmaceutically acceptable carriers or diluents as well as any other known adjuvants and excipients should be suitable for the humanized or chimeric antibody of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a humanized or chimeric antibody of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intra-arterial, intrathecal, intracapsular, intraorbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption-delaying agents, and the like that are physiologically compatible with a humanized or chimeric antibody of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. When referring to the "active compound" it is contemplated to also refer to the humanized or chimeric antibody according to the present invention.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The humanized or chimeric antibody of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-orthoesters, and polylactic acid alone or with a wax, or other materials well known in the art. Methods for the preparation of such formulations are generally known to those skilled in the art (see e.g., [78]).

In one embodiment, the humanized or chimeric antibody of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Therapeutic Applications

In another aspect, the present invention relates to a humanized or chimeric antibody, or pharmaceutical composition of the invention as defined in any aspect or embodiment herein described, for use as a medicament.

In another aspect, the present invention relates to a humanized or chimeric antibody, or pharmaceutical composition of the invention as defined in any aspect or embodiment herein described, for use in the treatment of a disease.

The humanized or chimeric antibody or pharmaceutical composition of the invention can be used as in the treatment of any cancer wherein the effector mechanisms of cytotoxic T-cells are desired. For example, the humanized or chimeric antibody may be administered to cells in culture, e.g., in vitro or ex vivo, or to human subjects, e.g. in vivo, to treat or prevent disorders such as cancer, inflammatory or auto-immune disorders. As used herein, the term "subject" is typically a human which respond to the humanized or chimeric antibody, or pharmaceutical composition. Subjects may for instance include human patients having disorders that may be corrected or ameliorated by modulating a target function or by leading to killing of the cell, directly or indirectly.

In another aspect, the present invention provides methods for treating or preventing a disorder, such as cancer, wherein recruitment of T-cells would contribute to the treatment or prevention, which method comprises administration of a therapeutically effective amount of a humanized or chimeric antibody, or pharmaceutical composition of the present invention to a subject in need thereof. The method typically involves administering to a subject a humanized or chimeric antibody in an amount effective to treat or prevent the disorder.

In one particular aspect, the present invention relates to a method of treatment of cancer comprising administering the humanized or chimeric antibody or pharmaceutical composition of the invention as defined in any aspect and embodiments herein described, to a subject in need thereof.

In another aspect, the present invention relates to the use or the method as defined in any aspect or embodiments herein described wherein the humanized or chimeric antibody is a bispecific antibody specifically binding to both CD3 and a cancer-specific target, or a target that is overexpressed in cancer or associated with cancer, such as HER2, CD19, EpCAM, EGFR, CD66e (or CEA, CEACAM5), CD33, EphA2 or MCSP (or HMW-MAA) and wherein the disease is cancer, such as breast cancer, prostate cancer, non-small cell lung cancer, bladder cancer, ovarian cancer, gastric cancer, colorectal cancer, esophageal cancer and squamous cell carcinoma of the head & neck, cervical cancer, pancreatic cancer, testis cancer, malignant melanoma, a soft-tissue cancer (e.g., synovial sarcoma), an indolent or aggressive form of B-cell lymphoma, chronic lymphatic leukemia or acute lymphatic leukemia.

The efficient dosages and dosage regimens for the humanized or chimeric antibody depend on the disease or condition to be treated and may be determined by the persons skilled in the art.

A physician having ordinary skill in the art may readily determine and prescribe the effective amount of the pharmaceutical composition required. For example, the physician could start doses of the humanized or chimeric antibody employed in the pharmaceutical composition at levels lower than that required in order to achieve the desired therapeutic effect and gradually increase the dosage until the desired effect is achieved. In general, a suitable dose of a composition of the present invention will be that amount of the humanized or chimeric antibody which is the lowest dose effective to produce a therapeutic effect according to a particular dosage regimen. Such an effective dose will generally depend upon the factors described above.

For example, an "effective amount" for therapeutic use may be measured by its ability to stabilize the progression of disease. The ability of a compound to inhibit cancer may, for example, be evaluated in an animal model system predictive of efficacy in human tumors. Alternatively, this property of a composition may be evaluated by examining the ability of the humanized or chimeric antibody to inhibit cell growth or to induce cytotoxicity by in vitro assays known to the skilled practitioner. A therapeutically effective amount of a therapeutic compound, i.e. a therapeutic humanized or chimeric antibody, or pharmaceutical composition according to the invention, may decrease tumor size, or otherwise ameliorate symptoms in a subject. One of ordinary skill in the art would be able to determine such amounts based on such factors as the subject's size, the severity of the subject's symptoms, and the particular composition or route of administration selected.

An exemplary, non-limiting range for a therapeutically effective amount of a humanized or chimeric antibody of the invention is about 0.001-30 mg/kg, such as about 0.001-20 mg/kg, such as about 0.001-10 mg/kg, such as about 0.001-5 mg/kg, for example about 0.001-2 mg/kg, such as about 0.001-1 mg/kg, for instance about 0.001, about 0.01, about 0.1, about 1, about 5, about 8, about 10, about 12, about 15, about 18 mg/kg.

Administration may e.g. be intravenous, intramuscular, intraperitoneal, or subcutaneous, and for instance administered proximal to the site of the target.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation.

In one embodiment, the efficacy of the treatment is monitored during the therapy, e.g. at predefined points in time.

If desired, an effective daily dose of a pharmaceutical composition may be administered as two, three, four, five, six or more sub-doses administered separately at appropriate intervals throughout the day, optionally, in unit dosage forms. In another embodiment, the humanized or chimeric antibody, or pharmaceutical composition is administered by slow continuous infusion over a long period, such as more than 24 hours, in order to minimize any unwanted side effects.

While it is possible for a humanized or chimeric antibody of the present invention to be administered alone, it is preferable to administer the humanized or chimeric antibody as a pharmaceutical composition as described above.

An effective dose of a humanized or chimeric antibody of the invention may also be administered using a weekly, biweekly or triweekly dosing period. The dosing period may be restricted to, e.g., 8 weeks, 12 weeks or until clinical progression has been established. Alternatively, an effective dose of a humanized or chimeric antibody of the invention may be administered every second, third or fourth week.

In one embodiment, the humanized or chimeric antibody may be administered by infusion in a weekly dosage of calculated by mg/m$^2$. Such dosages can, for example, be based on the mg/kg dosages provided above according to the following: dose (mg/kg)×70: 1.8. Such administration may be repeated, e.g., 1 to 8 times, such as 3 to 5 times. The administration may be performed by continuous infusion over a period of from 2 to 24 hours, such as of from 2 to 12 hours. In one embodiment, the humanized or chimeric antibody may be administered by slow continuous infusion over a long period, such as more than 24 hours, in order to reduce toxic side effects.

In one embodiment, the humanized or chimeric antibody may be administered in a weekly dosage of calculated as a fixed dose for up to 8 times, such as from 4 to 6 times when given once a week. Such regimen may be repeated one or more times as necessary, for example, after 6 months or 12 months. Such fixed dosages can, for example, be based on the mg/kg dosages provided above, with a body weight estimate of 70 kg. The dosage may be determined or adjusted by measuring the amount of humanized or chimeric antibody of the present invention in the blood upon administration by for instance taking out a biological sample and using anti-idiotypic antibodies which target the binding region of the humanized or chimeric antibodies of the present invention.

In one embodiment, the humanized or chimeric antibody may be administered by maintenance therapy, such as, e.g., once a week for a period of 6 months or more.

A humanized or chimeric antibody may also be administered prophylactically in order to reduce the risk of developing cancer, delay the onset of the occurrence of an event in cancer progression, and/or reduce the risk of recurrence when a cancer is in remission.

Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

A humanized or chimeric antibody may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

Diagnostic Applications

The humanized or chimeric antibody of the invention may also be used for diagnostic purposes, using a composition comprising a humanized or chimeric antibody as described herein. Accordingly, the invention provides diagnostic methods and compositions using the humanized or chimeric antibodies described herein. Such methods and compositions can be used for purely diagnostic purposes, such as detecting or identifying a disease, as well as for monitoring of the progress of therapeutic treatments, monitoring disease progression, assessing status after treatment, monitoring for recurrence of disease, evaluating risk of developing a disease, and the like.

In one aspect, the present invention relates to a method of diagnosing a disease characterized by involvement or accumulation of CD3-expression cells, comprising administering the humanized or chimeric antibody according to the invention, the composition according to the invention, or the pharmaceutically composition according to the invention to a subject, optionally wherein said humanized or chimeric antibody is labeled with a detectable agent.

In one aspect, the humanized or chimeric antibody of the present invention is used ex vivo, such as in diagnosing a disease in which cells expressing a specific target of interest and to which the humanized or chimeric antibody binds, are indicative of disease or involved in the pathogenesis, by detecting levels of the target or levels of cells which express the target of interest on their cell surface in a sample taken from a patient. This may be achieved, for example, by contacting the sample to be tested, optionally along with a control sample, with the humanized or chimeric antibody according to the invention under conditions that allow for binding of the antibody to the target. Complex formation can then be detected (e.g., using an ELISA). When using a control sample along with the test sample, the level of humanized or chimeric antibody or antibody-target complex is analyzed in both samples and a statistically significant higher level of humanized or chimeric antibody or antibody-target complex in the test sample indicates a higher level of the target in the test sample compared with the control sample.

Examples of conventional immunoassays in which humanized or chimeric antibodies of the present invention can be used include, without limitation, ELISA, RIA, FACS assays, plasmon resonance assays, chromatographic assays, tissue immunohistochemistry, Western blot, and/or immunoprecipitation.

Accordingly, in one embodiment, the present invention relates to a method of diagnosing a disease characterized by involvement or accumulation of CD3-expressing cells, comprising administering an antibody, bispecific antibody, composition or pharmaceutical composition according to any aspect or embodiment herein described, to a subject, optionally wherein the antibody is labeled with a detectable label.

In one embodiment, the invention relates to a method for detecting the presence of a target, or a cell expressing the target, in a sample comprising:

contacting the sample with a humanized or chimeric antibody of the invention under conditions that allow for binding of the humanized or chimeric antibody to the target in the sample; and analyzing whether a complex has been formed. Typically, the sample is a biological sample.

In one embodiment, the sample is a tissue sample known or suspected of containing a specific target and/or cells expressing the target. For example, in situ detection of the target expression may be accomplished by removing a histological specimen from a patient, and providing the humanized or chimeric antibody of the present invention to such a specimen. The humanized or chimeric antibody may be provided by applying or by overlaying the humanized or chimeric antibody to the specimen, which is then detected using suitable means. It is then possible to determine not only the presence of the target or target-expressing cells, but also the distribution of the target or target-expressing cells in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

In the above assays, the humanized or chimeric antibody can be labeled with a detectable substance to allow bound antibody to be detected. Alternatively, bound (primary) specific humanized or chimeric antibody may be detected by an antibody which is labeled with a detectable substance and which binds to the primary specific humanized or chimeric antibody. Furthermore, in the above assays, a diagnostic composition comprising an antibody or bispecific antibody according to any aspect or embodiments herein described may be used. Thus, in one aspect, the present invention relates to a diagnostic composition comprising an antibody or bispecific antibody according to any aspect or embodiment herein described.

The level of target in a sample can also be estimated by a competition immunoassay utilizing target standards labeled with a detectable substance and an unlabeled target-specific humanized or chimeric antibody. In this type of assay, the biological sample, the labeled target standard(s) and the target-specific humanized or chimeric antibody are combined, and the amount of labeled target standard bound to the unlabeled target-specific humanized or chimeric antibody is determined. The amount of target in the biological sample is inversely proportional to the amount of labeled target standard bound to the target-specific humanized or chimeric antibody.

Suitable labels for the target-specific humanized or chimeric antibody, secondary antibody and/or target standard used in in vitro diagnostic techniques include, without limitation, various enzymes, prosthetic groups, fluorescent materials, luminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; and examples of suitable radioactive material include $^{125}$I, $^{131}$I, $^{35}$S, and $^{3}$H.

In one aspect, the target-specific humanized or chimeric antibody of the invention is used in the in vivo imaging of target-expressing tissues such as tumors. For in vivo methods, antibody fragments such as, e.g., (Fab')$_2$, Fab and Fab' fragments, are particularly advantageous because of their rapid distribution kinetics.

In vivo imaging can be performed by any suitable technique. For example, a target-specific humanized or chimeric antibody (e.g., an antibody or a fragment) labeled with $^{99}$Tc, $^{131}$I, $^{111}$In or other gamma-ray emitting isotope may be used to image target-specific antibody accumulation or distribution in target-expressing tissues such as tumors with a gamma scintillation camera (e.g., an Elscint Apex 409ECT device), typically using low-energy, high resolution collimator or a low-energy all-purpose collimator. Alternatively, labeling with $^{89}$Zr, $^{76}$Br, $^{18}$F or other positron-emitting radionuclide may be used to image target-specific humanized or chimeric antibody, or antibody fragment distribution in tumors using positron emission tomography (PET). The images obtained by the use of such techniques may be used to assess biodistribution of target in a patient, mammal, or tissue, for example in the context of using target as a biomarker for the presence of cancer/tumor cells. Variations on this technique may include the use of magnetic resonance imaging (MRI) to improve imaging over gamma camera techniques. Conventional immunoscintigraphy methods and principles are described in, e.g., [79], [80], and [81]. Moreover, such images may also, or alternatively, serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer).

In one embodiment, the present invention provides an in vivo imaging method wherein a target-specific humanized or chimeric antibody of the present invention is conjugated to a detection-promoting radio-opaque agent, the conjugated humanized or chimeric antibody is administered to a host, such as by injection into the bloodstream, and the presence and location of the labeled humanized or chimeric antibody in the host is assayed. Through this technique and any other diagnostic method provided herein, the present invention provides a method for screening for the presence of disease-related cells in a human patient or a biological sample taken from a human patient and/or for assessing the distribution of target-specific humanized or chimeric antibody prior to target-specific ADC therapy.

For diagnostic imaging, radioisotopes may be bound to a target-specific humanized or chimeric antibody either directly or indirectly by using an intermediary functional group. Useful intermediary functional groups include chelators, such as ethylenediaminetetraacetic acid and diethylenetriaminepentaacetic acid (see for instance [82]).

In addition to radioisotopes and radio-opaque agents, diagnostic methods may be performed using target-specific antibodies that are conjugated to dyes (such as with the biotin-streptavidin complex), contrast agents, fluorescent compounds or molecules and enhancing agents (e.g. paramagnetic ions) for magnetic resonance imaging (MRI) (see, e.g., [83], which describes MRI techniques and the preparation of antibodies conjugated to a MRI enhancing agent). Such diagnostic/detection agents may be selected from agents for use in MRI, and fluorescent compounds. In order to load a target-specific humanized or chimeric antibody with radioactive metals or paramagnetic ions, it may be necessary to react it with a reagent having a long tail to which a multiplicity of chelating groups are attached for binding the ions. Such a tail may be a polymer such as a polylysine, polysaccharide, or another derivatized or derivatizable chain having pendant groups to which may be bound chelating groups such as, e.g., porphyrins, polyamines, crown ethers, bisthiosemicarbazones, polyoximes, and like groups known to be useful for this purpose. Chelates may be coupled to target-specific humanized or chimeric antibodies using standard chemistries.

Thus, the present invention provides a diagnostic target-specific humanized or chimeric antibody, wherein the target-specific humanized or chimeric antibody is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope.

In one aspect, the present invention relates to a diagnostic composition comprising an antibody or bispecific antibody according to the invention.

In a further aspect, the invention relates to a kit for detecting the presence of target antigen or a cell expressing the target, in a sample, comprising:
 a target-specific humanized or chimeric antibody of the invention; and
 instructions for use of the kit.

Thus, in one aspect, the present invention provides a kit for detecting the presence of a CD3 antigen, or a cell expressing CD3, in a sample comprising the steps of;
a) contacting the sample with an antibody or bispecific antibody according to the invention, under conditions that allow for formation of a complex between the antibody or bispecific antibody and CD3; and
b) analyzing whether a complex has been formed.

In one embodiment, the present invention provides a kit for diagnosis of cancer comprising a container comprising a target-specific humanized or chimeric antibody, and one or more reagents for detecting binding of the target-specific humanized or chimeric antibody to the target. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. In one embodiment, the present invention provides a diagnostic kit comprising one or more target-specific humanized or chimeric antibodies of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with a target-specific humanized or chimeric antibody, such as a labeled target-specific antibody, for the detection of the presence of the target in a tissue sample or host. In such diagnostic kits, as well as in kits for therapeutic uses described elsewhere herein, a target-specific humanized or chimeric antibody typically may be provided in a lyophilized form in a container, either alone or in conjunction with additional antibodies specific for a target cell or peptide. Typically, a pharmaceutically acceptable carrier (e.g., an inert diluent) and/or components thereof, such as a Tris, phosphate, or carbonate buffer, stabilizers, preservatives, biocides, inert proteins, e.g., serum albumin, or the like, also are included (typically in a separate container for mixing) and additional reagents (also typically in separate container(s)). In certain kits, a secondary antibody capable of binding to the target-specific humanized or chimeric antibody, which typically is present in a separate container, is also included. The second antibody is typically conjugated to a label and formulated in a manner similar to the target-specific humanized or chimeric antibody of the present invention. Using the methods described above and elsewhere herein, target-specific humanized or chimeric antibodies may be used to define subsets of cancer/tumor cells and characterize such cells and related tumor tissues.

Anti-Idiotypic Antibodies

In a further aspect, the invention relates to an anti-idiotypic antibody which binds to a humanized or chimeric antibody of the invention as described herein.

An anti-idiotypic (Id) antibody is an antibody which recognizes unique determinants generally associated with the antigen-binding site of an antibody. An anti-Id antibody may be prepared by immunizing an animal of the same species and genetic type as the source of a CD3 monoclonal antibody with the monoclonal antibody to which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original monoclonal antibody, which induced the anti-Id antibody. Thus, by using antibodies to the idiotypic determinants of a monoclonal antibody, it is possible to identify other clones expressing antibodies of identical specificity. Anti-Id antibodies may be varied (thereby producing anti-Id antibody variants) and/or derivatized by any suitable technique, such as those described elsewhere herein with respect to CD3-specific antibodies of the present invention. For example, a monoclonal anti-Id antibody may be coupled to a carrier such as keyhole limpet hemocyanin (KLH) and used to immunize BALB/c mice. Sera from these mice typically will contain anti-anti-Id antibodies that have the binding properties similar, if not identical, to an original/parent CD3 antibody.

Sequences

TABLE 1

| SEQ ID NO: | Clone name | Sequence |
| --- | --- | --- |
| SEQ ID NO: 1 | huCD3 VH CDR1 | GFTFNTYA |
| SEQ ID NO: 2 | huCD3 VH CDR2 | IRSKYNNYAT |
| SEQ ID NO: 3 | huCD3 VH CDR3 | VRHGNFGNSYVSWFAY |
| SEQ ID NO: 4 | huCD3 VL CDR1 | TGAVTTSNY |
|  | huCD3 VL CDR2 | GTN |
| SEQ ID NO: 5 | huCD3 VL CDR3 | ALWYSNLWV |
| SEQ ID NO: 6 | huCD3 VH1 | EVKLVESGGGLVQPGGSLRLSCAASGFTFNTYAMNWVRQA PGKGLEWVARIRSKYNNYATYYADSVKDRFTISRDDSKSSL YLQMNNLKTEDTAMYYCVRHGNFGNSYVSWFAYWGQGTL VTVSS |
| SEQ ID NO: 7 | huCD3 VH2 | EVKLVESGGGLVKPGRSLRLSCAASGFTFNTYAMNWVRQA PGKGLEWVARIRSKYNNYATYYADSVKDRFTISRDDSKSIL YLQMNNLKTEDTAMYYCVRHGNFGNSYVSWFAYWGQGTL VTVSS |
| SEQ ID NO: 8 | huCD3 VH3 | EVKLVESGGGLVKPGRSLRLSCAASGFTFNTYAMNWVRQA PGKGLEWVARIRSKYNNYATYYADSVKDRFTISRDDSKSIL YLQMNSLKTEDTAMYYCVRHGNFGNSYVSWFAYWGQGTL VTVSS |
| SEQ ID NO: 9 | huCD3 VH4 | EVKLVESGGGLVKPGRSLRLSCAASGFTFNTYAMNWVRQA PGKGLEWVARIRSKYNNYATYYADSVKDRFTISRDDSKSIL YLQMNSLKTEDTAMYYCVRHGNFGNSYVSWFAYWGQGTM VTVSS |
| SEQ ID NO: 10 | huCD3 VL1 | QAVVTQEPSFSVSPGGTVTLTCRSSTGAVTTSNYANWVQQ TPGQAFRGLIGGTNKRAPGVPARFSGSLIGDKAALTITGAQA DDESIYFCALWYSNLWVFGGGTKLTVL |
| SEQ ID NO: 11 | huCD3 VL2 | QAVVTQEPSFSVSPGGTVTLTCRSSTGAVTTSNYANWVQQ TPGQAFRGLIGGTNKRAPGVPARFSGSILGNKAALTITGAQA DDESIYFCALWYSNLWVFGGGTKLTVL |
| SEQ ID NO: 12 | huCD3 VL3 | QAVVTQEPSFSVSPGGTVTLTCRSSTGAVTTSNYANWVQQ TPGQAFRGLIGGTNKRAPGVPARFSGSILGNKAALTITGAQA DDESDYYCALWYSNLWVFGGGTKLTVL |
| SEQ ID NO: 13 | Mature human CD3ε (epsilon) | QDGNEEMGGITQTPYKVSISGTTVILTCPQYPGSEILWQHN DKNIGGDEDDKNIGSDEDHLSLKEFSELEQSGYYVCYPRGS KPEDANFYLYLRARVCENCMEMDVMSVATIVIVDICITGGLL LLVYYWSKNRKAKAKPVTRGAGAGGRQRGQNKERPPPVPN PDYEPIRKGQRDLYSGLNQRRI |
| SEQ ID NO: 14 | Human CD3δ (delta) | FKIPIEELEDRVFVNCNTSITWVEGTVGTLLSDITRLDLGKRI LDPRGIYRCNGTDIYKDKESTVQVHYRMCQSCVELDPATVA GIIVTDVIATLLLALGVFCFAGHETGRLSGAADTQALLRNDQ VYQPLRDRDDAQYSHLGGNWARNK |
| SEQ ID NO: 15 | IgG1m(f) heavy chain constant region | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISRT PEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQ KSLSLSPGK |
| SEQ ID NO: 16 | IgG1m(f)-LFLEDA heavy chain constant region | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEFEGGPSVFLFPPKPKDTLMISRTPEVTC VVVAVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDS DGSFFLYSKLTVDKSRWQQGNVFSCSVMHEALHNHYTQKSLSLSPG K |
| SEQ ID NO: 17 | VH huCLB-T3/4 | EVQLVESGGGLVKPGGSLRLSCAASGFTFSSYGMFWVRQAPGKGLE WVATISRYSRYIYYPDSVKGRFTISRDNAKNSLYLQMNSLRAEDTAVY YCARRPLYGSSPDYWGQGTLVTVSS |

TABLE 1-continued

| SEQ ID NO: | Clone name | Sequence |
|---|---|---|
| SEQ ID NO: 18 | VL huCLB-T3/4 | EIVLTQSPATLSLSPGERATLSCSASSSVTYVHWYQQKPGQAPRLLIYD TSKLASGIPARFSGSGSGTDFTLTISSLEPEDFAVYYCFQGSGYPLTFGS GTKLEMR |
| SEQ ID NO: 19 | VH HER2 169 | QVQLVQSGAEVKKPGASVKVSCKASGYTFTNYGISWVRQAPGQGLE WMGWLSAYSGNTIYAQKLQGRVTMTTDTSTTTAYMELRSLRSDDT AVYYCARDRIVVRPDYFDYWGQGTLVTSS |
| SEQ ID NO: 20 | VL HER2 169 | EIVLTQSPATLSLSPGERATLSCRASQSVSSYLAWYQQKPGQAPRLLIY DASNRATGIPARFSGSGSGTDFTLTISSLEPEDFAVYYCQQRSNWPRT FGQGTKVEIK |
| SEQ ID NO: 21 | Mature cyno CD3ε (epsilon) | QDGNEEMGSITQTPYQVSISGTTVILTCSQHLGSEAQWQHNGKNKE DSGDRLFLPEFSEMEQSGYYVCYPRGSNPEDASHHLYLKARVCENC MEMDVMAVATIVIVDICITLGLLLLVYYWSKNRKAKAKPVTRGAGA GGRQRGQNKERPPPVPNPDYEPIRKGQQDLYSGLNQRRI |
| SEQ ID NO: 22 | Mature rhesus CD3ε (epsilon) | QDGNEEMGSITQTPYHVSISGTTVILTCSQHLGSEVQWQHNGKNKE DSGDRLFLPEFSEMEQSGYYVCYPRGSNPEDASHHLYLKARVCENC MEMDVMAVATIVIVDICITLGLLLLVYYWSKNRKAKAKPVTRGAGA GGRQRGQNKERPPPVPNPDYEPIRKGQQDLYSGLNQRRI |
| SEQ ID NO: 23 | IgG1m(f)-F405L | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDG SFLLYSKLTVDKSRWQQGNVFSCSVMHEALHNHYTQKSLSLSPGK |
| SEQ ID NO: 24 | IgG1m(f)-K409R | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDG SFFLYSRLTVDKSRWQQGNVFSCSVMHEALHNHYTQKSLSLSPGK |
| SEQ ID NO: 25 | IgG1m(f)-LFLEDA-F405L | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEFEGGPSVFLFPPKPKDTLMISRTPEVTC VVVAVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDS DGSFLLYSKLTVDKSRWQQGNVFSCSVMHEALHNHYTQKSLSLSPG K |
| SEQ ID NO: 26 | IgG1m(f)-LFLEDA-K409R | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEFEGGPSVFLFPPKPKDTLMISRTPEVTC VVVAVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDS DGSFFLYSRLTVDKSRWQQGNVFSCSVMHEALHNHYTQKSLSLSPG K |
| SEQ ID NO: 27 | Parent murine VH | EVKLLESGGGLVQPKGSLKLSC AAS<u>GFTFNTYAM</u>NWVRQAPGKG LEWVAR<u>IRSKYNNYATY</u>YADSV KDRFTISRDDSQSILYLQMNNL KTEDTAMYYC<u>VRHGNFGNSYVS WFAY</u>WGQGTLVTVSA |
| SEQ ID NO: 28 | Parent murine VL | QAVVTQESALTTSPGETVTLTC RSS<u>TGAVTTSNYAN</u>WVQEKPDH LFTGLIGG<u>TNK</u>RAPGVPARFSG SLIGDKAALTITGAQTEDEAIY FC<u>ALWYSNLWV</u>FGGGTKLTVL |
| SEQ ID NO: 29 | VH CD20-7D8 | EVQLVESGGGLVQPDRSLRLSCAASGFTFHDYAMHWVRQA PGKGLEWVSTISWNSGTIGYADSVKGRFTISRDNAKNSLYL QMNSLRAEDTALYYCAKDIQYGNYYYGMD VWGQGTTVTVSS |
| SEQ ID NO: 30 | VL CD20-7D8 | EIVLTQSPATLSLSPGERATLSCRASQSVSSYLAWYQQKPG QAPRLLIYDASNRATGIPARFSGSGSGTDFTLTISSLEPEDFA VYYCQQRSNWPITFGQGTRLEIK |
| SEQ ID NO: 31 | Human IgLC2/IgLC3 constant domain | GQPKAAPSVTLFPPSSEELQANKATLVCLISDFYPGAVTVAW KADSSPVKAGVETTTPSKQSNNKYAASSYLSLTPEQWKSHR SYSCQVTHEGSTVEKTVAPTECS |

TABLE 1-continued

| SEQ ID NO: | Clone name | Sequence |
|---|---|---|
| SEQ ID NO: 32 | VL huCD3-LKNH | QAVVTQEPSLSVSPGGTVTLTCRSSTGAVTTSNYANWVQQKPGQAFRGLIGGTNNRAPGVPARFSGSLIGDKAALTITGAQADDESIYFCALWYSNHVFGGGTKLTVL |
| SEQ ID NO: 33 | VL huCD3-T41K | QAVVTQEPSFSVSPGGTVTLTCRSSTGAVTTSNYANWVQQKPGQAFRGLIGGTNKRAPGVPARFSGSLIGDKAALTITGAQADDESIYFCALWYSNLWVFGGGTKLTVL |
| SEQ ID NO: 34 | VH CD20-7D8 CDR1 | GFTFHDYA |
| SEQ ID NO: 35 | VH CD20-7D8 CDR2 | ISWNSGTI |
| SEQ ID NO: 36 | VH CD20-7D8 CDR3 | AKDIQYGNYYYGMDV |
| SEQ ID NO: 37 | VL CD20-7D8 CDR1 | QSVSSY |
|  | VL CD20-7D8 CDR2 | DAS |
| SEQ ID NO: 38 | VL CD20-7D8 CDR3 | QQRSNWPIT |
| SEQ ID NO: 39 | VH CD20-2F2 | EVQLVESGGGLVQPGRSLRLSCAASGFTFNDYAMHWVRQAPGKGLEWVSTISWNSGSIGYADSVKGRFTISRDNAKKSLYLQMNSLRAEDTALYYCAKDIQYGNYYYGMDVWGQGTTVTVSS |
| SEQ ID NO: 40 | VL CD20-2F2 | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIK |
| SEQ ID NO: 41 | VH CD20-2F2 CDR1 | GFTFNDYA |
| SEQ ID NO: 42 | VH CD20-2F2 CDR2 | ISWNSGSI |
| SEQ ID NO: 43 | VH CD20-2F2 CDR3 | AKDIQYGNYYYGMDV |
| SEQ ID NO: 44 | VL CD20-2F2 CDR1 | QSVSSY |
|  | VL CD20-2F2 CDR2 | DAS |
| SEQ ID NO: 45 | VL CD20-2F2 CDR3 | QQRSNWPIT |
| SEQ ID NO: 46 | VH CD20-11B8 | EVQLVQSGGGLVHPGGSLRLSCTGSGFTFSYHAMHWVRQAPGKGLEWVSIIGTGGVTYYADSVKGRFTISRDNVKNSLYLQMNSLRAEDMAVYYCARDYYGAGSFYDGLYGMDVWGQGTTVTVSS |
| SEQ ID NO: 47 | VL CD20-11B8 | EIVLTQSPATLSLSPGERATLSCRASQSVSSYLAWYQQKPGQAPRLLIYDASNRATGIPARFSGSGSGTDFTLTISSLEPEDFAVYYCQQRSDWPLTFGGGTKVEIK |
| SEQ ID NO: 48 | VH CD20-11B8 CDR1 | GFTFSYHA |
| SEQ ID NO: 49 | VH CD20-11B8 CDR2 | IGTGGVT |
| SEQ ID NO: 50 | VH CD20-11B8 CDR3 | ARDYYGAGSFYDGLYGMDV |
| SEQ ID NO: 51 | VL CD20-11B8 CDR1 | QSVSSY |
|  | VL CD20-11B8 CDR2 | DAS |

TABLE 1-continued

| SEQ ID NO: | Clone name | Sequence |
|---|---|---|
| SEQ ID NO: 52 | VL CD20-11B8 CDR3 | QQRSDWPLT |
| SEQ ID NO: 53 | VH CD20-2C6 | AVQLVESGGGLVQPGRSLRLSCAASGFTFGDYTMHWVRQA PGKGLEWVSGISWNSGSIGYADSVKGRFTISRDNAKNSLY LQMNSLRAEDTALYYCTKDNQYGSGSTYGLGVWGQGTLVT VSS |
| SEQ ID NO: 54 | VL CD20-2C6 | EIVLTQSPATLSLSPGERATLSCRASQSVSSYLAWYQQKPG QAPRLLIYDASNRATGIPARFSGSGSGTDFTLTISSLEPEDFA VYYCQQRSNWPLTFGGGTKVEIK |
| SEQ ID NO: 55 | VH CD20-2C6 CDR1 | GFTFGDYT |
| SEQ ID NO: 56 | VH CD20-2C6 CDR2 | ISWNSGSI |
| SEQ ID NO: 57 | VH CD20-2C6 CDR3 | TKDNQYGSGSTYGLGV |
| SEQ ID NO: 58 | VL CD20-2C6 CDR1 | QSVSSY |
|  | VL CD20-2C6 CDR2 | DAS |
| SEQ ID NO: 59 | VL CD20-2C6 CDR3 | QQRSNWPLT |
| SEQ ID NO: 60 | VL huCD3-CDR3 | ALWYSNHWV |

The CDR regions have been annotated according to the IMGT definitions.

EXAMPLES

Example 1—Generation of Humanized CD3 Antibodies and Non-Activating Antibody Variants Humanization of CD3 Antibodies Humanization of a murine CD3 antibody (U.S. Pat. No. 8,236,308, described herein as IgG1-CD3) was performed by Antitope (Cambridge, UK) using their improved version of the germline humanization (CDR-grafting) technology (EP 0 629 240). Using this technology, 4 different VH chains (SEQ ID NOs:6, 7, 8, and 9) and 3 different VL chains (SEQ ID NOs:10, 11, and 12) were designed. By combining these 4 VH with the 3 VL chains, 12 different antibodies were generated. The humanized variants are described herein as huCD3. Thus, humanized variants comprising a VH and a VL according to the invention, are described as, e.g., IgG1-huCD3-H1L1 meaning that said specific variant is of the IgG1 isotype, is a humanized CD3 and comprises the VH amino acid sequence termed "H1" and is defined according to SEQ ID NO:6, and the VL amino acid sequence termed "L1" and is defined according to SEQ ID NO: 10. Thus, H1 refers to the variable heavy chain region VH1, L1 refers to the variable light chain region VL1, and so forth.

In particular, the variants IgG1-huCD3-H1L1 (humanized CD3 comprising the VH1 sequence set forth in SEQ ID NO:6 and the VL1 sequence set forth in SEQ ID NO:10), IgG1-huCD3-H1L2 (humanized CD3 comprising the VH1 sequence set forth in SEQ ID NO:6 and the VL2 sequence set forth in SEQ ID NO:11), IgG1-huCD3-H1L3 (humanized CD3 comprising the VH1 sequence set forth in SEQ ID NO:6 and the VL3 sequence set forth in SEQ ID NO:12), IgG1-huCD3-H3L3 (humanized CD3 comprising the VH3 sequence set forth in SEQ ID NO:8 and the VL3 sequence set forth in SEQ ID NO:12), IgG1-huCD3-H4L1 (humanized CD3 comprising the VH4 sequence set forth in SEQ ID NO:9 and the VL1 sequence set forth in SEQ ID NO:10), IgG1-huCD3-H3L1 (humanized CD3 comprising the VH3 sequence set forth in SEQ ID NO:8 and the VL1 sequence set forth in SEQ ID NO:10), IgG1-huCD3-H3L3 (humanized CD3 comprising the VH3 sequence set forth in SEQ ID NO:8 and the VL3 sequence set forth in SEQ ID NO:12), and IgG1-huCD3-H4L3 (humanized CD3 comprising the VH4 sequence set forth in SEQ ID NO:9 and the VL3 sequence set forth in SEQ ID NO:12) have been generated and tested in the herein described examples.

In some examples an antibody comprising the heavy and light chain variable region sequences of huCLB-T3/4 (SEQ ID NOs:17 and 18, respectively) were used as a control antibody (Labrijn et al., PNAS 2013, 110: 5145-50) and to verify different non-activating mutation combinations in the Fc region (see Examples 8 to 10). The huCBL-T3/4 is a humanized version of the murine CD3 antibody CLB-T3/4 (Parren et al., Res Immunol. 1991, 142(9):749-63). Both sequences (SEQ ID NOs:17 and 18) were cloned into the relevant pcDNA3.3 (Invitrogen) expression vectors and expressed by cotransfection in HEK293F cells. The resulting control antibody is described as IgG1-huCLB-T3/4.

In some examples an antibody comprising the heavy and light chain variable region sequences of the CD20 antibody 7D8 (SEQ ID NO: 29 corresponding to the VH sequence and SEQ ID NO:30 corresponding to the VL sequence) was used as a positive control. When used in the context of a positive control it is termed "IgG1-CD20".

These IgG1-CD3 (i.e. the chimeric, parental CD3 antibody), IgG1-huCD3 and IgG1-huCLB-T3/4 antibodies were used in monospecific and bispecific format, where the bispecific antibodies were generated as described below.

HER2 Antibody

In some of the examples an antibody against HER2 was used. The VH and VL sequences for this HER2-specific antibody (antibody 169, SEQ ID NOs:19 and 20, respectively) were described before (WO2012/143524 [Genmab]; Labrijn et al., PNAS 2013, 110: 5145-50). The antibody was used in both monospecific and bispecific formats, and is termed "IgG1-HER2".

b12 Antibody

In some of the examples the antibody b12, a gp120 specific antibody (Barbas, C F. J Mol Biol. 1993 Apr. 5; 230(3):812-23.) was used as a negative control, and is termed "IgG1-b12".

Expression

Antibodies were expressed as IgG1,κ or IgG1,λ, with or without the non-activating mutations described below and with a mutation in the CH3 domain enabling the generation of bispecific antibodies by the method described below: IgG1-HER2-K409R, IgG1-b12-K409R, IgG1-CD3-F405L. Plasmid DNA mixtures encoding both heavy and light chain of antibodies were transiently transfected to Freestyle HEK293F cells (Invitrogen, US) using 293fectin (Invitrogen, US) essentially as described by the manufacturer.

Purification of Antibodies

Culture supernatant was filtered over 0.2 μm dead-end filters, loaded on 5 mL MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH2PO4, 140 mM NaCl, pH 7.4 (B. Braun). Alternatively, subsequent to purification, the eluate was loaded on a HiPrep Desalting column and the antibody was exchanged into 12.6 mM NaH2PO4, 140 mM NaCl, pH 7.4 (B. Braun) buffer. After dialysis or exchange of buffer, samples were sterile filtered over 0.2 μm dead-end filters. Purity was determined by SDS-PAGE and concentration was measured by absorbance at 280 nm. Purified antibodies were stored at 2-8° C.

Generation of Bispecific Antibodies

Bispecific antibodies were generated in vitro using the DuoBody® platform technology, i.e. 2-MEA-induced Fab-arm exchange as described in WO 2011/147986 and Labrijn et al. (Labrijn et al., PNAS 2013, 110: 5145-50; Gramer et al., MAbs 2013, 5: 962-973). To enable the production of bispecific antibodies by this method, IgG1 molecules carrying a single mutation in the CH3 domain were generated: in one parental IgG1 antibody the F405L mutation (i.e. the IgG1-CD3 antibody), in the other parental IgG1 antibody the K409R mutation (i.e. the HER2 or b12 antibodies). To generate bispecific antibodies, these two parental antibodies, each antibody at a final concentration of 0.5 mg/mL, were incubated with 25 or 75 mM 2-mercaptoethylamine-HCl (2-MEA) in a total volume of 500 μL TE at 31° C. for 5 hours. The reduction reaction was stopped when the reducing agent 2-MEA is removed by using PD-10 columns (GE-healthcare, product #17-0851-01), equilibrated with 25 mL PBS. Prior to desalting, 2 mL PBS (B. Braun, product #3623140) was added to the samples to adjust the volume to 2.5 mL. Elution was done in 3.5 mL PBS. Samples were collected in Amicon Ultra centrifugal units (30 kD MWCO, Millipore, product #UFC803096) and concentrated by centrifuging 8 min at 3000×g. Volumes were adjusted to 500 μL (when needed) with PBS and samples were sterile-filtered over a 0.2 μm filter (Millex-GV, product #SLGV004SL). The bispecific products were stored at 2-8° C.

In an alternative way, yielding the same bispecific antibody, to generate bispecific antibodies 100 μg of the two parental antibodies were mixed and incubated with 75 mM 2-mercaptoethylamine-HCl (2-MEA) in a total volume of 400 μL PBS (B. Braun, product #3623140) at 31° C. for 5 hours. The reduction reaction was stopped when the reducing agent 2-MEA is removed by using Amicon Ultra 0.5 ml centrifugal units (10 kD MWCO, Millipore, product #UFC501096) and washing 4× with 400 μl PBS by centrifuging 10 min at 13000×g. Samples were collected in a new tube by inverting the filter and centrifuging 2 min at 1000 g. Volumes were adjusted to 200 μL (when needed) with PBS. The absorbance of 280 nm (A280) of bispecific products was measured to determine the final concentration. HPLC cation exchange chromatography (HPLC-CEX) (as described in WO 2013/060867) was performed to determine the amount of bispecific product. Samples were stored at 2-8° C.

The generated bispecific antibodies are described as "K409R IgG1 backbone" and "F405L IgG1 backbone" in the following.

Non-Activating Mutations

Several antibody variants were generated with one or more amino acid substitutions in the Fc region. A non-activating Fc region prevents the antibody from interacting with Fc-receptors present on blood cells, such as monocytes, or with C1q to activate the classical complement pathway. Reduction of the Fc activity was tested in antibody variants that contain different combinations of amino acid substitutions in the Fc region. Maximally five amino acid substitutions were introduced, which include the mutations N297Q, L234A, L235A, L234F, L235E, D265A, and P331S. Substitutions in one or more of these five amino acid positions were introduced in the K409R and/or F405L IgG1 backbone. The following Fc region variants of the huCLB-T3/4 antibody were generated: N297Q (refers to the N297Q substitution, termed IgG1-huCLB-T3/4-N297Q), LFLE (refers to the L234F/L235E substitutions, termed IgG1-huCLB-T3/4-LFLE), LALA (refers to the L234A/L235A substitutions, termed IgG1-huCLB-T3/4-LALA), LFLENQ (refers to the L234F/L235E/N297Q substitutions, termed IgG1-huCLB-T3/4-LFLENQ), LFLEDA (refers to the L234F/L235E/D265A substitutions, termed IgG1-huCLB-T3/4-LFLEDA), DA (refers to the D265A substitution, termed IgG1-huCLB-T3/4-DA), DAPS (refers to the D265A/P331S substitutions, termed IgG1-huCLB-T3/4-DAPS), DANQ (refers to the D265A/N297Q substitutions, termed IgG1-huCLB-T3/4-DANQ), LFLEPS (refers to the L234F/L235E/P331S substitutions, termed IgG1-huCLB-T3/4-LFLEPS), and LFLEDANQPS (refers to the L234F/L235E/D265A/N297Q/P331S substitutions, termed IgG1-huCLB-T3/4-LFLEDANQPS).

In particular, in the IgG1-huCD3 antibody variants a combination of three amino acid substitutions, which include the mutations L234F, L235E and D265A and is referred to as LFLEDA, were introduced in the K409R and F405L IgG1 backbones to generate antibodies with a non-activating Fc region. The resulting non-activating antibody variant is termed with the suffix "-LFLEDA".

Example 2—Binding of Humanized CD3 Antibodies and Non-Activating Variants Thereof to Human and Cynomolgous T-Cell Lines Expressing CD3

Binding of purified variants of humanized CD3 (huCD3) antibodies and bispecific (bs)IgG1-huCD3×HER2 molecules with or without LFLEDA mutations in the Fc region (see Example 1) to the human T-cell line Jurkat (Clone E6-1, ATCC® TIB-152™, LGC Standards GmbH, Wesel, Germany) or the cynomolgous T-cell line HSC-F (cat. no. JCRB1164; Health Science Research Resources Bank, Osaka, Japan) was analyzed by FACS analysis. In addition to the non-activating mutations, LFLEDA, the antibody variants contained F405L or K409R mutations as described in Example 1.

Cells ($1 \times 10^5$ cells/well) were incubated in polystyrene 96-well round-bottom plates (Greiner bio-one 650101) with serial dilutions of antibody preparations (range 5 to 10,000 ng/mL in 3-fold dilutions) in 100 µL PBS/0.1% BSA/0.02% azide at 4° C. for 30 min.

After washing twice in PBS/0.1% BSA/0.02% azide, cells were incubated in 100 µL with secondary antibody at 4° C. for 30 min. As a secondary antibody, R-Phycoerythrin (PE)-conjugated goat-anti-human IgG F(ab')2 (109-116-098, Jackson ImmunoResearch Laboratories, Inc., West Grove, Pa.) diluted 1/100 in PBS/0.1% BSA/0.02% azide, was used for all experiments. Next, cells were washed twice in PBS/0.1% BSA/0.02% azide, re-suspended in 150 µL PBS/0.1% BSA/0.02% azide and analyzed on a FACS Cantoll (BD Biosciences). Binding curves were analyzed using nonlinear regression (sigmoidal dose-response with variable slope) using GraphPad Prism V 5.04 software (GraphPad Software, San Diego, Calif., USA).

FIG. 1A shows that binding to Jurkat cells of the IgG1λ-huCD3 variants IgG1-huCD3-H1L1 (SEQ ID NOs:6 and 10, respectively), IgG1-huCD3-H1L2 (SEQ ID NOs:6 and 11, respectively), IgG1-huCD3-H1L3 (SEQ ID NOs:6 and 12, respectively), IgG1-huCD3-H3L3 (SEQ ID NOs:8 and 12, respectively), and IgG1-huCD3-H4L1 (SEQ ID NOs:9 and 10, respectively) with wild-type Fc region was observed for all variants, and that binding ability of IgG1-CD3-LFLEDA (parental CD3 antibody as described in Example 1 with non-activating LFLEDA mutations) and IgG1-huCD3-H3L1-LFLEDA with non-activating LFLEDA mutations were similar to huCD3 variants with wild-type Fc regions. Binding of IgG1-huCLB-T3/4, included as positive control, was strong to Jurkat cells in comparison with the IgG1-huCD3 variants. No binding was observed for the negative control antibody IgG1-b12.

Figure 6A:
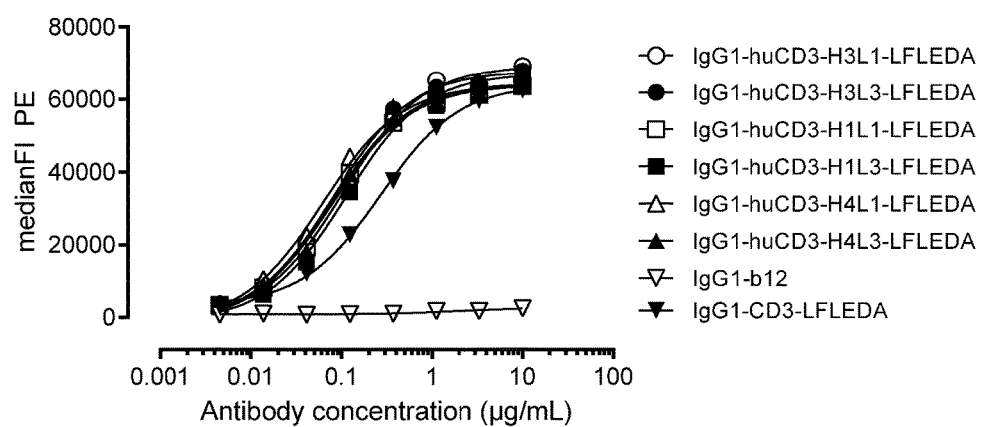
FIGS. 6A and 6B: Shows binding curves of non-activating, monospecific antibody variants of IgG1-huCD3 (FIG. 6A) and non-activating, bispecific antibody variants bsIgG1-huCD3×HER2 (FIG. 6B) to the human T-cell line Jurkat. Data shown are mean fluorescence intensities (MFI) of one representative experiment, as described in Example 2. The tables show the antibody concentrations (μg/mL) that result in half-maximal binding (EC50).

FIG. 6A shows that binding to Jurkat cells of the IgG1-CD3-LFLEDA (parental CD3 antibody as described in Example 1 with non-activating LFLEDA mutations), IgG1-huCD3-H3L1-LFLEDA, IgG1-huCD3-H3L3-LFLEDA, IgG1-3huCD3-H1L1-LFLEDA, IgG1-huCD3-H1L3-LFLEDA, IgG1-huCD3-H4L1-LFLEDA, and IgG1-huCD3-H4L3-LFLEDA with the non-activating LFLEDA mutations were similar to binding ability to huCD3 variants with wild-type Fc regions. Binding of IgG1-huCLB-T3/4, included as positive control, was stronger to Jurkat cells in comparison with the IgG1-huCD3 variants in low antibody concentrations but similar at higher antibody concentrations. Overall, the humanized CD3 variants have maintained the binding ability to CD3 as the IgG1-CD3 antibody. No binding was observed for the negative control antibody IgG1-b12.

Figure 1B:
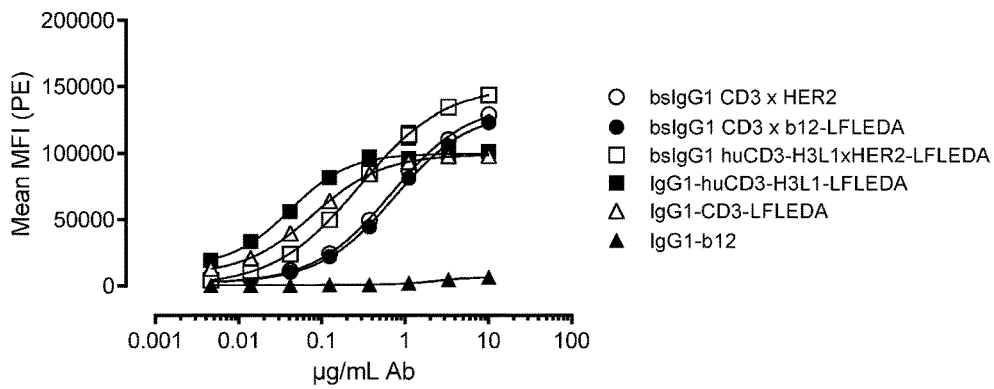

FIG. 1B shows that bispecific antibody variants bsIgG1 CD3×HER2, bsIgG1 CD3×b12-LFLEDA, and bsIgG1 huCD3-H3L1×HER2-LFLEDA also bind to Jurkat cells. The maximal binding values for these bispecific antibodies are higher than the maximal binding values of the monospecific antibodies. The EC50 concentrations of the bispecific antibodies were 6 to 10-fold higher. Again, no binding was observed for the negative control antibody IgG1-b12.

Figure 6B:
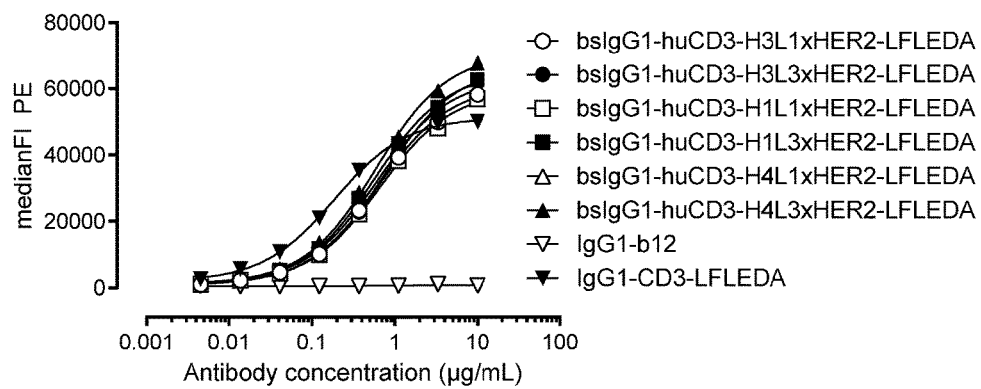

FIG. 6B shows that bispecific non-activating Fc antibody variants bsIgG1 huCD3-H3L1×HER2-LFLEDA, bsIgG1-huCD3-H3L3×HER2-LFLEDA, bsIgG1-huCD3-H1L1×HER2-LFLEDA, bsIgG1-huCD3-H1L3×HER2-LFLEDA, bsIgG1-huCD3-H4L1×HER2-LFLEDA, and bsIgG1-huCD3-H4L3×HER2-LFLEDA also bind to Jurkat cells. The maximal binding values for these bispecific antibodies are higher than the maximal binding values of the monospecific antibodies. The EC50 concentrations of the bispecific antibodies were 4 to 10-fold higher. Monovalent binding allows more antibodies to accumulate on the cell surface, thus, the higher binding values for the bispecific antibodies. Again, no binding were observed for the negative control antibody IgG1-b12.

Figure 2A:
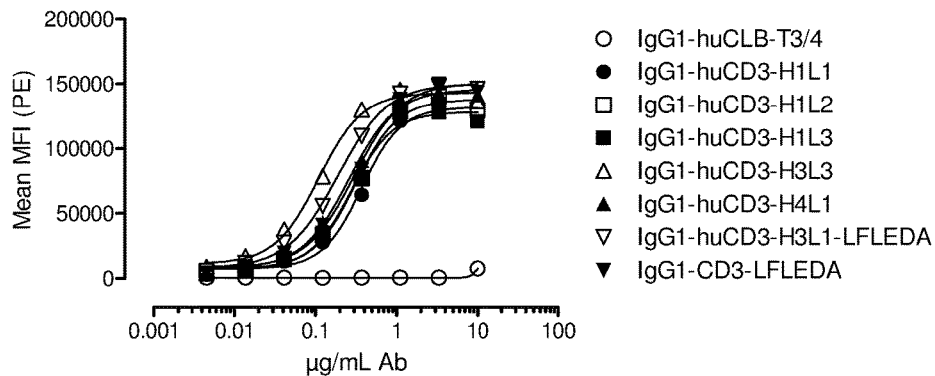
FIGS. 2A and 2B: Shows binding curves of (FIG. 2A) monospecific antibody variants of IgG1-huCD3 and (FIG. 2B) bispecific antibody variants bsIgG1 huCD3×HER2 to the cynomolgus T-cell line HSC-F. Data shown are mean fluorescence intensities (MFI) of one representative experiment, as described in Example 2.

FIG. 2A shows that binding of the IgG1-huCD3 variants IgG1-huCD3-H1L1, IgG1-huCD3-H1L2, IgG1-huCD3-H1L3, IgG1-huCD3-H3L3, and IgG1-huCD3-H4L1 with wild-type Fc region and IgG1-CD3-LFLEDA, IgG1-huCD3-H3L1-LFLEDA to the cynomolgus T-cell line HSC-F was similar. No binding was observed for the control antibody huCLB-T3/4, which does not cross-react with cynomolgus CD3, and the negative control antibody IgG1-b12.

Figure 7A:
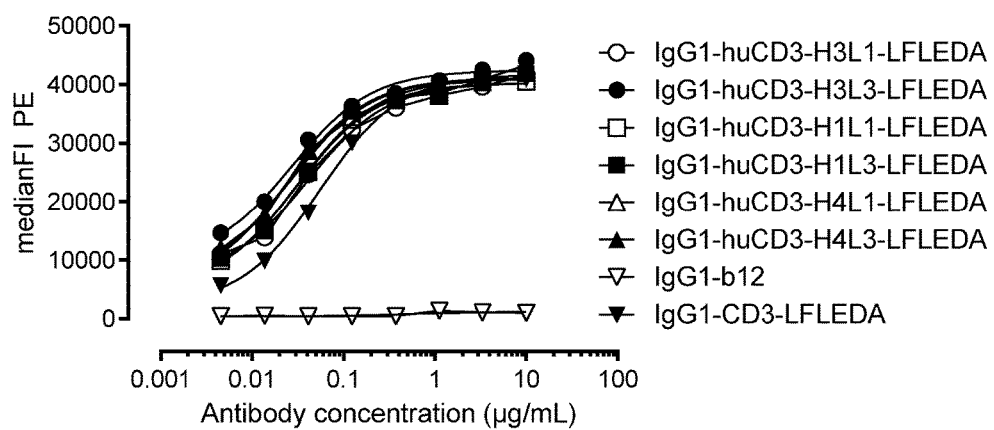
FIGS. 7A and 7B: Shows binding curves of non-activating, monospecific antibody variants of IgG1-huCD3 (FIG. 7A) and non-activating, bispecific antibody variants bsIgG1-huCD3×HER2 (FIG. 7B) to the cynomolgus T-cell line HSC-F. Data shown are mean fluorescence intensities (MFI) of one representative experiment, as described in Example 2. The tables show the antibody concentrations (μg/mL) that result in half-maximal binding (EC50).

FIG. 7A shows that binding of the IgG1-huCD3 variants IgG1-CD3-LFLEDA, IgG1-huCD3-H3L1-LFLEDA, IgG1-huCD3-H3L3-LFLEDA, IgG1-huCD3-H1L1-LFLEDA, IgG1-huCD3-H1L3-LFLEDA, IgG1-huCD3-H4L1-LFLEDA, and IgG1-huCD3-H4L3-LFLEDA to the cynomolgus T-cell line HSC-F was similar. No binding was observed for the negative control antibody IgG1-b12.

Figure 2B:
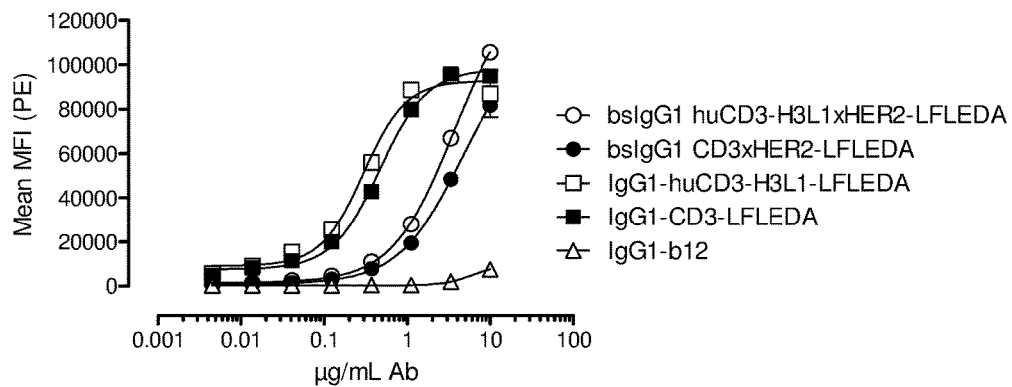
Figure 3A:
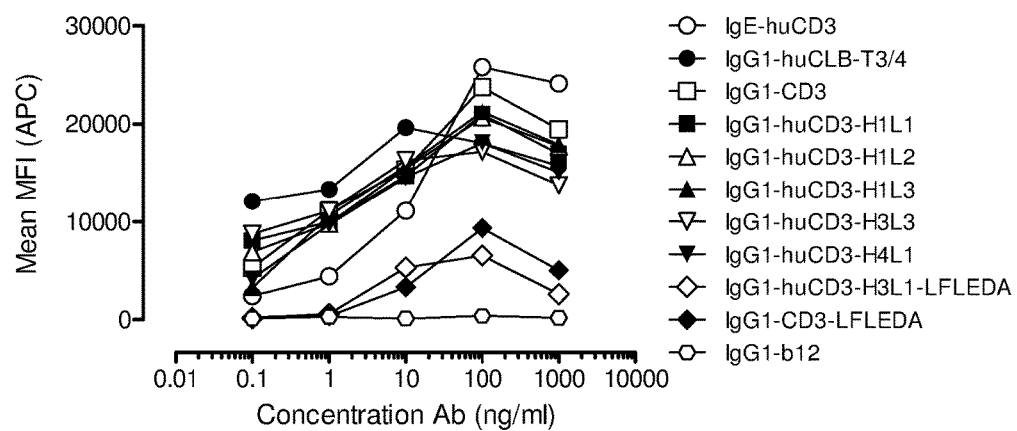
FIGS. 3A and 3B: T-cell activation by IgG1-huCD3 antibody variants. Expression of CD69 on T-cells from human (FIG. 3A) and cynomolgus (FIG. 3B) origin in PBMC culture was measured by FACS analysis, as described in Example 3. These experiments were performed twice and representative results from one experiment are shown.
Figure 3B:
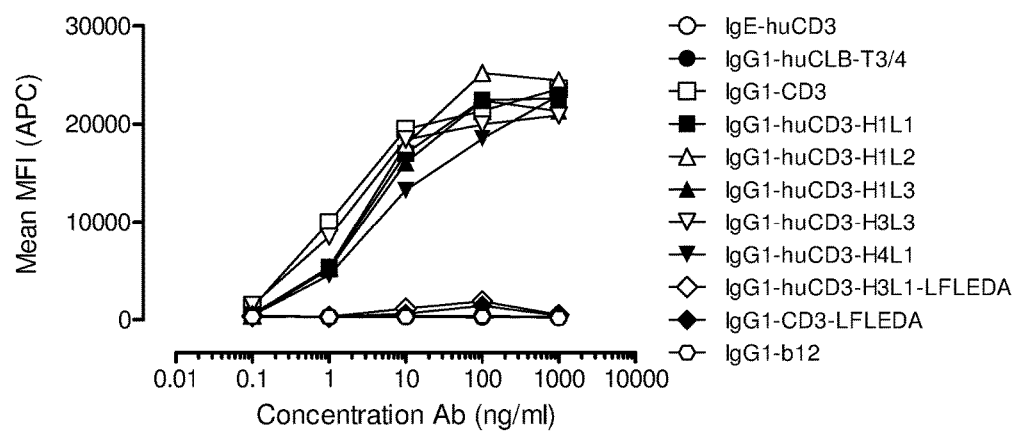
Figure 4A:
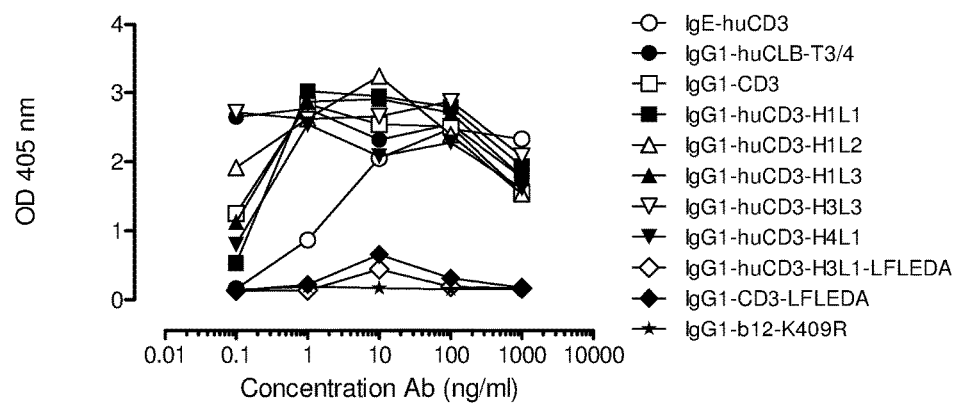
FIGS. 4A and 4B: T-cell proliferation induced by IgG1-huCD3 antibody variants. Human (FIG. 4A) or cynomolgus (FIG. 4B) PBMCs were incubated with IgG1-huCD3 antibody variants for 3 days, after which proliferation was measured by a cell proliferation ELISA, as described in Example 4. Representative results from two independent experiments are shown.
Figure 4B:
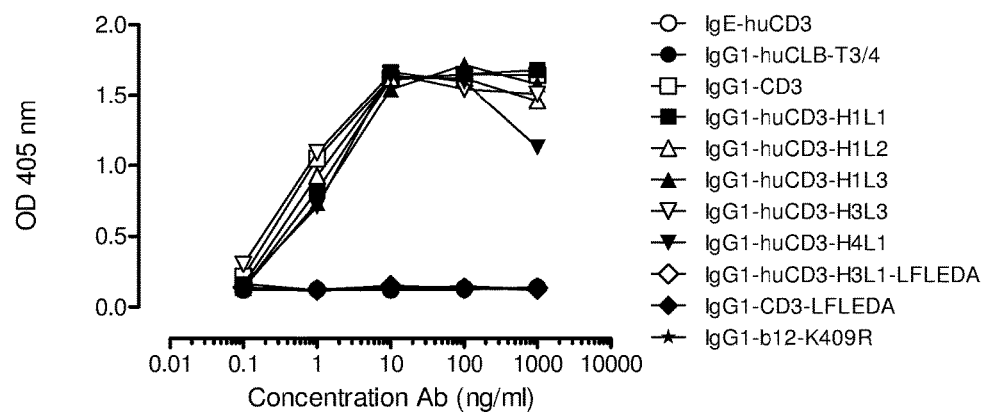

FIG. 2B shows that bispecific antibody variants bsIgG1 CD3×HER2 and bsIgG1 huCD3-H3L1-LFLEDA also bind to HSC-F cells. The maximal binding values for these bispecific antibodies are higher than the maximal binding values of the monospecific anti-CD3 variants. The EC50 concentrations of the bispecific antibodies were 10 to 12-fold higher than that of the monospecific anti-CD3 antibodies. Again, no binding was observed for the negative control antibody IgG1-b12.

Figure 7B:
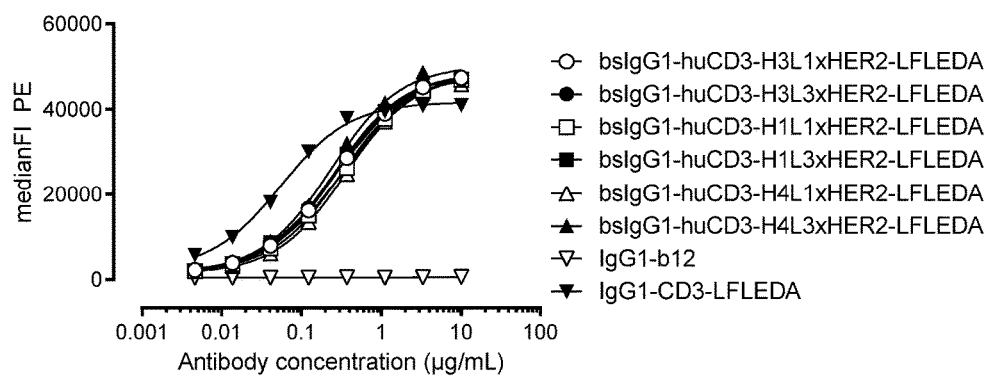

FIG. 7B shows that bispecific non-activating Fc antibodies variants bsIgG1 huCD3-H3L1×HER2-LFLEDA, bsIgG1-huCD3-H3L3×HER2-LFLEDA, bsIgG1-huCD3-H1L1×HER2-LFLEDA, bsIgG1-huCD3-H1L3×HER2-LFLEDA, bsIgG1-huCD3-H4L1×HER2-LFLEDA, and bsIgG1-huCD3-H4L3×HER2-LFLEDA also bind to HSC-F cells. The maximal binding values for these bispecific antibodies are higher than the maximal binding values of the monospecific anti-CD3 variants. The EC50 concentrations of the bispecific antibodies were 3 to 6-fold higher than that of the monospecific anti-huCD3 antibodies. Again, no binding was observed for the negative control antibody IgG1-b12.

Example 3—T-Cell Activation by Humanized CD3 Antibody Variants

CD69 expression is an early marker of T-cell activation. CD3 antibodies could mediate cross-linking of T-cells and immune cells through binding of CD3 expressed by T-cells and Fc receptors expressed by immune cells by the Fc region of the antibody, such as the IgG1 Fc region. This could lead to T-cell activation and induction of CD69. Antibody variants containing a non-activating Fc region (LFLEDA mutations) do not bind Fc receptors. Therefore, it was anticipated that non-activating CD3 antibodies do not induce T-cell activation and CD69 expression as the non-activating Fc region does not bind to Fc receptor expressing immune cells and thus cannot cross-link T-cells and immune cells.

CD69 expression on T-cells was evaluated by FACS analysis to determine early activation of T-cells after incubation with humanized CD3 (huCD3) variants with and without LFLEDA mutations in the Fc region. In addition to the non-activating mutations, LFLEDA variants contain F405L or K409R mutations as described in Example 1.

PBMCs were isolated from whole blood or buffy coat by density gradient separation using Leucosep tubes (#227290; Greiner Bio-one, Alphen a/d Rijn, The Netherlands), washed with PBS and re-suspended in culture medium.

A dose response series of huCD3 antibody variants, a negative control (IgG1-b12) and positive controls (IgE-huCD3 and parental IgG1-CD3) were prepared in culture medium (ranging from 0.1 to 1,000 ng/mL in 10-fold dilutions) and added to the wells of a 96-well round bottom plate containing human or cynomolgus PBMCs. After 16-24 hours incubation, cells were pelleted by centrifugation and supernatant (containing cytokines) was collected and stored at −20° C. Cells were then washed with PBS/0.1% BSA/0.02% azide and stained for 30 minutes at 4° C. with a mouse-anti-human CD28-PE (854.222.010; Sanquin, Amsterdam, The Netherlands; T-cell marker) and mouse-anti-human CD69-APC antibody (340560; BD Biosciences, Franklin Lakes, N.J.), which are cross-reactive with cynomolgus CD28 and CD69, respectively. Unbound antibodies were removed by washing twice with PBS/0.1% BSA/0.02% azide. Cells were re-suspended in 150 µL/well and CD69-expression on CD28 positive cells was measured on FACS Canto II (BD Biosciences).

FIG. 3 shows that IgG1-CD3 (as described in Example 1) and humanized IgG1-huCD3 variants with wild-type IgG1 Fc region induced similar levels of CD69 expression on T-cells from human (FIG. 3A) and cynomolgus (FIG. 3B) origin. Non-activating (LFLEDA) IgG1-CD3-LFLEDA and IgG1-huCD3-H3L1 variants induced low levels of CD69 expression in human T-cells. No expression of CD69 was induced by the non-activating IgG1-huCD3 variants in cynomolgus T-cells. The control antibody IgG1-b12 also did not induce expression of CD69 in human or cynomolgus T-cells.

FIG. 8 shows that non-activating (LFLEDA) IgG1-huCD3-H3L1-LFLEDA, IgG1-huCD3-H3L3-LFLEDA, IgG1-3huCD3-H1L1-LFLEDA, IgG1-huCD3-H1L3-LFLEDA, IgG1-huCD3-H4L1-LFLEDA, and IgG1-huCD3-H4L3-LFLEDA variants induced low levels of CD69 expression in human T-cells. FIGS. 8A and 8B show induction of CD69 expression on T-cells from cynomolgus monkey. The minor activation by non-activating variants observed may be due to cross-linking of CD3 molecules through bivalent binding of CD3 antibodies. Such explanation is supported by the observation that the activation is reduced at the highest concentration where antibody binding is monovalent. The control antibody IgG1-b12 also did not induce expression of CD69 in human or cynomolgus T-cells.

Figure 8A:
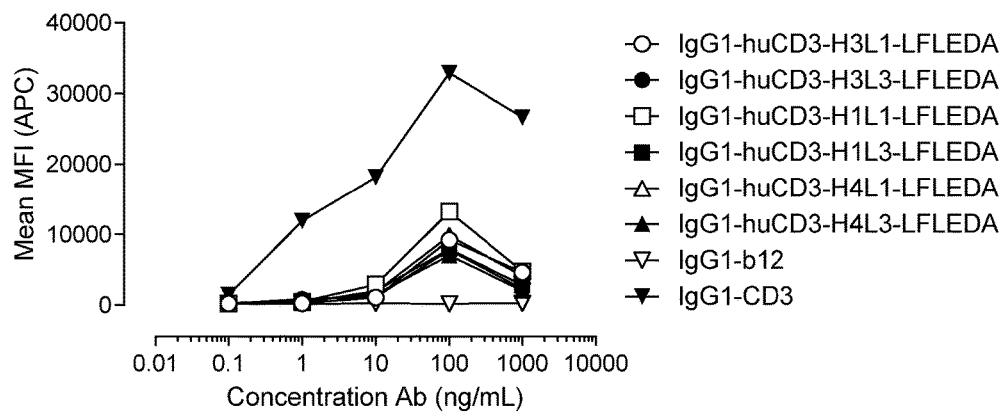
FIGS. 8A-8D: T-cell activation by non-activating monospecific IgG1-huCD3 (FIGS. 8A and 8B) or non-activating bispecific bsIgG1-huCD3×HER2 antibody variants (FIGS. 8C and 8D). Expression of CD69 on T-cells from human (FIGS. 8A and 8C) and cynomolgus (FIGS. 8B and 8D) origin in PBMC culture was measured by FACS analysis, as described in Example 3. These experiments were performed twice and representative results from one experiment are shown.
Figure 8B:
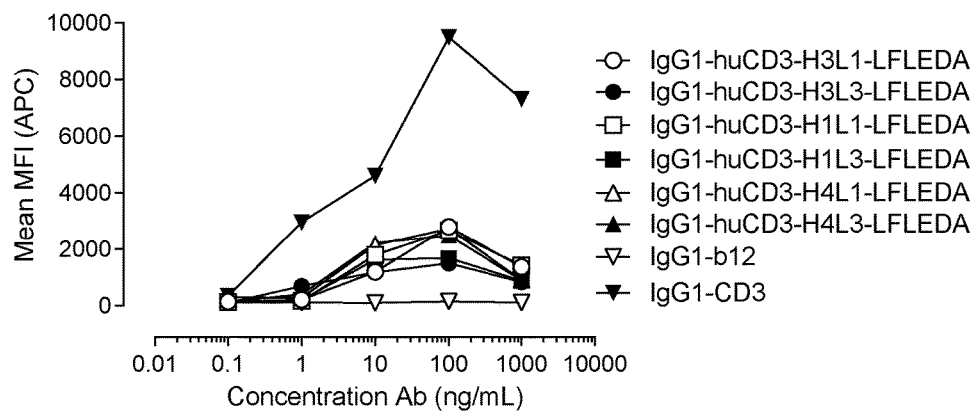
Figure 8C:
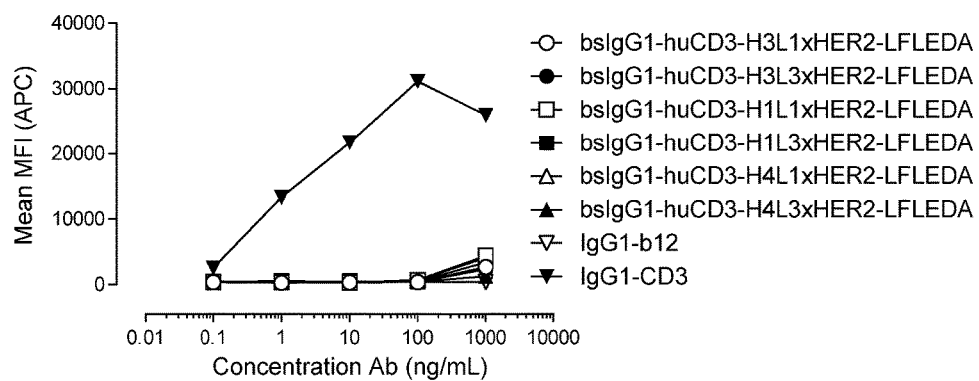
Figure 8D:
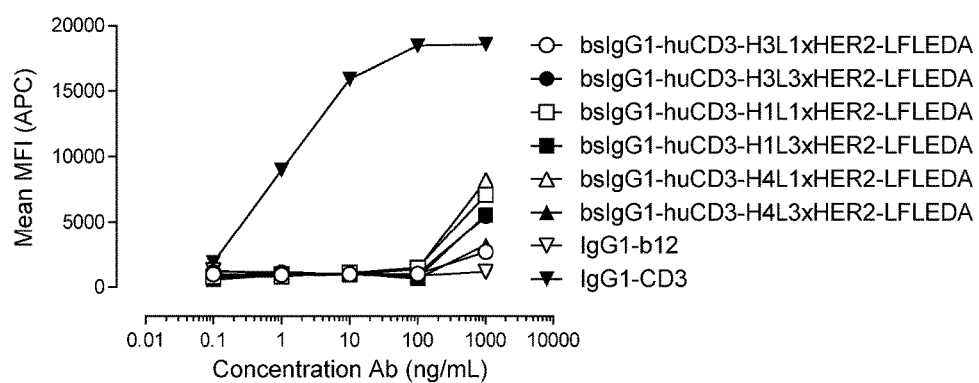

FIGS. 8C and 8D show that non-activating bispecific antibody variants bsIgG1-huCD3-H3L1×HER2-LFLEDA, bsIgG1-huCD3-H3L3×HER2-LFLEDA, bsIgG1-huCD3-H1L1×HER2-LFLEDA, bsIgG1-huCD3-H1L3×HER2-LFLEDA, bsIgG1-huCD3-H4L1×HER2-LFLEDA, and bsIgG1-huCD3-H4L3×HER2-LFLEDA do not induce expression of CD69 in T-cells from humans (FIG. 8C) or cynomolgus monkeys (FIG. 8D). However, at the higher antibody concentrations some induction of CD69 expression was observed.

Example 4—T-Cell Proliferation Induced by Humanized CD3 Antibody Variants

The effect of humanized CD3 (huCD3) antibody variants (described in Example 1) on the proliferation of human and cynomolgus T-cells was evaluated by the Cell proliferation ELISA kit from Roche Applied Science (Cell Proliferation ELISA, BrdU kit, #11647229001; Roche Applied Science, Mannheim, Germany), which was performed according to the manufacturer's instructions.

Human or cynomolgus PBMCs, isolated from whole blood or buffy coat, were incubated in 96-well culture plates with dilution series (ranging from 0.1 to 1,000 ng/mL in 10-fold dilutions) of IgG1 huCD3 antibody variants. IgE-CD3 and IgG1-huCLB-T3/4 were included as positive controls and IgG1-b12 as negative control. After 3 days of incubation with the antibodies, BrdU (Roche Applied Science, Mannheim, Germany) was added to the medium and plates were incubated for 5 hours. Cells were then pelleted by centrifugation and supernatant collected and stored at −20° C. Plates were dried and stored at 4° C. until ELISA was performed.

BrdU incorporation in the DNA was determined by ELISA according to the manufacturer's instructions (Roche Applied Science). Cells were fixed to the plates, where after the plates were incubated for 90 minutes at RT with an anti-BrdU antibody conjugated with peroxidase. Plates were washed with PBST and binding was detected using ABTS buffer (instead of the TMB solution provided with the kit). Color development was stopped after 30 min by adding 2% oxalic acid to the wells. OD405 nm was then measured on an EL808 ELISA-reader.

Figure 9A:
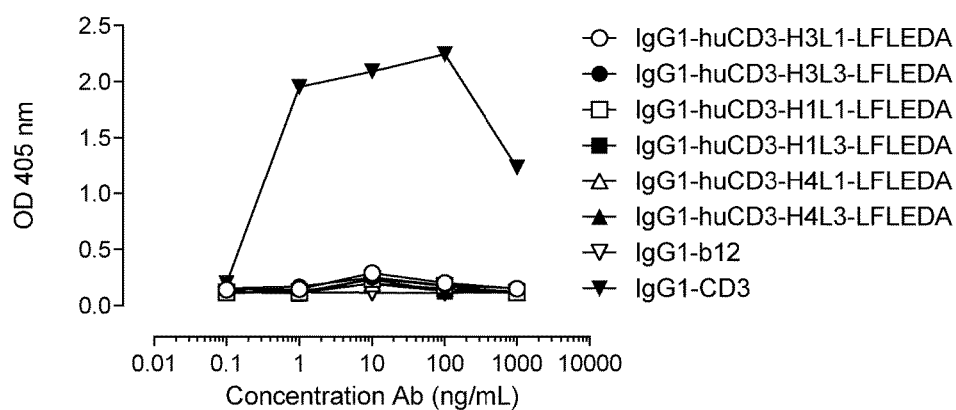
FIGS. 9A-9D: T-cell proliferation induced by non-activating monospecific IgG1-huCD3 (FIGS. 9A and 9B) or non-activating bispecific bsIgG1-huCD3×HER2 antibody variants (FIGS. 9C and 9D). T-cell proliferation was measured in human (FIGS. 9A and 9C) or cynomolgus (FIGS. 9B and 9D) PBMCs that were incubated with various antibody variants for 3 days, after which proliferation was measured by a cell proliferation ELISA, as described in Example 4. Representative results from two independent experiments are shown.
Figure 9B:
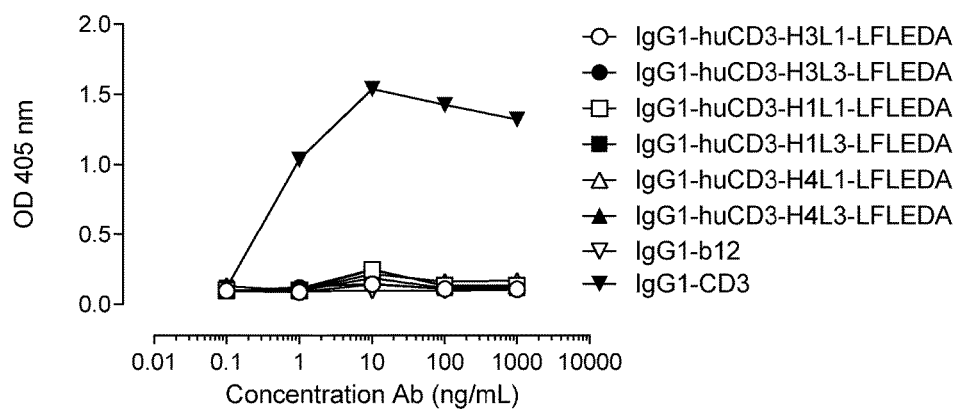

FIG. 4 shows that incubation of PBMCs with parental IgG1-CD3 and humanized IgG1-huCD3 variants with wild-type IgG1 Fc region induced strong proliferation of human (FIG. 4A) and cynomolgus (FIG. 4B) T-cells, even at very low concentrations of antibody. Incubation with non-activating LFLEDA variants of the IgG1-huCD3 antibodies did not induce proliferation of human T-cells (FIGS. 4A and 9A) or cynomolgus T-cells (FIGS. 4B and 9B). Thus, although the non-activating variants of the IgG1-huCD3 antibodies induced low levels of CD69 expression in human T-cells (as shown in Example 3), no proliferation of human T-cells was induced by these non-activating IgG1-huCD3 variants.

Figure 9C:
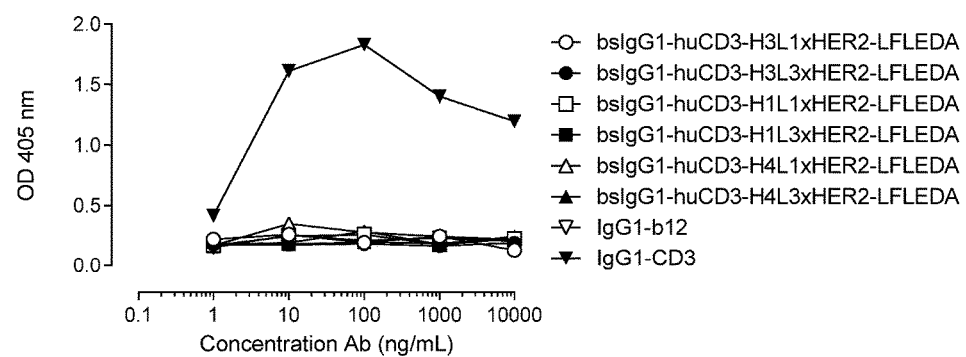
Figure 9D:
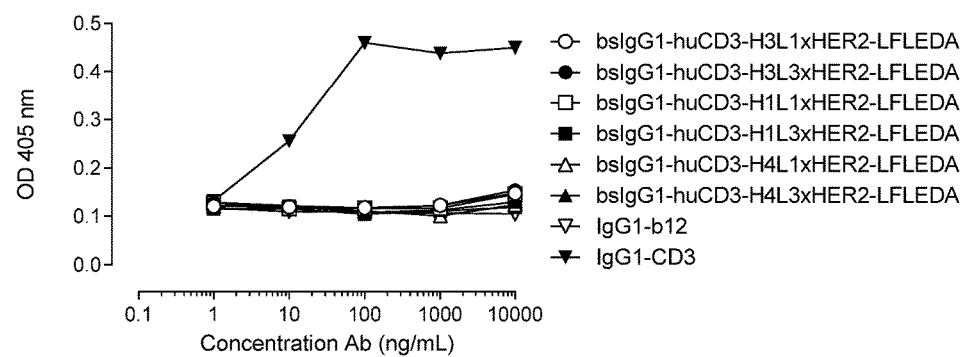

FIGS. 9C and 9D show that non-activating bispecific antibody variants bsIgG1-huCD3-H3L1×HER2-LFLEDA, bsIgG1-huCD3-H3L3×HER2-LFLEDA, bsIgG1-huCD3-H1L1×HER2-LFLEDA, bsIgG1-huCD3-H1L3×HER2-LFLEDA, bsIgG1-huCD3-H4L1×HER2-LFLEDA, and bsIgG1-huCD3-H4L3×HER2-LFLEDA do not induce proliferation of T-cells isolated from humans (FIG. 9C) or cynomolgus monkeys (FIG. 9D).

Example 5—In Vitro T-Cell-Mediated Cytotoxicity Induced by Humanized CD3 Antibody Variants Tumor-specific T-cell cytotoxicity can be mediated by bispecific antibodies that bind with one arm to CD3 and the other arm to a tumor-specific target, such as HER2. Simultaneous binding of bispecific antibodies to both T-cells and tumor cells will lead to T-cell activation and tumor cell specific cytotoxicity. In this Example, T-cell mediated cytotoxicity against HER2-positive tumor cells was evaluated using bispecific antibodies against CD3 (humanized variants) and HER2.

Therefore, AU565 (human breast carcinoma) cells were cultured in RPMI 1640 supplemented with 10% (vol/vol)

heat inactivated CCS, 1.5 g/L sodium bicarbonate (Lonza), 1 mM sodium pyruvate, 4.5 g/L glucose (Sigma), 50 IU/mL penicillin, and 50 µg/mL streptomycin. The cell line was maintained at 37° C. in a 5% (vol/vol) $CO_2$ humidified incubator. AU565 cells were cultured to near confluency, after which cells were trypsinized, re-suspended in culture medium and passed through a cell strainer to obtain a single cell suspension. $5 \times 10^4$ cells were seeded in each well of a 96-well culture plate, and cells were incubated at least 3 hrs at 37° C., 5% $CO_2$ to allow adherence to the plate.

Human or cynomolgus PBMCs were isolated from whole blood or buffy coat. Isolated PBMCs were washed with PBS, re-suspended in culture medium and added in a 1:1 ratio to the AU565 tumor cells in the 96-well plates. The percentage of T-cells present in PBMCs was measured by FACS-analysis, using a mouse anti-human CD3-PerCP (BD, #345766) antibody (for staining T-cells), which is cross-reactive with cynomolgus CD3. The T-cell content in the population of used PBMCs was typically 50 to 60%.

Dilution series (final concentrations ranging from 0.001 up to 10,000 ng/mL) of bispecific antibody variants bsIgG1 CD3×HER2-LFLEDA, bsIgG1 CD3×b12-LFLEDA, bsIgG1 huCD3-H3L1×HER2-LFLEDA, bsIgG1-huCD3-H3L3×HER2-LFLEDA, bsIgG1-huCD3-H1L1×HER2-LFLEDA, bsIgG1-huCD3-H1L3×HER2-LFLEDA, bsIgG1-huCD3-H4L1×HER2-LFLEDA, and bsIgG1-huCD3-H4L3×HER2-LFLEDA were prepared in culture medium and added to the plates. IgG1-HER2-LFLEDA and IgG1-b12 were included as controls. In addition to the non-activating mutations, LFLEDA antibody variants contain F405L or K409R mutations for preparation in bispecific format (see Example 1). Plates were incubated for 3 days at 37° C., 5% $CO_2$. Incubation of cells with 1 µM staurosporin (#S6942-200, Sigma) was used as reference for 100% tumor cell kill. Plates were washed twice with PBS, and 150 µL culture medium containing 10% Alamar blue was added to each well. Plates were incubated for 4 hours at 37° C., 5% $CO_2$. Absorbance at 590 nm was measured (Envision, Perkin Elmer, Waltham, Mass.).

Figure 5A:
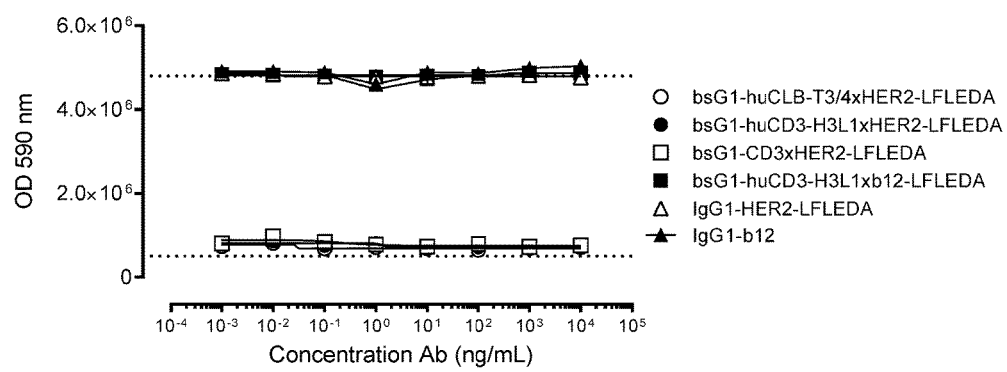
FIGS. 5A and 5B: Induction of human (FIG. 5A) and cynomolgus (FIG. 5B) T-cell-mediated cytotoxicity by huCD3 antibody variants with non-activating LFLEDA mutations were determined as explained in Example 5. Representative results from two independent experiments performed in duplo are shown.
Figure 5B:
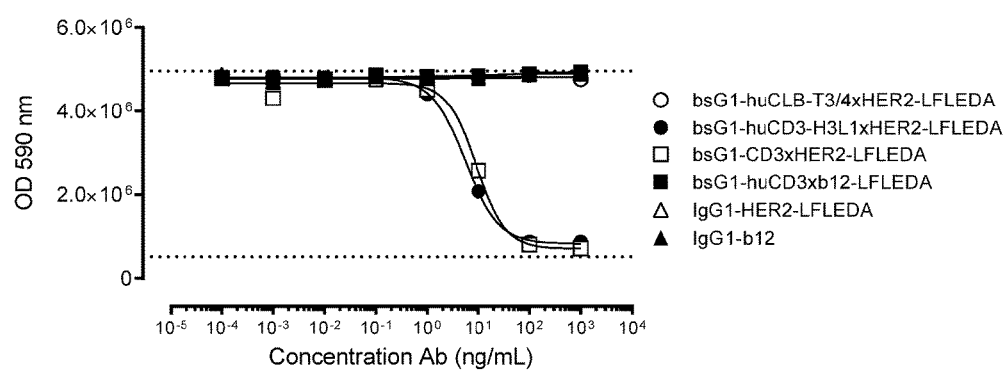

Bispecific CD3×HER2-LFLEDA antibody variants (bsIgG1-huCLB-T3/4×HER2-LFLEDA and bsIgG1-CD3×HER2-LFLEDA) induced killing of AU565 cells at low concentrations using human effector cells (FIG. 5A) or cynomolgus effector cells (FIG. 5B). The CD3 bispecific control antibody huCLB-T3/4×HER2-LFLEDA, which shows no cross-reactivity with cynomolgus CD3, only induced killing of AU565 cells when human PBMCs were used (FIG. 5A). Thus, no killing of target cells was observed when cynomolgus effector cells were used in the assay (FIG. 5B). Incubation with monospecific IGG1-b12 or IgG1-HER2-LFLEDA or bsIgG1-CD3×b12-LFLEDA antibodies did not induce unspecific killing of target cells.

Figure 10A:
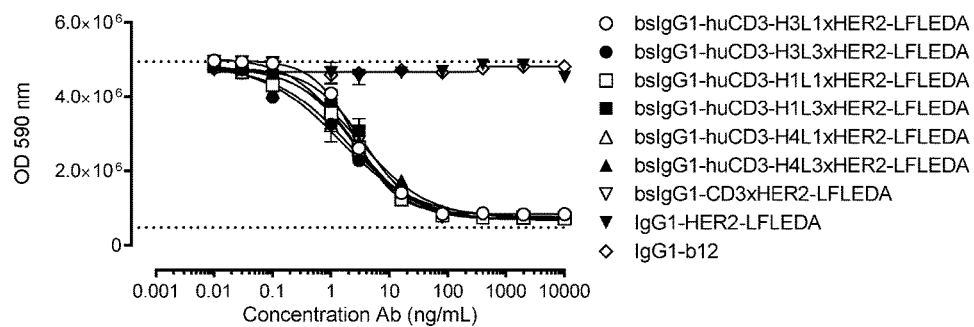
FIGS. 10A and 10B: Induction of human (FIG. 10A) and cynomolgus (FIG. 10B) T-cell-mediated cytotoxicity by huCD3 antibody variants with non-activating LFLEDA mutations were determined as explained in Example 5. Representative results from two independent experiments performed in duplo are shown.
Figure 10B:
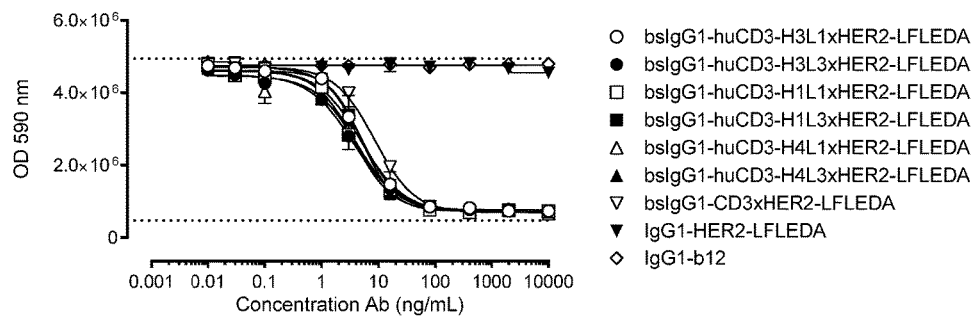

Bispecific antibody variants bsIgG1 huCD3-H3L1×HER2-LFLEDA, bsIgG1-huCD3-H3L3×HER2-LFLEDA, bsIgG1-huCD3-H1L1×HER2-LFLEDA, bsIgG1-huCD3-H1L3×HER2-LFLEDA, bsIgG1-huCD3-H4L1×HER2-LFLEDA, and bsIgG1-huCD3-H4L3×HER2-LFLEDA induced killing of AU565 cells at low concentrations using human effector cells (FIG. 10A) or cynomolgus effector cells (FIG. 10B). Incubation with monospecific IgG1-b12 or IgG1-HER2-LFLEDA antibodies did not induce unspecific target cell killing (FIGS. 10A and B). Thus, the humanized CD3 variants comprising the non-activating Fc region do not induce unspecific target cell killing, which indicates that the variants comprising a non-activating Fc region can be used to ensure targeted T-cell activation and thus avoid non-targeted T-cell activation.

Example 6—Rhesus T-Cell Activation by Humanized CD3 Antibody Variants

CD69 expression on rhesus T-cells was evaluated to determine early activation of T-cells after incubation with humanized CD3 (huCD3) antibody variants with wild-type IgG1 Fc region. Isolation of rhesus PBMCs and evaluation of CD69 expression by flow cytometry was performed as described in Example 3.

Figure 11:
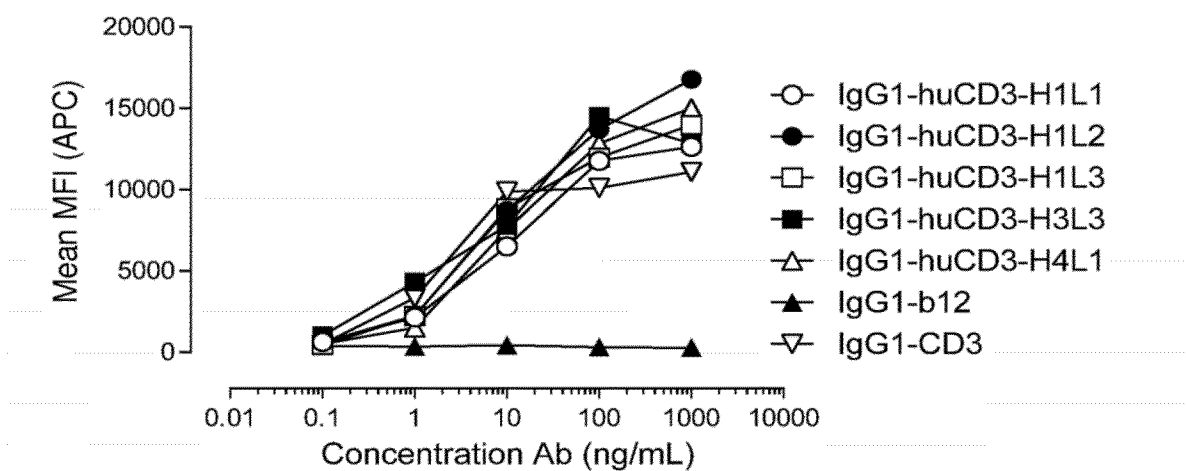
FIG. 11: Rhesus T-cell activation by IgG1-huCD3 antibody variants. Expression of CD69 on T-cells from rhesus origin in PBMC culture was measured by FACS analysis, as described in Example 6.
Figure 12A:
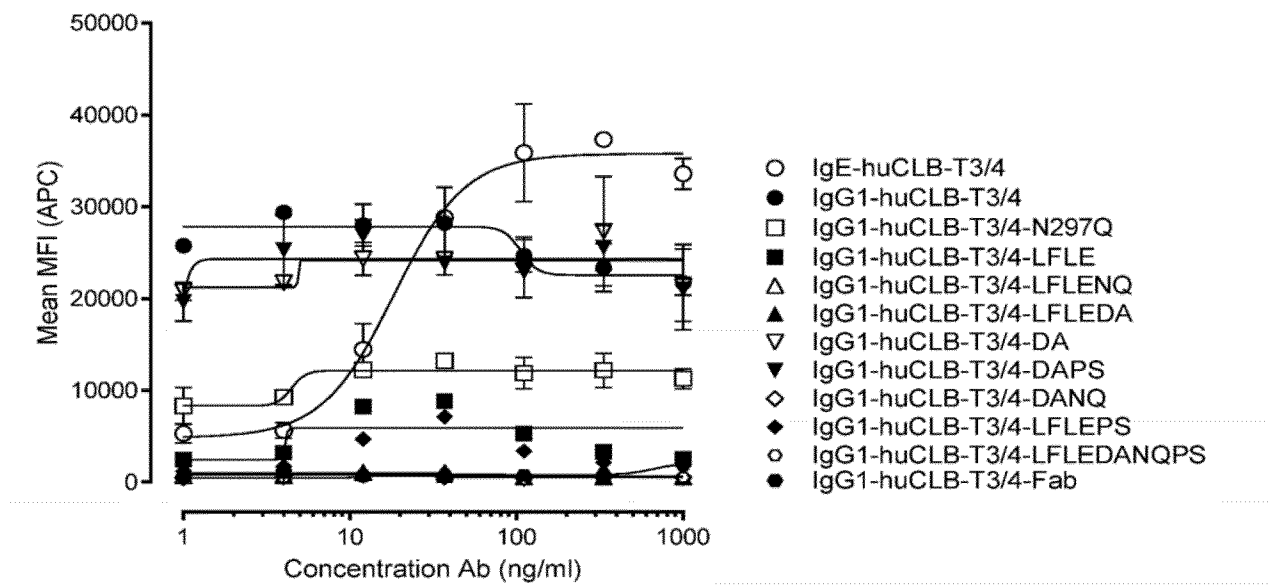
Figure 12B:
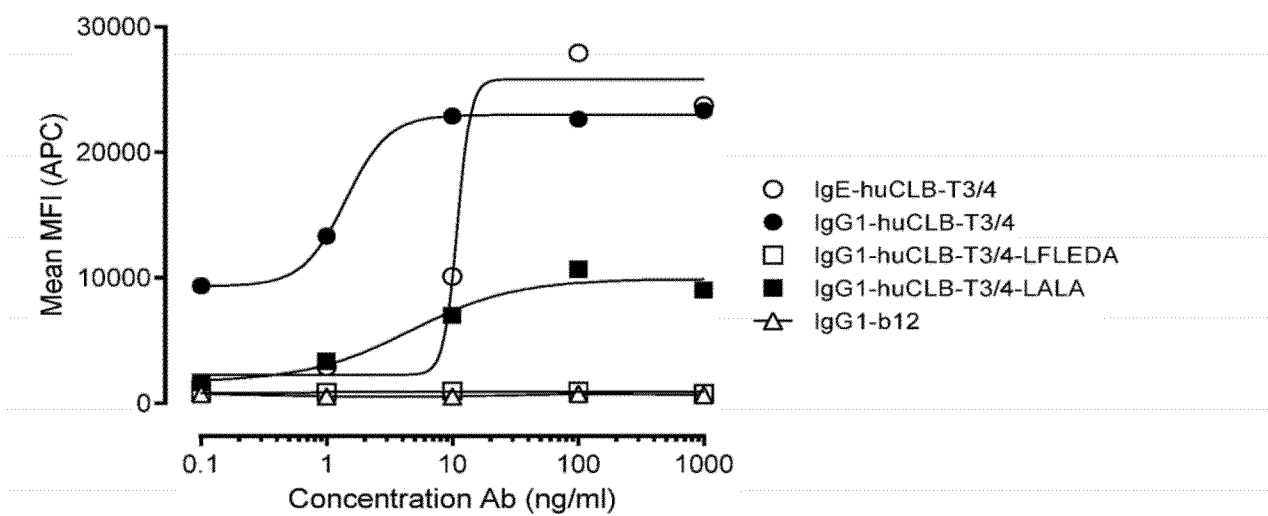
Figure 13A:
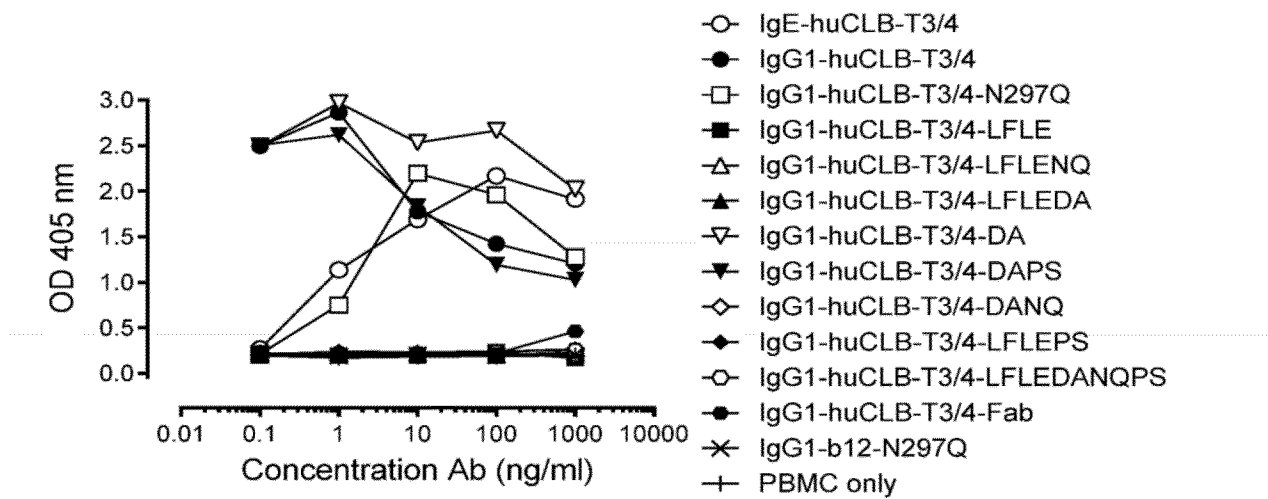
Figure 13B:
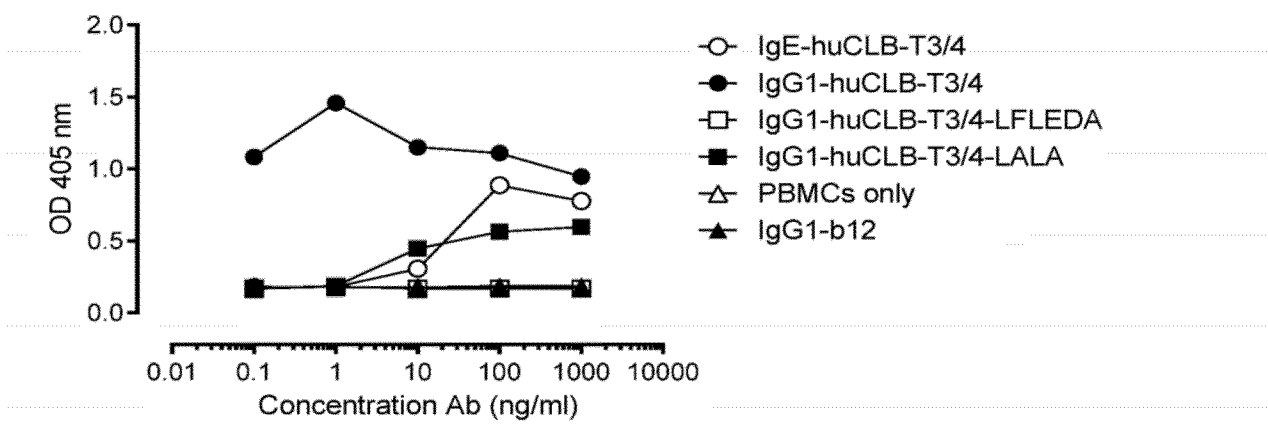
Figure 14A:
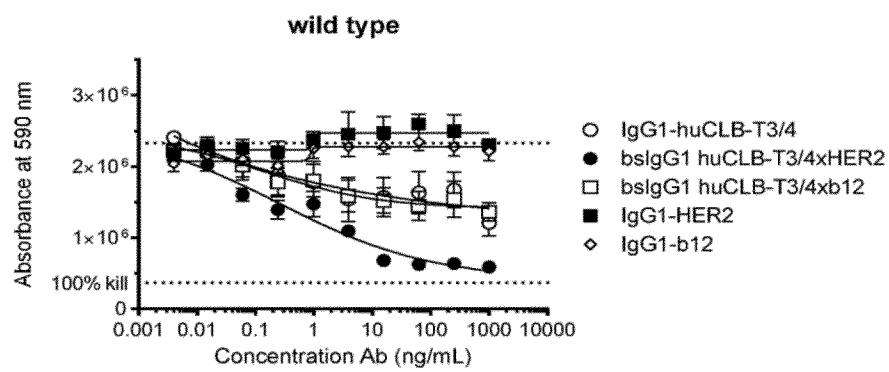
Figure 14B:
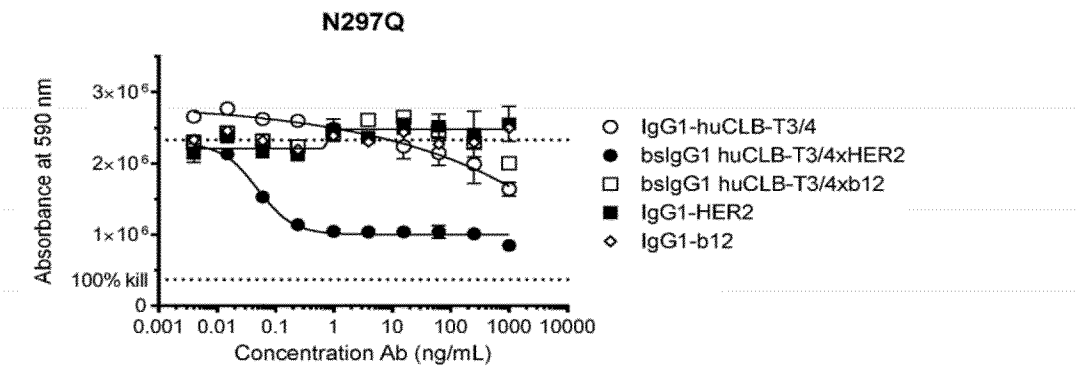
Figure 14C:
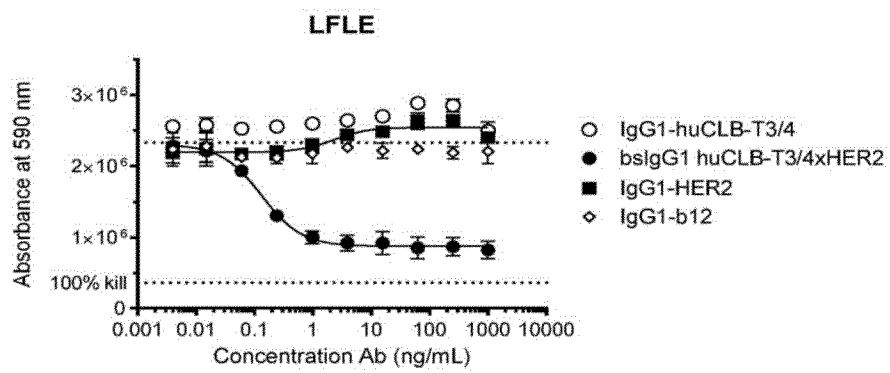
Figure 14D:
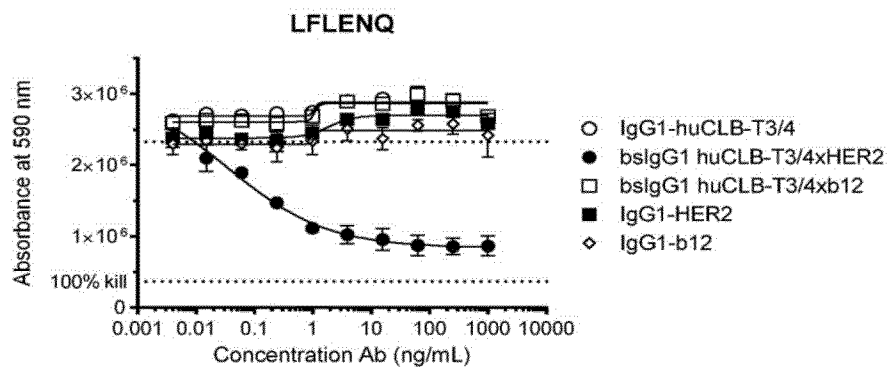
Figure 14E:
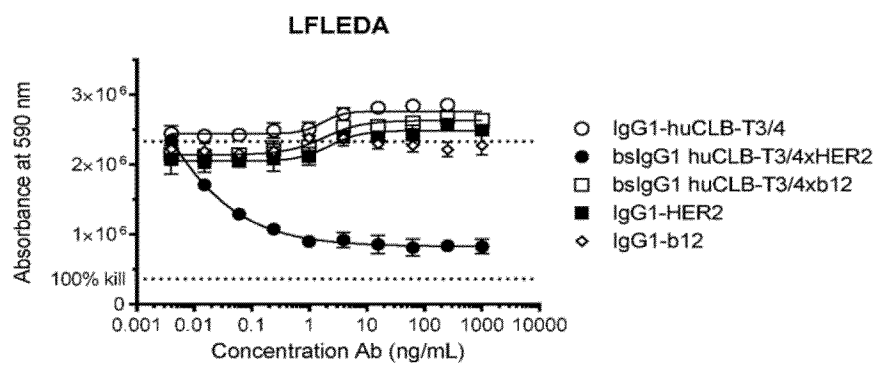
Figure 14F:
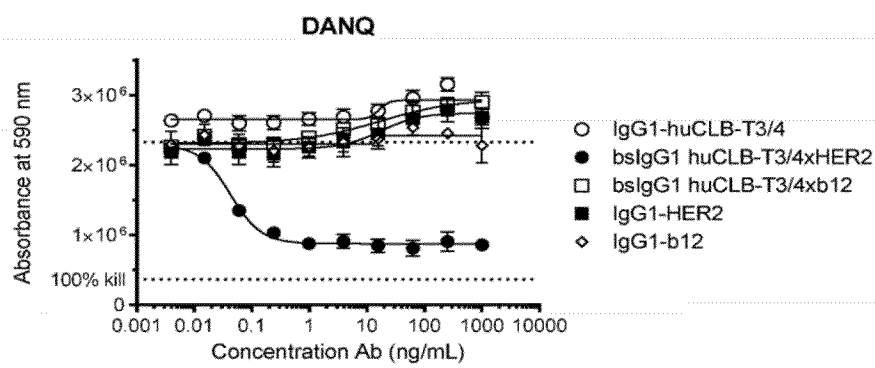
Figure 14G:
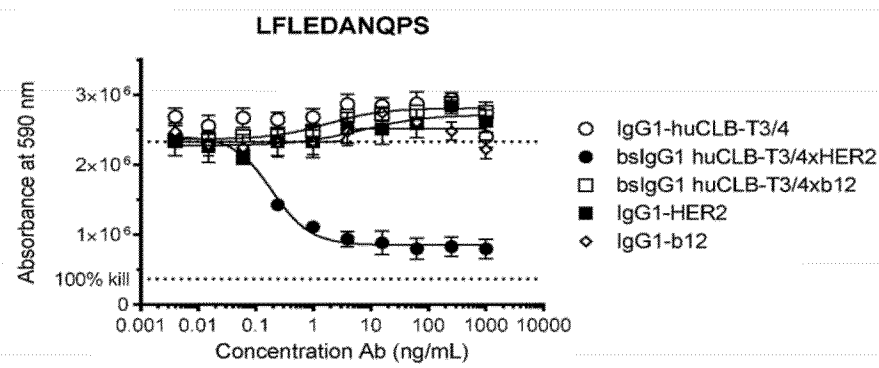
Figure 15A:
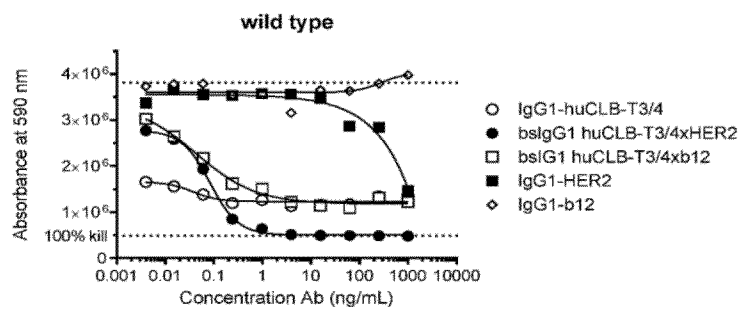
Figure 15B:
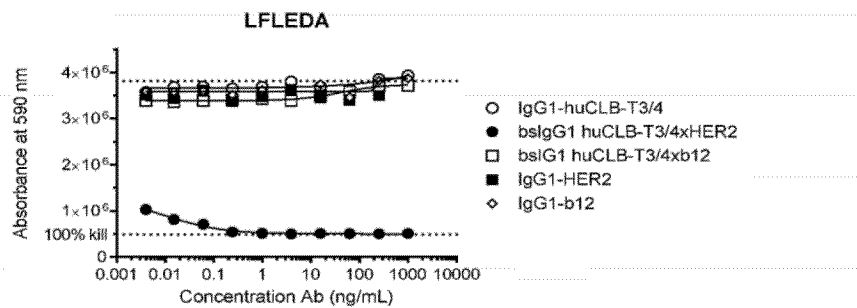
Figure 15C:
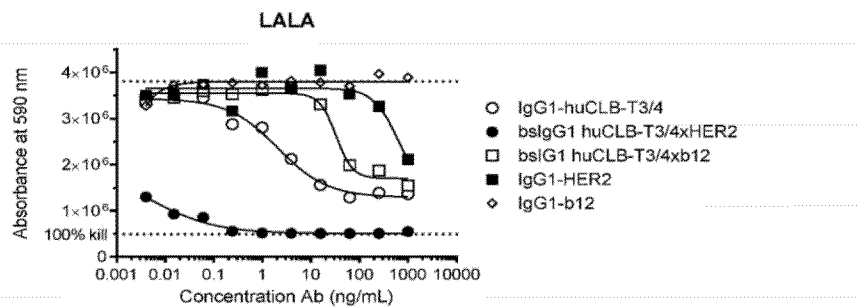
Figure 16A:
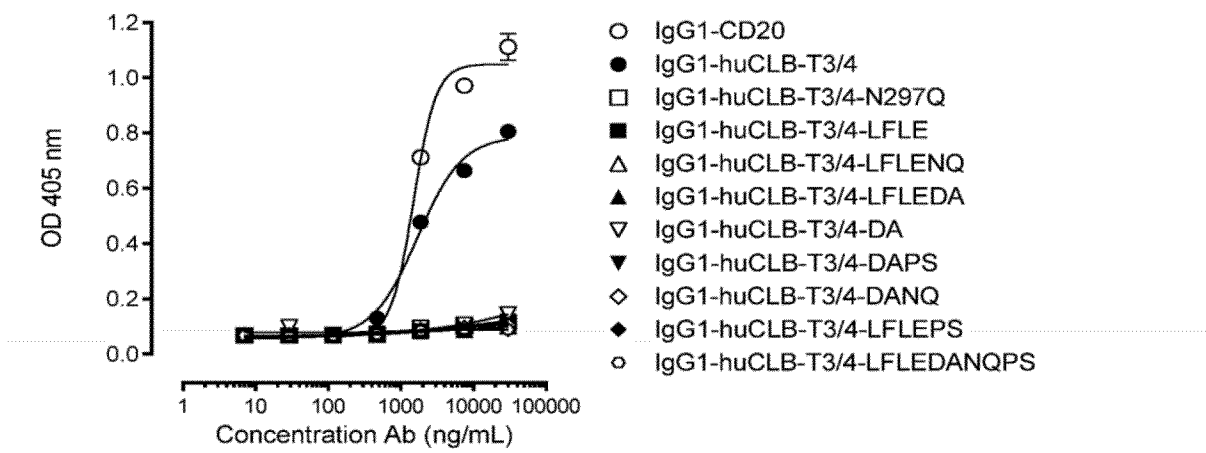
Figure 16B:
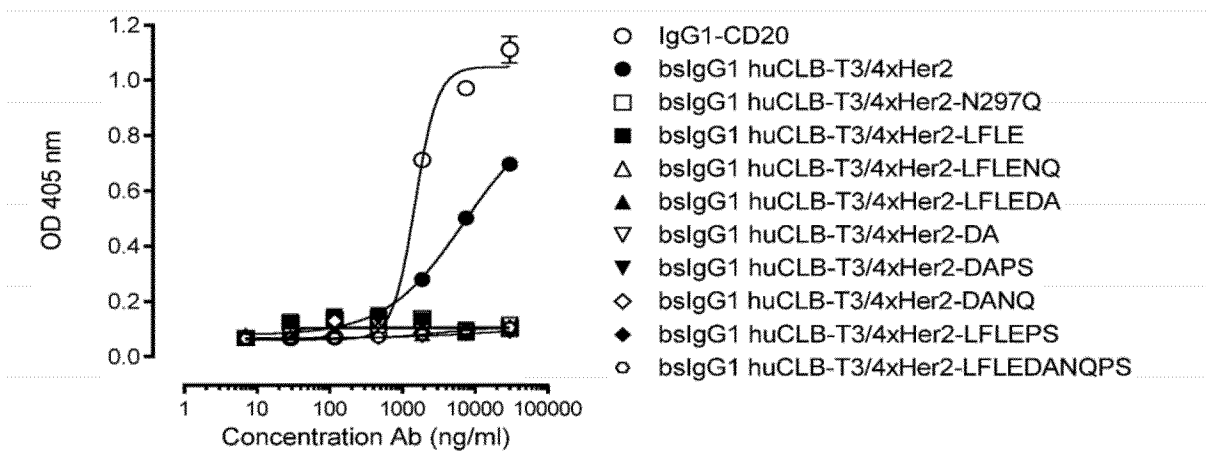
Figure 16C:
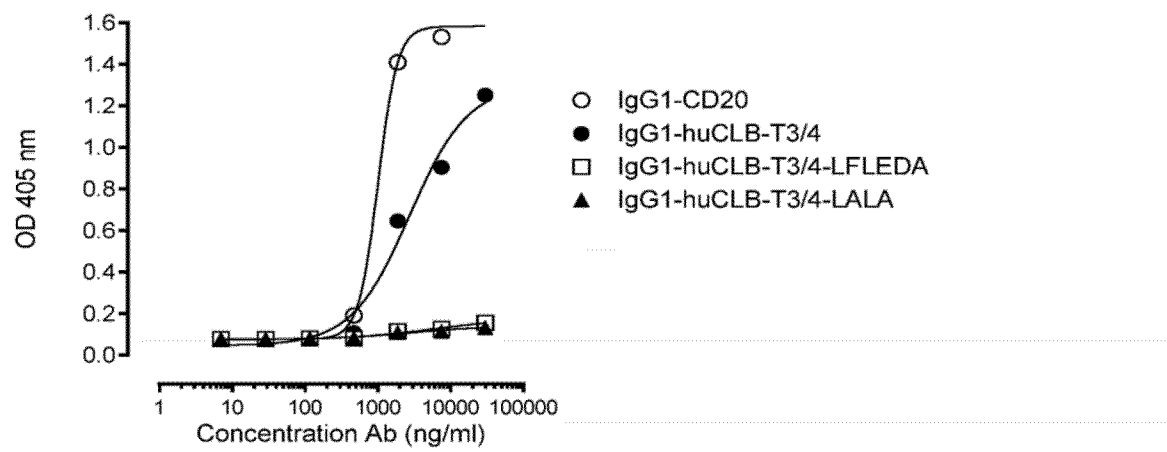
Figure 16D:
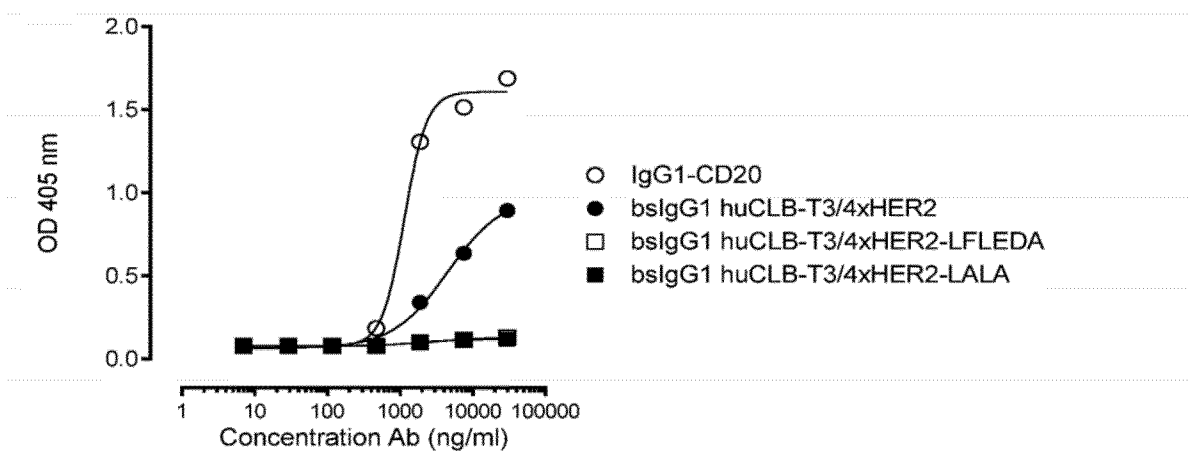
Figure 17A:
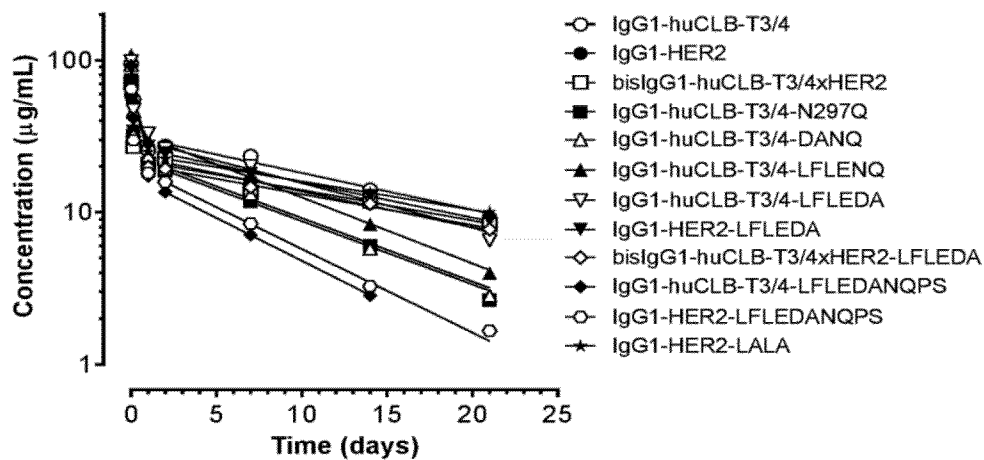
Figure 17B:
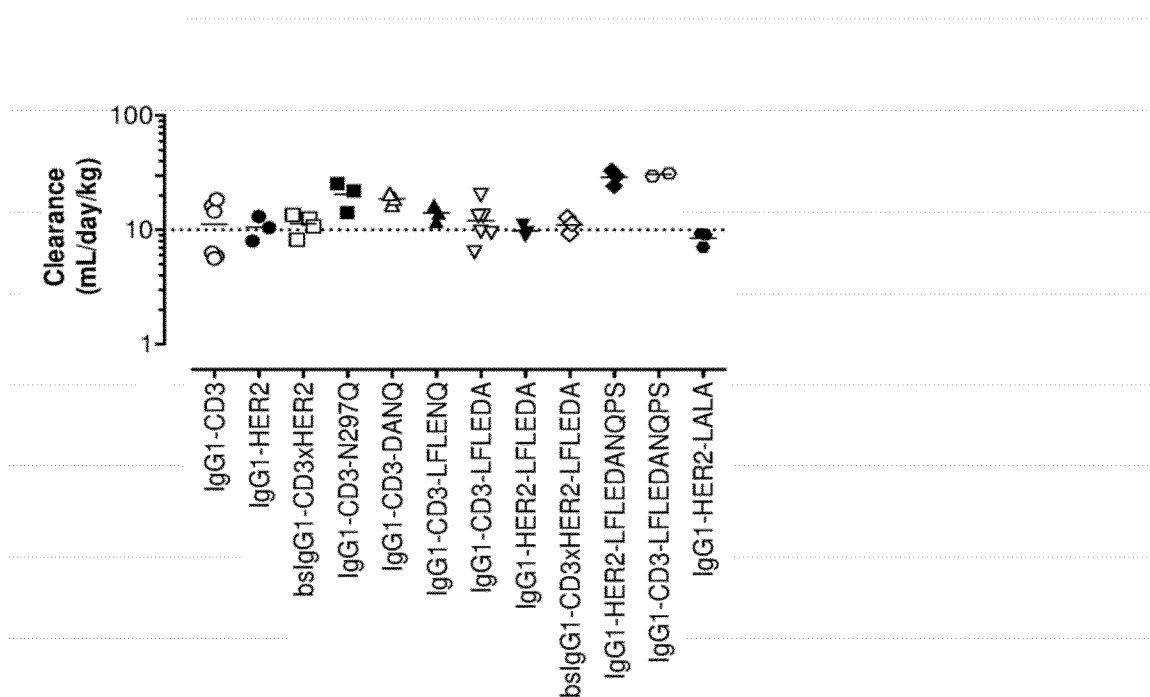

FIG. 11 shows that humanized CD3 antibody variants IgG1-huCD3-H1L1, IgG1-huCD3-H1L2, IgG1-huCD3-H1L3, IgG1-huCD3-H3L3, and IgG1-huCD3-H4L1 induced CD69 expression on T-cells from rhesus origin to similar levels as IgG1-CD3 (as described in Example 1). The negative control antibody IgG1-b12 did not induce expression of CD69 in rhesus T-cells. Thus, the huCD3 variants according to the present invention may be used in experiments involving rhesus monkey CD3. The huCD3 variants are cross-reactive with rhesus monkey CD3.

Example 7—T-Cell Activation by Non-Activating Variants of huCLB-T3/4

CD69 expression on T-cells was evaluated by FACS analysis to determine early activation of T-cells after incubation with IgG1-huCLB-T3/4 variants with mutations in the Fc region (see Example 1).

PBMCs were isolated from whole blood or buffy coat by density gradient separation using Leucosep tubes (#227290; Greiner Bio-one, Alphen a/d Rijn, The Netherlands), washed with PBS and resuspended in culture medium.

A dose response series of IgG1-huCLB-T3/4 variants, a negative control (IgG1-huCLB-T3/4-Fab) and positive control (IgE-huCLB-T3/4) were prepared in culture medium (ranging from 1 to 1000 ng/mL in 3-fold dilutions) and added to the wells of a 96-well round bottom plate containing the PBMCs. After 16-24 hours incubation, cells were pelleted by centrifugation and supernatant (containing cytokines) collected and stored at −20° C. Cells were then washed with PBS/0.1% BSA/0.02% azide and stained for 30 minutes at 4° C. with a mouse-anti-human CD28-PE (854.222.010; Sanquin, Amsterdam, The Netherlands; T-cell marker) and mouse-anti-human CD69-APC antibody (340560; BD Biosciences, Franklin Lakes, N.J.). Unbound antibodies were removed by washing twice with PBS/0.1% BSA/0.02% azide. Cells were resuspended in 150 µL/well and CD69-expression on CD28 positive cells was measured on FACS Canto II (BD Biosciences).

Figure 12A:
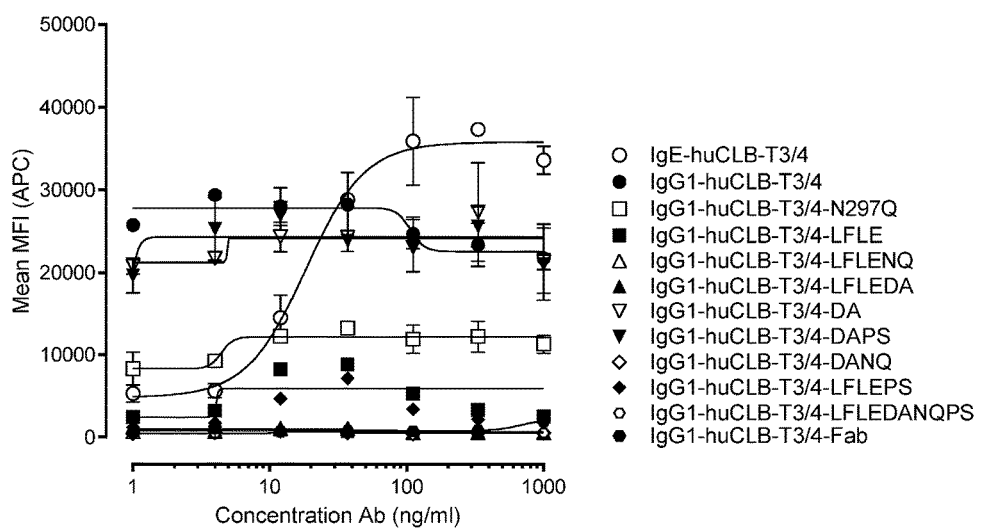
FIGS. 12A and 12B: T-cell activation by non-activating variants of huCLB-T3/4 antibody. IgG1-huCLB-T3/4 variants were titrated on PBMCs. Expression of CD69 on T-cells in PBMC culture was measured by FACS analysis, as described in Example 7. Representative examples of 3 experiments are shown.

FIG. 12A shows that CD69 expression was high on cells which were incubated with IgE-huCLB-T3/4, IgG1-huCLB-T3/4, IgG1-huCLB-T3/4-DA and IgG1-huCLB-T3/4-DAPS. Incubation with IgG1-huCLB-T3/4-N297Q induced somewhat lower expression levels of CD69 compared to wild-type IgG1-huCLB-T3/4, and incubation with IgG1-huCLB-T3/4-LFLE and IgG1-huCLB-T3/4-LFLEPS induced CD69 to a lesser extent. Incubation of PBMCs with IgG1-CD3 Fab, IgG1-huCLB-T3/4-LFLEDA, IgG1-huCLB-T3/4-LFLENQ, IgG1-huCLB-T3/4-DANQ and IgG1-huCLB-T3/4-LFLEDANQPS antibodies did not induce any expression of CD69 on T-cells.

Figure 12B:
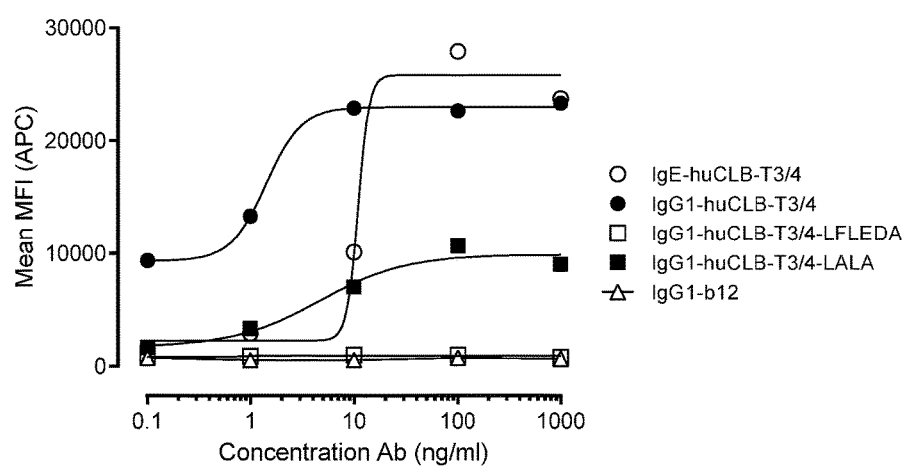

FIG. 12B shows that CD69 expression was high on cells which were incubated with IgE-huCLB-T3/4 and IgG1-huCLB-T3/4. Incubation with IgG1-huCLB-T3/4-LALA induced somewhat lower expression levels of CD69 compared to wild-type IgG1-huCLB-T3/4, and incubation with IgG1-huCLB-T3/4-LFLEDA and IgG1-b12 (negative control) did not induce any expression of CD69 on T-cells.

Example 8—T-Cell Proliferation by Non-Activating Variants of huCLB-T3/4

The effect of huCLB-T3/4 variants (described in Example 1) on the proliferation of T-cells was evaluated by the Cell proliferation ELISA kit from Roche Applied Science (Cell Proliferation ELISA, BrdU kit, #11647229001; Roche Applied Science, Mannheim, Germany), which was performed according to the manufacturer's instructions.

PBMCs, isolated from whole blood or buffy coat, were incubated in 96-well culture plates with dilution series (ranging from 0.1 to 1000 ng/mL) of IgG1-CD3 variants. IgE-CD3 and IgG1-CD3 were included as positive controls and IgG1-b12 (with K409R mutation for generation of bispecific antibodies) as a negative control. After 3 days of incubation with the antibodies, BrdU (Roche Applied Science, Mannheim, Germany) was added to the medium and plates were incubated for 5 hours. Cells were then pelleted by centrifugation and supernatant collected and stored at −20° C. Plates were dried and stored at 4° C. until ELISA was performed.

BrdU incorporation in the DNA was determined by ELISA according to the manufacturer's instructions (Cell Proliferation ELISA, BrdU kit, #11647229001; Roche Applied Science). Cells were fixed to the plates, where after the plates were incubated for 90 minutes at room temperature (RT) with an anti-BrdU antibody conjugated with peroxidase. Plates were washed with PBST and binding was detected using ABTS buffer (instead of the TMB solution provided with the kit). Color development was stopped after 30 min by adding 2% oxalic acid to the wells. OD405 nm was then measured on an EL808 ELISA-reader.

Figure 13A:
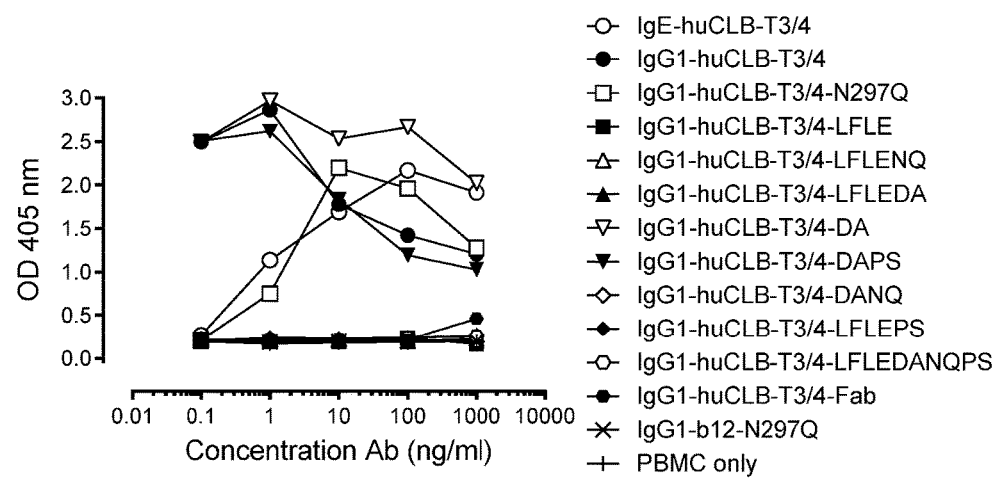
FIGS. 13A and 13B: T-cell proliferation by non-activating variants of huCLB-T3/4 antibody. PBMCs were incubated with antibodies for three days, after which proliferation was measured by a cell proliferation ELISA, as described in Example 8. Representative results from two independent experiments are shown.

FIG. 13A shows that incubation of PBMCs with IgG1-huCLB-T3/4, IgG1-huCLB-T3/4-DA and IgG1-huCLB-T3/4-DAPS induced strong proliferation of T-cells, even at very low concentrations of antibody. Incubation with IgG1-huCLB-T3/4-N297Q induced dose-dependent proliferation, which was comparable to the IgE-huCLB-T3/4 positive control. Incubation of PBMCs with IgG1-huCLB-T3/4-Fab, IgG1-b12-N297Q, IgG1-huCLB-T3/4-LFLE, IgG1-huCLB-T3/4-LFLEDA, IgG1-huCLB-T3/4-LFLENQ, IgG1-huCLB-T3/4-LFLEPS, IgG1-huCLB-T3/4-DANQ and IgG1-huCLB-T3/4-LFLEDANQPS antibodies did not induce proliferation of T-cells.

Figure 13B:
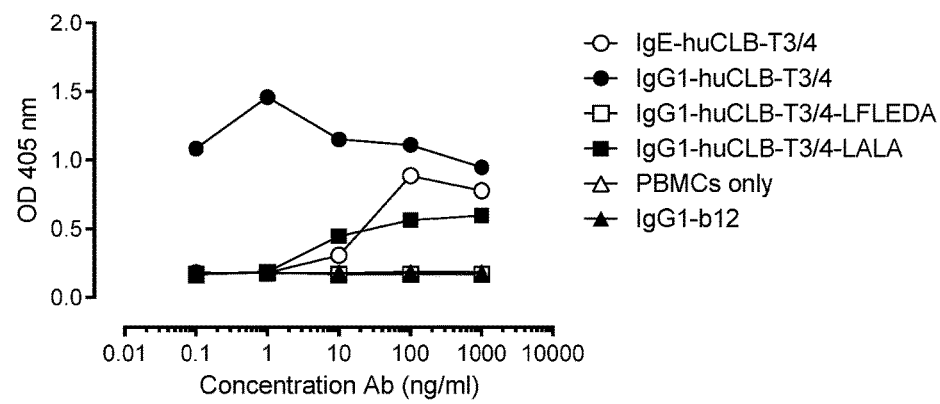
Figure 14A:
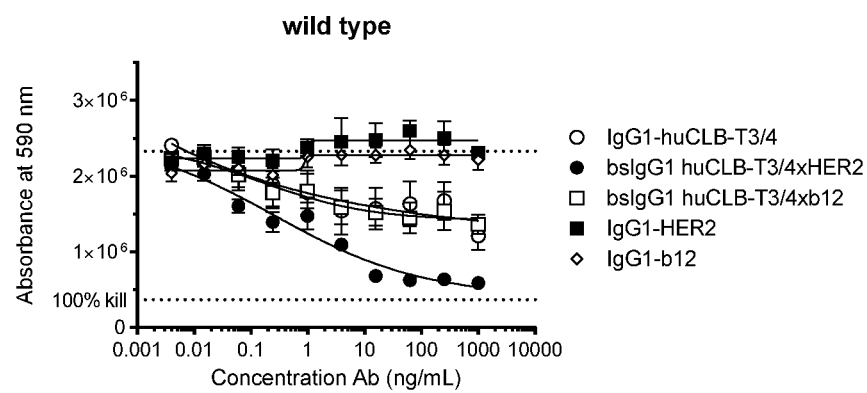
FIGS. 14A-14G: In vitro T-cell-mediated cytotoxicity induced by non-activating antibody variants of a CD3 antibody. Induction of T-cell-mediated cytotoxicity by antibody variants (N297Q, LFLE, LFLENQ, LFLEDA, DANQ, LFLEDANQPS [FIGS. 14A-14G]) was determined as explained in Example 9. The averages from two experiments performed in duplo are shown.
Figure 14B:
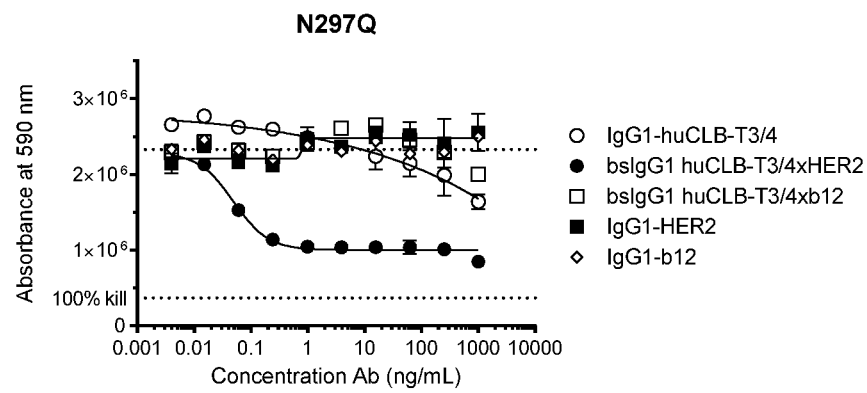
Figure 14C:
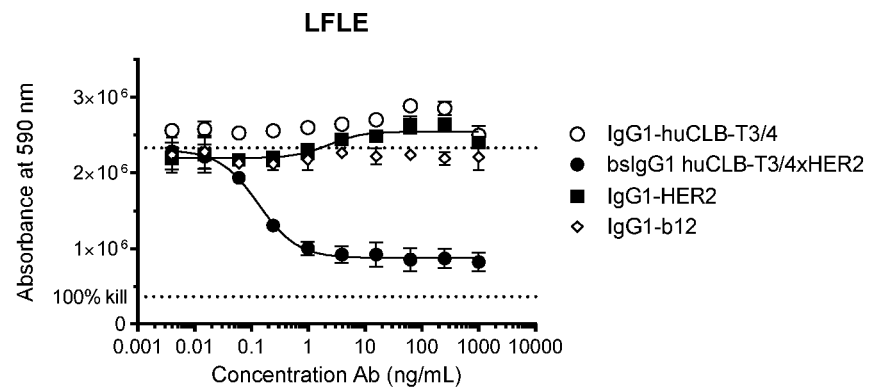
Figure 14D:
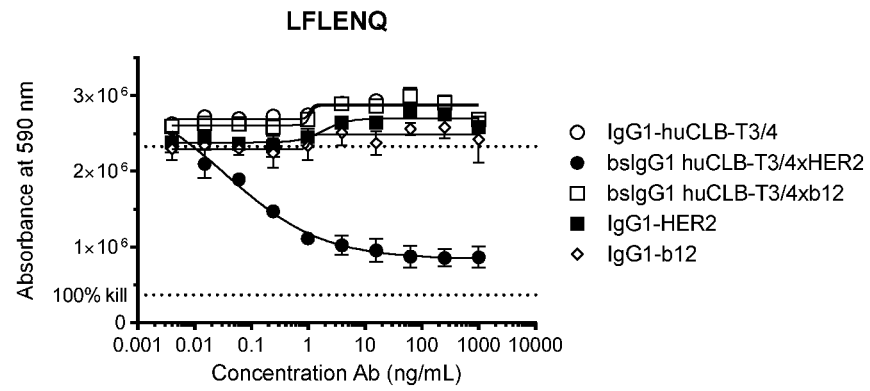
Figure 14E:
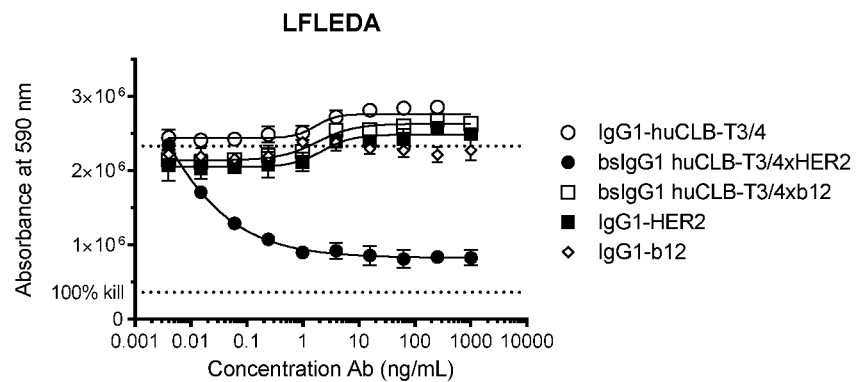
Figure 14F:
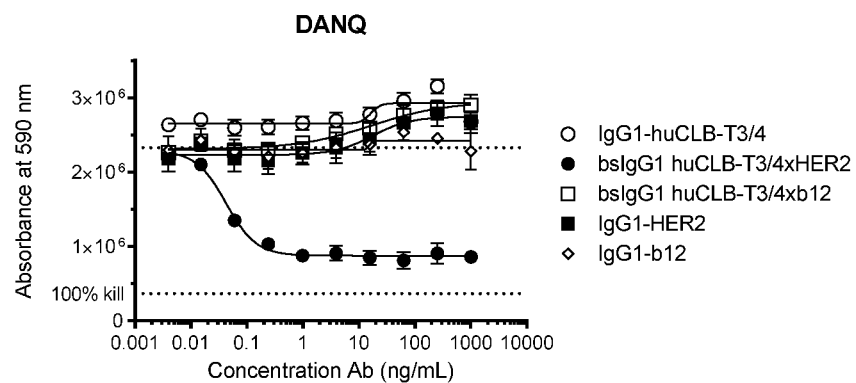
Figure 14G:
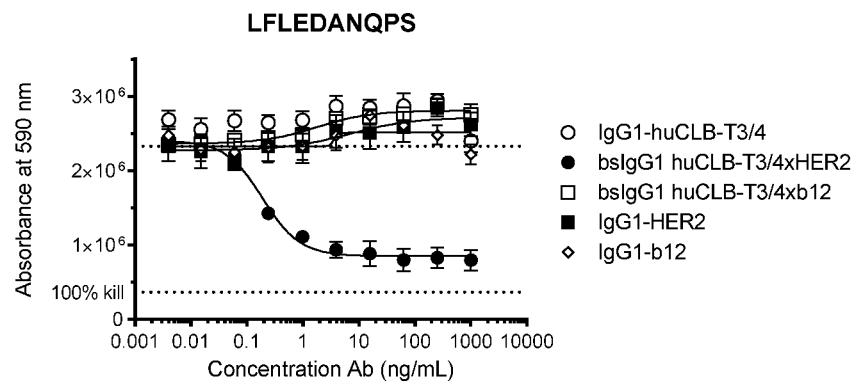

FIG. 13B shows that incubation of PBMCs with IgG1-huCLB-T3/4 induced strong proliferation of T-cells, even at very low concentrations of antibody. Incubation with IgE-huCLB-T3/4 (positive control) and IgG1-huCLB-T3/4-LALA induced dose-dependent proliferation. Incubation of PBMCs with IgG1-huCLB-T3/4-LFLEDA did not induce proliferation of T-cells.

Based on the results from Examples 7 and 8, a subset of mutants that were considered least activating, was subjected to further analysis.

Example 9—In Vitro T-Cell-Mediated Cytotoxicity Induced by Non-Activating Antibody Variants huCLB-T3/4

AU565 (human breast carcinoma) cells were cultured in RPMI 1640 supplemented with 10% (vol/vol) heat inactivated CCS, 1.5 g/L sodium bicarbonate (Lonza), 1 mM sodium pyruvate, 4.5 g/L glucose (Sigma), 50 IU/mL penicillin, and 50 µg/mL streptomycin. The cell line was maintained at 37° C. in a 5% (vol/vol) $CO_2$ humidified incubator. AU565 cells were cultured to near confluency. Cells were trypsinized, re-suspended in culture medium and passed through a cell strainer to obtain a single cell suspension. $5 \times 10^4$ cells were seeded in each well of a 96-well culture plate, and cells were incubated at least 3 hrs. at 37° C., 5% CO2 to allow adherence to the plate.

Peripheral blood mononuclear cells (PBMC) were isolated from blood from healthy volunteers using Leucosep 30 mL tubes, according to the manufacturer's protocol (Greiner Bio-one). Isolated PBMCs were washed with PBS, re-suspended in culture medium and added in a 1:1 ratio to the AU565 tumor cells in the 96-well plates. The percentage of T-cells present in PBMCs was measured by FACS-analysis, using a mouse anti-human CD3-PerCP (BD, #345766) antibody (for staining T-cells). The T-cell content in the population of used PBMCs was typically 50 to 60%.

Dilution series (final concentrations ranging from 0.004 to 1000 ng/mL) of IgG1-b12, IgG1-huCLB-T3/4, IgG1-HER2, and bispecific huCLB-T3/4×b12 and huCLB-T3/4×HER2 antibodies expressed as different Fc-variants, wild type, N297Q, LFLE, LALA, LFLENQ, LFLEDA, DANQ, and LFLEDENQPS, were prepared in culture medium and added to the plates. Plates were incubated for 3 days at 37° C., 5% $CO_2$. Incubation of cells with 1 µM staurosporin (#S6942-200, Sigma) was used as reference for 100% tumor cell kill. After incubation, supernatants were removed and stored at −20° C. Plates were washed twice with PBS, and 150 µL culture medium containing 10% Alamar blue was added to each well. Plates were incubated for 4 hours at 37° C., 5% $CO_2$. Absorbance at 590 nm was measured (Envision, Perkin Elmer, Waltham, Mass.).

Figure 15A:
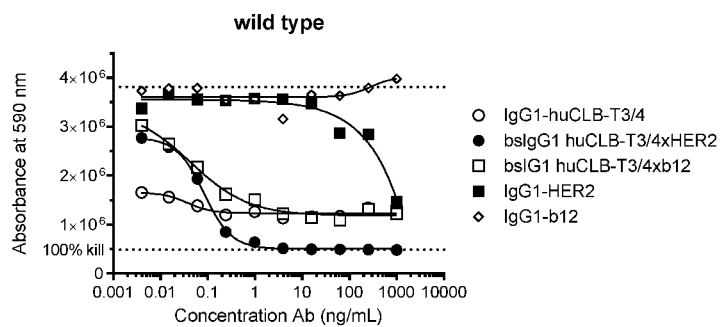
FIGS. 15A-15C: In vitro T-cell mediated cytotoxicity induced by non-activating huCLB-T3/4 variants. Induction of T-cell mediated cytotoxicity by antibody variants (LFLEDA LAL [FIGS. 15A-15C] was determined as described in Example 9. The averages from one experiment performed in duplet are shown.
Figure 15B:
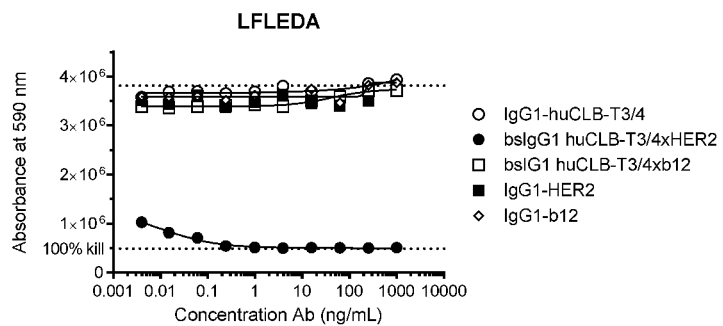
Figure 15C:
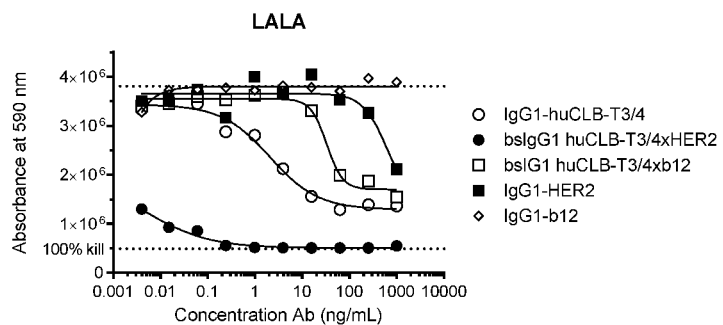

Two experiments were performed using PBMCs from different donors. In the first experiment Fc-variants N297Q, LFLE, LFLENQ, LFLEDA, DANQ, and LFLEDANQPS were tested (FIG. 14A-G). In the second experiment Fc-variants LFLEDA and LALA were tested (FIG. 15A-C). Antibodies with wild-type Fc-domains were included in both experiments as reference. Incubation with wild-type monospecific IgG1-huCLB-T3/4 or bispecific huCLB-T3/4×b12 antibodies induced unspecific killing of target cells (FIGS. 14A-G and 15A-C). The monospecific IgG1-huCLB-T3/4 and bsIgG1-huCLB-T3/4×b12 variants N297Q (FIG. 14A-G) and LALA (FIG. 15A-C) still induced some unspecific target cell killing, albeit to a lesser extent than the wild-type antibody tested in the same experiment. Unspecific target cell killing was not induced by any of the other tested IgG1-huCLB-T3/4 or bsIgG1-huCLB-T3/4×b12 antibodies with non-activating mutations (FIGS. 14A-G and 15A-C).

All bispecific huCLB-T3/4×HER2 antibodies induced dose-dependent killing of AU565 cells with at least comparable efficacy compared to the wild type bispecific huCLB-T3/4×HER2 antibody without non-activating mutations (FIGS. 14A-G and 15A-C). Maximum killing occurred at very low concentrations.

No cytotoxicity was induced by wild-type or non-activating variants of the monospecific b12 or HER2 antibodies (FIGS. 14A-G and 15A-C), which was as expected.

Example 10—Evaluation of Binding of C1q to Non-Activating Antibody Variants of huCLB-T3/4

Interaction of C1q with antibodies bound to a target cell is the first step in the classical pathway of complement activation. Since wild-type IgG1 harbors the interaction site for C1q, the interaction of C1q to these non-activating IgG1 variants by an ELISA was evaluated.

Dilution series (range 7-30,000 ng/mL in 4-fold dilutions) of IgG1-huCLB-T3/4, bsIgG1-huCLB-T3/4×HER2 and IgG1-CD20 (positive control) and non-activating antibody variants as described above in Example 1 thereof were coated on 96-well Microlon ELISA plates (Greiner, Germany) overnight at 4° C. Plates were washed and blocked with PBS supplemented with 0.025% Tween 20 and 0.1% gelatine. With washings in between incubations, plates were sequentially incubated with 3% pooled human serum (Sanquin, product #M0008) for 1 h at 37° C., with 100 µL/well rabbit anti-human C1q (DAKO, product #A0136, 1/4,000) for 1 h at RT, and with 100 µL/well swine anti-rabbit IgG-HRP (DAKO, P0399, 1:10,000) as detecting antibody for 1 h at RT. Detection was performed by addition of 1 mg/mL 2,2'-azino-bis (3-ethylbenzothiazoline-6-sulfonic acid) (ABTS; Roche, Mannheim, Germany) for about 30 min. The reaction was stopped by the addition of 100 µL 2% oxalic acid. Absorbance was measured at 405 nm in a microplate reader (Biotek, Winooski, Vt.). Log transformed data were analyzed by fitting sigmoidal dose-response curves with variable slope using GraphPad Prism software.

Figure 16A:
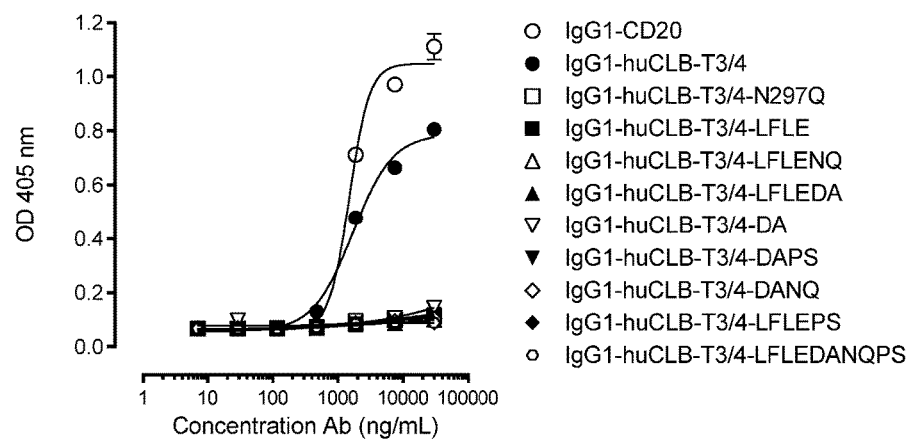
FIGS. 16A-16D: Evaluation of binding of C1q to non-activating huCLB-T3/4 antibody variants. Binding of C1q to monospecific IgG1 huCLB-T3/4 (FIGS. 16A-16C) and bsIgG1-huCLB-T3/4×HER2 (FIGS. 16B-16D) and non-activating antibody variants thereof was evaluated by ELISA as described in Example 10. The results in the graphs are representative for n=2 experiments.

FIG. 16A shows that the antibodies with wild-type IgG1 Fc regions, IgG1-CD20 and IgG1-huCLB-T3/4 showed C1q binding. No binding of C1q was detected on all evaluated antibody variants with non-activating mutations (N297Q, LFLE, LFLENQ, LFLEDA, DA, DAPS, DANQ, LFLEPS, LFLEDANQPS, LALA).

Figure 16B:
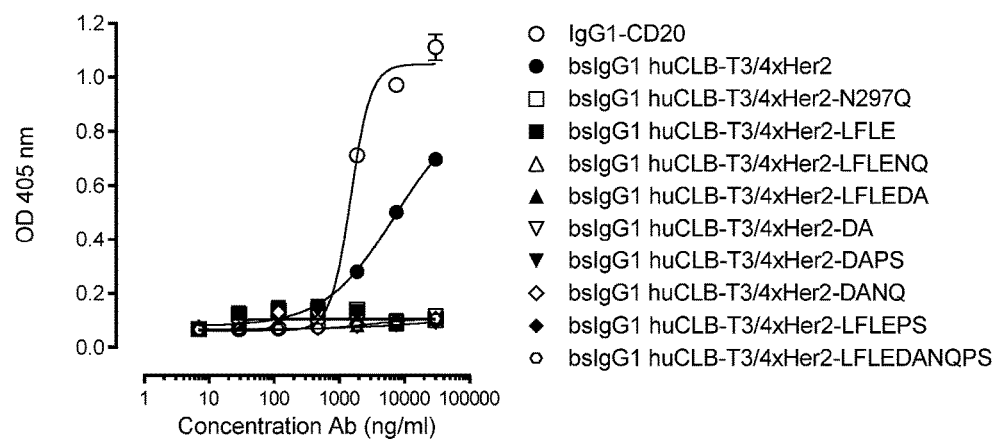

FIG. 16B shows that the antibody with wild-type IgG1 Fc reigon bsIgG1-huCLB-T3/4×HER2 showed C1q binding. No binding of C1q was detected on all evaluated antibody variants with non-activating mutations (N297Q, LFLE, LFLENQ, LFLEDA, DA, DAPS, DANQ, LFLEPS, LFLEDANQPS, LALA).

Figure 16C:
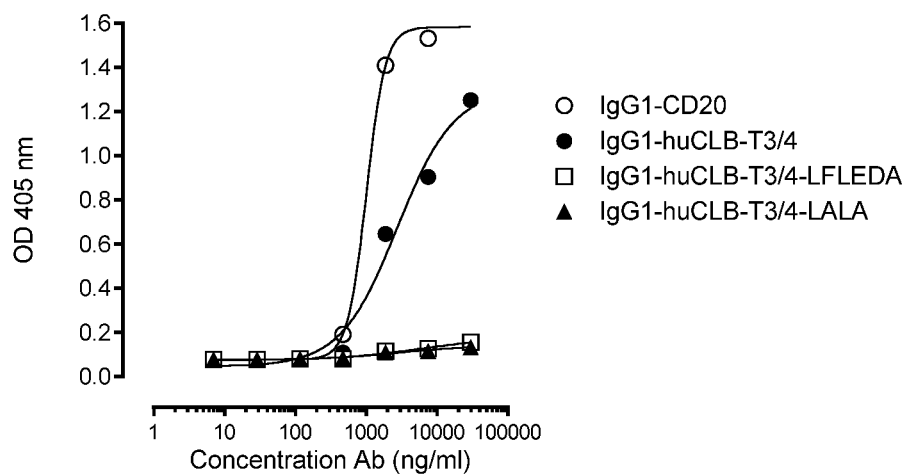
Figure 16D:
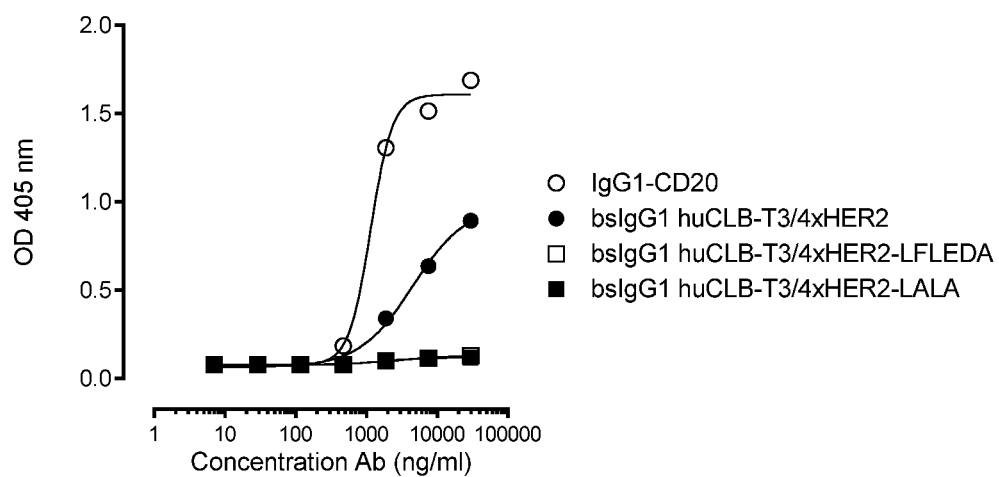

FIG. 16C and FIG. 16D show that the antibodies with wild-type IgG1 Fc regions, IgG1-CD20, IgG1-huCLB-T3/4, and bsIgG1-huCLB-T3/4×HER2 showed C1q binding. No binding of C1q was detected on the antibody variants with non-activating mutations (LFLEDA and LALA).

Example 11—Pharmacokinetic (PK) Analysis of Non-Activating Antibody Variants

The mice in this study were housed in a barrier unit of the Central Laboratory Animal Facility (Utrecht, The Netherlands) and kept in filter-top cages with water and food provided ad libitum. All experiments were approved by the Utrecht University animal ethics committee. 7-10 Weeks old C.B-17 SCID mice (C.B-17/Icr-Prkdc<Scid>/IcrIcoCrl, Charles-River) were injected intravenously with 100 µg wild-type antibody (IgG1-huCLB-T3/4, IgG1-HER2, or bsIgG-huCLB-T3/4×HER2) or non-activating variants thereof (LALA, LFLEDA, LFLENQ, DANQ or LFLEDANQPS) using 3 mice per group. 50 µL blood samples were collected from the saphenous vein at 10 minutes, 4 hours, 1 day, 2 days, 7 days, 14 days and 21 days after antibody administration. Blood was collected into heparin containing vials and centrifuged for 5 minutes at 10,000×g. Plasma was stored at −20° C. until determination of antibody concentrations.

Human IgG concentrations were determined using a total hIgG sandwich ELISA. For this assay, mouse mAb anti-human IgG-kappa clone MH16 (#M1268, CLB Sanquin, The Netherlands), coated to 96-well Microlon ELISA plates (Greiner, Germany) at a concentration of 2 µg/mL was used as capturing antibody. After blocking plates with PBS supplemented with 0.2% bovine serum albumin, samples were added, serially diluted with ELISA buffer (PBS supplemented with 0.05% Tween 20 and 0.2% bovine serum albumin), and incubated on a plate shaker for 1 h at room temperature (RT). Plates were subsequently incubated with goat anti-human IgG immunoglobulin (#109-035-098, Jackson, West Grace, Pa.) and developed with 2,2'-azino-bis (3-ethylbenzthiazoline-6-sulfonic acid) (ABTS; Roche, Mannheim, Germany). The reaction was stopped after 30 min by adding 2% oxalic acid to the wells. Absorbance was measured in a microplate reader (Biotek, Winooski, Vt.) at 405 nm.

Plasma clearance rates (mL/day/kg) were calculated based on the area under the curve (AUC), according to the following equation:

$$\text{Plasma clearance} = \frac{\text{Dose}(\mu g/kg)}{AUC(\mu g/mL/day)}$$

Data analysis was performed using Graphpad prism software.

Figure 17A:
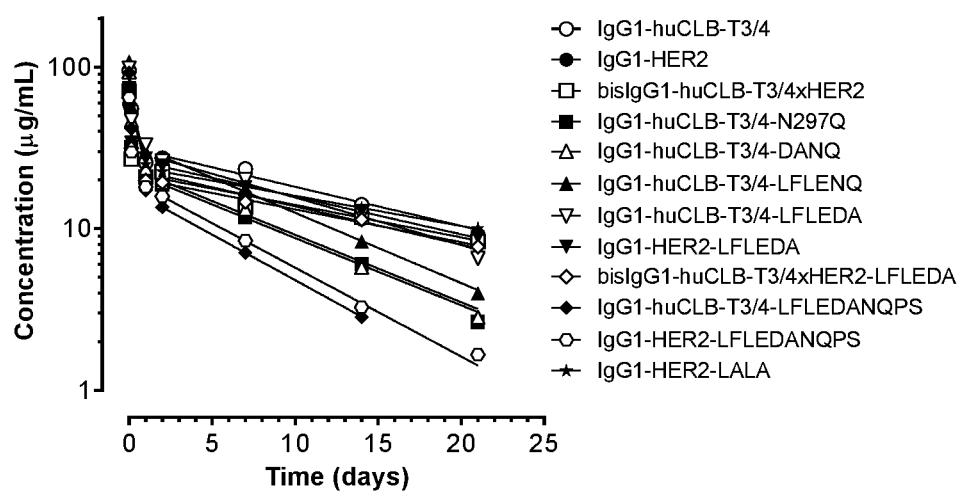
FIGS. 17A and 17B: Pharmacokinetic (PK) analysis of non-activating huCLB-T3/4 antibody variants were compared to that of wild-type IgG1-huCLB-T3/4 antibody as described in Example 11. Plasma concentration of human IgG1 was plotted against time (FIG. 17A). Plasma clearance rate calculated as described in Example 11 (FIG. 17B). The horizontal dotted line represents the average clearance rate of human IgG1 antibodies in SCID mice (10 mL/day/kg).

FIG. 17A shows that the plasma human IgG concentrations were lower for antibody variants N297Q, DANQ, LFLENQ, and LFLEDANQPS when compared to wild-type antibodies, suggesting a faster clearance. The human IgG concentrations in plasma for antibody variants LFLEDA and LALA were similar to those of wild-type antibodies.

Figure 17B:
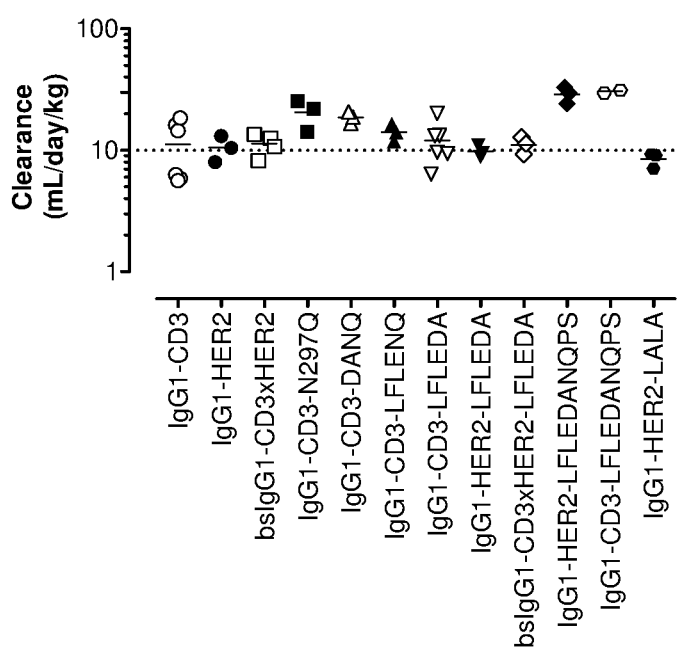
Figure 23A:
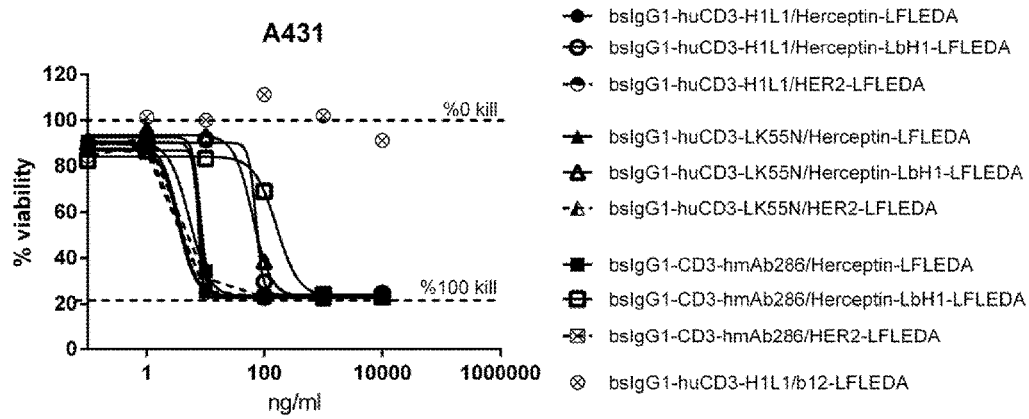
FIGS. 23A and 23B: Cytotoxicity of huCD3×HER2 antibody affinity variants on A431 cells (low HER2 expressing cells) (FIG. 23A) and AU565 cells (high HER2 expressing cells) (FIG. 23B) treated with CD3 and HER2 affinity variants.
Figure 23B:
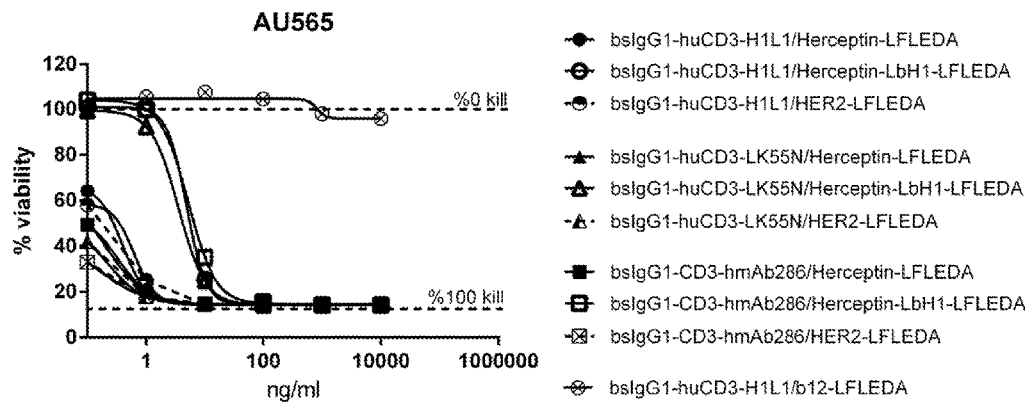
Figure 24A:
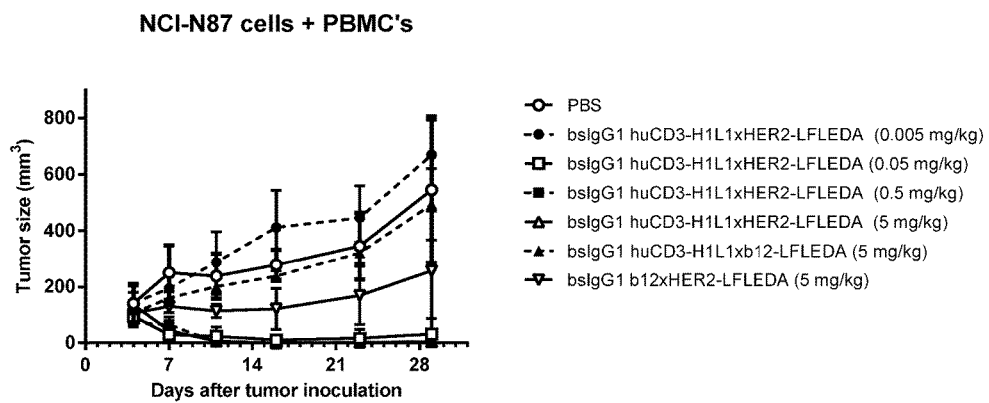
FIGS. 24A and 24B: Reduction of tumor size in NOD-SCID mice by huCD3-H1L1×HER2-LFLEDA 7, 14, 21 and 28 days after tumor inoculation (FIG. 24A), and at day 29 (FIG. 24B).
Figure 24B:
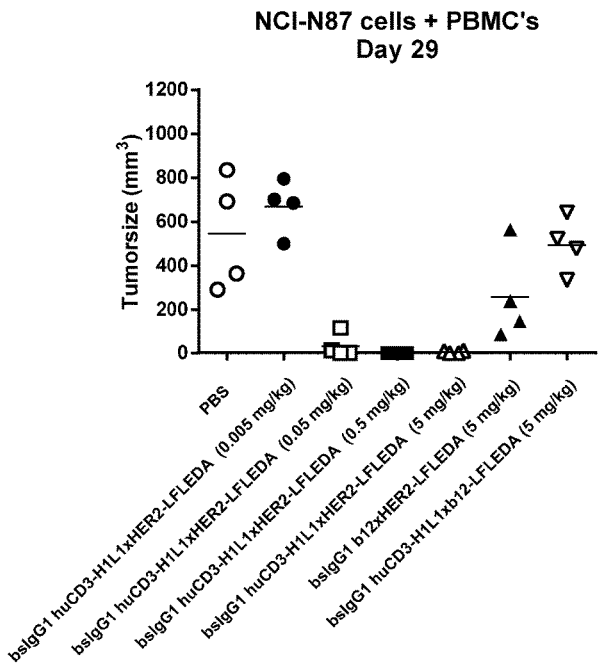

FIG. 17B shows that the plasma clearance rates of antibody variants N297Q, DANQ and LFLENQ were 2 to 3-fold higher than that of wild-type antibody. The clearance rate of antibody variant LFLEDANQPS was 3-5 times higher than that of wild-type antibody. Plasma clearance rates of antibody variants LFLEDA and LALA were similar to that of wild-type antibody.

Example 12—In Vitro Immunogenicity Assessment of the IgG1-LFLEDA Backbone

In order to determine the potential for clinical immunogenicity of the IgG1-LFLEDA-K409R backbone, Antitope's EpiScreen™ platform was applied to IgG1-HER2-LFLEDA. In short, PBMCs were isolated from a cohort of 50 HLA-typed healthy donors representing the European and North American population. After CD8+ T-cell depletion the PBMC preparations were individually frozen and stored. Thawed PBMCs were subsequently cultured and incubated with IgG1-HER2-LFLEDA-K409R or one of the control samples (IgG1-HER2 or IgG1-HER2-LFLE-K409R) for 5 to 8 days. The ability of the samples to induce CD4+ T-cells responses was assessed by measuring cell proliferation ([$3^H$]-Thymidine incorporation) and IL-2 production (ELISpot assay). Donors showing responses with a stimulation index (SI; signal/baseline signal)≥1.9 in both assays were considered positive.

Figure 18:
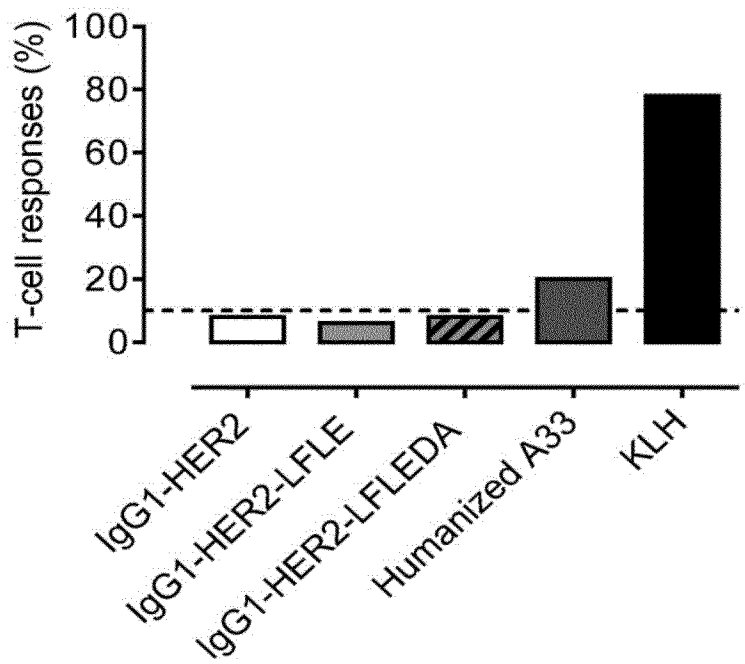
FIG. 18: The frequency of positive T-cell responses among healthy HLA-typed donors. SI indexes of ≥1.9 in both proliferation and IL-2 secretion assays were considered positive responses. Humanized A33 was used as clinical benchmark control antibody that shows high level of immunogenicity in the clinic and routinely induces 20-30% T-cell responses in the EpiScreen Assay. KLH responses were included to check PBMC quality (after thawing).

EpiScreen™ analysis showed that for IgG1-HER2-LFLEDA, 4 donors (8%) showed positive CD4+ T-cell responses, which was comparable to 4 (8%) and 3 (6%) positive responses for IgG1-HER2 and IgG1-HER2-LFLE, respectively (FIG. 18). Thus, IgG1-HER2-LFLEDA-K409R (as well as IgG1-HER2 and IgG1-HER2-LFLE-K409R) showed low potential for immunogenicity with frequencies of responses below 10%. The positive control humanized A33 (e.g. [84]) was used as clinical benchmark control antibody that shows high levels of immunogenicity in the clinic and routinely induces 20-30% T-cell responses in the EpiScreen Assay.

Example 13—Generation of Mutants to Optimize the Production of the Humanized CD3 Antibodies Generation of huCD3-L1 Mutant Plasmids Several IgG1-huCD3-L1 LC mutants were generated in order to improve the expression levels of IgG1-huCD3-H1L1 in transient transfection assays, cf. Table 2. The selection of residues was based on comparisons with germline sequences or screening for the presence of rare residues in huCD3-L1 in combination with crystal structures from homologous antibodies. The selected sequences were synthesized at GeneArt (Life Technologies, Germany). p33L encodes the constant domain of the human IgLC2/IgLC3 lambda light chain of SEQ ID NO:31. p33G1f encodes the IgG1m(f) heavy chain constant region of SEQ ID NO:15.

μg/mL) including the T41K mutation amongst other mutations. The other mutations in these constructs did not show expression enhancement when tested individually (IgG1-huCD3-H1L1-LF10L, IgG1-huCD3-H1L1-LK55N, IgG1-huCD3-H1L1-LL97H) compared to IgG1-huCD3-H1L1.

A second set of expression enhancing mutations was observed for the combination of R23A and A35P. While IgG1-huCD3-H1L1-LLTGPEAEY format lacking R23A and A35P did not show enhanced expression (83 μg/mL), IgG1-huCD3-H1L1-LLAPTGPEAEY containing the additional R23A and A35P mutations did show a 3-fold increase in expression (237 μg/mL). Individually, R23A or A35P did not show enhanced expression levels (56 and 81 μg/mL, respectively).

TABLE 2

| LC constructs | LC Mutants | Antibody name after co-expression with HC VH1 encoding plasmid |
|---|---|---|
| p33L-huCD3-VL1 | — | IgG1-huCD3-H1L1 |
| p33L-huCD3-VL1-F10L | F10L | IgG1-huCD3-H1L1-LF10L |
| p33L-huCD3-VL1-R23A | R23A | IgG1-huCD3-H1L1-LR23A |
| p33L-huCD3-VL1-A35P | A35P | IgG1-huCD3-H1L1-LA35P |
| p33L-huCD3-VL1-T41K | T41K | IgG1-huCD3-H1L1-LT41K |
| p33L-huCD3-VL1-K55N | K55N | IgG1-huCD3-H1L1-LK55N |
| p33L-huCD3-VL1-L97H | L97H | IgG1-huCD3-H1L1-LL97H |
| p33L-huCD3-VL1-LKNH | F10L, T41K, K55N, L97H | IgG1-huCDS-H1L1-LLKNH |
| p33L-huCD3-VL1-LTGPEAEY | F10L, R47T, D71G, A82P, D83E, S86A, I87E, F89Y | IgG1-huCD3-H1L1-LLTGPEAEY |
| p33L-huCD3-VL1-LAPTGPEAEY | F10L, R23A, A35P, R47T, D71G, A82P, D83E, S86A, I87E, F89Y | IgG1-huCD3-H1L1-LLAPTGPEAEY |

Transient Expression in Expi293F Cells

For a single antibody, the plasmids encoding heavy chain (HC) and light chain (LC) were transiently transfected in Freestyle Expi293F cells (Life technologies, USA) using ExpiFectamine 293 (Life technologies). In total 1.5 μg HC encoding plasmid and 1.5 μg LC encoding plasmid (Table 2) were diluted in 150 μL Opti-MEM (Gibco, USA). To prepare the transfection mix, 8 μL ExpiFectamine 293 was diluted in 150 μL Opti-MEM and incubated for 5 minutes at room temperature. Next, the DNA/Opti-MEM and ExpiFectamine 293/Opti-MEM solutions were mixed, incubated for 20 minutes at room temperature and added to 2.55 mL Expi293 Expression Medium containing $7.5 \times 10^6$ Expi293F cells and 50 U/mL Pen-Strep. The cells were incubated at 37° C., 8% CO2 and shaken at 200 rpm. To enhance expression, 21 hours after transfection, 15 μL enhancer mix 1 and 150 μL enhancer mix 2 were added. The cells were incubated for 4 days followed by the harvest of the supernatant. Supernatants were spun at 3,000×g and filter sterilized over a 0.2 μm filter. The IgG expression levels were measured on the Octet RED (ForteBio, US) using anti-human IgG sensors (ForteBio, USA).

IgG Concentration Analysis

Figure 20:
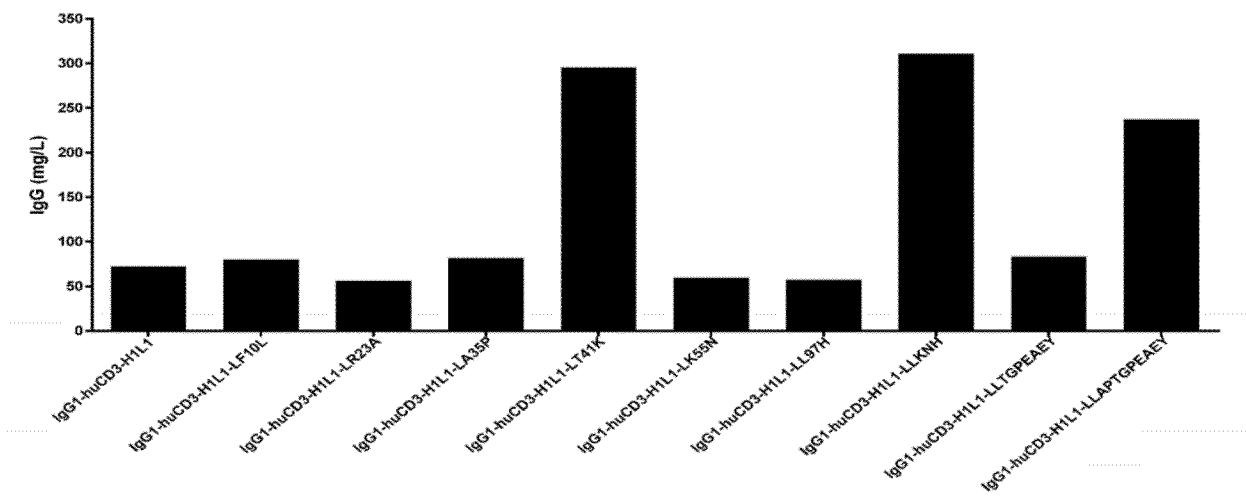
FIG. 20: Expression levels of IgG1-huCD3-H1L1 variants in Expi293F supernatants as measured by Octet RED using anti human IgG immobilized sensors.

For all mutants listed the IgG expression levels were measured individually or in combination. FIG. 20 shows the measured IgG expression level in supernatant for the panel of expressed antibodies listed in Table 2. The IgG1-huCD3-H1L1 antibody expressed to 72 μg/mL. A 4-fold increase in IgG expression was observed for the IgG1-huCD3-H1L1-LT41K mutant (295 μg/mL). Similar expression levels were observed for IgG1-huCD3-H1L1-LLKNH mutant (311

Example 14—Binding of huCD3-H1L1-LFLEDA Variants to Jurkat Cells

The apparent binding affinities of the huCD3-H1L1-LFLEDA variants to Jurkat cells were tested. IgG1-CD3-hmAb286 disclosed in US2012038219 was used as a reference antibody.

Jurkat cells (DSMZ, Brunswick, Germany) were thawed at 37° C. and washed once in 30 mL PBS and spun for 10 minutes at 300×g at 4° C. Cell pellet was resuspended in 25 mL of PBS/0.1% BSA/0.02% azide at a final concentration of $0.8 \times 10^6$ cells/mL. 100 μL of this cell suspension ($0.8 \times 10^5$ cells/well) was transferred into polystyrene 96-well round-bottom plates (Greiner Bio-one, Alphen a/d Rijn, The Netherlands) and incubated with serial dilutions of supernatant preparations (range 3 to 10,000 ng/mL in 3-fold dilutions) in PBS/0.1% BSA/0.02% azide at 4° C. for 30 minutes. After washing three times in PBS/0.1% BSA/0.02% azide, Jurkat cells were incubated in 50 μL with secondary antibody at 4° C. for 30 min. As a secondary antibody, R-Phycoerythrin (PE)-conjugated goat-anti-human IgG F(ab')2 (Jackson ImmunoResearch Laboratories, Inc., West Grove, Pa.) diluted 1/200 in PBS/0.1% BSA/0.02% azide, was used for all experiments. Next, Jurkat cells were washed twice in PBS/0.1% BSA/0.02% azide, re-suspended in 150 μL PBS/0.1% BSA/0.02% azide and analyzed on a FACS Cantoll (BD Biosciences). Binding curves were analyzed using nonlinear regression (sigmoidal dose-response with variable slope) using GraphPad Prism V 5.04 software (GraphPad Software, San Diego, Calif., USA).

Figure 21:
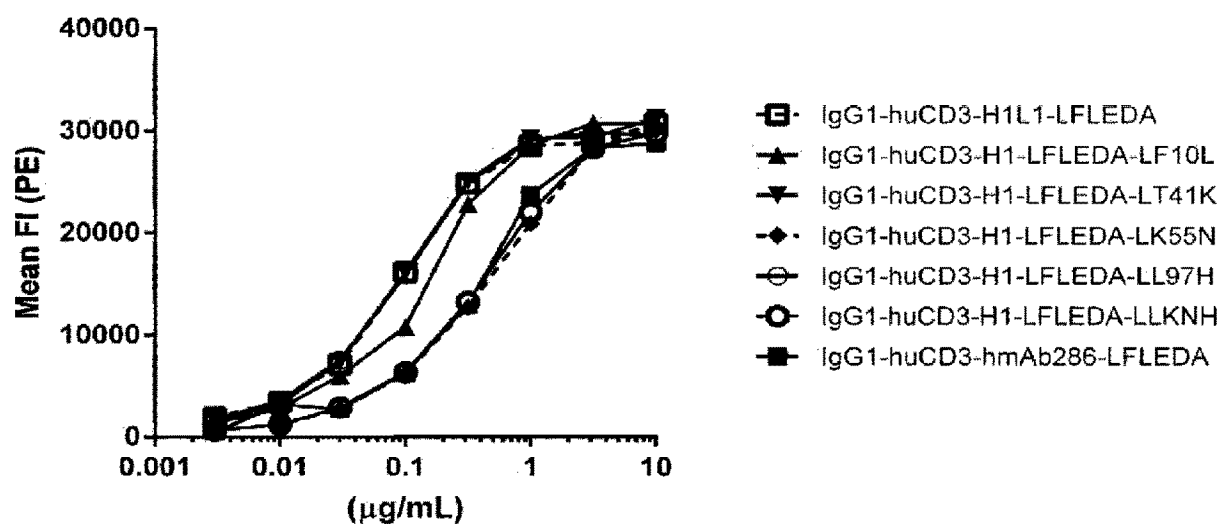
FIG. 21: Binding of IgG1-huCD3-H1L1-LFLEDA mutants to Jurkat cells.

FIG. 21 shows the binding curves, and Table 3 shows the EC$_{50}$ values of the IgG1-huCD3-H1L1-LFLEDA mutants. The T41K mutation had no effect on binding affinity whereas the K55N and LKNH mutants showed a 5-fold lower apparent affinity in comparison with wild type IgG1-huCD3-H1L1-LFLEDA. The affinity of the reference antibody IgG1-CD3-hmAb286-LFLEDA was lower in comparison to IgG1-huCD3-H1L1-LFLEDA, and was similar to the IgG1-huCD3-H1L1-LFLEDA variants containing the K55N mutation.

TABLE 3

| Antibodies | EC$_{50}$ (μg/mL) |
| --- | --- |
| IgG1-huCD3-H1L1-LFLEDA | 0.096 |
| IgG1-huCD3-H1-LFLEDA-LF10L | 0.169 |
| IgG1-huCD3-H1-LFLEDA-LT41K | 0.096 |
| IgG1-huCD3-H1-LFLEDA-LK55N | 0.531 |
| IgG1-huCD3-H1-LFLEDA-LL97H | 0.095 |
| IgG1-huCD3-H1-LFLEDA-LLKNH | 0.438 |
| IgG1-CD3-hmAb286-LFLEDA | 0.397 |

Example 15—Binding of Bispecific huCD3×HER2 Affinity Variants on T Cells

Binding of purified affinity variants of bispecific (bs) IgG1-huCD3×HER2 molecules with or without LFLEDA mutations in the Fc region to the human T-cells isolated from a buffy coat (donor no: N001814268806, purchased from Sanquin, Amsterdam, The Netherlands) was analyzed by FACS analysis. T cells were isolated via StemSep™ Human T cell Enrichment Kit (Stem Cell Technologies, Vancouver, Canada) according to provider's instructions. Herceptin-LbH1-mutations were identified from published data from Bostrom et al. (85, 86) and had lower affinity to HER2 in comparison to Herceptin (trastuzumab).

To assess binding, isolated T cells (1×10$^5$ cells/well) were incubated in polystyrene 96-well round-bottom plates (Greiner bio-one 650101) with serial dilutions of antibody preparations (range 6.4 to 10,000 ng/mL in 5-fold dilutions) in 100 μL PBS/0.1% BSA/0.02% azide at 4° C. for 30 minutes. After washing twice in PBS/0.1% BSA/0.02% azide, T cells were incubated in 50 μL with secondary antibody at 4° C. for 30 minutes. As a secondary antibody, R-Phycoerythrin (PE)-conjugated goat-anti-human IgG F(ab')2 (Jackson ImmunoResearch Laboratories, Inc., West Grove, Pa.) diluted 1/200 in PBS/0.1% BSA/0.02% azide, was used for all experiments. Next, T cells were washed twice in PBS/0.1% BSA/0.02% azide, re-suspended in 100 μL PBS/0.1% BSA/0.02% azide and analyzed on a FACS Cantoll (BD Biosciences). Binding curves were analyzed using nonlinear regression (sigmoidal dose-response with variable slope) using GraphPad Prism V 5.04 software (GraphPad Software, San Diego, Calif., USA).

Figure 22:
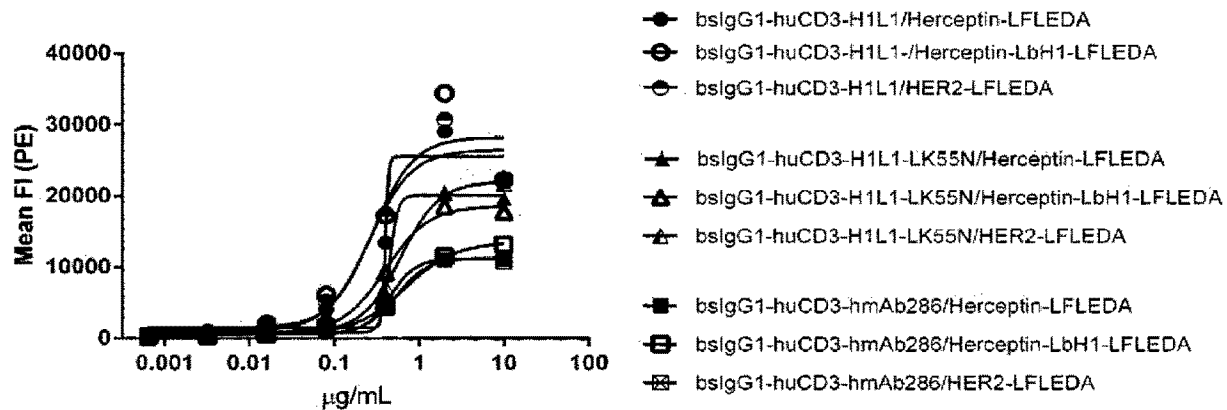
FIG. 22: Binding of the CD3 bispecific antibody variants to human T cells. The circles depict the binding of the huCD3-H1L1-LFLEDA variants, the triangles depict the binding of the huCD3-H1L1-LFLEDA-LK55N variants and the squares depict the binding of the CD3-hmAb286-LFLEDA variants.
Figure 23A:
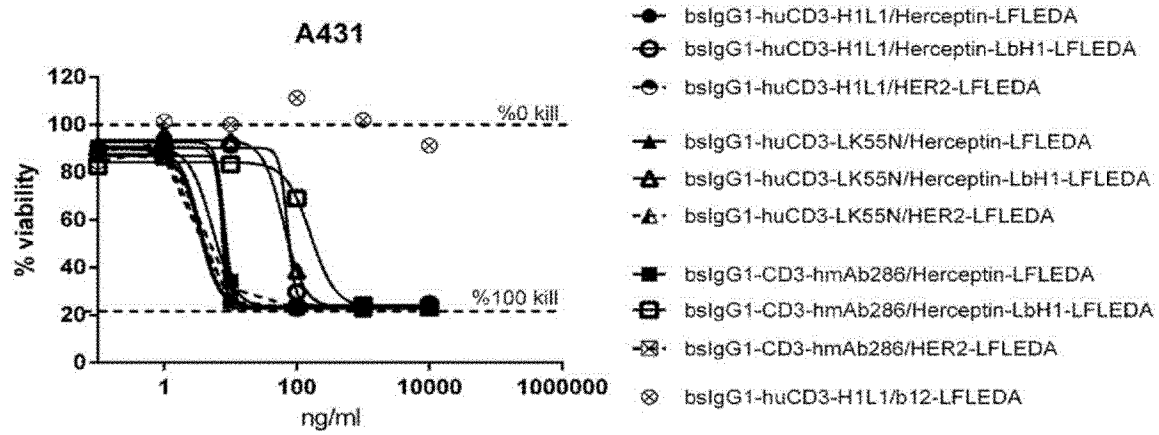
Figure 23B:
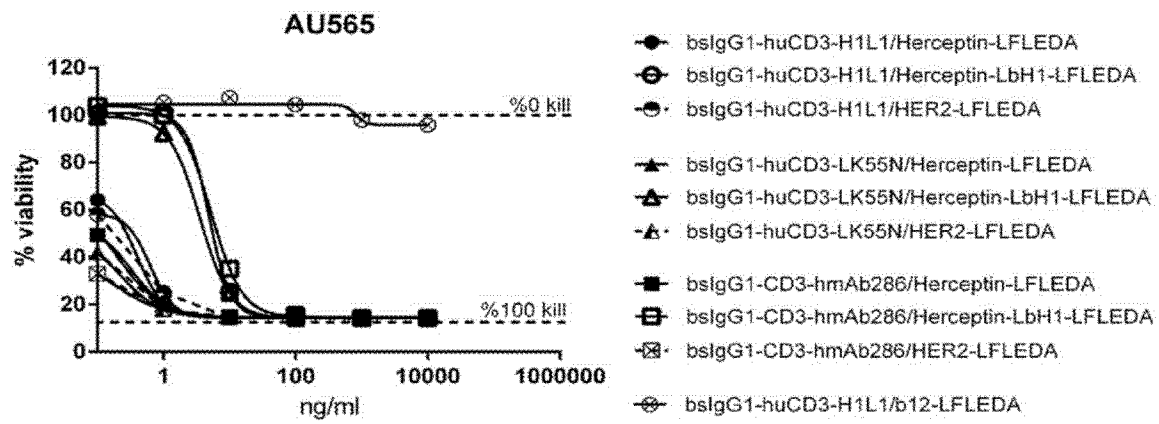
Figure 24A:
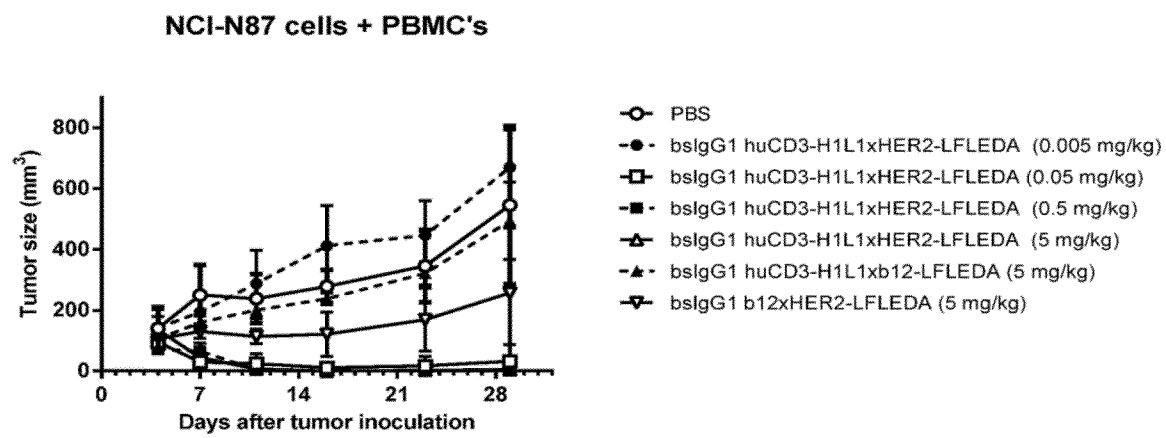
Figure 24B:
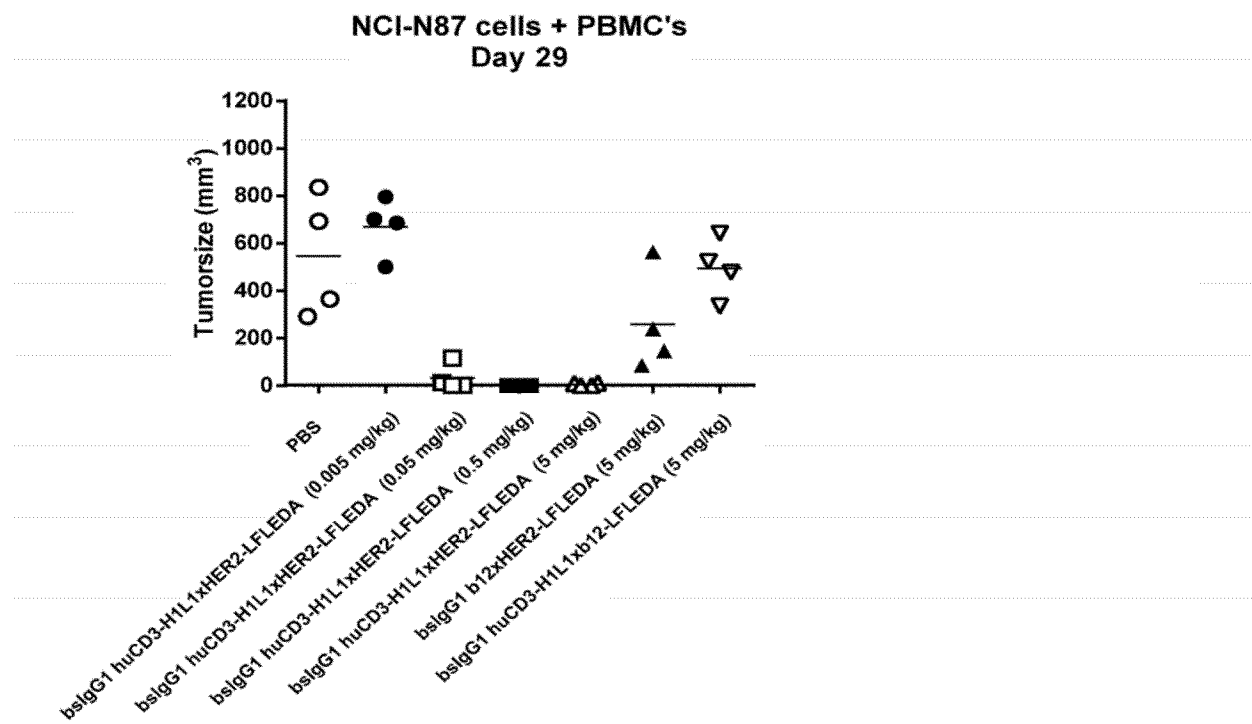
Figure 25A:
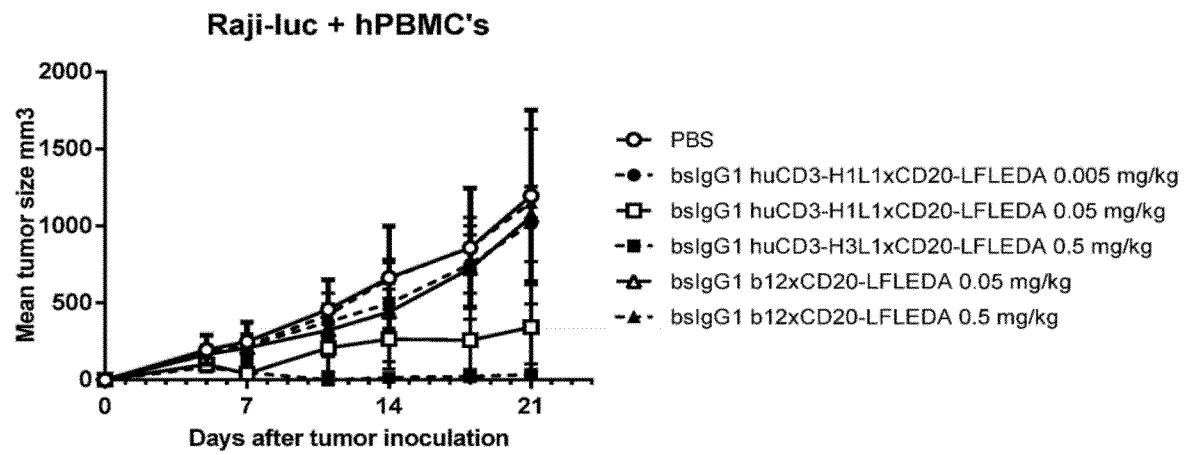
Figure 25B:
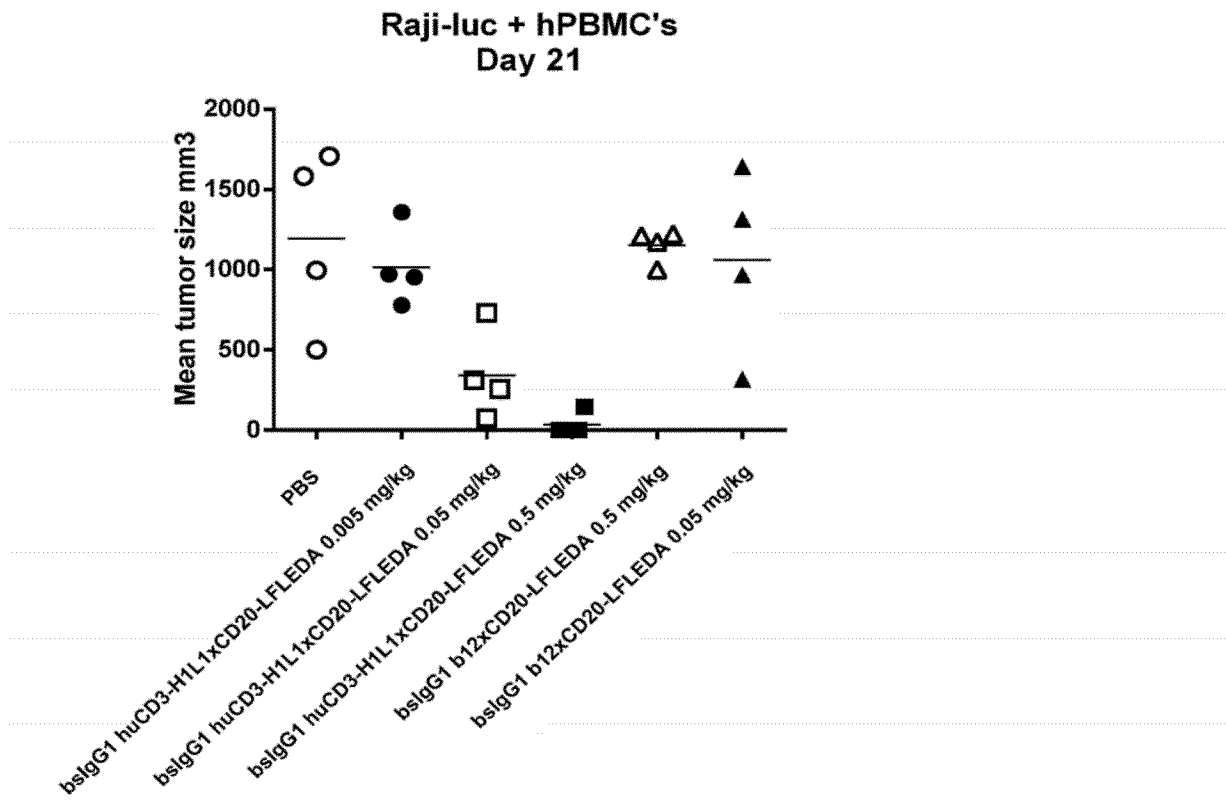

The binding curves results are shown in FIG. 22, and the EC$_{50}$ values are shown in Table 4. As can be seen the maximal difference between EC$_{50}$ values of the CD3 variants is a factor 2.

TABLE 4

| Antibodies | EC$_{50}$ (μg/mL) |
| --- | --- |
| bsIgG1-huCD3-H1L1/Herceptin-LFLEDA | ~0.40 |
| bsIgG1-huCD3-H1L1/Herceptin-LbH1 -LFLEDA | ~0.28 |
| bsIgG1-huCD3-H1L1/HER2-LFLEDA | 0.26 |
| bsIgG1-huCD3-H1L1-LK55N/Herceptin-LFLEDA | ~0.44 |

TABLE 4-continued

| Antibodies | EC$_{50}$ (μg/mL) |
| --- | --- |
| bsIgG1-huCD3-H1L1-LK55N/Herceptin-LbH1 -LFLEDA | 0.40 |
| bsIgG1-huCD3-H1L1-LK55N/HER2-LFLEDA | 0.61 |
| bsIgG1-huCD3-hmAb286/Herceptin-LFLEDA | 0.53 |
| bsIgG1-huCD3-hmAb286/Herceptin-LbH1 -LFLEDA | 0.68 |
| bsIgG1-huCD3-hmAb286/HER2-LFLEDA | 0.46 |

Example 16—In Vitro T-Cell-Mediated Cytotoxicity Induced by huCD3 Antibody Affinity Variants In this Example, T-cell mediated cytotoxicity against HER2-positive tumor cells was evaluated using bispecific antibodies with different affinities against huCD3 and HER2. The bispecific antibodies were prepared as described above, and contained the F405L mutation in the CD3 arm, and the K409R mutation in the HER2 arm. A431 and AU565 (human breast carcinoma) cells with different HER2 expression levels were used in this assay. HER2 copy numbers are ~20,000 for A431 cells and ~1,000,000 for AU565 cells. AU565 cells were cultured in RPMI 1640 with HEPES and L-glutamine (Lonza, Basel Switzerland) supplemented with 10% (vol/vol) bovine serum with iron (Life Technologies, Germany), 1.5 g/L sodium bicarbonate (Lonza, Germany), 1 mM sodium pyruvate (Lonza, Germany), 4.5 g/L glucose (Sigma), 50 IU/mL penicillin, and 50 μg/mL streptomycin (Lonza, Basel, Switzerland). A431 (ATCC, epidermoid carcinoma) cells were cultured in RPMI 1640 with HEPES and L-glutamine (Lonza, Basel, Switzerland) supplemented with 10% (vol/vol) bovine serum with iron (Life Technologies, Germany), 50 IU/mL penicillin, and 50 μg/mL streptomycin (Lonza, Basel, Switzerland). The cell lines were maintained at 37° C. in a 5% (vol/vol) CO2 humidified incubator. AU565 and A431 cells were cultured to near confluency, after which cells were trypsinized, re-suspended in culture medium and passed through a cell strainer to obtain a single cell suspension. AU565 and A431 cells were seeded 3×10$^4$ and 1.6×10$^4$ cells/well, respectively in 96-well culture plates, and incubated at least 3 hours at 37° C., 5% CO2 to allow adherence to the plate.

Human T cells were isolated from a buffy coat as mentioned in Example 15. Isolated T cells were washed with PBS, re-suspended in culture medium (RPMI 1640, 10% serum) and added in 1:3 ratio to the AU565 or 1:10 ratio to A431 cells in the 96-well plates.

Dilution series (final concentrations ranging from 0.1 up to 10,000 ng/mL) of bispecific antibody variants bsIgG1-huCD3/Herceptin-LFLEDA, bsIgG1-huCD3/Herceptin-LbH1-LFLEDA, bsIgG1-huCD3-H1L1/HER2-LFLEDA, bisIgG1-huCD3-LK55N/Herceptin-LbH1-LFLEDA, bsIgG1-huCD3-LK55N/HER2-LFLEDA, bsIgG1-huCD3-hmAb286/Herceptin-LFLEDA, bsIgG1-huCD3-hmAb286/Herceptin-LbH1-LFLEDA, bsIgG1-CD3-hmAb286/HER2-LFLEDA and bsIgG1-huCD3-H1L1/b12-LFLEDA were prepared in culture medium and added to the plates. Plates were incubated for 3 days at 37° C., 5% CO2. Incubation of cells with 1 μM staurosporine (Sigma) was used as reference for 100% tumor cell kill. Plates were washed twice with PBS, and 150 μL culture medium containing 10% Alamar blue (Life Technologies, Germany) was added to each well. Plates were incubated for 4 hours at 37° C., 5% CO2. Absorbance at 590 nm was measured (Envision, Perkin Elmer, Waltham, Mass.).

FIG. 23 shows the viability of A431 cells (FIG. 23A) and AU565 cells (FIG. 23B) treated with CD3 and HER2 affinity variants. Lower HER2 affinity in combination with high and low CD3 affinity results in lower efficacy in both cell lines (shown as open symbols in both graphs). The bispecific antibodies with a similar high affinity to HER2 (Herceptin and HER2) in combination with wild type huCD3-H1L1, huCD3-LK55N or CD3-hmAb286 CD3 arm showed similar efficacy on A431 cells. The affinity variation in the CD3 arm had no effect on the efficacy on A431 cells. The bispecific antibodies with a similar high affinity to HER2 (Herceptin and HER2) in combination with CD3-hmAb286 CD3 arm, the huCD3-LK55N arm and wild type huCD3-H1L1 arm showed similar efficacies on AU565 cells with the CD3 hmAb286 CD3 arm showing a relatively higher efficacy. A lower binding affinity for the CD3 arm was more beneficial in AU565 cells which had a higher HER2 expression compared to the A431 cells.

Example 17—In Vivo Tumor Killing Effect of huCD3-H1L1×HER2-LFLEDA and huCD3-H1L1×CD20-LFLEDA in NOD-SCID Mice The in vivo anti-tumor efficacy of the bispecific CD3×HER2 antibody bsIgG1-huCD3-H1L1×HER2-LFLEDA was evaluated in a subcutaneous NCI-N87 xenograft model. In this model human, unstimulated PBMCs, as a source of human T cells, were co-inoculated with tumor cells, analogous to the model described by Brischwein et al., (Mol. Immunol. 43 (2006), 1129-1143). In these experiments six to eleven weeks old female NOD-SCID (NOD.CB17-Prkdcscid/NcrCrl) mice were used. Human PBMCs from healthy donors were isolated from a buffy coat as described in Example 15. At day 0, a mixture containing 5×10$^6$ cells of both PBMCs and NCI-N87 cells were inoculated subcutaneously in 200 μL in the right flank of each mouse. Within one hour of injection, the mice were randomly assigned to seven different treatment groups (n=4 per donor). Each group was injected intravenously (i.v.) with a single dose of (bispecific) antibody. Treatment groups are shown in Table 5. Tumor growth was evaluated twice per week using caliper (PLEXX) until an endpoint tumor volume of 1500 mm$^3$, until tumors showed ulcerations or until the end of the study.

The results are shown in FIG. 24. As can be seen from FIG. 24A, huCD3-H1L1×HER2-LFLEDA efficiently reduced the tumor size at all three tested concentrations. FIG. 24B shows the tumor size 29 days after tumor inoculation. Tumor formation was significantly inhibited (p<0.0001, Tukeys multiple comparison test) in mice treated with bsIgG1-huCD3-H1L1×HER2-LFLEDA at doses of 0.05 mg/kg, 0.5 mg/kg and 5 mg/kg compared to the PBS control group, whereas treatment with 0.005 mg/kg did not affect tumor formation. Treatment with 5 mg/kg of the control antibody bsIgG1-huCD3-H1L1×b12-LFLEDA did not inhibit tumor formation, whereas treatment with bsIgG1-b12×HER2-LFLEDA seemed to induce some tumor growth inhibition compared to the PBS control, but this was not significant according to the One-Way Anova, Tukey's multiple comparison test.

TABLE 5

| Group | Antibody | Dose |
|---|---|---|
| 1 | PBS | |
| 2 | bsIgG1- huCD3-H1L1×HER2-LFLEDA | 0.1 μg (=0.005 mg/kg) |
| 3 | bsIgG1- huCD3-H1L1×HER2-LFLEDA | 1 μg (=0.05 mg/kg) |
| 4 | bsIgG1- huCD3-H1L1×HER2-LFLEDA | 10 μg (=0.5 mg/kg) |
| 5 | bsIgG1- huCD3-H1L1×HER2-LFLEDA | 100 μg (=5 mg/kg) |
| 6 | bsIgG1- huCD3-H1L1×b12-LFLEDA | 100 μg (=5 mg/kg) |
| 7 | bsIgG1- b12×HER2-LFLEDA | 100 μg (=5 mg/kg) |

The in vivo anti-tumor efficacy of bispecific CD20×CD3 antibody huCD3-H1L1×CD20-LFLEDA was evaluated in a subcutaneous Raji xenograft model. In this model human, unstimulated PBMCs, as a source of human T cells, were co-inoculated with tumor cells, analogous to the model described by Brischwein et al., (Mol. Immunol. 43 (2006), 1129-1143). Six to eleven weeks old female NOD-SCID (NOD.CB17-Prkdcscid/NcrCrl) mice were used. Human PBMC from healthy donors were isolated from a buffy coat, washed and resuspended with PBS-0.1% BSA. At day 0, a mixture containing 5×10$^6$ cells of both PBMCs and Raji cells were inoculated subcutaneously in 200 μL in the right flank of each mouse. Within one hour of injection, the mice were sorted into seven groups (n=4 per donor) and each group was injected intravenously (i.v.) with a single dose of (bispecific) antibody. Treatment groups are shown in Table 6. Tumor growth was evaluated twice per week using caliper (PLEXX) until an endpoint tumor volume of 1500 mm$^3$, until tumors showed ulcerations or until the end of the study.

The results are shown in FIG. 25. As can be seen from FIG. 25A, huCD3-H1L1×CD20-LFLEDA efficiently reduced the tumor size at the two higher tested doses (0.5 mg/kg and 0.05 mg/kg) of huCD3-H1L1×CD20-LFLEDA.

Figure 25A:
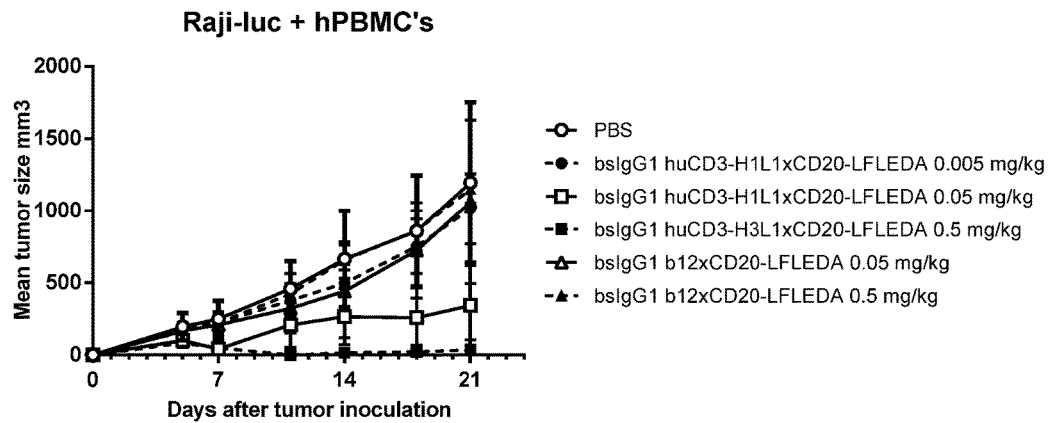
FIGS. 25A and 25B: Reduction of tumor size in NOD-SCID mice by huCD3-H1L1×CD20-LFLEDA 7, 14, and 21 days after tumor inoculation (FIG. 25A), and at day 21 (FIG. 25B).
Figure 25B:
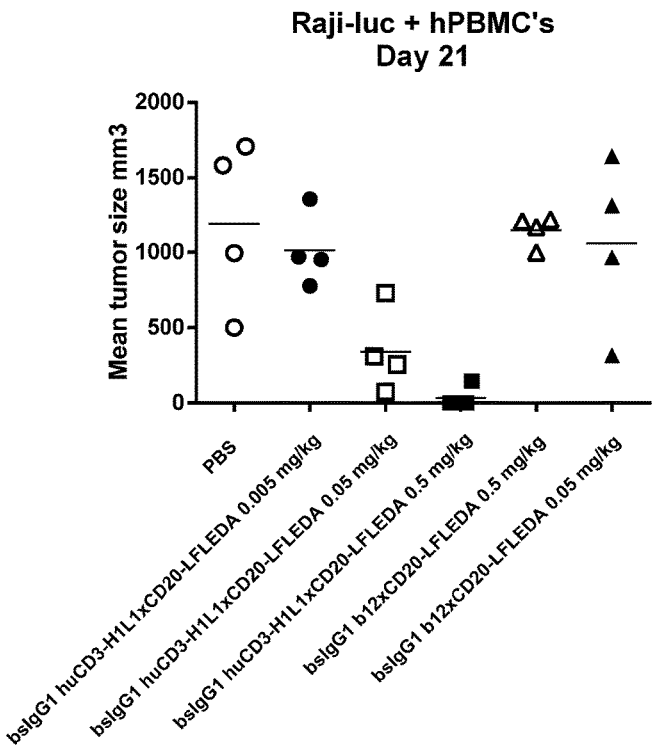
Figure 1A:
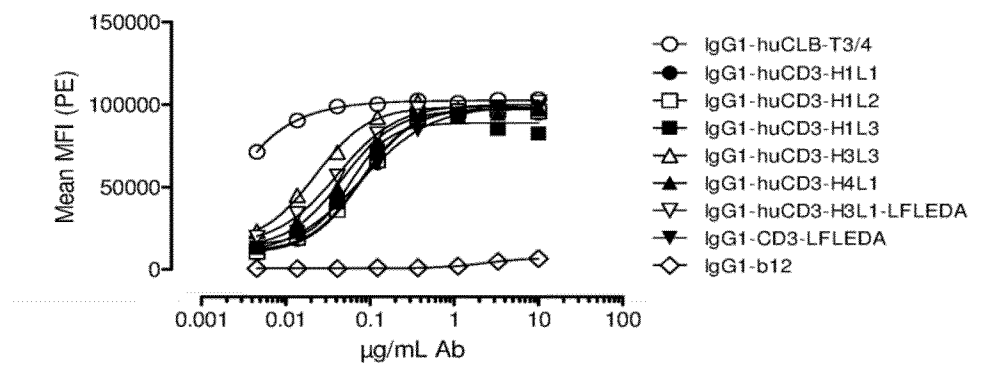
Figure 1B:
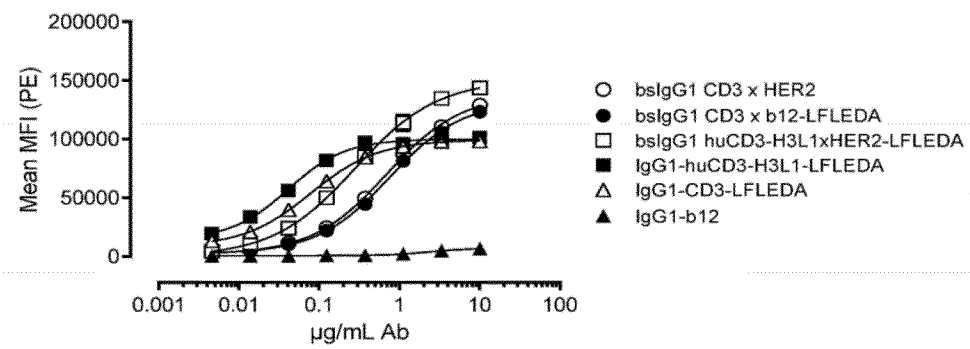
Figure 2A:
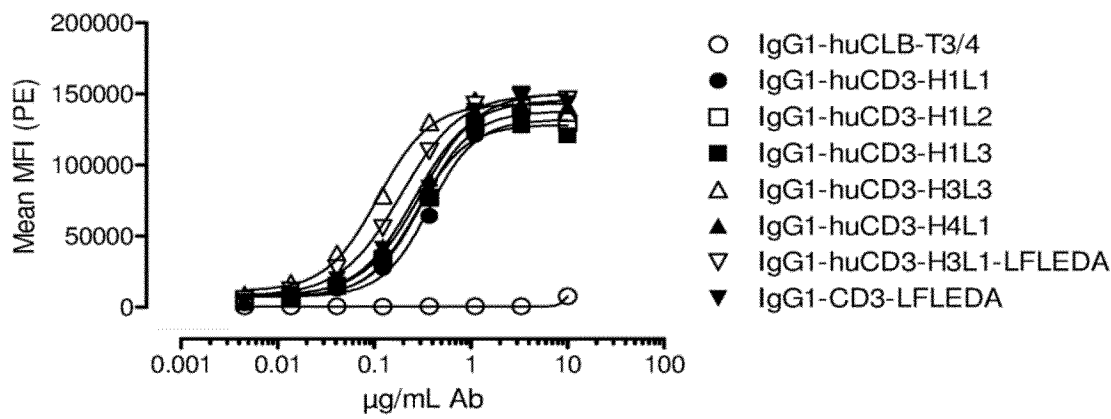
Figure 2B:
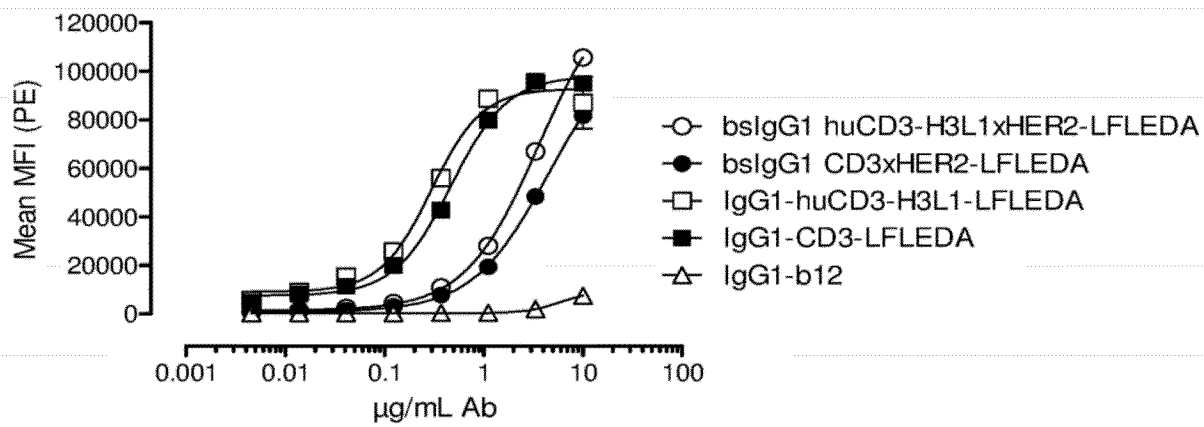
Figure 3A:
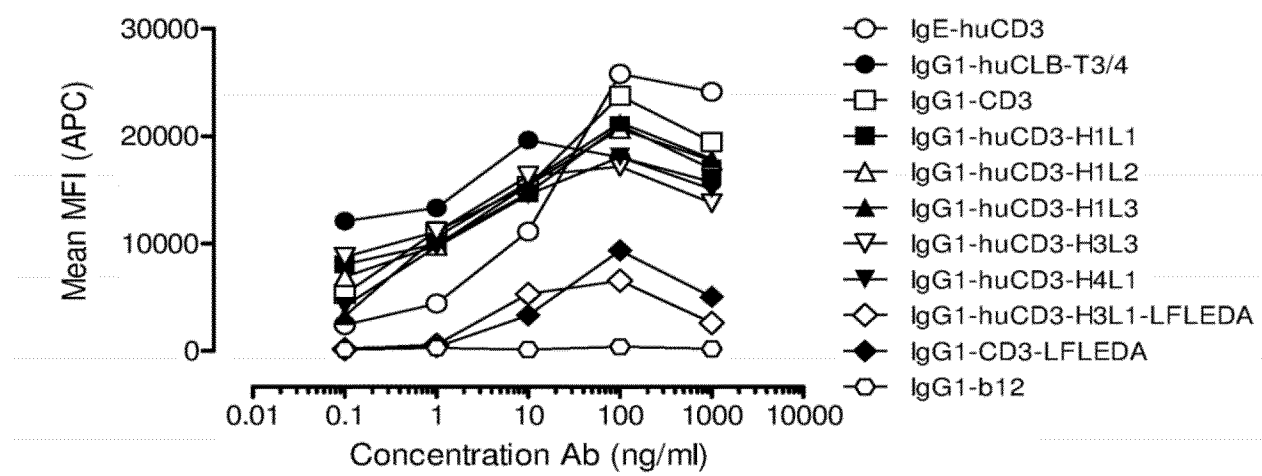
Figure 3B:
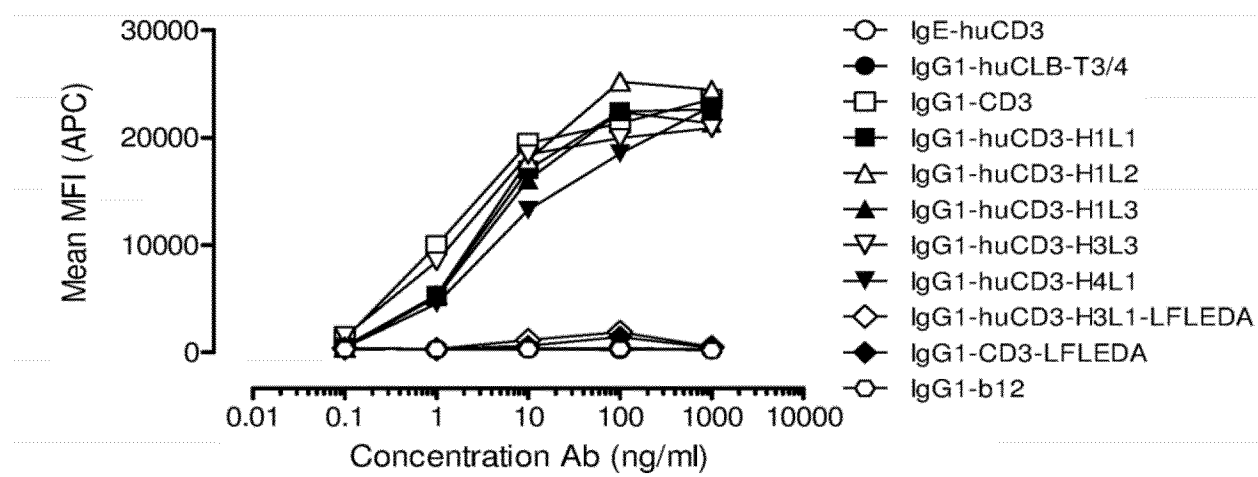
Figure 4A:
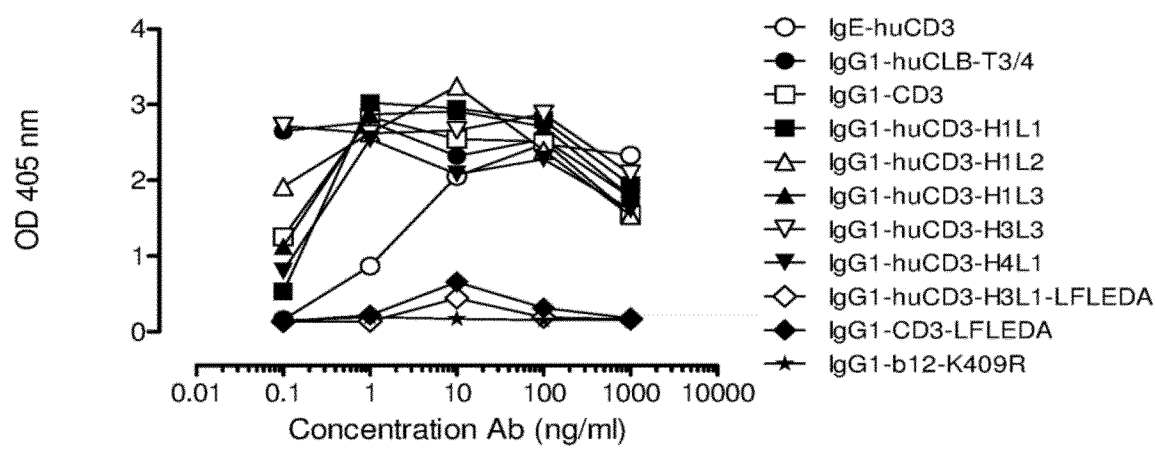
Figure 4B:
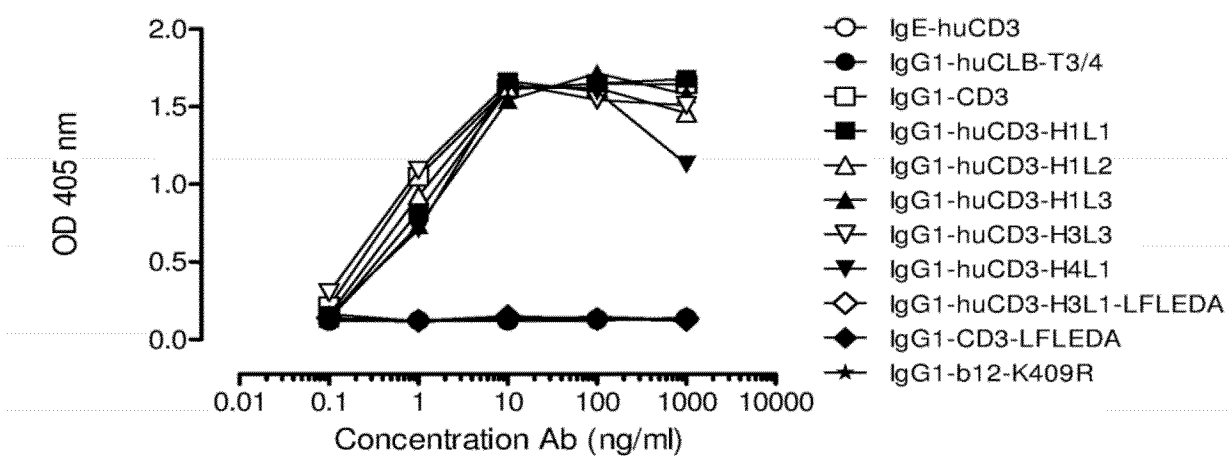
Figure 5A:
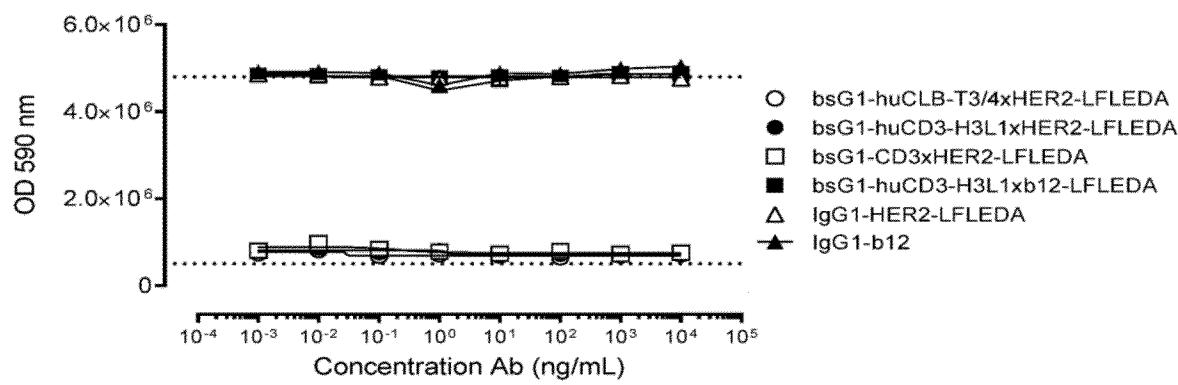
Figure 5B:
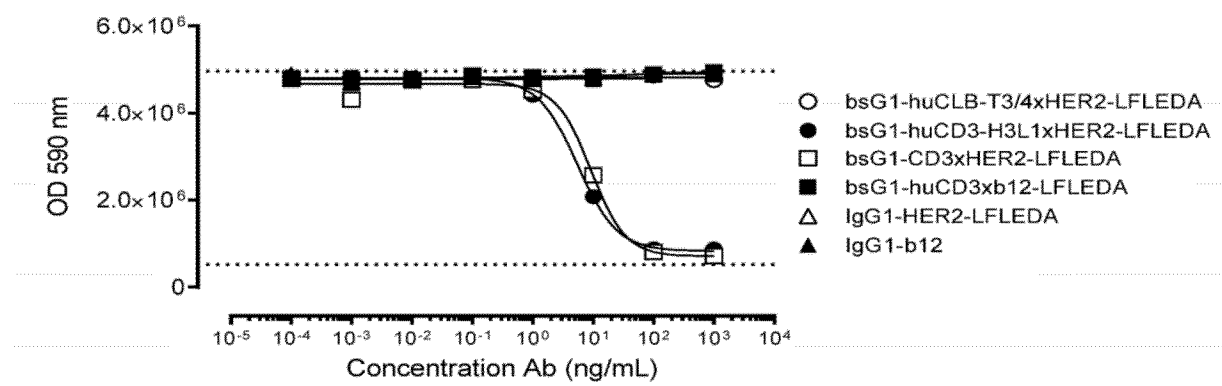
Figure 6A:
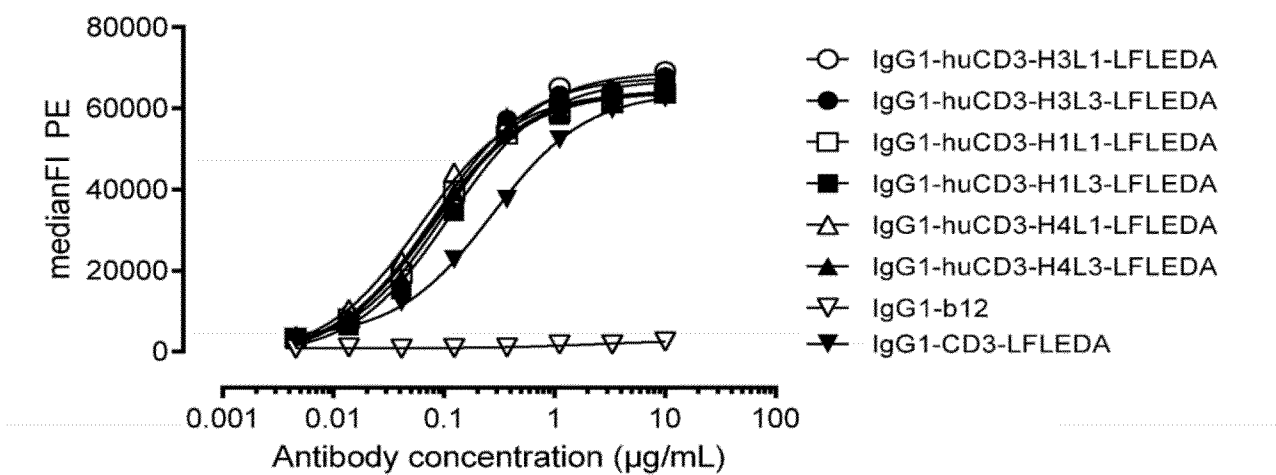
Figure 6B:
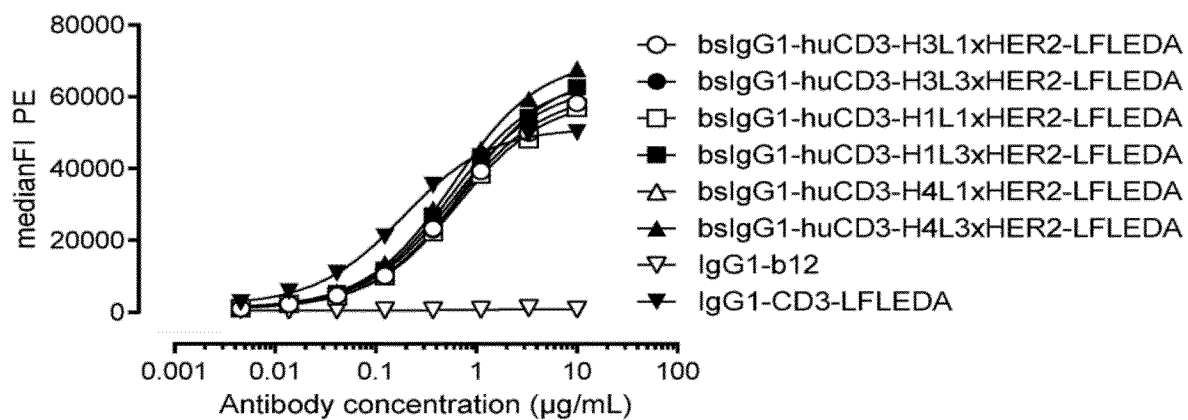
Figure 7A:
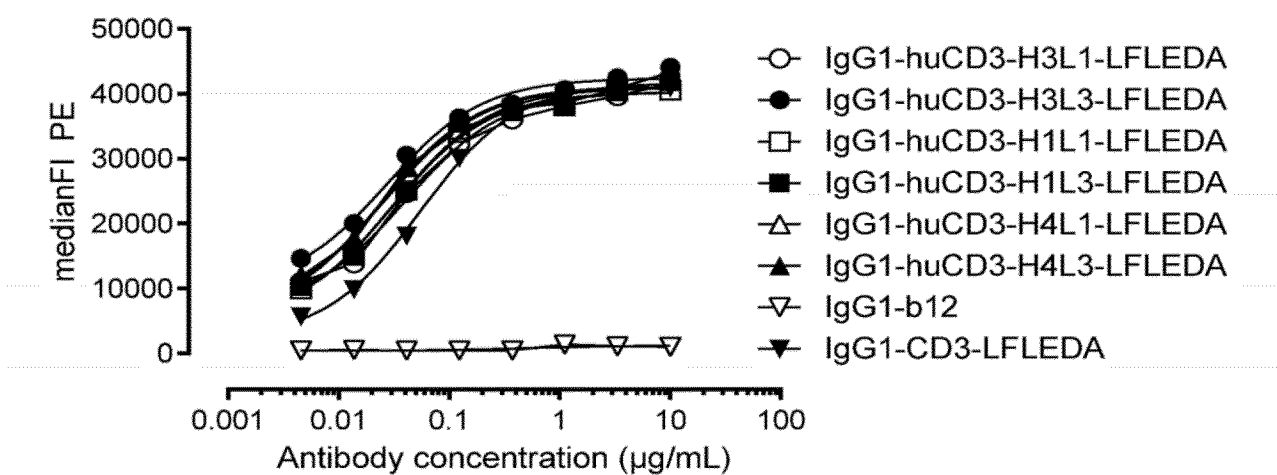
Figure 7B:
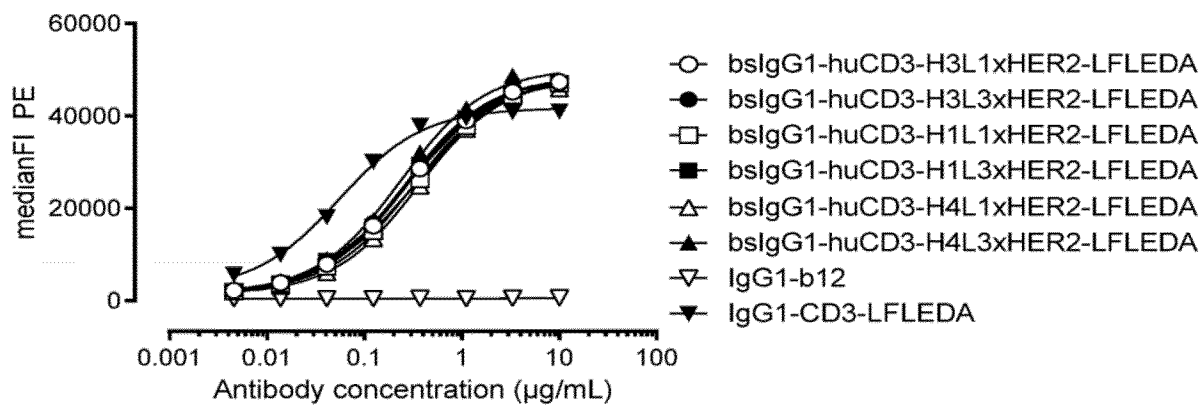
Figure 8A:
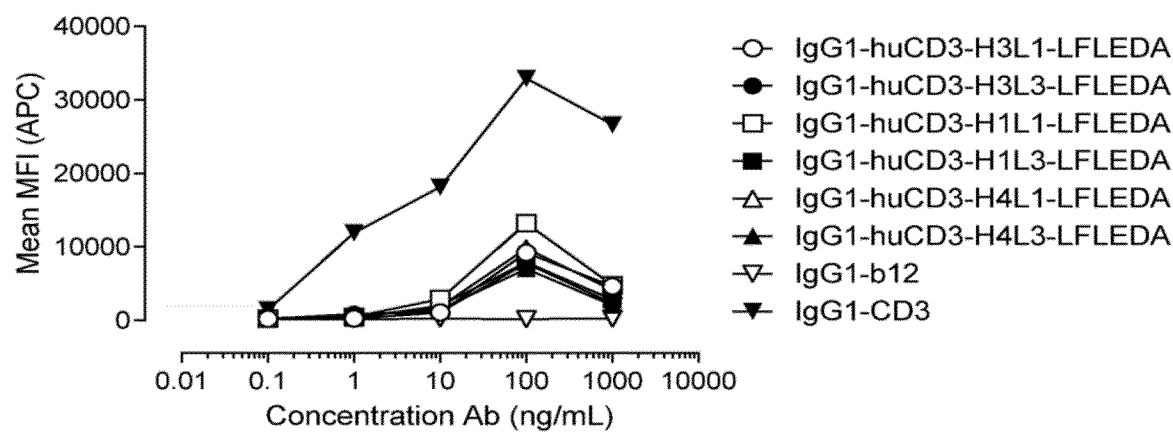
Figure 8B:
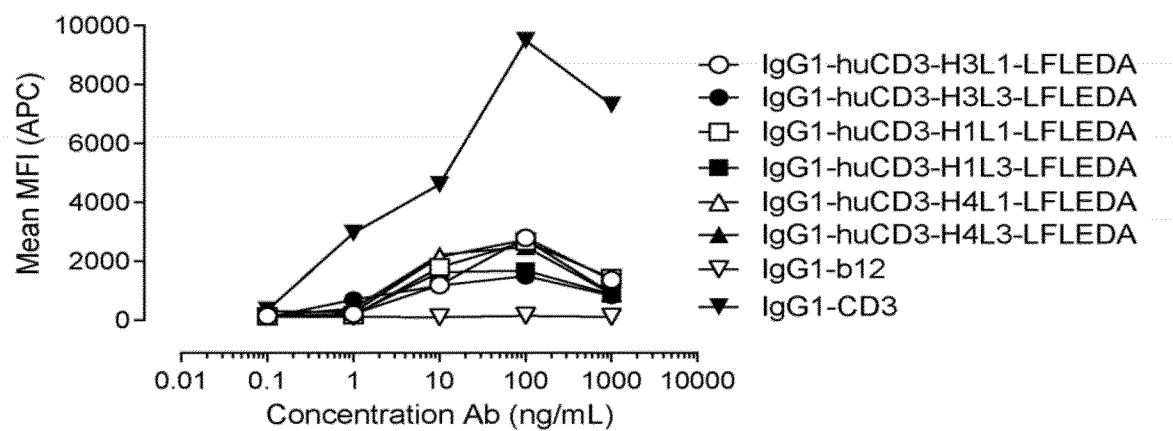
Figure 8C:
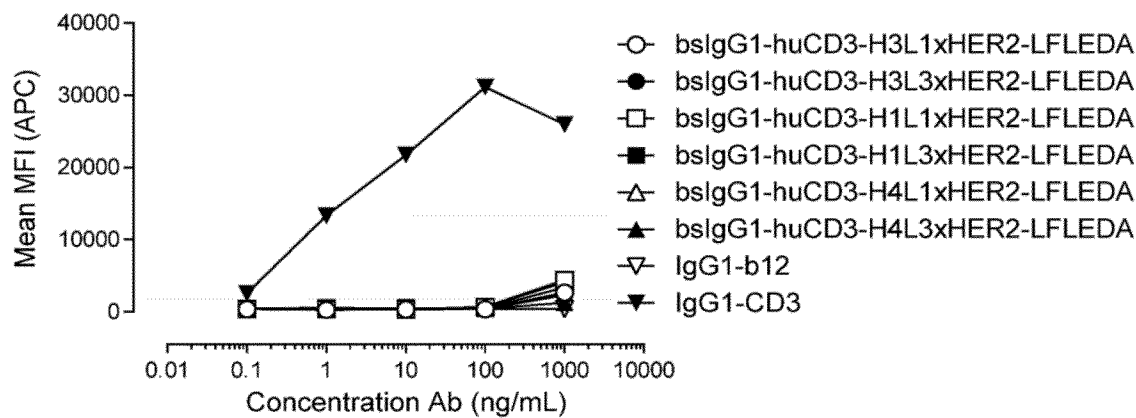
Figure 8D:
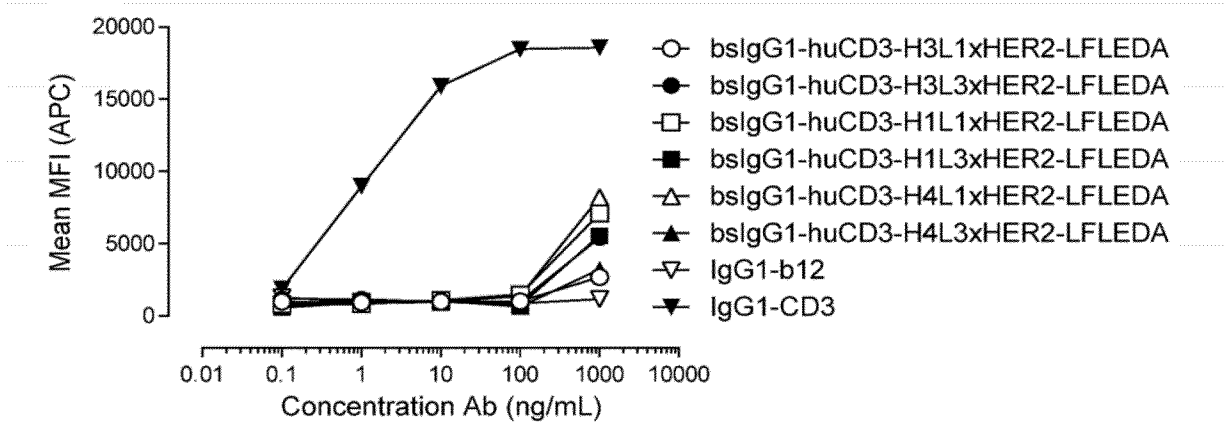
Figure 9A:
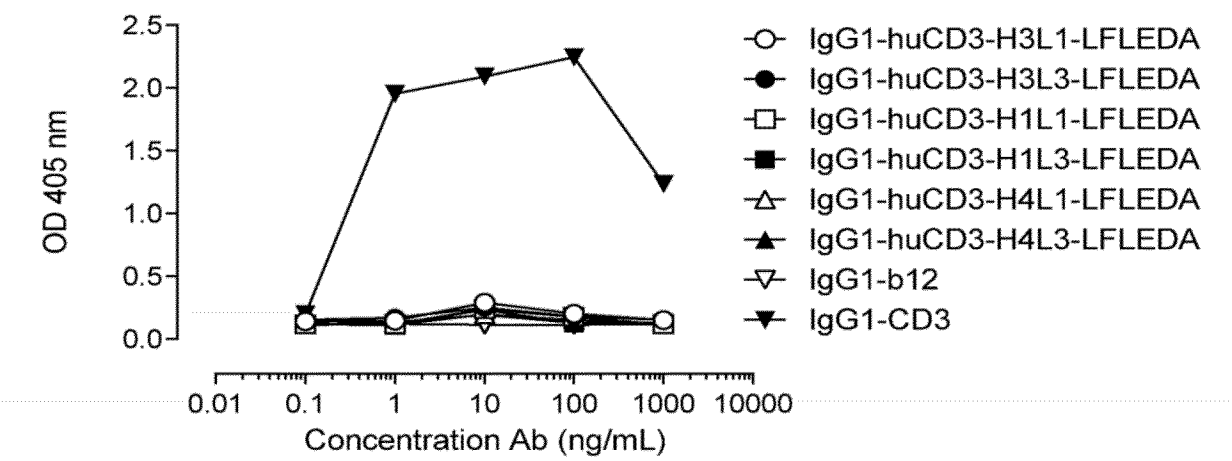
Figure 9B:
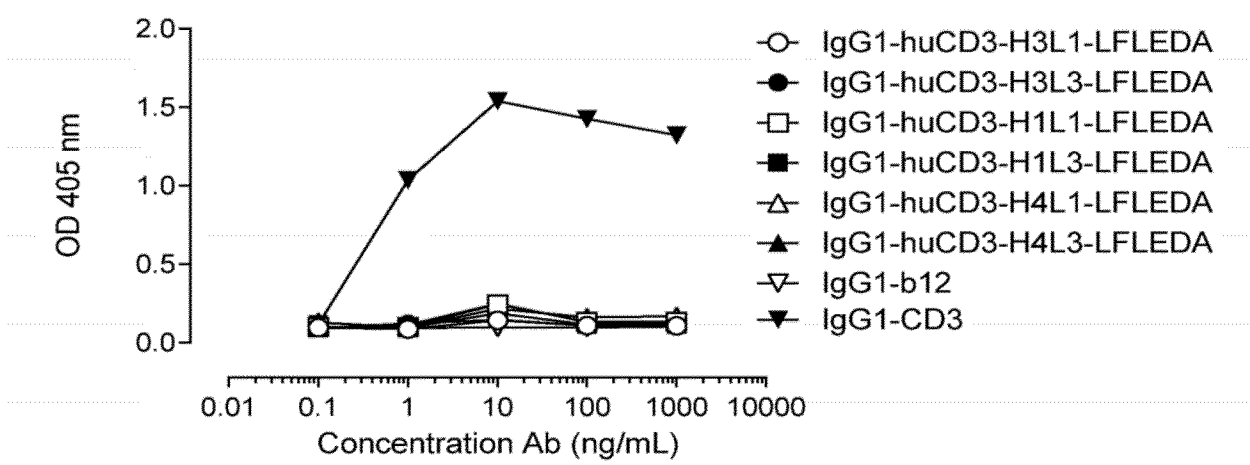
Figure 9C:
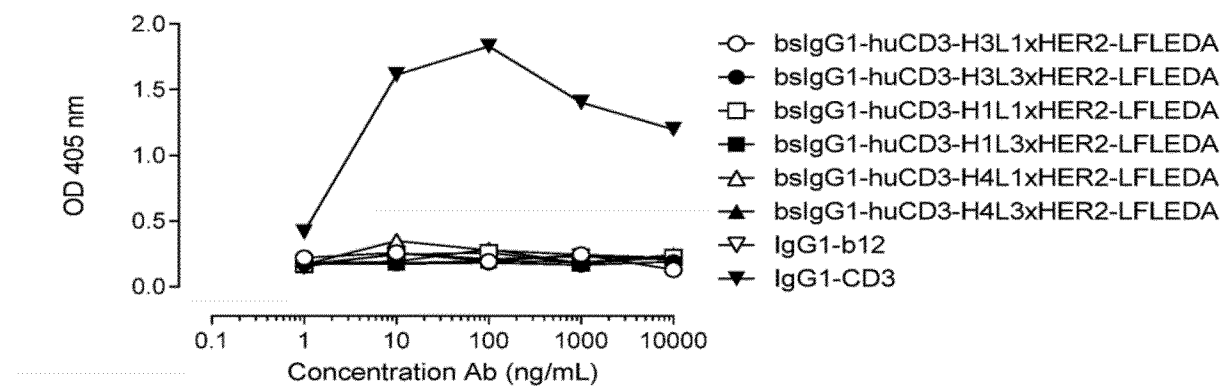
Figure 9D:
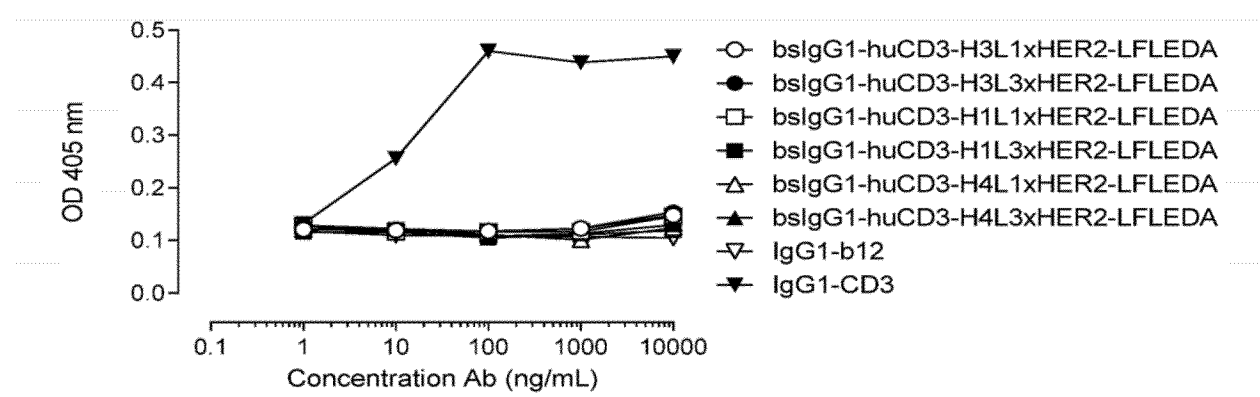
Figure 10A:
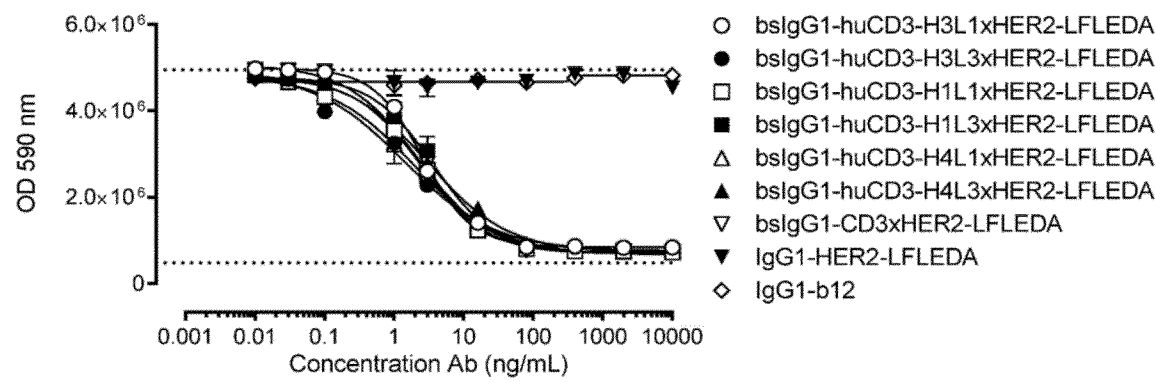
Figure 10B:
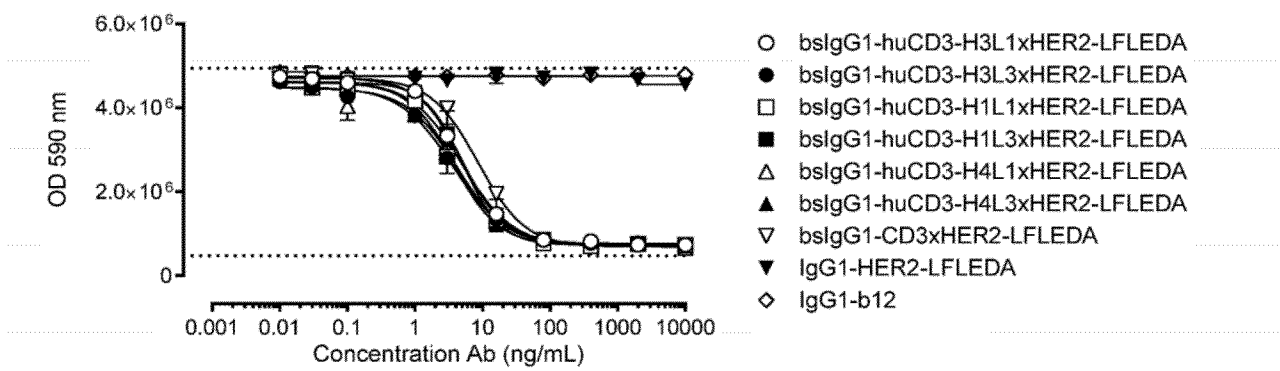

In FIG. 25B, the tumor size of the individual mice are indicated at the last day the groups were intact (day 21). Tumor formation is significantly inhibited in mice treated with huCD3-H1L1×CD20-LFLEDA at doses of 0.05 mg/kg and 0.5 mg/kg compared to the PBS control group (p-values were p<0.05 and p<0.01, respectively, when assessed with a One-Way Anova, Tukey's multiple comparison test). Treatment with 0.005 mg/kg did not affect tumor formation. Treatment with 0.5 mg/kg and 0.05 of the control antibody b12×CD20 (bsIgG1-b12×CD20-LFLEDA) did not significantly inhibit tumor formation compared to the PBS control (One-Way Anova, Tukey's multiple comparison test).

TABLE 6

| Group | Antibody | Dose |
|---|---|---|
| 1 | PBS | |
| 2 | bsIgG1- huCD3-H1L1×CD20-LFLEDA | 0.1 μg (=0.005 mg/kg) |
| 3 | bsIgG1- huCD3-H1L1×CD20-LFLEDA | 1 μg (=0.05 mg/kg) |
| 4 | bsIgG1- huCD3-H1L1×CD20-LFLEDA | 10 μg (=0.5 mg/kg) |
| 5 | bsIgG1- b12×CD20-LFLEDA | 1 μg (=0.05 mg/kg) |
| 6 | bsIgG1- b12×CD20-LFLEDA | 10 μg (=0.5 mg/kg) |

LIST OF REFERENCES

[1] Xu et al., 2000, Cell Immunol. 200(1):16-26
[2] Herold et al., 2005, Diabetes, 54(6):1763-9

[3] Staerz, et. al., 1985, Nature 314:628-631
[4] Muller and Kontermann, 2010, BioDrugs 24: 89-98
[5] Lum and Thakur, 2011, BioDrugs 25: 365-379
[6] Linke et al., 2010, MAbs 2: 129-136
[7] Ruf et al., 2010, Br J Clin Pharmacol 69: 617-625
[8] Bokemeyer et al., 2009, J Clin Oncol (Meeting Abstracts), 3036
[9] Heiss et al., 2010, Int J Cancer 127: 2209-2221
[10] Jones et al., 2009, Lancet Oncol 10:1179-1187
[11] Kiewe et al., 2006, Clin Cancer Res 12:3085-3091
[12] WO 2012/162067
[13] WO 2008/119567
[14] Fundamental Immunology Ch. 7, Paul, W., ed., 2nd ed. Raven Press, N.Y. (1989)
[15] Lefranc M P, et al., 2003, Dev Comp Immunol. January; 27(1):55-77
[16] Brochet, X. et al., 2008, Nucl. Acids Res. 36, W503-508
[17] Giudicelli, V., Brochet, X, Lefranc, M.-P., 2011, Cold Spring Harb Protoc. Jun. 1, 2011(6)
[18] Sambrook et al., 1989, Molecular Cloning: A laboratory Manual, New York: Cold Spring Harbor Laboratory Press, Ch. 15
[19] WO92/22653
[20] EP 0 629 240
[21] E. Meyers and W. Miller, 1988, Comput. Appl. Biosci 4, 11-17
[22] Needleman and Wunsch, 1970, J. Mol. Biol. 48, 444-453
[23] Clustal W algorithm, Thompson, 1994
[24] T cell Epitope Database from e.g. http://www.iedb.org/
[25] Perry et al., 2008 Drugs R D 9 (6):385-396
[26] Bryson et al., 2010, Biodrugs 24 (1):1-8
[27] Kabat, E. A. et al., 1991, Sequences of proteins of immunological interest. 5th Edition—US Department of Health and Human Services, NIH publication No. 91-3242, pp 662, 680, 689
[28] Oganesyan et al., 2008, Acta Cryst. (D64):700-4
[29] Canfield et al., 1991, J. Exp. Med. (173):1483-91
[30] Duncan et al., 1988, Nature (332):738-40
[31] Shields et al., 2001, J. Biol. Chem. (276):6591-604
[32] Idusogie E E, et al., 2000, J Immunol. 164: 4178-84
[33] Leabman et al., 2013, MAbs; 5(6):896-903
[34] Parren et al., 1992, J. Clin Invest. 90: 1537-1546
[35] Bruhns et al., 2009, Blood 113: 3716-3725
[36] WO 2011/066501
[37] Lightle, S., et al., 2010, Protein Science (19):753-62
[38] Brekke et al., 2006, J Immunol 177:1129-1138
[39] Dall'Acqua W F, et al., 2006, J Immunol 177:1129-1138
[40] Wu et al., 2010, Generation and Characterization of a Dual Variable Domain Immunoglobulin (DVD-Ig™) Molecule, In: Antibody Engineering, Springer Berlin Heidelberg
[41] WO 2011/131746
[42] WO 2002/020039
[43] WO 98/050431
[44] WO 2011/117329
[45] EP 1 870 459
[46] WO 2009/089004
[47] US 2010 00155133
[48] WO 2010/129304
[49] WO 2007/110205
[50] WO 2010/015792
[51] WO 2011/143545
[52] WO 2012/058768
[53] WO 2011/028952
[54] WO 2008/003116
[55] U.S. Pat. No. 7,262,028
[56] U.S. Pat. No. 7,612,181
[57] WO 2010/0226923
[58] U.S. Pat. No. 7,951,918
[59] CN 102250246
[60] WO 2012/025525
[61] WO 2012/025530
[62] WO 2008/157379
[63] WO 2010/080538
[64] Sykes and Johnston, 1997, Nat Biotech 17, 355-59
[65] U.S. Pat. No. 6,077,835
[66] WO 2000/70087
[67] Schakowski et al., 2001, Mol Ther 3, 793-800
[68] WO 2000/46147
[69] Benvenisty and Reshef, 1986, PNAS USA 83, 9551-55
[70] Wigler et al., 1978, Cell 14, 725
[71] Coraro and Pearson, 1981, Somatic Cell Genetics 7, 603
[72] U.S. Pat. No. 5,589,466
[73] U.S. Pat. No. 5,973,972
[74] Van Heeke & Schuster, 1989, J Biol Chem 264, 5503-5509
[75] F. Ausubel et al., 1987, ed. Current Protocols in Molecular Biology, Greene Publishing and Wiley Inter-Science New York
[76] Grant et al., 1987, Methods in Enzymol 153, 516-544
[77] Remington: The Science and Practice of Pharmacy, 19th Edition, Gennaro, Ed., Mack Publishing Co., Easton, Pa., 1995
[78] Sustained and Controlled Release Drug Delivery Systems, J. R. Robinson, ed., Marcel Dekker, Inc., New York, 1978
[79] Srivastava (ed.), Radiolabeled Monoclonal Antibodies For Imaging And Therapy, Plenum Press 1988
[80] Chase, "Medical Applications of Radioisotopes," in Remington's Pharmaceutical Sciences, 18th Edition, Gennaro et al., (eds.), pp. 624-652, Mack Publishing Co., 1990
[81] Brown, "Clinical Use of Monoclonal Antibodies," in Biotechnology And Pharmacy 227-49, Pezzuto et al., (eds.), Chapman & Hall 1993
[82] U.S. Pat. No. 5,057,313
[83] U.S. Pat. No. 6,331,175
[84] Ritter G, et al.; 2001, Cancer Res., 61:6851-9
[85] Bostrom et al, Science. 2009; 323(5921):1610-4
[86] Bostrom et al, PLosOne. 2011; 6(4)e17887

The invention claimed is:

1. A humanized or chimeric antibody which binds to human CD3 and comprises heavy chain variable region CDR1, CDR2, and CDR3 domains comprising the amino acid sequences set forth in SEQ ID NOs: 1, 2, and 3, respectively, and a light chain comprising the amino acid sequence of SEQ ID NO: 10, wherein the amino acid in the position corresponding to position T41 in SEQ ID NO: 10 is not T.

2. A humanized or chimeric antibody which binds to human CD3 and comprises heavy chain variable region CDR1, CDR2, and CDR3 domains comprising the amino acid sequences set forth in SEQ ID NOs: 1, 2, and 3, respectively, and a light chain comprising the amino acid sequence of SEQ ID NO: 10, wherein the amino acid in the position corresponding to position F10 in SEQ ID NO: 10 is not F, and wherein one or more of the amino acid positions corresponding to the positions T41, K55, and L97 in SEQ ID NO: 10 are not T, K, and L, respectively.

3. The antibody according to claim 2, wherein the amino acids in the positions corresponding to positions F10, T41, K55, and L97 in SEQ ID NO: 10 are not F, T, K, and L, respectively.

4. A humanized or chimeric antibody which binds to human CD3 and comprises heavy chain variable region CDR1, CDR2, and CDR3 domains comprising the amino acid sequences set forth in SEQ ID NOs: 1, 2, and 3, respectively, and a light chain comprising the amino acid sequence of SEQ ID NO: 10, wherein the amino acids in the positions corresponding to positions R23 and A35 in SEQ ID NO: 10 are not R and A, respectively.

5. The antibody according to claim 4, wherein the amino acids in the positions corresponding to positions F10, R23, A35, R47, D71, A82, D83, S86, I87, and F89 in SEQ ID NO: 10 are not F, R, A, R, D, A, D, S, I, and F, respectively.

6. The antibody according to claim 5, wherein
   i. the amino acid in the position corresponding to position F10 in SEQ ID NO: 10 is not F, or
   ii. the amino acid in the position corresponding to position K55 in SEQ ID NO: 10 is not K, or
   iii. the amino acid in the position corresponding to position F10 in SEQ ID NO: 10 is not F, and the amino acid in the position corresponding to position K55 in SEQ ID NO: 10 is not K.

7. The antibody according to claim 6, wherein
   (i) the amino acid in the position corresponding to position F10 in SEQ ID NO: 10 is L, or
   (ii) the amino acid in the position corresponding to position K55 in SEQ ID NO: 10 is N, or
   (iii) the amino acid in the position corresponding to position F10 in SEQ ID NO: 10 is L, and the amino acid in the position corresponding to position K55 in the lambda light chain of SEQ ID NO: 10 is N.

8. A humanized or chimeric antibody which binds to human CD3 and comprises heavy chain variable region CDR1, CDR2, and CDR3 domains comprising the amino acid sequences set forth in SEQ ID NOs: 1, 2, and 3, respectively, and light chain variable region CDR1, CDR2, and CDR3 domains comprising the amino acid sequences set forth in SEQ ID NO: 4, GTN, and SEQ ID NO: 5 or 60, respectively, wherein said antibody comprises a constant heavy chain and a constant light chain, wherein the positions corresponding to positions L234, L235, and D265 in the human IgG1 heavy chain of SEQ ID NO: 15 are F, E, and A, respectively, and wherein the position corresponding to F405 in the human IgG1 heavy chain of SEQ ID NO: 15 is L, and wherein (i) the positions corresponding to positions F10, T41, K55, and L97 in the lambda light chain of SEQ ID NO: 10 are L, K, N, and H, respectively, or (ii) the position corresponding to position T41 in the lambda light chain of SEQ ID NO: 10 is K.

9. A composition comprising the antibody of claim 1 and a carrier.

10. The antibody of claim 1, wherein the heavy chain variable region comprises an amino acid sequence selected from the group consisting of SEQ ID NOs: 6-9.

11. The antibody of claim 2, wherein the heavy chain variable region comprises an amino acid sequence selected from the group consisting of SEQ ID NOs: 6-9.

12. The antibody of claim 4, wherein the heavy chain variable region comprises an amino acid sequence selected from the group consisting of SEQ ID NOs: 6-9.

13. The antibody of claim 8, wherein the heavy chain variable region comprises an amino acid sequence selected from the group consisting of SEQ ID NOs: 6-9.

14. The antibody of claim 1, which is a full length antibody.

15. The antibody of claim 2, which is a full length antibody.

16. The antibody of claim 4, which is a full length antibody.

17. A composition comprising the antibody of claim 2 and a carrier.

18. A composition comprising the antibody of claim 4 and a carrier.

19. A composition comprising the antibody of claim 8 and a carrier.

* * * * *

UNITED STATES PATENT AND TRADEMARK OFFICE
CERTIFICATE OF CORRECTION

PATENT NO. : 10,407,501 B2
APPLICATION NO. : 15/110414
DATED : September 10, 2019
INVENTOR(S) : Edward Norbert Van Den Brink et al.

Page 1 of 33

It is certified that error appears in the above-identified patent and that said Letters Patent is hereby corrected as shown below:

On the Title Page

Under abstract "19 Claims, 26 Drawing Sheets" should read --19 Claims, 32 Drawing Sheets--.

In the Drawings

Please replace FIGS. 1-26 with FIGS. 1-32 as shown on the attached pages.

In the Claims

At Column 133, Claim number 5, Line number 57, delete "A35, R47, D71, A82, D83, S86, 187, and F89 in SEQ ID" and insert --A35, R47, D71, A82, D83, S86, I87, and F89 in SEQ ID--.

Signed and Sealed this
Twenty-second Day of September, 2020

Andrei Iancu
*Director of the United States Patent and Trademark Office*

| Antibody | EC50 (μg/mL) |
|---|---|
| IgG1-huCD3-H1L1 | 0.07 |
| IgG1-huCD3-H1L2 | 0.08 |
| IgG1-huCD3-H1L3 | 0.06 |
| IgG1-huCD3-H3L3 | 0.02 |
| IgG1-huCD3-H4L1 | 0.05 |
| IgG1-huCD3-H3L1-LFLEDA | 0.04 |
| IgG1-CD3-LFLEDA | 0.08 |

| Antibody | EC50 (μg/mL) |
|---|---|
| bsIgG1 CD3 x HER2 | 0.68 |
| bsIgG1 CD3 x b12-LFLEDA | 0.75 |
| bsIgG1 huCD3-H3L1xHER2-LFLEDA | 0.28 |
| IgG1-huCD3-H3L1-LFLEDA | 0.04 |
| IgG1-CD3-LFLEDA | 0.07 |

| Antibody | EC50 (µg/mL) |
|---|---|
| IgG1-huCD3-H1L1 | 0.37 |
| IgG1-huCD3-H1L2 | 0.31 |
| IgG1-huCD3-H1L3 | 0.28 |
| IgG1-huCD3-H3L3 | 0.11 |
| IgG1-huCD3-H4L1 | 0.26 |
| IgG1-huCD3-H3L1-LFLEDA | 0.19 |
| IgG1-CD3-LFLEDA | 0.30 |

| Antibody | EC50 (µg/mL) |
|---|---|
| bsIgG1 CD3xHER2-LFLEDA | 4.46 |
| bsIgG1 huCD3-H3L1xHER2-LFLEDA | 3.54 |
| IgG1-CD3-LFLEDA | 0.47 |
| IgG1-huCD3-H3L1-LFLEDA | 0.30 |

| Antibody | EC50 (µg/mL) |
|---|---|
| IgG1-huCD3-H3L1-LFLEDA | 0.04 |
| IgG1-huCD3-H3L3-LFLEDA | 0.03 |
| IgG1-huCD3-H1L1-LFLEDA | 0.03 |
| IgG1-huCD3-H1L3-LFLEDA | 0.03 |
| IgG1-huCD3-H4L1-LFLEDA | 0.03 |
| IgG1-huCD3-H4L3-LFLEDA | 0.02 |
| IgG1-CD3-LFLEDA | 0.06 |

| Antibody | EC50 (µg/mL) |
|---|---|
| bsIgG1-huCD3-H3L1xHER2-LFLEDA | 0.28 |
| bsIgG1-huCD3-H3L3xHER2-LFLEDA | 0.26 |
| bsIgG1-huCD3-H1L1xHER2-LFLEDA | 0.32 |
| bsIgG1-huCD3-H1L3xHER2-LFLEDA | 0.25 |
| bsIgG1-huCD3-H4L1xHER2-LFLEDA | 0.36 |
| bsIgG1-huCD3-H4L1xHER2-LFLEDA | 0.24 |
| IgG1-CD3-LFLEDA | 0.06 |

Figure 19

VH
VH3 EVKLVESGGGLVKPGRSLRLSCAASGFTFNTYAMNWVRQAPGKGLEWVARIRSKYNNVATYYADSVKDRFTISRDDSKSILYLQMNSLKTEDTAMYYCVRHGNFGNSYVSWFAYWGQGTLVTVSS
VH2 ----------------------------------------------------------------N--------------------------------------------------------- 99%
VH4 ------------------------------------------------------------------------------------------------------------M------------- 99%
VH1 ------Q-G----------------------------------------------------S---------N--------------------------------------------------- 97%

VL
VL1 QAVVTQEPSFSVSPGGTVTLTCRSSTGAVTTSNYANWVQQTPGQAFRGLIGTNKRAPGVPARFSGSLIGDKAALTITGAQADDESIYFCALWYSNLWVFGGGTKLTVL
VL2 -----------------------------------------------------------------------------------IL-N------------------- 97%
VL3 -----------------------------------------------------------------------------------IL-N----------D-Y------ 95%